(12) United States Patent
Abreu

(10) Patent No.: US 12,295,880 B2
(45) Date of Patent: May 13, 2025

(54) DEVICES CONFIGURED TO MONITOR BIOLOGICAL PARAMETERS, AND TO PROVIDE TREATMENT, AT AN ABREU BRAIN THERMAL TUNNEL

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

( * ) Notice: Subject to any disclaimer, the term of this patent is extended or adjusted under 35 U.S.C. 154(b) by 0 days.

(21) Appl. No.: 18/367,783

(22) Filed: Sep. 13, 2023

(65) Prior Publication Data

US 2023/0414407 A1    Dec. 28, 2023

Related U.S. Application Data

(60) Division of application No. 16/281,800, filed on Feb. 21, 2019, now Pat. No. 11,786,394, which is a
(Continued)

(51) Int. Cl.
| | | |
|---|---|---|
| *A61F 7/02* | (2006.01) | |
| *A61F 7/00* | (2006.01) | |
| *A61F 7/10* | (2006.01) | |

(52) U.S. Cl.
CPC ........ *A61F 7/02* (2013.01); *A61F 2007/0003* (2013.01); *A61F 2007/0004* (2013.01); *A61F 2007/0006* (2013.01); *A61F 2007/0007* (2013.01); *A61F 2007/0054* (2013.01); *A61F 2007/0059* (2013.01); *A61F 2007/0063* (2013.01); *A61F 2007/0071* (2013.01); *A61F 2007/0075* (2013.01);
(Continued)

(58) Field of Classification Search
CPC ..... A61F 7/02; A61F 7/007; A61F 2007/0071
See application file for complete search history.

(56) References Cited

U.S. PATENT DOCUMENTS

| | | |
|---|---|---|
| 3,173,419 A | 3/1965 | Dubilier et al. |
| 3,463,885 A | 8/1969 | Upton |

(Continued)

FOREIGN PATENT DOCUMENTS

| | | |
|---|---|---|
| CN | 2398565 Y | 9/2000 |
| CN | 2446955 Y | 9/2001 |

(Continued)

OTHER PUBLICATIONS

RCA Technical Notes, Contact Lens Tonometer by Robert E. Morey, RCA TN No. 602, dated Dec. 1964, 2 pages.
(Continued)

*Primary Examiner* — Kaitlyn E Smith
(74) *Attorney, Agent, or Firm* — Studebaker Brackett PLLC

(57) ABSTRACT

Devices for therapeutic interaction with an Abreu brain thermal tunnel (ABTT) terminus. Such devices provide heat to or remove heat from the ABTT terminus, and may also provide heat to or remove heat from veins connected to the ABTT. Therapeutic devices for engaging with the ABTT terminus benefit from diagnostics obtained at the ABTT terminus, or from other locations on the body.

7 Claims, 85 Drawing Sheets

Related U.S. Application Data continuation of application No. 14/594,122, filed on Jan. 10, 2015, now Pat. No. 10,251,776.

(60) Provisional application No. 61/930,262, filed on Jan. 22, 2014, provisional application No. 61/926,159, filed on Jan. 10, 2014.

(52) U.S. Cl.
CPC ............. A61F 2007/0076 (2013.01); A61F 2007/0093 (2013.01); A61F 2007/0094 (2013.01); A61F 2007/0096 (2013.01); A61F 2007/0228 (2013.01); A61F 2007/108 (2013.01)

(56) References Cited

U.S. PATENT DOCUMENTS

| | | |
|---|---|---|
| 3,531,642 A | 9/1970 | Barnes et al. |
| 3,545,260 A | 12/1970 | Lichtenstein et al. |
| 3,585,849 A | 6/1971 | Grolman |
| 3,626,757 A | 12/1971 | Benzinger |
| 3,724,263 A | 4/1973 | Rose et al. |
| 3,769,961 A | 11/1973 | Fatt et al. |
| 3,897,272 A | 7/1975 | Medlar |
| 3,897,790 A | 8/1975 | Magilton et al. |
| 3,963,019 A | 6/1976 | Quandt |
| 4,186,184 A | 1/1980 | Zaffaroni |
| 4,231,052 A | 10/1980 | Day et al. |
| 4,297,685 A | 10/1981 | Brainard, II |
| 4,305,399 A | 12/1981 | Beale |
| 4,312,358 A | 1/1982 | Barney |
| 4,321,261 A | 3/1982 | Ellis et al. |
| 4,330,299 A | 5/1982 | Cerami |
| 4,331,161 A | 5/1982 | Patel |
| 4,344,315 A | 8/1982 | Moxon et al. |
| 4,344,438 A | 8/1982 | Schultz |
| 4,386,831 A | 6/1983 | Grounauer |
| 4,444,990 A | 4/1984 | Villar |
| 4,485,820 A | 12/1984 | Flower |
| 4,488,558 A | 12/1984 | Simbruner et al. |
| 4,595,020 A | 6/1986 | Palti |
| 4,597,392 A | 7/1986 | Opitz et al. |
| 4,628,938 A | 12/1986 | Lee |
| 4,629,424 A | 12/1986 | Lauks et al. |
| 4,771,792 A | 9/1988 | Seale |
| 4,784,149 A | 11/1988 | Berman et al. |
| 4,830,014 A | 5/1989 | Goodman et al. |
| 4,846,196 A | 7/1989 | Wiksell et al. |
| 4,860,755 A | 8/1989 | Erath |
| 4,922,913 A | 5/1990 | Waters, Jr. et al. |
| 4,944,303 A | 7/1990 | Katsuragi |
| 4,947,849 A | 8/1990 | Takahashi et al. |
| 4,951,671 A | 8/1990 | Coan |
| 4,979,831 A | 12/1990 | Schertz et al. |
| 5,005,577 A | 4/1991 | Frenkel |
| 5,046,482 A | 9/1991 | Everest |
| 5,062,432 A | 11/1991 | James et al. |
| 5,076,274 A | 12/1991 | Matsumoto |
| 5,109,852 A | 5/1992 | Kaye et al. |
| 5,115,815 A | 5/1992 | Hansen |
| 5,148,807 A | 9/1992 | Hsu |
| 5,165,409 A | 11/1992 | Coan |
| 5,179,953 A | 1/1993 | Kursar |
| 5,183,044 A | 2/1993 | Nishio et al. |
| 5,190,039 A | 3/1993 | Takeuchi et al. |
| 5,209,231 A | 5/1993 | Cote et al. |
| 5,217,015 A | 6/1993 | Kaye et al. |
| 5,222,495 A | 6/1993 | Clarke et al. |
| 5,222,809 A | 6/1993 | Ehrenkranz |
| 5,246,867 A | 9/1993 | Lakowicz et al. |
| 5,251,627 A | 10/1993 | Morris |
| 5,255,979 A | 10/1993 | Ferrari |
| 5,295,495 A | 3/1994 | Maddess |
| 5,297,554 A | 3/1994 | Glynn et al. |
| 5,341,805 A | 8/1994 | Stavridi et al. |
| 5,342,283 A | 8/1994 | Good |
| 5,342,789 A | 8/1994 | Chick et al. |
| 5,352,411 A | 10/1994 | Khuri |
| 5,356,780 A | 10/1994 | Robinson et al. |
| 5,375,595 A | 12/1994 | Sinha et al. |
| 5,383,452 A | 1/1995 | Buchert |
| 5,433,197 A | 7/1995 | Stark |
| 5,435,307 A | 7/1995 | Friauf et al. |
| 5,441,476 A | 8/1995 | Kitado et al. |
| 5,503,770 A | 4/1996 | James et al. |
| 5,522,662 A | 6/1996 | Shiokawa |
| 5,636,635 A | 6/1997 | Massie et al. |
| 5,653,239 A | 8/1997 | Pompei et al. |
| 5,664,578 A | 9/1997 | Boczan |
| 5,673,692 A | 10/1997 | Schulze et al. |
| 5,711,915 A | 1/1998 | Siegmund et al. |
| 5,796,341 A | 8/1998 | Stratiotis |
| 5,813,982 A | 9/1998 | Baratta |
| 5,817,008 A | 10/1998 | Rafert et al. |
| 5,820,557 A | 10/1998 | Hattori et al. |
| 5,830,139 A | 11/1998 | Abreu |
| 5,833,633 A | 11/1998 | Sarvazyan |
| 5,854,078 A | 12/1998 | Asher et al. |
| 5,860,934 A | 1/1999 | Sarvazyan |
| 5,862,803 A | 1/1999 | Besson et al. |
| 5,898,004 A | 4/1999 | Asher et al. |
| 5,984,880 A | 11/1999 | Lander et al. |
| 5,994,701 A | 11/1999 | Tsuchimoto et al. |
| 6,011,984 A | 1/2000 | Van Antwerp et al. |
| 6,028,323 A | 2/2000 | Liu |
| 6,040,194 A | 3/2000 | Chick et al. |
| 6,042,266 A | 3/2000 | Cheslock et al. |
| 6,047,203 A | 4/2000 | Sackner et al. |
| 6,072,180 A | 6/2000 | Kramer et al. |
| 6,120,460 A | 9/2000 | Abreu |
| 6,123,668 A | 9/2000 | Abreu |
| 6,126,595 A | 10/2000 | Amano et al. |
| 6,135,968 A | 10/2000 | Brounstein |
| 6,152,875 A | 11/2000 | Hakamata |
| 6,178,346 B1 | 1/2001 | Amundson et al. |
| 6,181,957 B1 | 1/2001 | Lambert et al. |
| 6,187,599 B1 | 2/2001 | Asher et al. |
| 6,196,714 B1 | 3/2001 | Bellifemine et al. |
| 6,197,534 B1 | 3/2001 | Lakowicz et al. |
| 6,197,928 B1 | 3/2001 | Tsien et al. |
| 6,203,193 B1 | 3/2001 | Egawa |
| 6,213,943 B1 | 4/2001 | Abreu |
| 6,256,522 B1 | 7/2001 | Schultz |
| 6,290,658 B1 | 9/2001 | Kolich |
| 6,292,685 B1 | 9/2001 | Pompei |
| 6,300,871 B1 | 10/2001 | Irwin et al. |
| 6,312,393 B1 | 11/2001 | Abreu |
| 6,319,540 B1 | 11/2001 | Van Antwerp et al. |
| 6,385,473 B1 | 5/2002 | Haines et al. |
| 6,385,474 B1 | 5/2002 | Rather et al. |
| 6,423,001 B1 | 7/2002 | Abreu |
| 6,432,050 B1 | 8/2002 | Porat et al. |
| 6,470,893 B1 | 10/2002 | Boesen |
| 6,529,617 B1 | 3/2003 | Prokoski |
| 6,536,945 B2 | 3/2003 | Rolston |
| 6,542,081 B2 | 4/2003 | Torch |
| 6,543,933 B2 | 4/2003 | Stergiopoulos et al. |
| 6,544,193 B2 | 4/2003 | Abreu |
| 6,681,127 B2 | 1/2004 | March |
| 6,731,976 B2 | 5/2004 | Penn et al. |
| 6,789,901 B1 | 9/2004 | Kormos |
| 6,791,087 B1 | 9/2004 | Okumura |
| 6,846,106 B1 | 1/2005 | Chen et al. |
| 7,187,960 B2 | 3/2007 | Abreu |
| 7,340,293 B2 | 3/2008 | McQuilkin |
| 7,346,386 B2 | 3/2008 | Pompei |
| 7,515,054 B2 | 4/2009 | Torch |
| 7,597,668 B2 | 10/2009 | Yarden |
| 7,621,877 B2 | 11/2009 | Schnall |
| 7,689,437 B1 | 3/2010 | Teller et al. |
| 7,756,559 B2 | 7/2010 | Abreu |
| 7,787,938 B2 | 8/2010 | Pompei |
| 7,837,623 B2 | 11/2010 | Aubry et al. |

(56) References Cited

U.S. PATENT DOCUMENTS

| | | |
|---|---|---|
| 8,103,071 B2 | 1/2012 | Schnell et al. |
| 8,172,459 B2 | 5/2012 | Abreu |
| 8,328,420 B2 | 12/2012 | Abreu |
| 8,500,271 B2 | 8/2013 | Howell et al. |
| 8,527,022 B1 | 9/2013 | Lash et al. |
| 8,721,562 B2 | 5/2014 | Abreu |
| 8,834,020 B2 | 9/2014 | Abreu |
| 8,849,379 B2 | 9/2014 | Abreu |
| 9,007,220 B2 | 4/2015 | Johns et al. |
| 10,251,776 B2 * | 4/2019 | Abreu ................ A61F 7/02 |
| 11,786,394 B2 * | 10/2023 | Abreu ................ A61F 7/02 607/104 |
| 2001/0028309 A1 | 10/2001 | Torch |
| 2002/0026119 A1 | 2/2002 | Pompei |
| 2002/0035340 A1 | 3/2002 | Fraden et al. |
| 2002/0049374 A1 | 4/2002 | Abreu |
| 2002/0049389 A1 | 4/2002 | Abreu |
| 2002/0068876 A1 | 6/2002 | Pompei et al. |
| 2002/0111657 A1 | 8/2002 | Dae et al. |
| 2002/0126731 A1 | 9/2002 | Stergiopoulos et al. |
| 2003/0055473 A1 | 3/2003 | Ramsden et al. |
| 2003/0060863 A1 | 3/2003 | Dobak |
| 2003/0067958 A1 | 4/2003 | Jang |
| 2003/0108223 A1 | 6/2003 | Prokoski |
| 2003/0111605 A1 | 6/2003 | Sato et al. |
| 2003/0179094 A1 | 9/2003 | Abreu |
| 2003/0210146 A1 | 11/2003 | Tseng |
| 2003/0212340 A1 | 11/2003 | Lussier et al. |
| 2004/0039298 A1 | 2/2004 | Abreu |
| 2004/0059212 A1 | 3/2004 | Abreu |
| 2004/0076316 A1 | 4/2004 | Fauci |
| 2004/0082862 A1 | 4/2004 | Chance |
| 2004/0125996 A1 | 7/2004 | Eddowes et al. |
| 2004/0152991 A1 | 8/2004 | Pompei |
| 2004/0154550 A1 | 8/2004 | McQuilkin |
| 2004/0170216 A1 | 9/2004 | Russak et al. |
| 2004/0210159 A1 | 10/2004 | Kibar |
| 2004/0246548 A1 | 12/2004 | Papuchon et al. |
| 2005/0250996 A1 | 11/2005 | Shirai et al. |
| 2006/0122473 A1 | 6/2006 | Kill et al. |
| 2006/0215728 A1 | 9/2006 | Jang |
| 2006/0264726 A1 | 11/2006 | Mannheimer et al. |
| 2007/0055171 A1 | 3/2007 | Fraden |
| 2007/0219434 A1 | 9/2007 | Abreu |
| 2008/0043809 A1 | 2/2008 | Herbert |
| 2008/0200830 A1 | 8/2008 | Pompei |
| 2008/0214949 A1 | 9/2008 | Stivoric et al. |
| 2009/0105605 A1 * | 4/2009 | Abreu .................. A61B 5/0075 600/549 |
| 2009/0157056 A1 | 6/2009 | Ferren et al. |
| 2010/0022909 A1 | 1/2010 | Padiy |
| 2010/0113894 A1 | 5/2010 | Padiy |
| 2010/0204765 A1 | 8/2010 | Hall et al. |
| 2011/0024626 A1 | 2/2011 | O'Donnell et al. |
| 2011/0040161 A1 | 2/2011 | Abreu |
| 2011/0077546 A1 | 3/2011 | Fabian |
| 2011/0092822 A1 | 4/2011 | Pompei |
| 2012/0031405 A1 | 2/2012 | Geist et al. |
| 2012/0136285 A1 | 5/2012 | Korb et al. |
| 2013/0124039 A1 | 5/2013 | Abreu |
| 2013/0172790 A1 | 7/2013 | Badawi |
| 2013/0215928 A1 | 8/2013 | Bellifemine |
| 2013/0292571 A1 | 11/2013 | Mukherjee et al. |

FOREIGN PATENT DOCUMENTS

| | | |
|---|---|---|
| CN | 1328432 A | 12/2001 |
| DE | 4433104 C1 | 5/1996 |
| EP | 0236028 A2 | 9/1987 |
| EP | 0411121 A2 | 2/1991 |
| EP | 2 120 681 B1 | 7/2011 |
| EP | 1 951 110 B1 | 10/2012 |
| JP | S61-48369 A | 3/1986 |
| JP | H10-075934 A | 3/1998 |
| JP | H10-239158 A | 9/1998 |
| JP | H11-164826 A | 6/1999 |
| JP | 2001-500394 A | 1/2001 |
| JP | 2001/031151 A | 2/2001 |
| JP | 2002-525132 A | 8/2002 |
| JP | 3885024 B2 | 2/2007 |
| WO | 93/01745 A1 | 2/1993 |
| WO | 97/19188 A1 | 5/1997 |
| WO | 98/22820 A1 | 5/1998 |
| WO | 99/51142 A2 | 10/1999 |
| WO | 00/10007 A2 | 2/2000 |
| WO | 00/13580 A1 | 3/2000 |
| WO | 00/16051 A1 | 3/2000 |
| WO | 00/16099 A1 | 3/2000 |
| WO | 00/18237 A1 | 4/2000 |
| WO | 00/64492 A1 | 11/2000 |
| WO | 02/03855 A1 | 1/2002 |
| WO | 02/28271 A2 | 4/2002 |
| WO | 02/067688 A1 | 9/2002 |
| WO | 2005/015163 A2 | 2/2005 |
| WO | 2010-042738 A2 | 4/2010 |

OTHER PUBLICATIONS

Ophthal. Physiol. Opt., 1989, vol. 9, April, Research Note, Multiple Applications of the NCT: An Assessment of Instrument's Effect on IOP by G.E Russell and J.P.G. Bergmanson, pp. 212-214.

Arch Ophthalmol—vol. 97, Mar. 1979, The Pneumatonograph—A Laboratory Study, by Robert A. Moses, M.D. and Walter J. Grodzki Jr., D.D.S., pp. 547-552.

IEEE Transactions on bio-Medical Engineering, vol. BME-14, No. 2, Apr. 1967, Miniature Passive Pressure Transensor for Implanting in the Eye, by C.C. Collins, pp. 74-83.

Trans. Amer. Acad. of O. & O., Jan.-Feb. 1957, Tonometer Calibration, An Attempt to Remove Discrepancies Found in the 1954 Calibration Scale for Schiotz Tonometers by Jonas S. Friedenwald, M.D., pp. 108-123.

Investigative Ophthalmology, Feb. 1962, The Relationship Between Pressure and Volume Changes in Living and Dead Rabbit Eyes, by John E. Eisenlohr and Maurice E. Langham, pp. 63-77.

Investigative Ophthalmology, Sep. 1971, vol. 10, No. 9, Theory and Calibration of the Schiotz Tonometer VII. Experimental Results of Tonometric Measurements: Scale Reading Versus Indentation Volume by Robert A. Moses and Walter J. Grodzki, pp. 716-723.

The British Journal of Ophthalmology, Jun. 1920, Communications—Tonometry, by HJ. Schiötz, pp. 249-261.

American Journal of Opthalmology, vol. 20, No. 10, Oct. 1937, Contribution to the Theory and Practice of Tonometry by Jonas S. Friedenwald, M.D., pp. 985-1024.

Ophthalmologica vol. 150, No. 5, (1965), Rheology of the Human Sclera, Unifying Formulation of Ocular Rigidity, by W.K. McEwen and Roger St. Helen, pp. 321-346.

A.M.A. Archives of Ophthalmology, vol. 57, Apr. 1957, Tonometer Calibration, by Earle H. McBain, M.D., pp. 520-531.

The Photonics Dictionary, 1996 Book 4, 42nd Edition, pp. D-24, D153.

Manual of Skin Diseases, Fifth Edition, Gordon C. Sauer, MD., 1985, pp. 204, 373.

Textbook of Biochemistry With Clinical Correlations, Second Edition, Thomas M. Devlin, Ph.D., 1986, pp. 118, 139.

Physical Optics, Third Revised Edition, Robert W. Wood, 1961, pp. 650-651.

An Examiner's First Report; issued by the Australian Government, IP Australia dated Dec. 18, 2008, which corresponds to Australian Patent Application No. 2004263812.

An Examiner's First Report; issued by the Australian Government, IP Australia dated Mar. 10, 2010, which corresponds to Australian Patent Application No. 2009212808.

An Examiner's First Report; issued by the Australian Government, IP Australia dated Feb. 19, 2010, which corresponds to Australian Patent Application No. 2009212861.

An Examiner's First Report; issued by the Australian Government, IP Australia dated Nov. 4, 2013, which corresponds to Australian Patent Application No. 2012247045.

(56) References Cited

OTHER PUBLICATIONS

An Office Action issued by the Canadian Intellectual Property Office dated May 3, 2012, which corresponds to Canadian Patent Application No. 2,517,869.
English translation of a First Office Action and Search Report; issued by the State Intellectual Property Office of the People's Republic of China dated Jul. 21, 2014, which corresponds to Chinese Patent Application No. 201310097177.3.
English translation of a First Office Action and Search Report; issued by the State Intellectual Property Office of the People's Republic of China dated Jul. 22, 2014, which corresponds to Chinese Patent Application No. 201310097142.
A supplementary European Search Report; issued by the European Patent Office dated Oct. 17, 2008, which corresponds to European Patent Application No. 04785841.0-1265.
A "Communication pursuant to Article 94(3) EPC," issued by the European Patent Office dated Jan. 27, 2009, which corresponds to European Patent Application No. 04785841.0-1265.
A "Communication pursuant to Article 94(3) EPC," issued by the European Patent Office dated Sep. 12, 2013, which corresponds to European Patent Application No. 04785841.0-1657.
English Translation of Relevant Portion of Office Action; issued by the State of Israel Department of Justice, Patent Office dated Jul. 3, 2013, which corresponds to Israeli Patent Application No. 1704896.
English translation of Notification of Reasons for Refusal; issued by the Japanese Patent Office dated Jun. 11, 2009, which corresponds to Japanese Patent Application No. 2006-508817.
English translation of Notification of Reasons for Refusal; issued by the Japanese Patent Office dated Jan. 12, 2010, which corresponds to Japanese Patent Application No. 2006-508817.
A Summarized English Translation of Office Action; issued by the Instituto Mexicano de la Propiedad Industrial dated Jul. 4, 2008, which corresponds to Mexican National Phase Patent Application No. PA/a/2005/009159.
An Office Action; issued by the Instituto Mexicano de la Propiedad Industrial dated Sep. 25, 2009, which corresponds to Mexican National Phase Patent Application No. PA/a/2005/009159.
International Search Report & Written Opinion; PCT/US2004/005496; dated May 6, 2005.
English translation of an Office Action; issued by the Japanese Patent Office dated Jan. 22, 2009, which corresponds to Japanese Patent Application No. 2004-515642.
English translation of an Office Action; issued by the National Institute of Industrial Property dated Jul. 1, 2013, which corresponds to Brazilian Patent Application PI0309578-9.
English translation of the "First Office Action," and "Search Report," issued by the State Intellectual Property Office of the People's Republic of China dated Jun. 4, 2014, which corresponds to Chinese Application No. 201210361917.5.
A "Communication pursuant to Article 94(3) EPC," issued by the European Patent Office dated Jan. 27, 2009, which corresponds to European Patent Application No. 03 754 363.4-1265.
A second "Communication pursuant to Article 94(3) EPC," issued by the European Patent Office dated Sep. 13, 2013, which corresponds to European Patent Application No. 03 754 363.4-1657.
A third "Communication pursuant to Article 94(3) EPC," issued by the European Patent Office dated Mar. 4, 2014, which corresponds to European Patent Application No. 03 754 363.4-1657.
A fourth "Communication pursuant to Article 94(3) EPC," issued by the European Patent Office dated Sep. 24, 2014, which corresponds to European Patent Application No. 03 754 363.4-1657.
English translation of an Office Action; issued by the State of Israel Department of Justice, Patent Office dated Nov. 26, 2008, which corresponds to Israeli Patent Application No. 164685.

English translation of an Office Action; issued by the Korean Intellectual Property Office dated Dec. 26, 2011, which corresponds to Korean Patent Application No. 10-2010-7018173.
International Search Report; PCT/US03/12382; dated May 13, 2005.
International Search Report; PCT/US2006/041238; dated Aug. 31, 2007.
An Office Action issued by the Canadian Intellectual Property Office dated Aug. 2, 2011, which corresponds to Canadian Patent Application No. 2,627,278.
A Second Office Action issued by the Canadian Intellectual Property Office dated Mar. 14, 2012, which corresponds to Canadian Patent Application No. 2,627,278.
A "Communication pursuant to Particle 94(3) EPC," issued by the European Patent Office dated May 13, 2011, which corresponds to European Patent Application No. 06 826 452.2-2319.
English translation of an Office Action; issued by the State of Israel Department of Justice, Patent Office dated Jun. 23, 2011, which corresponds to Israeli Patent Application No. 191039.
An Examiner's First Report; issued by the Australian Government, IP Australia dated Jan. 13, 2012, which corresponds to Australian Patent Application No. 2011202015.
Patent Examination Report No. 1; issued by the Australian Government, IP Australia dated Dec. 13, 2013, which corresponds to Australian Patent Application No. 2012203667.
An Examiner's First Report; issued by the Australian Government, IP Australia dated Apr. 21, 2009, which corresponds to Australian Patent Application No. 2006306422.
An Examiner's Report No. 2; issued by the Australian Government, IP Australia dated Nov. 10, 2010, which corresponds to Australian Patent Application No. 2006306422.
English translation of an Office Action; issued by the Korean Intellectual Property Office dated Jun. 21, 2013, which corresponds to Korean Patent Application No. 10-2008-7012335.
English translation of an Office Action; issued by the Japanese Patent Office dated Nov. 17, 2011, which corresponds to Japanese Patent Application No. 2008-537828.
English translation of a Second Office Action; issued by the Japanese Patent Office dated Nov. 13, 2012, which corresponds to Japanese Patent Application No. 2008-537828.
English translation of a Third Office Action; issued by the Japanese Patent Office dated Nov. 26, 2013, which corresponds to Japanese Patent Application No. 2008-537828.
Overton, Staci. "Brain Temperature Tunnel Discovered." Medical Breakthroughs Reported by Ivanhoe, Jun. 2, 2003.
International Search Report; PCT/US2014/060199; dated Jan. 8, 2015.
International Search Report; PCT/US2014/060201; dated Mar. 3, 2015.
Dittmar, A et al., A Non Invasive Wearable Sensor for the Measurement of Brain Temperature. Proceedings of the 28th IEEE EMBS Annual International Conference. Aug. 30-Sep. 3, 2006. pp. 900-902, New York City, USA.
An Office Action and Examination Search Report issued by the Canadian Intellectual Property Office dated Mar. 26, 2015, which corresponds to Canadian Patent Application No. 2,627,278.
International Search Report; PCTUS2015/010873; dated Apr. 10, 2015.
International Preliminary Report on Patentability; PCT/US2015/012546 dated Aug. 26, 2016; and is related to U.S. Appl. No. 14/594,122.
Written Opinion of the International Searching Authority; PCT/US15/12546 dated Feb. 26, 2016, and is related to U.S. Appl. No. 14/594,122.
The International Search Report dated Jun. 12, 2015, which corresponds to International Patent Application No. PCT/US15/10938 and is related to U.S. Appl. No. 14/594, 122.

\* cited by examiner

FIG. 14
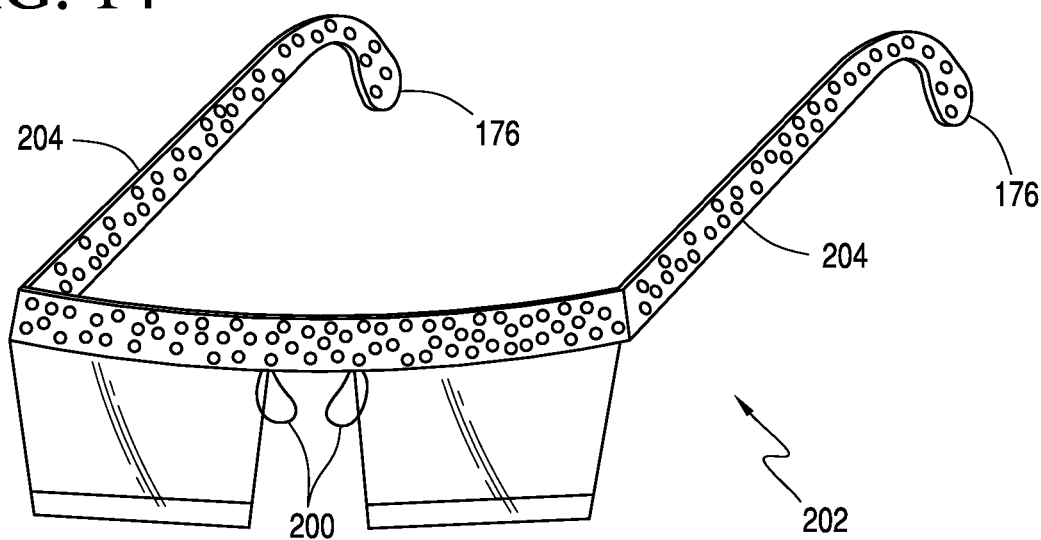
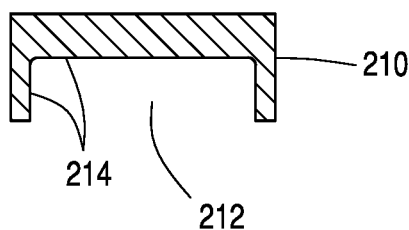
FIG. 16
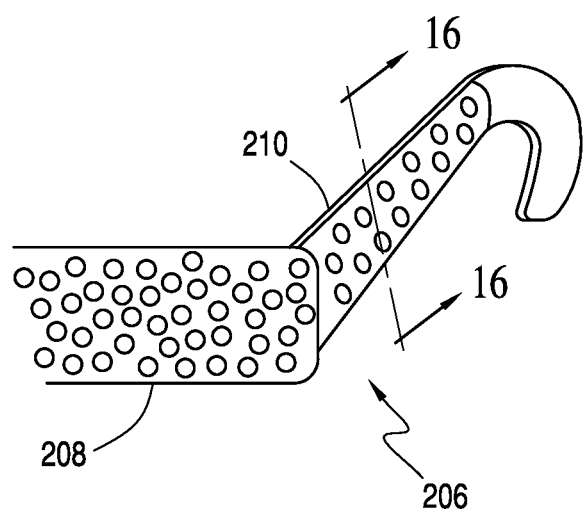
FIG. 15

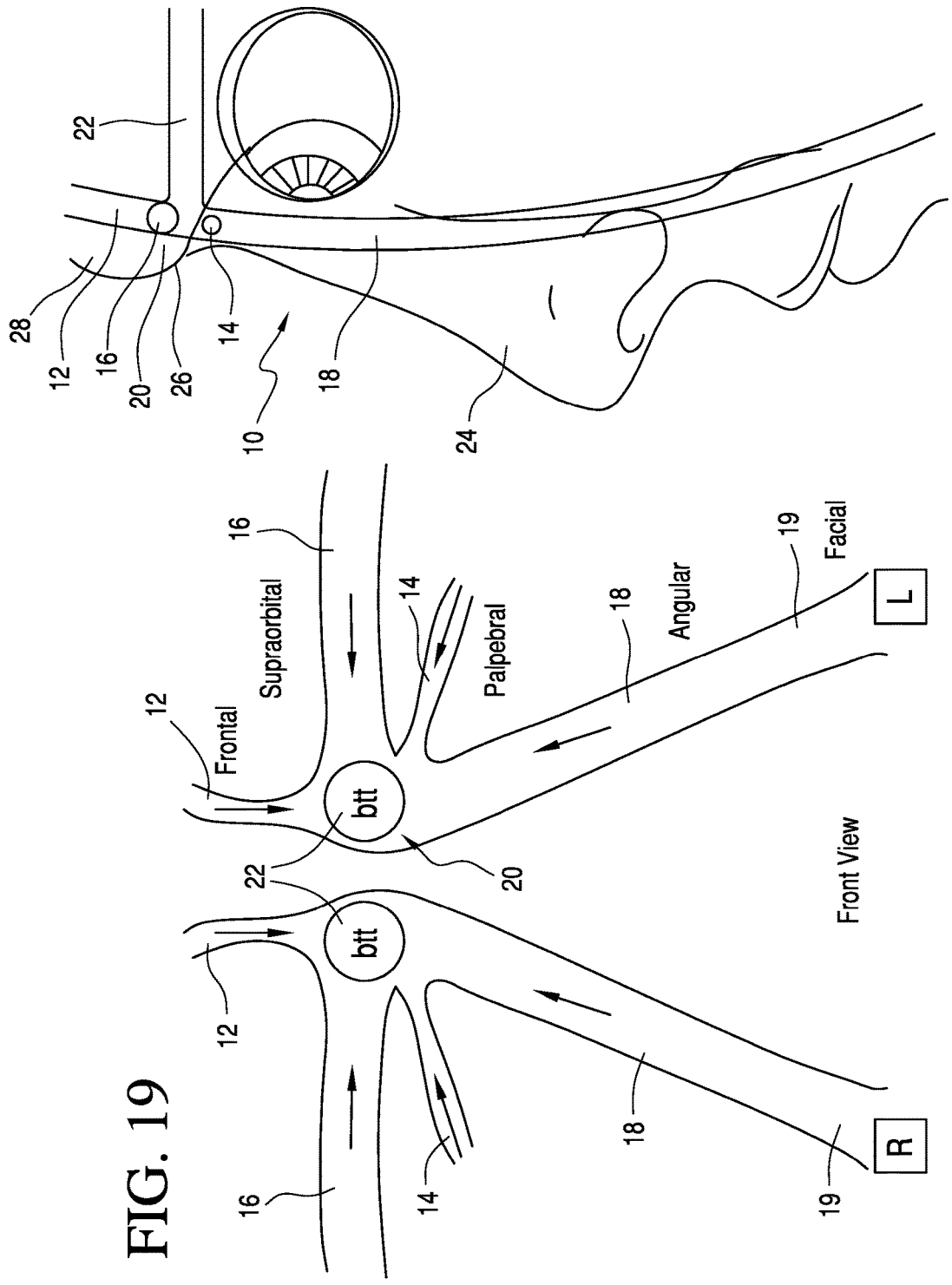

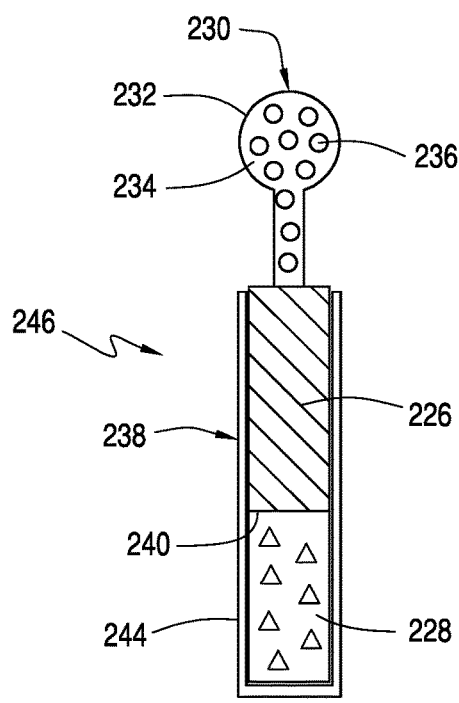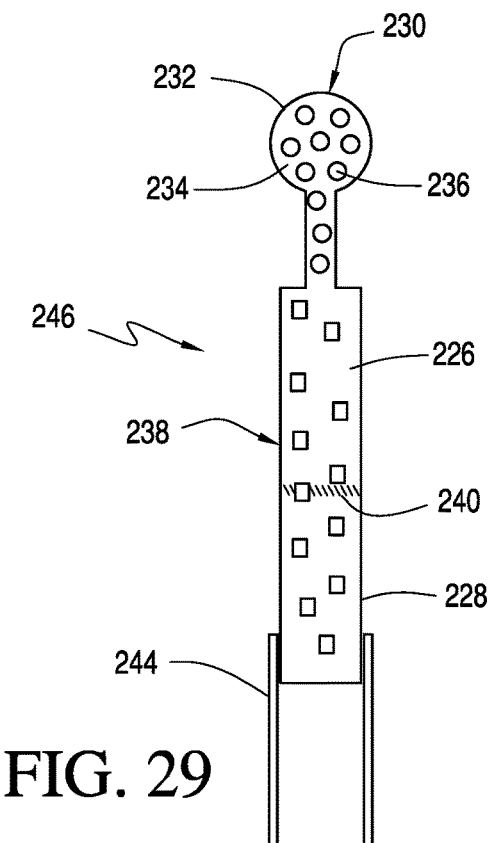
FIG. 28  FIG. 29
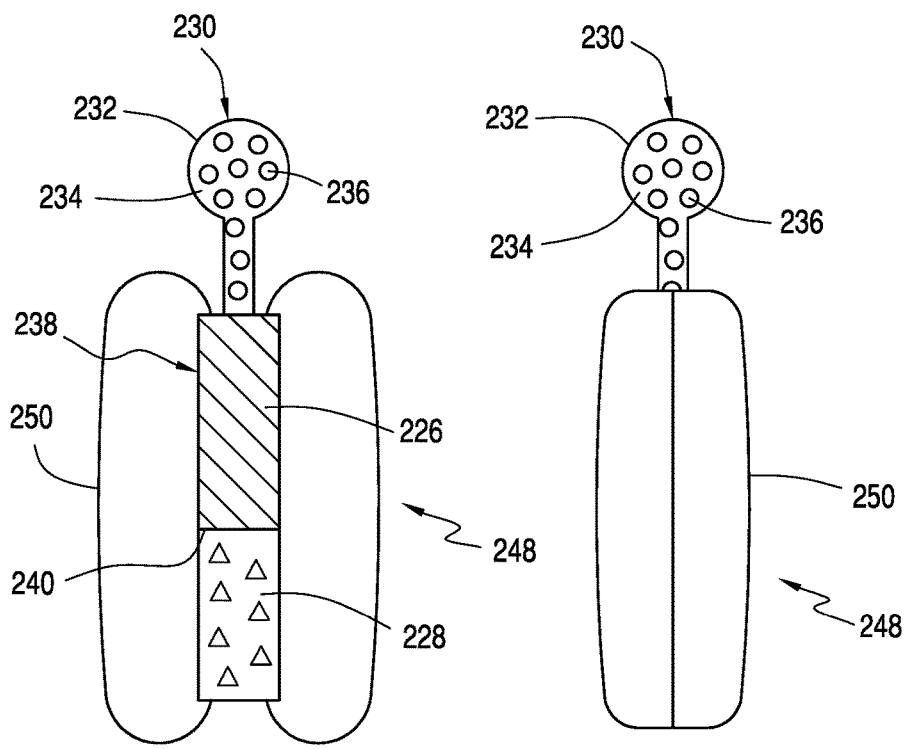
FIG. 30  FIG. 31

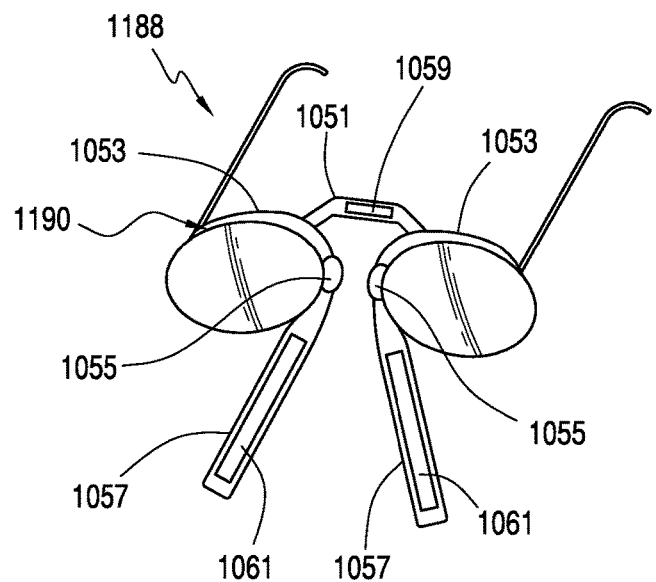
FIG. 36
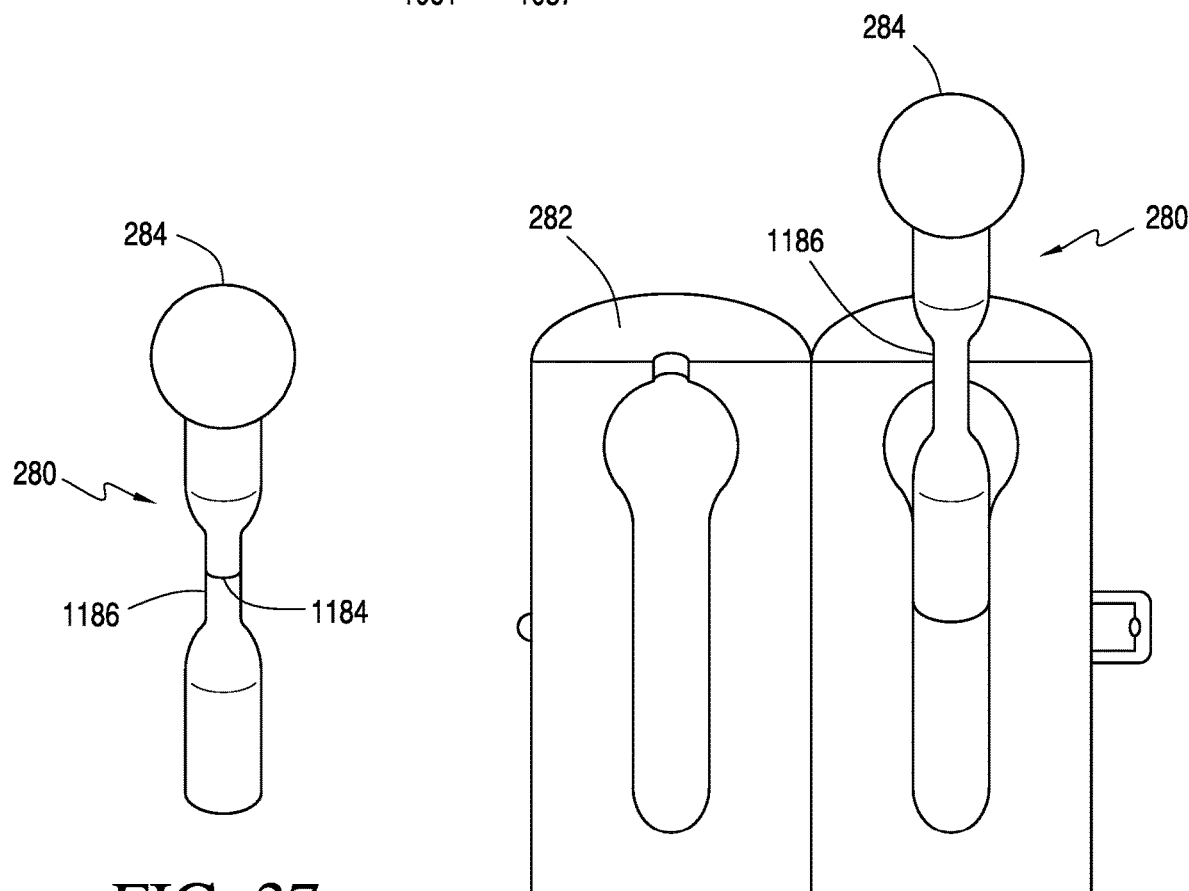
FIG. 37
FIG. 38

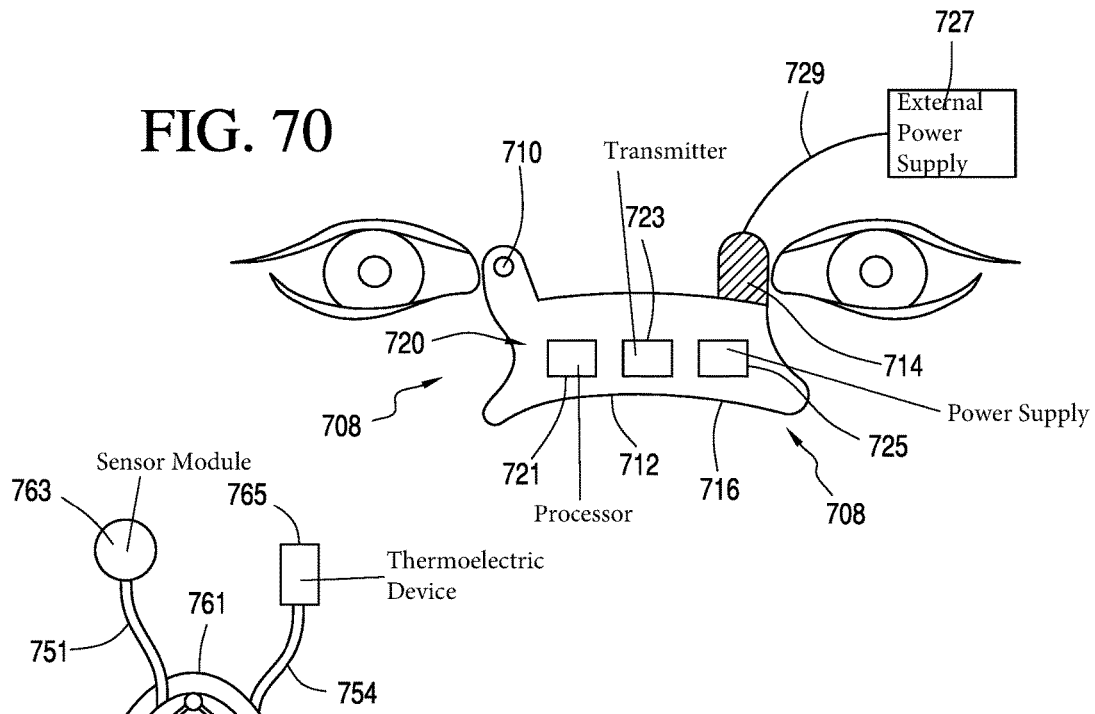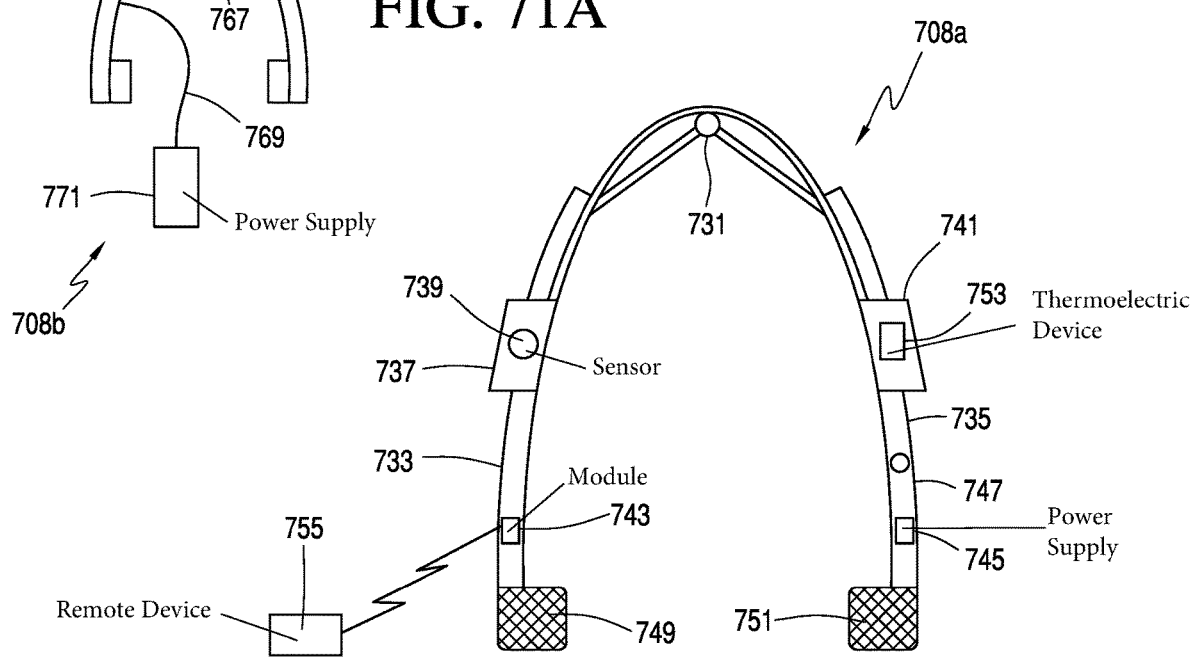

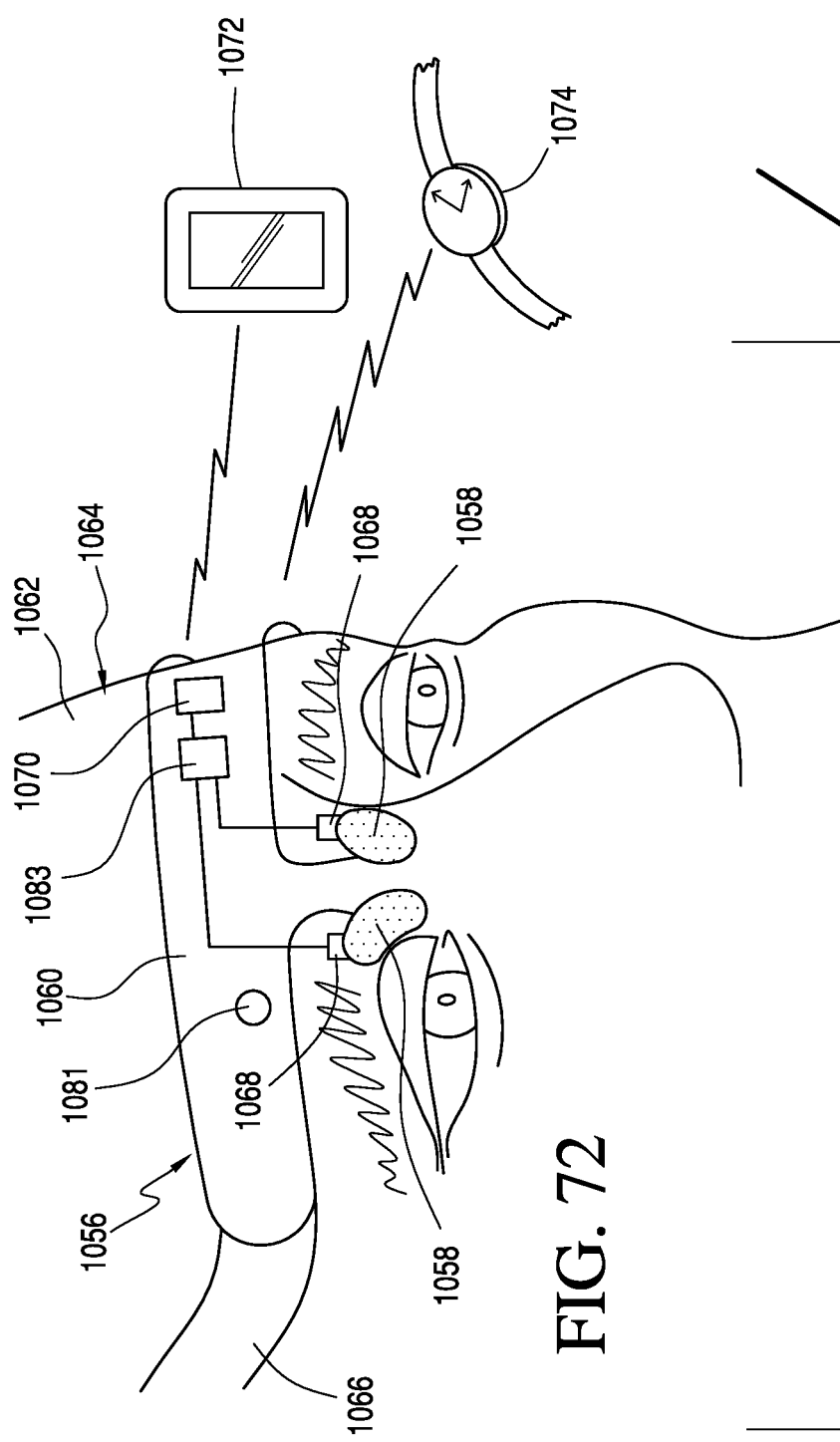

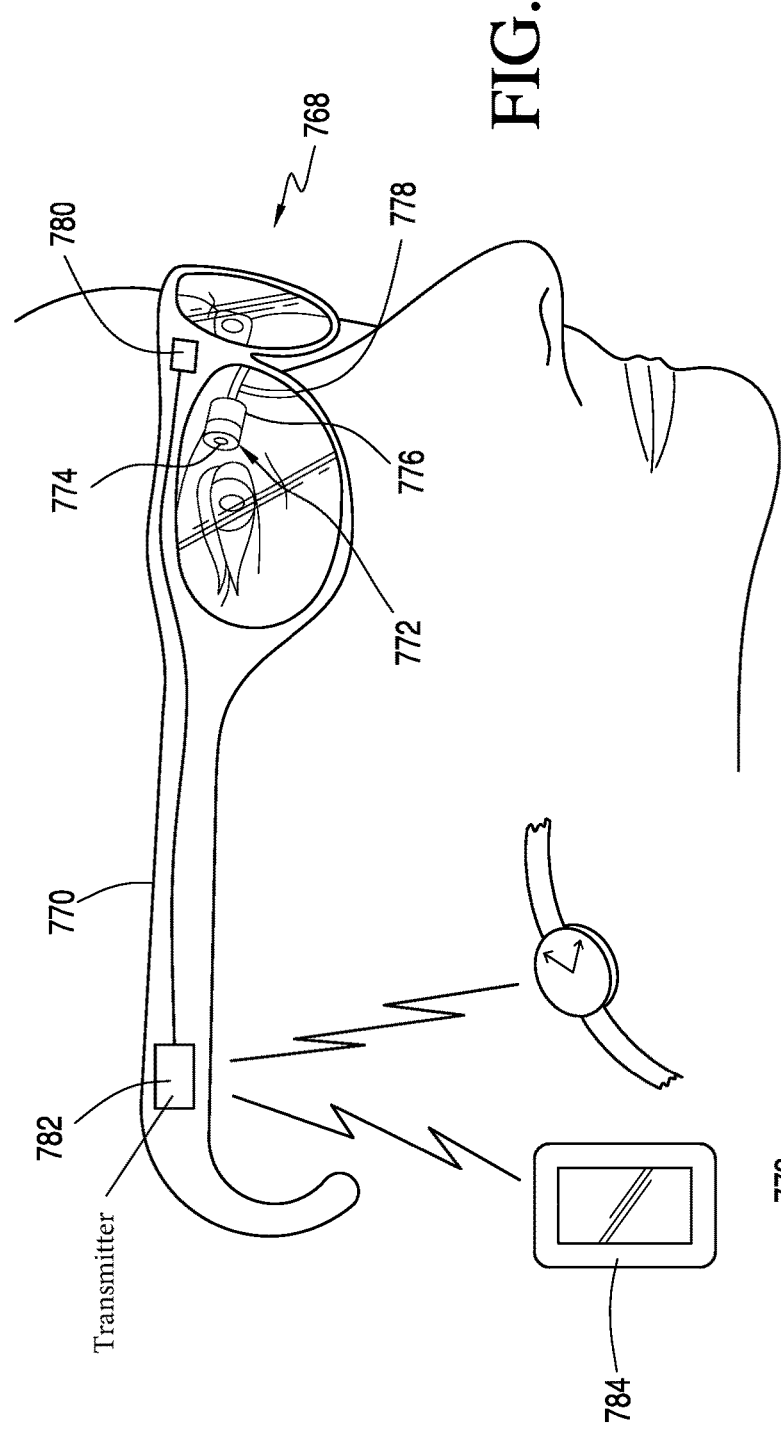
FIG. 77
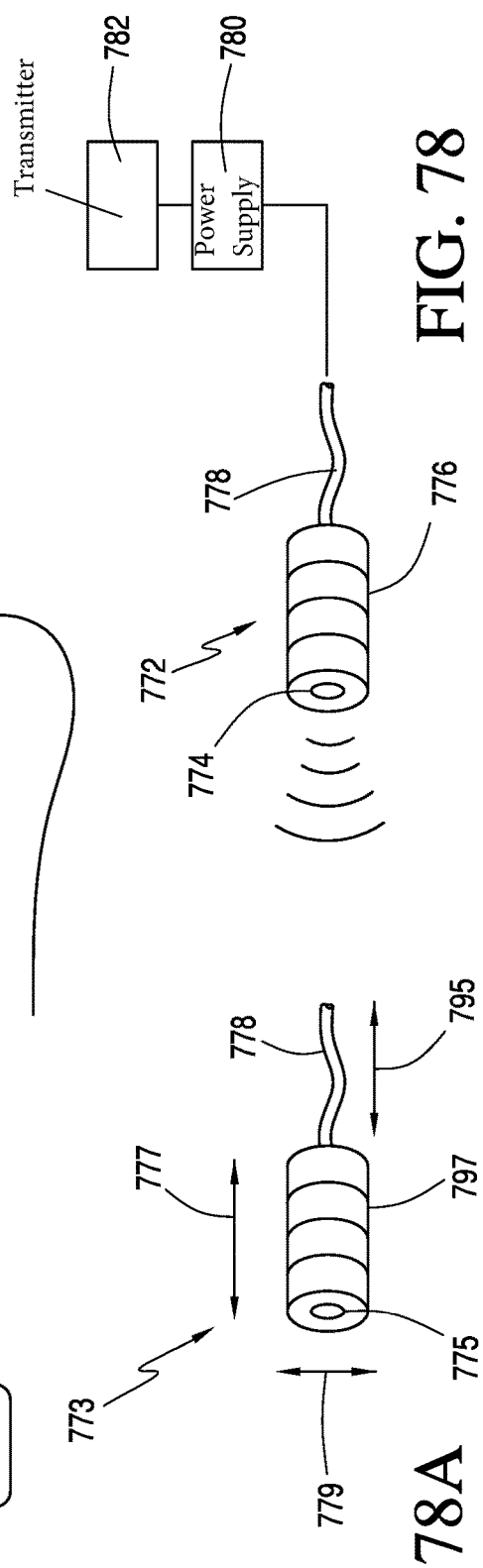
FIG. 78
FIG. 78A

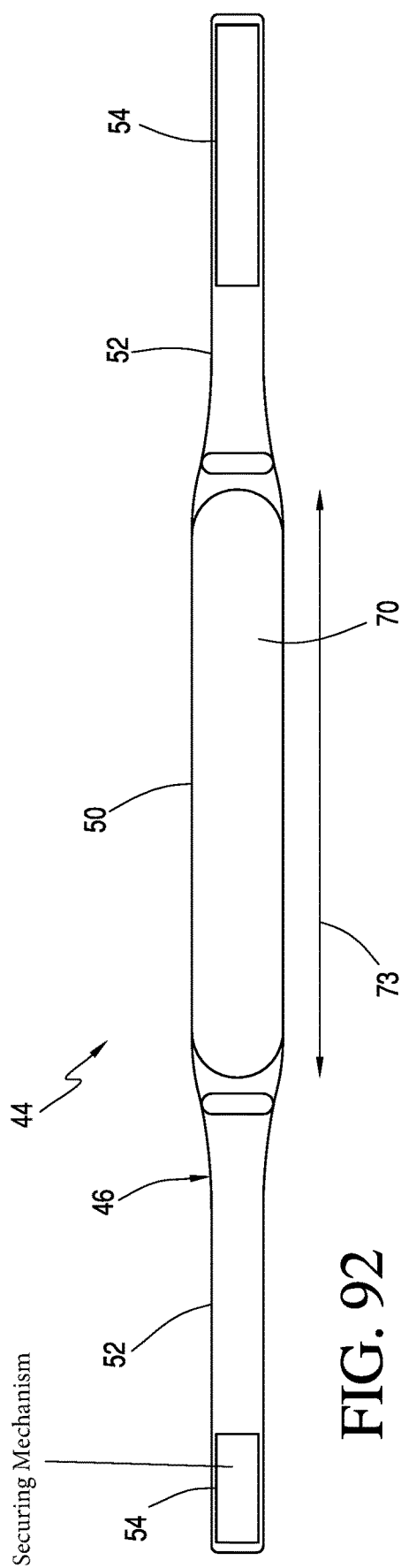
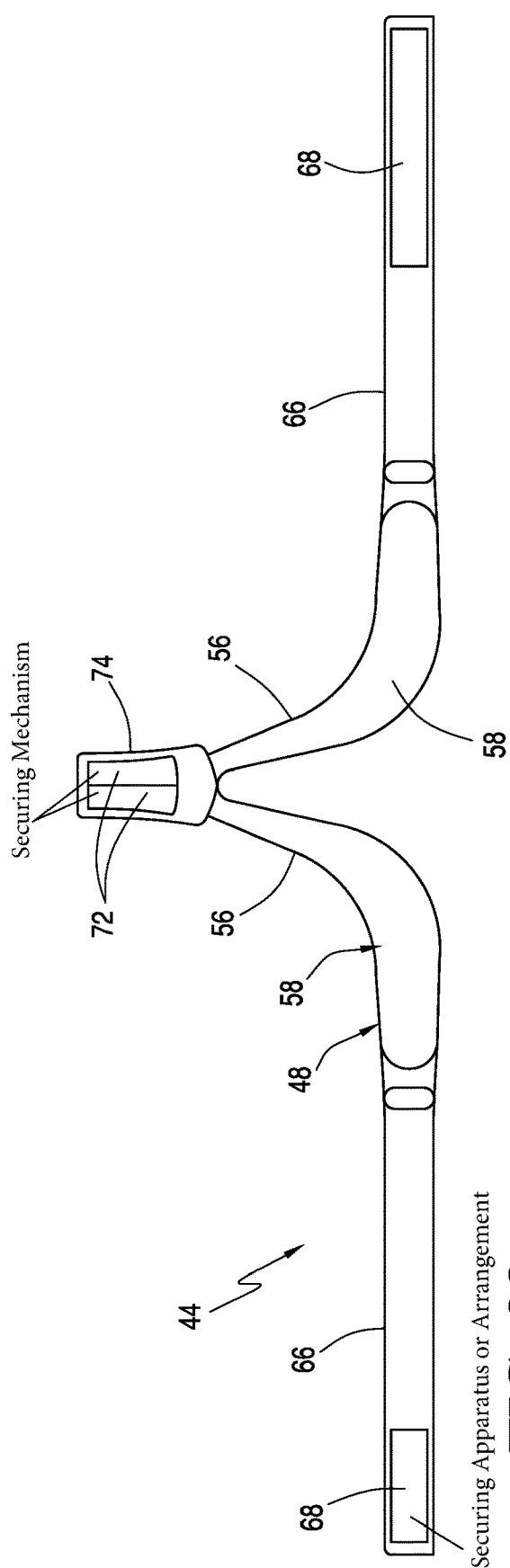
FIG. 92
FIG. 93

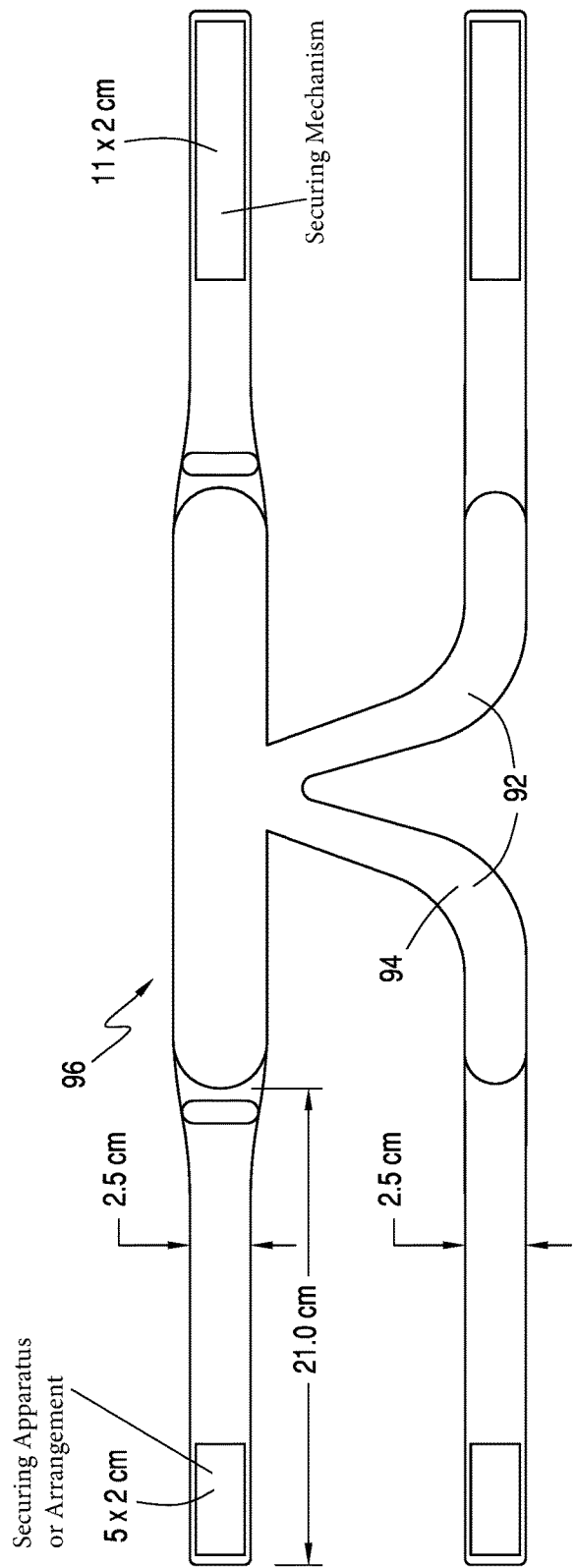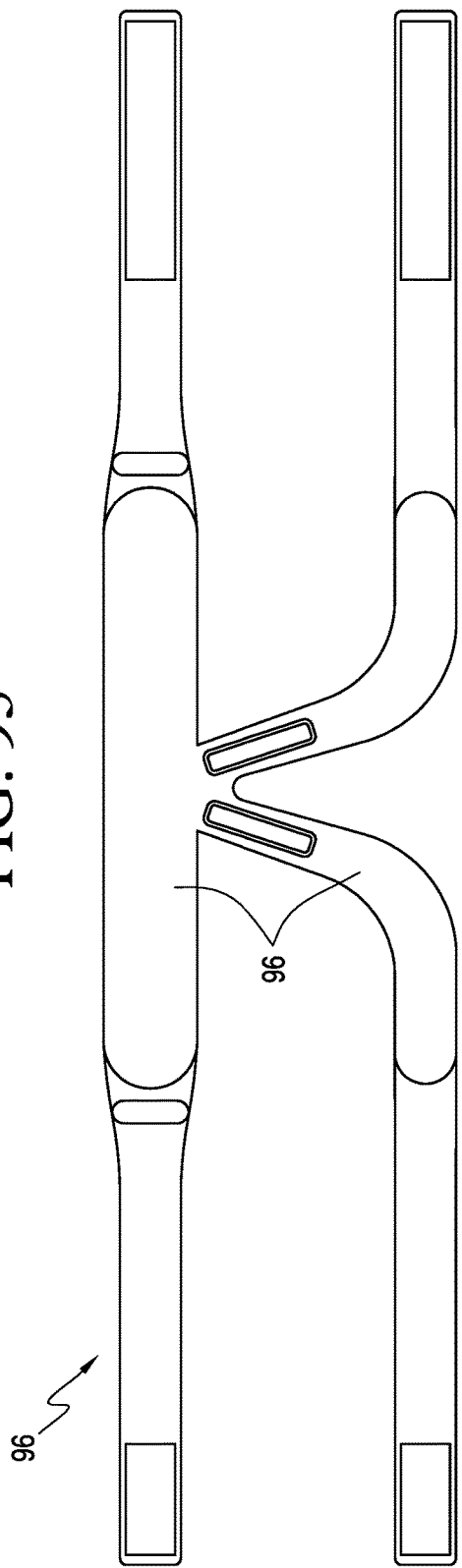
FIG. 95
FIG. 96

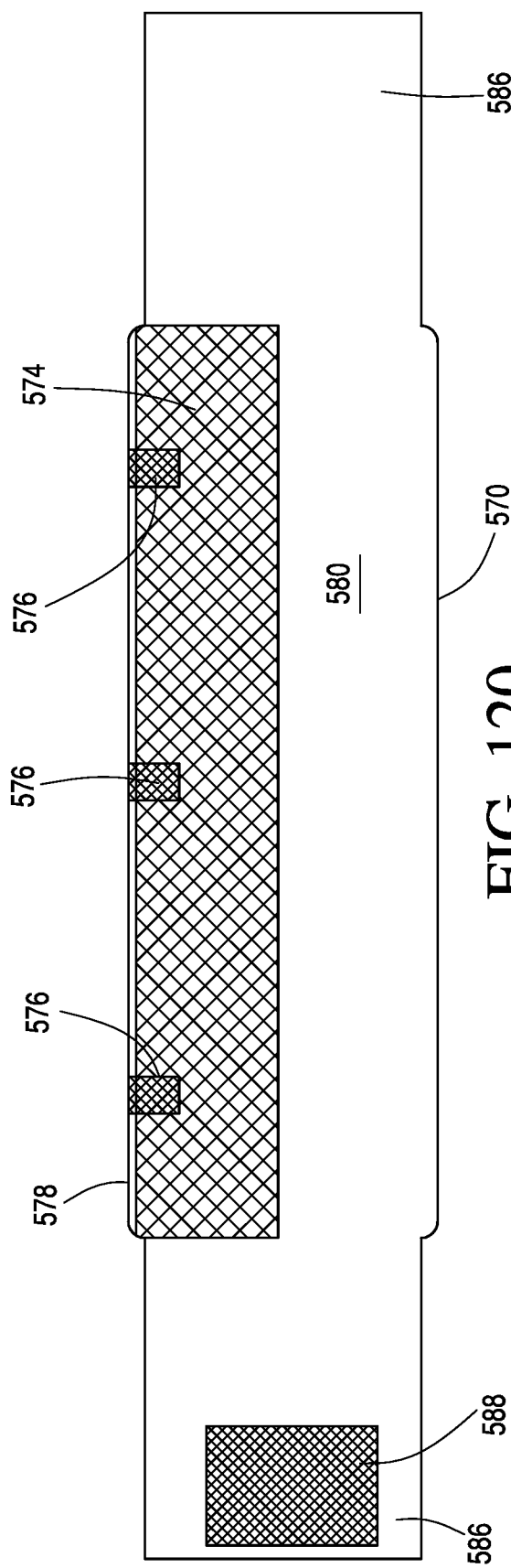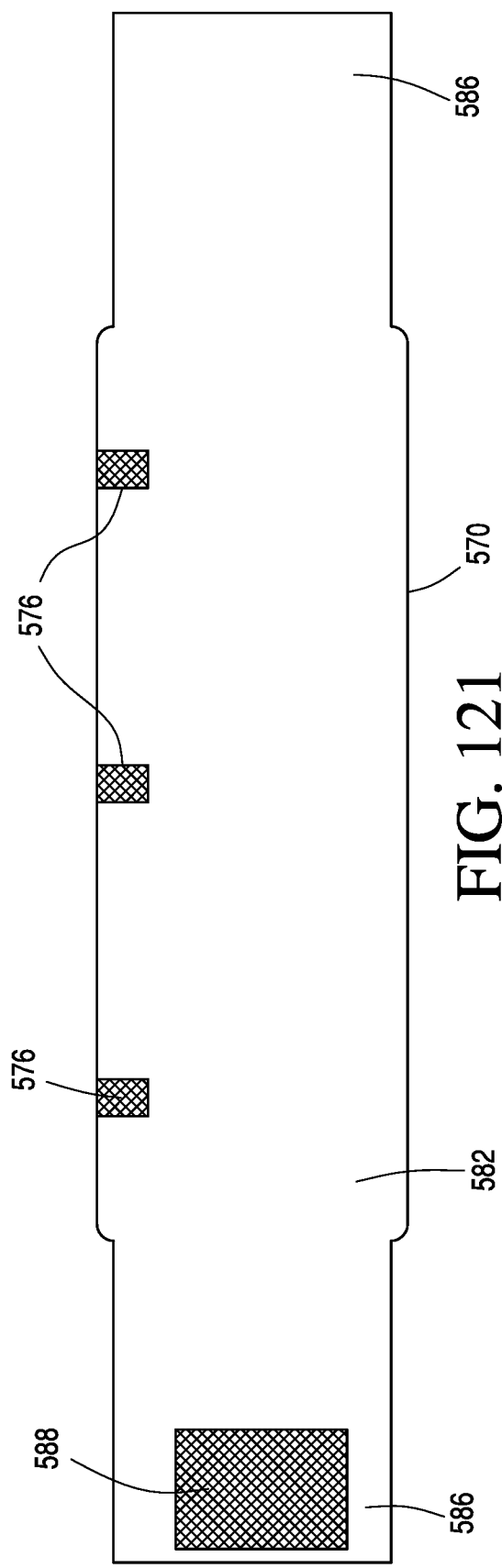

FIG. 125
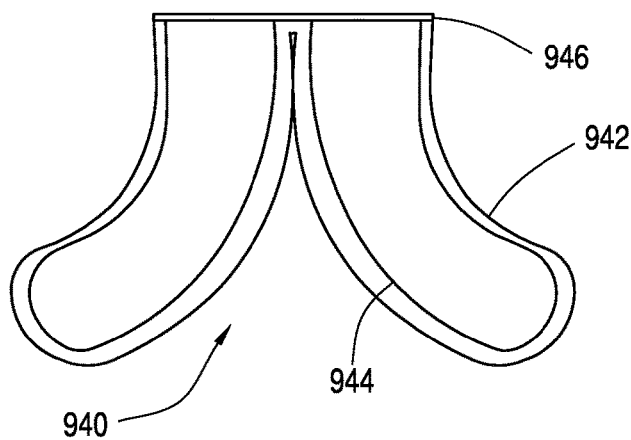
FIG. 126
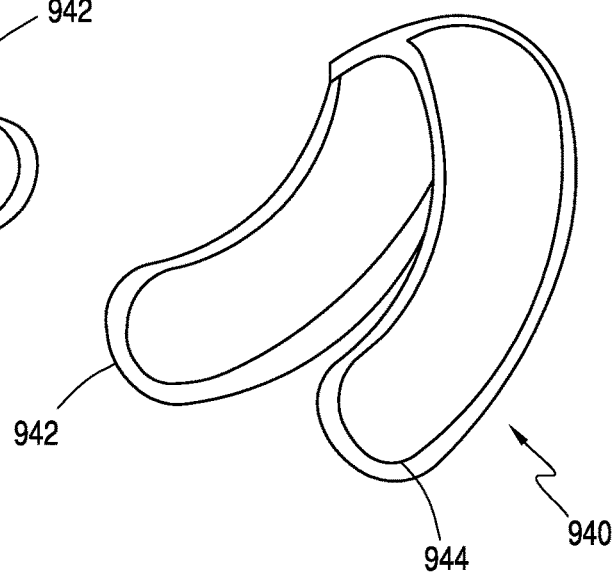
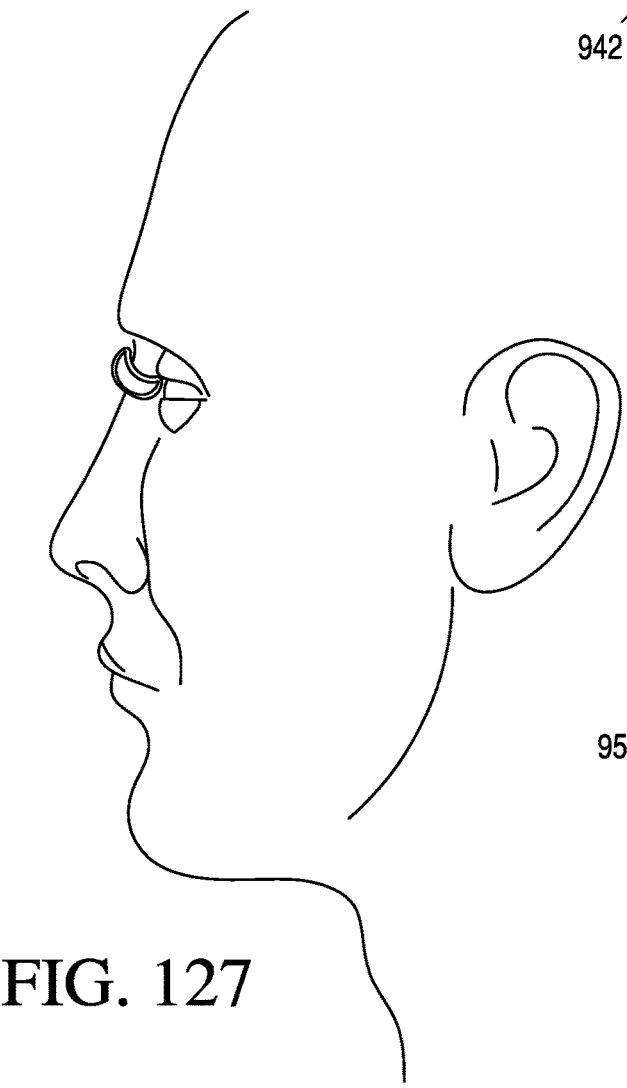
FIG. 127
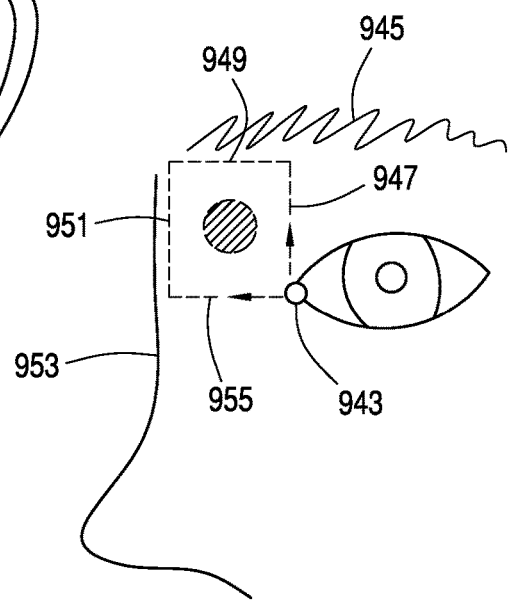
FIG. 125A

DEVICES CONFIGURED TO MONITOR BIOLOGICAL PARAMETERS, AND TO PROVIDE TREATMENT, AT AN ABREU BRAIN THERMAL TUNNEL

CROSS-REFERENCE TO RELATED APPLICATIONS

This application is a divisional of U.S. patent application Ser. No. 16/281,800, filed on Feb. 21, 2019, which is a continuation of U.S. patent application Ser. No. 14/594,122, filed on Jan. 10, 2015, which claims the benefit of priority to U.S. Provisional Patent Application Nos. 61/926,159, filed on Jan. 10, 2014, and 61/930,262, filed on Jan. 22, 2014, which are hereby incorporated by reference in their entirety.

TECHNICAL FIELD

This disclosure relates to medical devices configured to monitor biological parameters non-invasively and to provide therapeutic applications of heat and cold to the skin on, over, or adjacent to an Abreu brain thermal tunnel (ABTT) terminus.

BACKGROUND

Hypothermia and hyperthermia, which are conditions created by thermal disturbances, are caused when a body's core temperature lowers to such an extreme temperature that metabolic functions cannot occur, or more heat is absorbed or generated by the body than it can dissipate. Both thermal disturbances are common and can be life-threatening if not properly and quickly diagnosed and treated. The risk of hyperthermia, which can lead to heat exhaustion and heat stroke, is high among groups that participate in strenuous physical activities such as competitive athletics, and those that work outdoors when the temperature may be dangerously high, such as construction workers. Outdoors enthusiasts who spend a large amount of time in cold-weather climates, or those that participate in water sports, are prone to hypothermia. Heat and cold-related conditions are also common among military personnel who serve in extreme climate areas such as the desert and the arctic.

Although the brain is the organ that is most sensitive to temperature-induced damage, this damage is conventionally treated by raising or lowering body temperature by affecting the temperature of the entire body as opposed to the head, because it is conventionally understood that layers of insulation surrounding the brain make removing heat from or applying heat to the brain via the head is ineffective and slow. Conventional treatments include removing or adding additional clothing, placing the entire body or a portion thereof in a bath of cold or warm water, drinking cold or warm liquids, and resting or moving the body to increase or decrease body activity. Often individual body parts are cooled or heated using ice, an electric heating pad, or reusable packs filled with a thermally retentive substance such as polypropylene glycol gel, which may be heated, cooled, or frozen for both hot and cold applications. People affected by heatstroke are also placed in cooled or refrigerated areas. Likewise, people suffering from hypothermia are placed in warm or hot rooms.

Many significant drawbacks are associated with conventional methods of treating thermal-related conditions. Conventional methods and devices have severe limitations as they all work against the biology of the human body. In some cases, drawbacks accrue because of the mechanism of heating or cooling. Consider, for example, gel packs. The gel substance in a gel pack is generally encased within a very thin layer of plastic or other, similar material. This configuration allows for adequate thermal transfer or exchange either to or from the skin, but can also allow for excess thermal transfer or exchange with the environment, causing some of the heating or cooling capability of the gel pack to be lost to the environment, instead of being transferred to the part of the body to which it is being applied.

When the core temperature of the body is dangerously low, i.e., hypothermic, a conventional therapeutic treatment approach is to heat the entire body in the belief that the core temperature will be raised to a safe level. However, testing by Applicant indicates that heating the entire body may only result in raising the temperature of the body's extremities rather than the core temperature, and raising core temperature is the only effective way to treat hypothermia. By heating the body surface, the peripheral thermal receptors located in the extremities, send signals to the brain that the body is too hot, in which case the brain will respond by cooling the core temperature even more. Thus, the brain may negate the effects of a whole body thermal treatment and may even cause the person suffering from hypothermia to decrease core temperature further, even though his or her extremities seem to be warming.

On the other hand, if, for example, an athlete suffers hyperthermia as a result of too strenuous an activity, and the athlete's entire body is cooled or the skin of the body is cooled, the athlete's body runs a risk of fatally overheating as a result of activating thermal receptors which detect cooling. The brain reads the cool temperature of the skin surface as a signal that the body is too cold, causing the brain to activate mechanisms to deleteriously increase the core temperature.

A major drawback of conventional methods of changing body core temperature is the stimulation of thermal peripheral receptors on the skin. This stimulus sends a signal to the brain. If cold is applied, the signal will cause the brain to produce heat, which is the reason people shiver when exposed to cold; e.g., a cold wind, cold ambient temperature, cold water, etc. Shivering occurs as a result of the brain sending impulses for muscles to contract because muscle contraction generates heat. In addition to the production of heat, the brain sends a signal to the blood vessels on the surface of the body to contract, i.e., vasoconstriction. Vasoconstriction reduces heat loss and increases the internal or core temperature of the body. Muscle, heart, and vasculature all work at full force to generate heat when the peripheral skin receptors are activated, which is the reason a soldier or an athlete, for example, dies from heatstroke, despite immersion of their body in ice water. There are cases of overheated athletes who perished once taken to a room with an air conditioner and a low temperature. The brain of the athletes responded to cold stimuli by having the body produce more heat, causing the death of a person who was already very hot because the brain was hot before coming into the air conditioned room, and after entering the air conditioned room, the brain, misreading skin sensor input, increased its temperature even further, leading to metabolic shutdown and death.

Thus, conventional approaches to raising body temperature can cause heatstroke to be a fatal condition in many cases, and is one of the most lethal conditions experienced by a human being given that conventional attempts to resolve the overheating condition causes a further increase of body internal temperature. A similar situation occurs with hypothermia, since during warming of the body the brain, which is already cold, will send signals for the body to counteract the effects of the heat being applied. In this situation, the brain instructs the body to promote peripheral vasodilation to release heat, to reduce or stop metabolic functions, and to reduce muscle activity to reduce production of heat. Thus, conventional approaches to warming a hypothermic person can further reduce the temperature of the brain, causing in many instances the demise of the person.

The inadvertent causing of death of conventionally treated patients is compounded by other factors. One such factor is that the body is covered by fat, the tissue with the lowest thermal conductivity, and which has a thermal conductivity similar to oak, where k=0.00004 Kcal/(s·N·C). Therefore, cooling or warming up the skin not only is ineffective as far as heat or cold being transmitted through the skin into the body because of the thermal insulation of fat, but also because the cooling or warming up of peripheral thermal receptors causes the brain to generate the opposite thermal response, as described above.

The brain is the organ most affected during thermal disturbances, i.e., heatstroke or hyperthermia, or hypothermia, with the extreme effect being death, so many attempts to cool or warm up the brain involve the cooling or warming up the head. The challenge of conventional techniques of warming the brain is compounded by the body surface being covered by fat. Therefore, attempts to cool or warm the head are also ineffective and equally dangerous as cooling and warming the whole body, limbs, or the body surface as described hereinabove, and can just as quickly lead to brain damage and death. Attempts to cool or warm up the brain are affected because of the presence of fat, and the stimulation of skin receptors on the head causes the brain to generate the opposite response, similar to the situation that occurs when trying to heat or cool the extremities, as described herein. Also similar to cooling or heating the entire body, a change in temperature of peripheral receptors on the face and head results in an opposite reaction of the brain. In fact, the brain overcompensates for the change in temperature of the peripheral receptors, which can cause damaging effects to the brain.

Damage to the brain caused by thermal disturbances can also occur in medical operating room environments. A patient undergoing surgery runs a risk of suffering from hypothermia if the operating room is not kept warm enough during the procedure. Maintaining a high environmental temperature in the operating room allows the patient's body to remain warm while the patient is under general anesthesia, and allows the patient's organs to remain warm even while exposed. However, in such a hot working environment, physicians and staff in the operating room are often uncomfortably warm and may suffer from hyperthermia because of the clothing typically worn in such environments, in addition to a risk of infection as pathogens grow in warm temperatures.

Several remedies to this difficulty have been previously presented. For example, one such proposed solution is to use a heating device to warm the patient's body, so that the operating room may be kept at a comfortably cool temperature for the surgeons and staff. Such an approach has been implemented using a disposable, electrically heated blanket to cover the patient's body. However, the blanket does not completely prevent the patient's body heat from escaping into the environment, and the patient's temperature still lowers. Similarly, it has been proposed that the patient's body be completely enveloped in a garment that circulates warmed fluid between a heat source and the body through a series of serpentine tubes. However, a blanket or garment designed to heat the patient's body may obstruct the regions that must be accessed by the surgeon to complete a surgery successfully. If the blanket or garment comprises an open front to give the surgeon easier access, then the patient's body may lose much needed thermal energy through the opening. An alternate solution is to cool surgeon and staff's bodies individually so that a warmer room temperature may be maintained. Such an approach can be obtained by a conventional cooling vest that can be worn by each surgeon or staff person, but the same issues as cooling skin surface occurs, in addition to infection risk in a warm environment, as described hereinabove.

Conventional treatments involving directly heating or cooling the brain have relied on invasive methods with injection of fluid. For example, medical professionals currently employ the technique of cooling the brains of patients who have suffered cardiac arrests to reduce the amount of oxygen the brain and heart need to keep working. The conventional approach to cooling the brain in this situation is by covering the patient's body with thermal transfer vests or blankets, configured to cool the body, or by injecting cold fluid into the patient's body. However, such approaches have been shown to be ineffective as patients tend to shiver intensely during the procedure, which equates to high heat production.

The challenges associated with methods for treating cardiac arrest patients, and for warming or cooling surgeons or patients in operating room environments using thermal energy, are similar to those discussed above related to thermal disturbance treatments. Warming or cooling the patient's entire body may cause peripheral or internal receptors to signal to the brain that it must overcompensate with an opposite change in brain temperature, resulting in hyperthermia or hypothermia. Moreover, in the case of cardiac arrest patients, the temperature of extremely cool fluid cannot be regulated, thus there is a risk that the cool fluid may result in excessive cooling of the body. Thus, conventional solutions to cooling the brain can result in unforeseen overcompensation and may cause thermal disturbances opposite to those that they are proposed to correct, thus exacerbating the very situation that was being corrected.

Controlling core brain temperature is also important in patients suffering from traumatic brain injury. However, the same limitations and drawbacks of conventional approaches to controlling core brain temperature described herein prevent a predictably successful outcome, and brain injury remains a common complication.

SUMMARY

This disclosure provides a device configured to control the temperature of the brain noninvasively, comprising at least one of a heating apparatus and a cooling apparatus, a controller, and a temperature measurement apparatus. The at least one heating apparatus and cooling apparatus is configured to be applied directly to an Abreu brain thermal tunnel (ABTT) terminus. The controller is configured to actuate the at least one heating apparatus and cooling apparatus. The temperature measurement apparatus is configured to measure a temperature of the brain. The controller is configured to operate the at least one heating apparatus and cooling apparatus to provide heat to or remove heat from the ABTT terminus until the temperature measurement apparatus measures a predetermined temperature of the brain.

This disclosure also provides a device configured to apply heat or cold to an Abreu brain thermal tunnel (ABTT) noninvasively, the device comprising a support structure and a thermoelectric device. The thermoelectric device is positioned on the support structure and configured to provide heat to an ABTT terminus located on, over, or adjacent to the ABTT terminus when the support structure is worn by a user.

This disclosure also provides a device configured to apply heat or cold to an Abreu brain thermal tunnel (ABTT) noninvasively, the device comprising an eyeglass frame. The eyeglass frame includes at least one thermally retentive substance positioned to contact an ABTT terminus on, over, or adjacent to the ABTT when the eyeglass frame positioned on a person's face. The thermally retentive substance is heated or cooled prior to placing the eyeglass frame on the person's face.

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 14 is a view of a further heating or cooling mechanism configured to be integral with an eyeglass frame that includes lenses, in accordance with an exemplary embodiment of the present disclosure.

FIG. 15 is a view of a portion of an ABTT and Vein Thermal Pack (ABVTP) mask, with a thermal transfer device positioned in a cavity of a frame, in accordance with an exemplary embodiment of the present disclosure.

FIG. 16 is a cross-sectional view of a frame of FIG. 15 along the line 16-16, in accordance with an exemplary embodiment of the present disclosure.

FIG. 19 is a simplified view of the ABTT and facial veins associated with the ABTT.

FIG. 20 is a simplified partial cross-sectional view through a human skull in a vertical direction, showing the Abreu brain thermal tunnel and certain other facial features.

FIG. 28 is a schematic view of an alternative hand held thermal transfer device, in accordance with an exemplary embodiment of the present disclosure.

FIG. 29 is another view of the alternative hand held thermal transfer device of FIG. 28, in a second position, in accordance with an exemplary embodiment of the present disclosure.

FIG. 30 is a view of yet another alternative hand held thermal transfer device, in accordance with an exemplary embodiment of the present disclosure.

FIG. 31 is a view of the hand held thermal transfer device of FIG. 30, with insulation covering a body portion of the device, in accordance with an exemplary embodiment of the present disclosure.

FIG. 36 is a view an active thermal exchange device, in accordance with an exemplary embodiment of the present disclosure.

FIG. 37 is a stylistic representation of a circuit of an active thermal transfer device in a closed position, in accordance with an exemplary embodiment of the present disclosure.

FIG. 38 is a view of the active thermal transfer device of FIG. 37 in an open position, in accordance with an exemplary embodiment of the present disclosure.

FIG. 70 is a view of a patient wearing an active heat exchange device in accordance with an exemplary embodiment of the present disclosure.

FIG. 71 is a side or edge view of the active heat exchange device of FIG. 70.

FIG. 71A is a side or edge view of another active heat exchange device of the present disclosure.

FIG. 72 is a view of a patient wearing an active heat exchange device in accordance with an exemplary embodiment of the present disclosure.

FIG. 73 is a graph of a nominal or statistically normal temperature rise of a pad positioned in contact with the ABTT terminus, in response to an application of a predetermined temperature to the ABTT terminus.

FIG. 74 is a graph of a temperature rise of a pad positioned in contact with the ABTT terminus, in response to an application of a predetermined temperature to the ABTT terminus, indicating a medical condition of the measured subject.

FIG. 77 is a view of an active thermal exchange device in accordance with an exemplary embodiment of the present disclosure.

FIG. 78 is a view of a portion of the active thermal exchange device of FIG. 77.

FIG. 78A is a view of another active thermal exchange device in accordance with an exemplary embodiment of the present disclosure.

FIG. 92 is a support structure in the form of a headband, in accordance with an exemplary embodiment of the present disclosure.

FIG. 93 is a thermal exchange system configured to be positioned on the support structure of FIG. 92, in accordance with an exemplary embodiment of the present disclosure.

FIG. 95 is view of a first, skin side of the thermal exchange system FIG. 94, in accordance with an exemplary embodiment of the present disclosure.

FIG. 96 is view of a second side of the thermal exchange system of FIG. 94, in accordance with an exemplary embodiment of the present disclosure.

FIG. 100 is a view of a user wearing an ABVTP in accordance with an exemplary embodiment of the present disclosure.

FIG. 101 is a view of a user wearing an ABVTP in accordance with an exemplary embodiment of the present disclosure.

FIG. 102 is a view of a user wearing the ABVTP of FIG. 101.

FIG. 103 is a view of the ABVTP shown in FIGS. 101 and 102.

FIG. 104 is a front view of a thermally retentive headband cover, in accordance with an exemplary embodiment of the present disclosure.

FIG. 105 is a front view of a thermal pack device configured to be attached to the headband cover of FIG. 104, in accordance with an exemplary embodiment of the present disclosure.

FIG. 106 is a view of a person wearing the headband cover and thermal pack device of FIGS. 104 and 105.

FIG. 107 is a view of a node of FIG. 104.

FIG. 108 is another view of nodes of FIG. 104.

FIG. 109 is a view of another embodiment of a headband cover that has slots for sunglass or eyeglass lenses, in accordance with an exemplary embodiment of the present disclosure.

FIG. 110 is a front view of another embodiment thermal pack headband and a face mask, in accordance with an exemplary embodiment of the present disclosure.

FIG. 111 is a view of a person wearing the thermal pack headband and face mask of FIG. 110.

Figure 112:
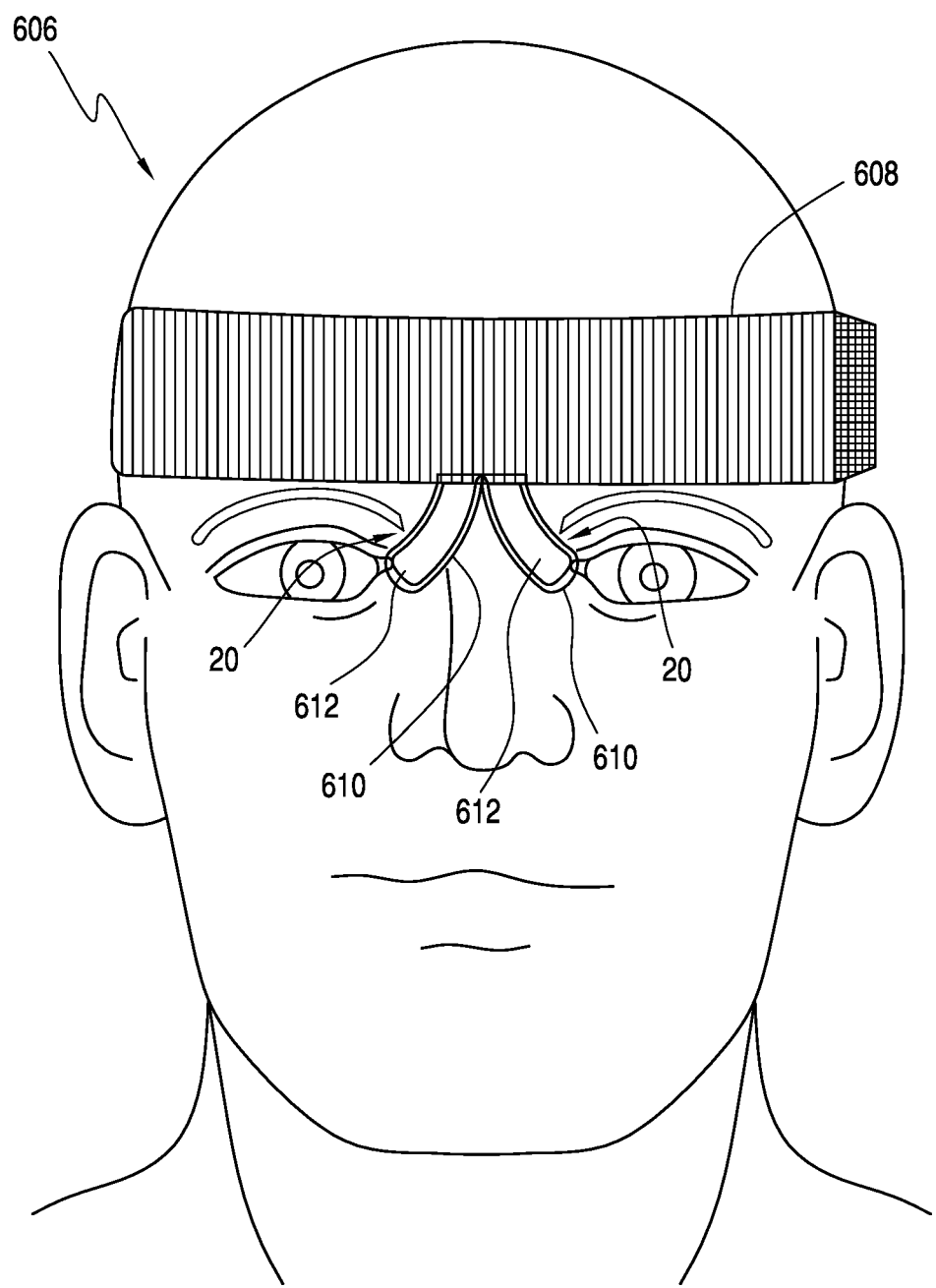

FIG. 112 is a view of a person wearing a thermoelectric cooling/heating headband with nodes, in accordance with an exemplary embodiment of the present disclosure.

Figure 113:
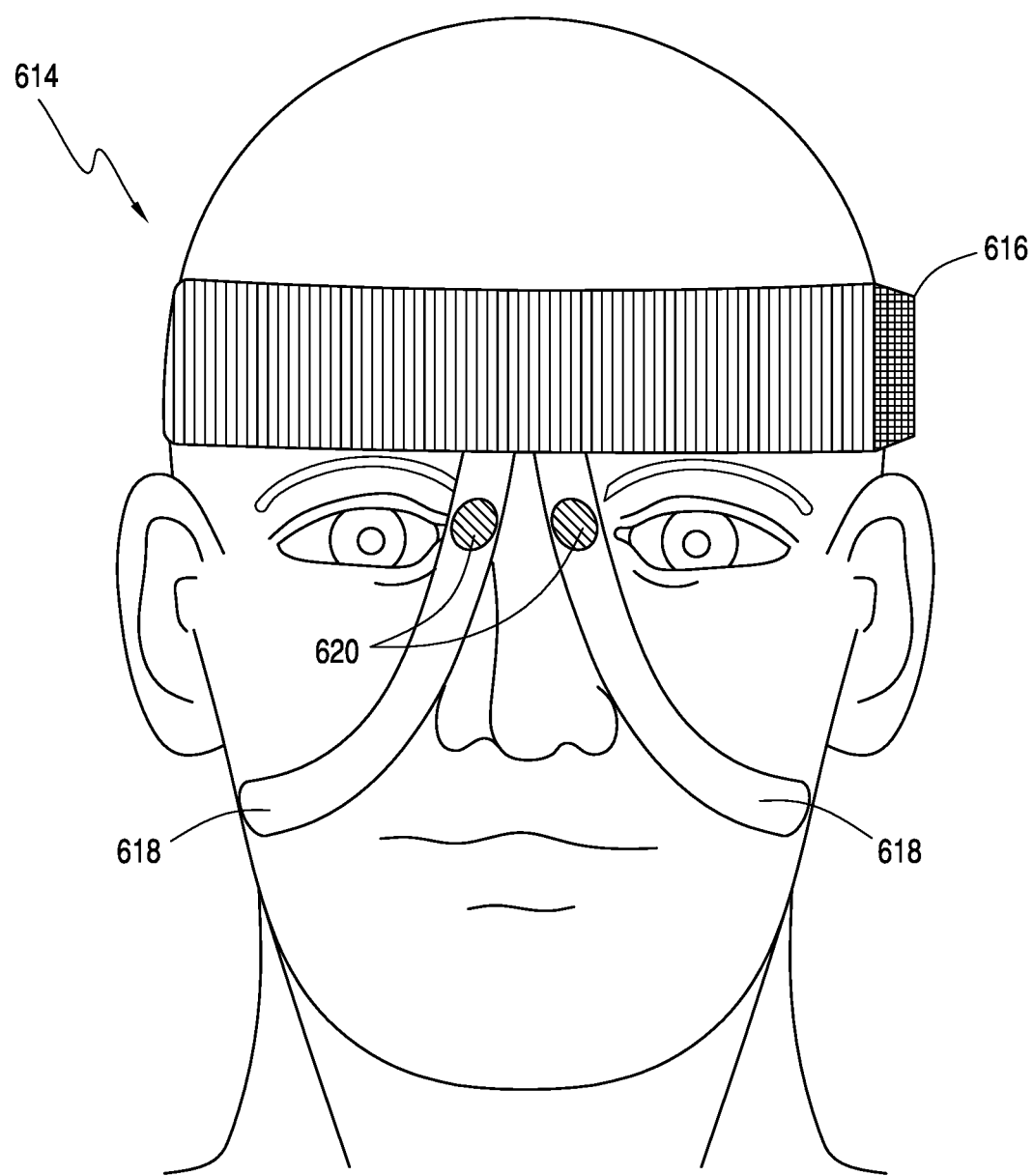

FIG. 113 is a view of a person wearing a thermoelectric cooling/heating headband with a thermal pack, in accordance with an exemplary embodiment of the present disclosure.

Figure 114:
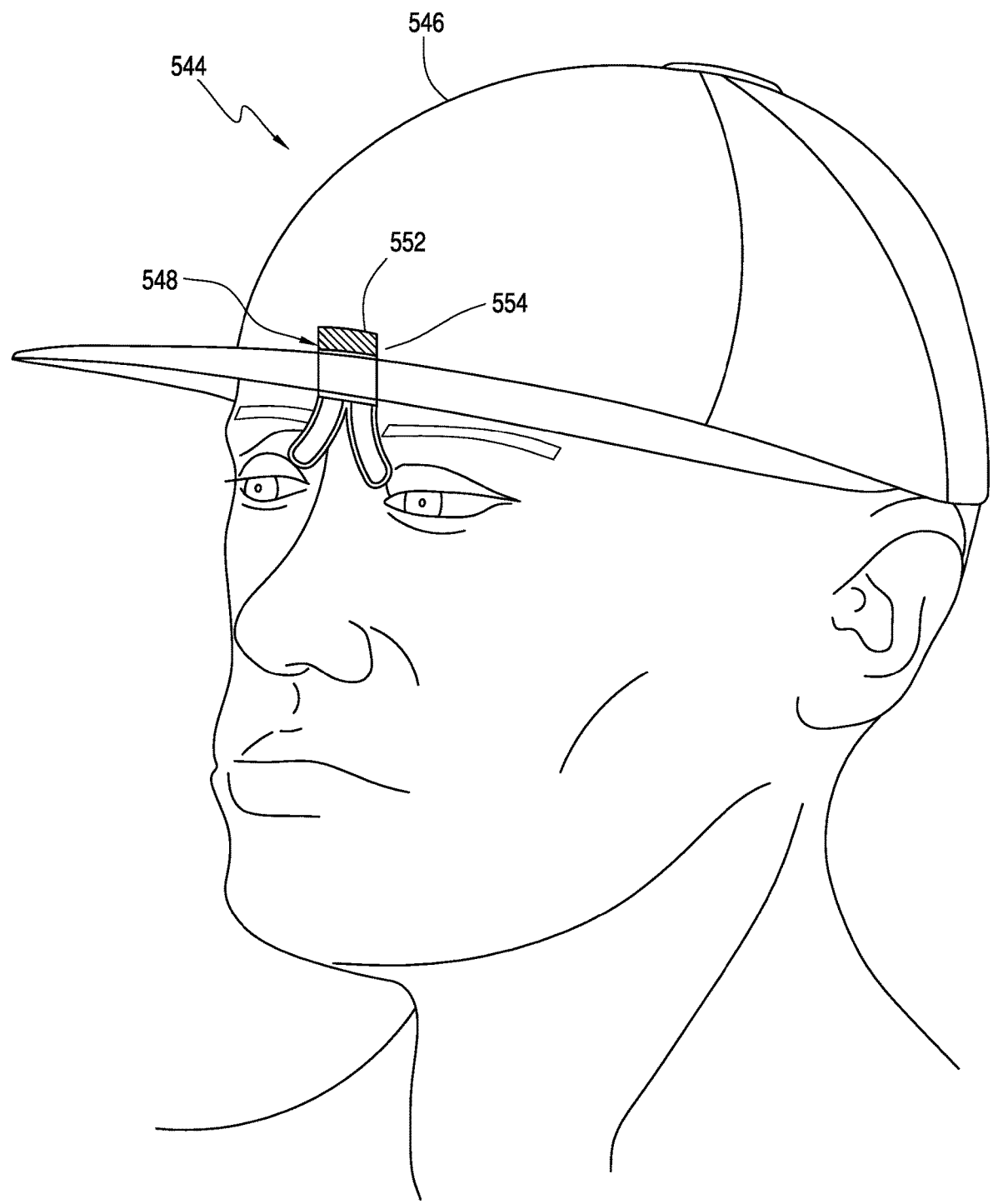

FIG. 114 is a view of a person wearing a baseball cap with detachable nodes, in accordance with an exemplary embodiment of the present disclosure.

Figure 115:
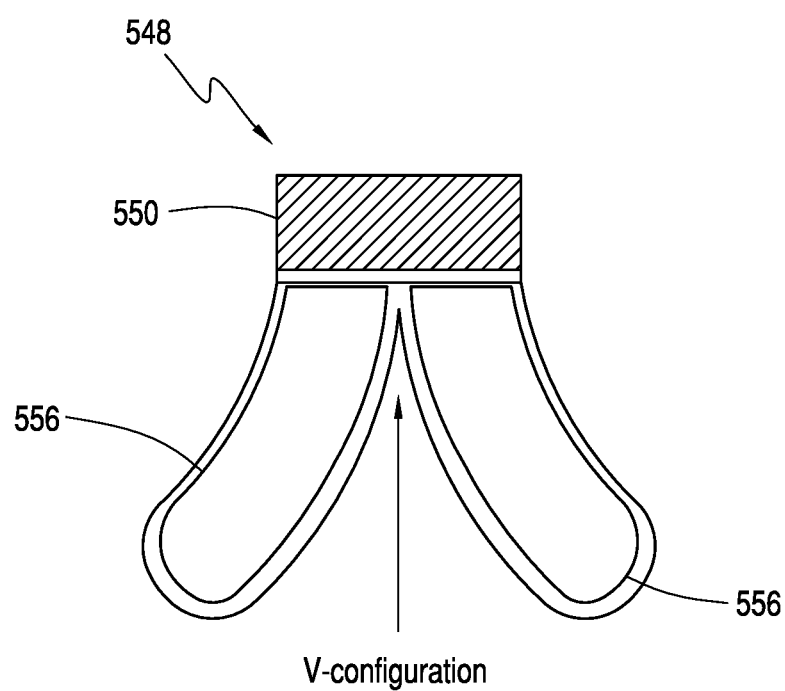

FIG. 115 is a view the detachable nodes of FIG. 114, in accordance with an exemplary embodiment of the present disclosure.

Figure 116:
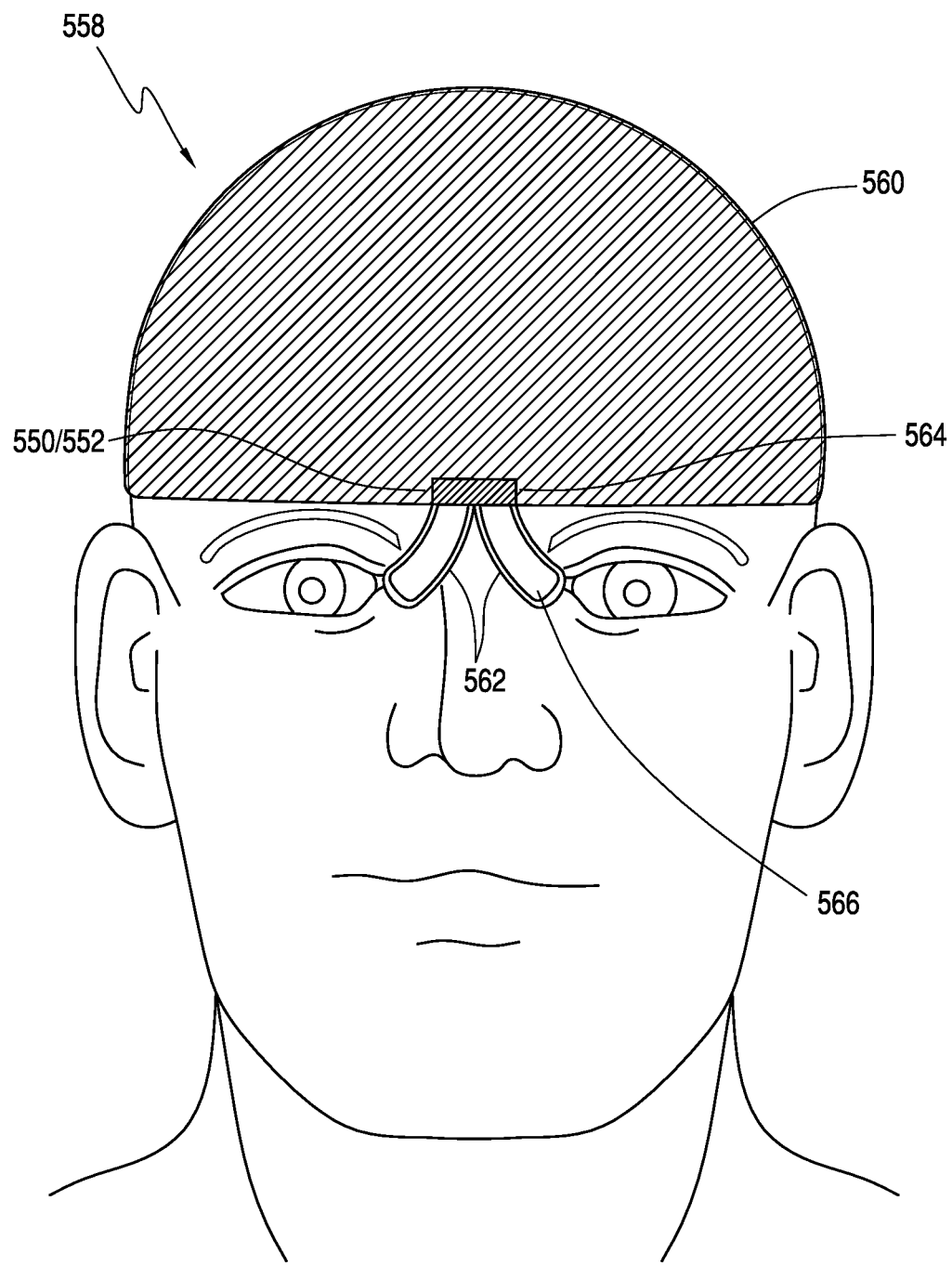

FIG. 116 is a view of a person wearing a fitted cooling cap with detachable nodes, in accordance with an exemplary embodiment of the present disclosure.

Figure 117:
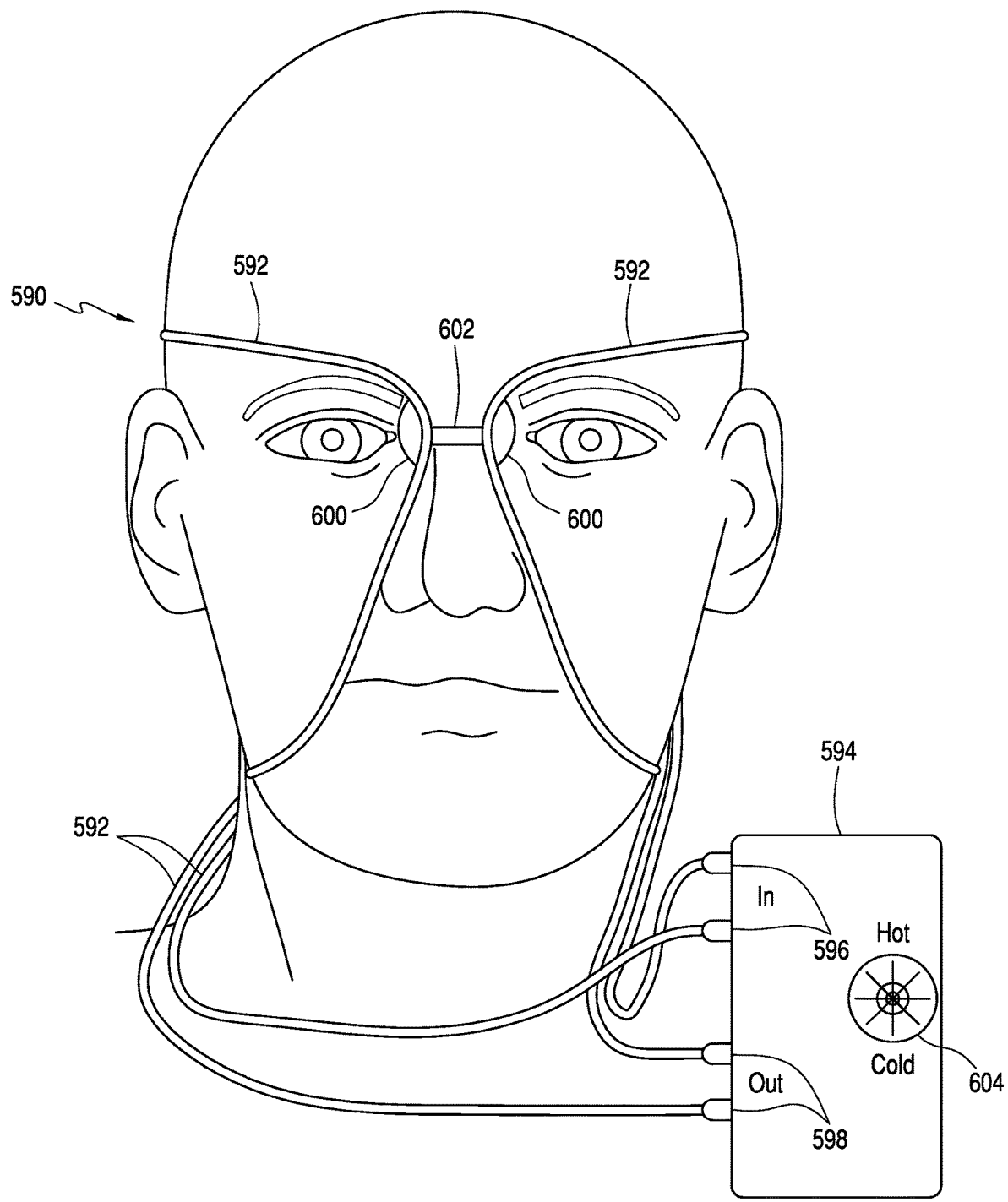

FIG. 117 is a view of a person wearing a serpentine tube that carries heated/cooled fluid supplied by a pumping mechanism with a power source, in accordance with an exemplary embodiment of the present disclosure.

Figure 106:
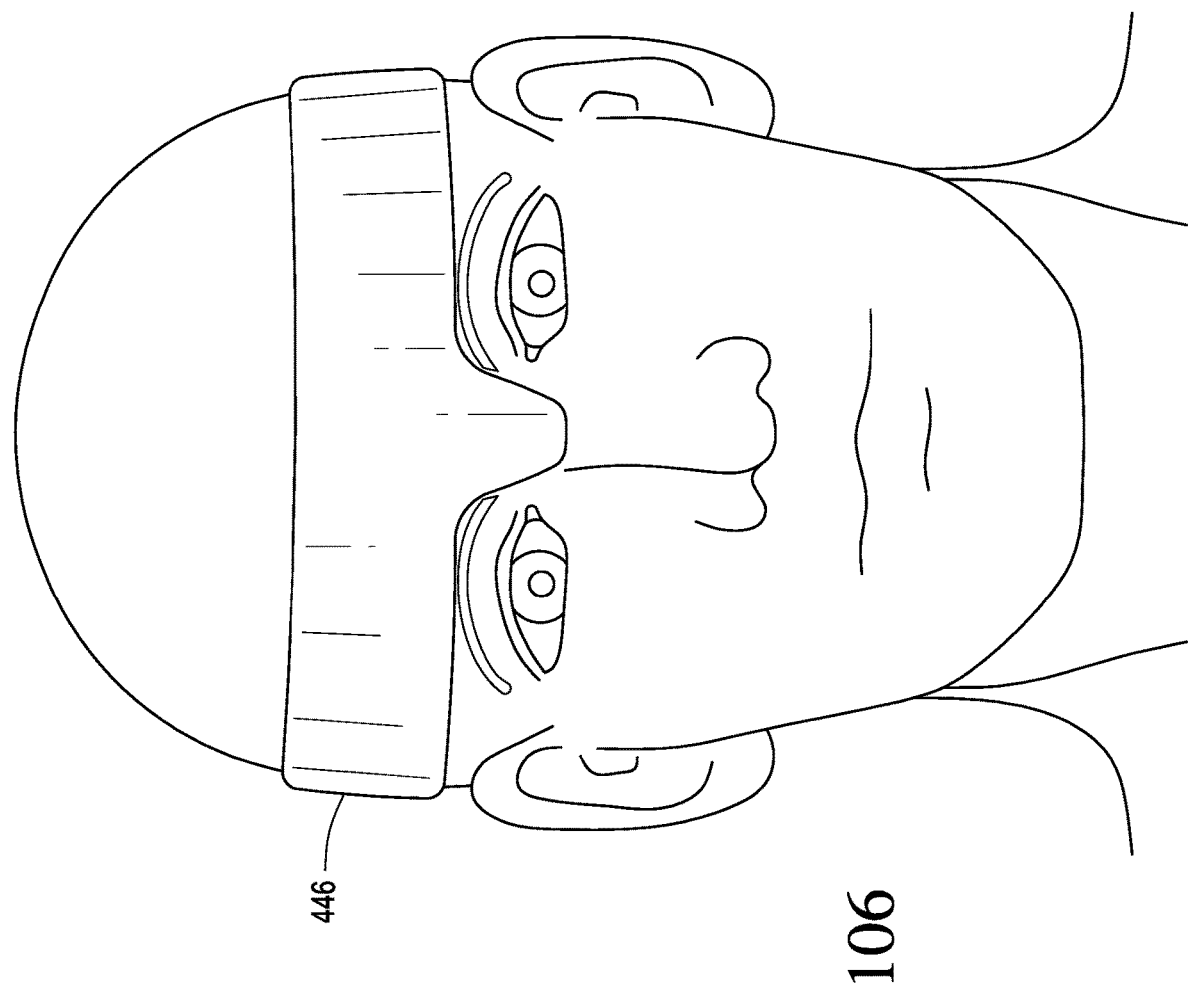
Figure 118A:
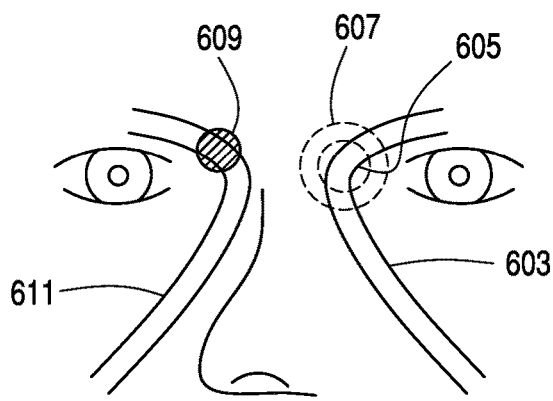
Figure 118:
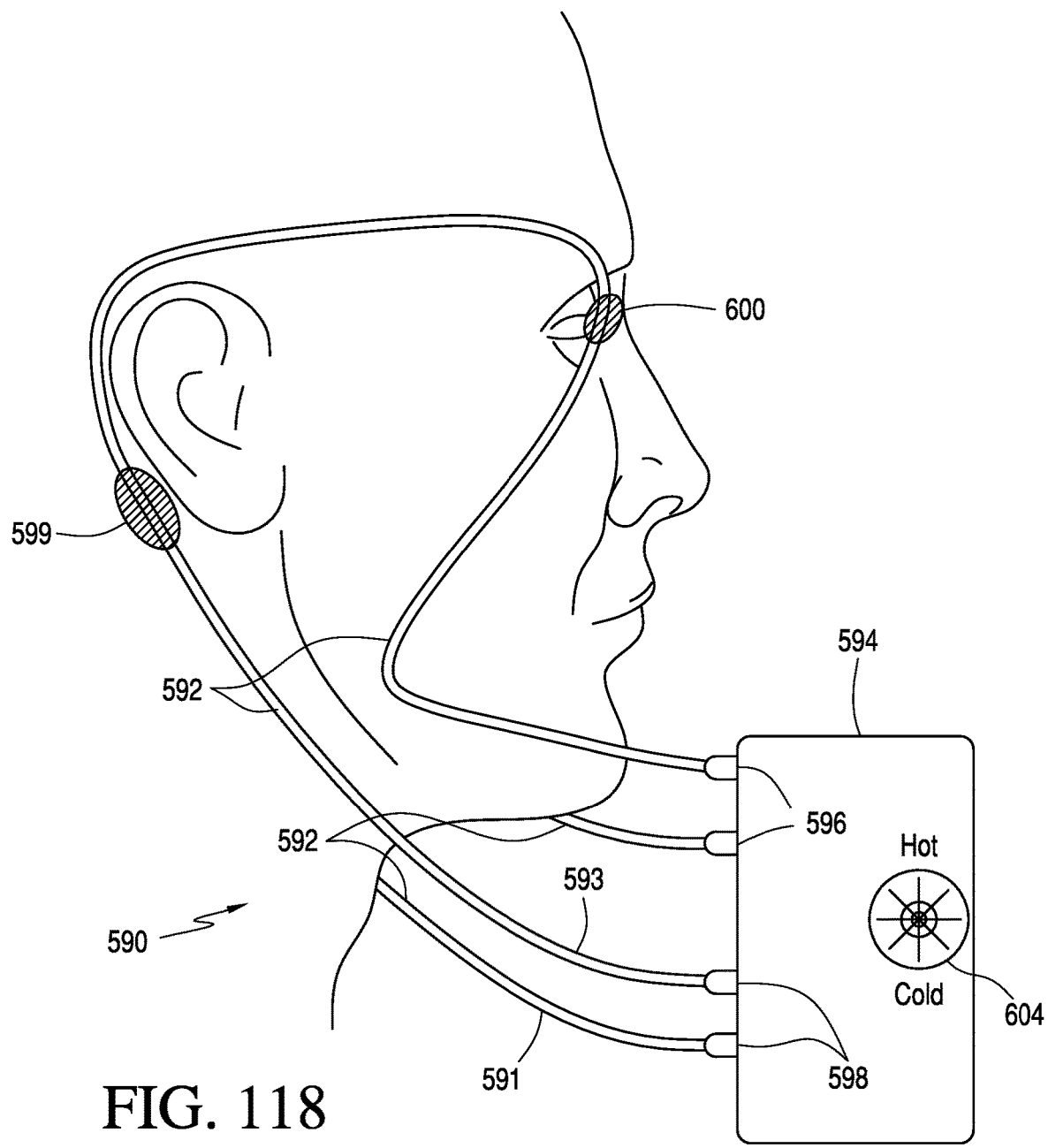

FIG. 118 is another view of the person in FIG. 106.

FIG. 118A is a view of another active thermal exchange device in accordance with an exemplary embodiment of the present disclosure.

Figure 119:
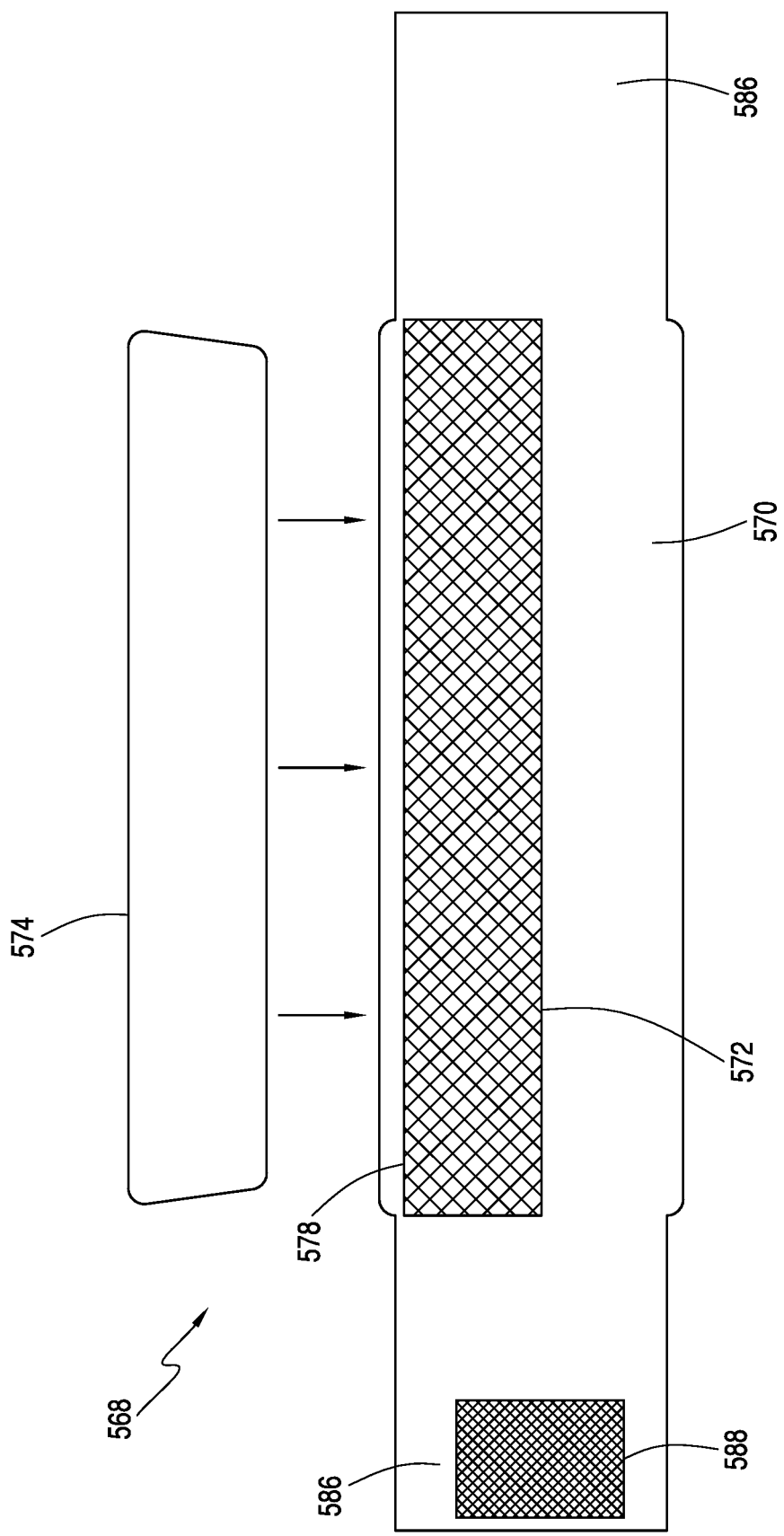

FIG. 119 is a an exploded view of a body of a thermal pack device and a back of a thermally retentive soft cloth with a mesh pouch for the thermal pack body, in accordance with an exemplary embodiment of the present disclosure.

FIG. 120 is another view of the thermal pack device secured in the mesh pouch of the thermally retentive soft cloth of FIG. 119.

FIG. 121 is a front view of the thermally retentive soft cloth of FIG. 120.

Figure 122:
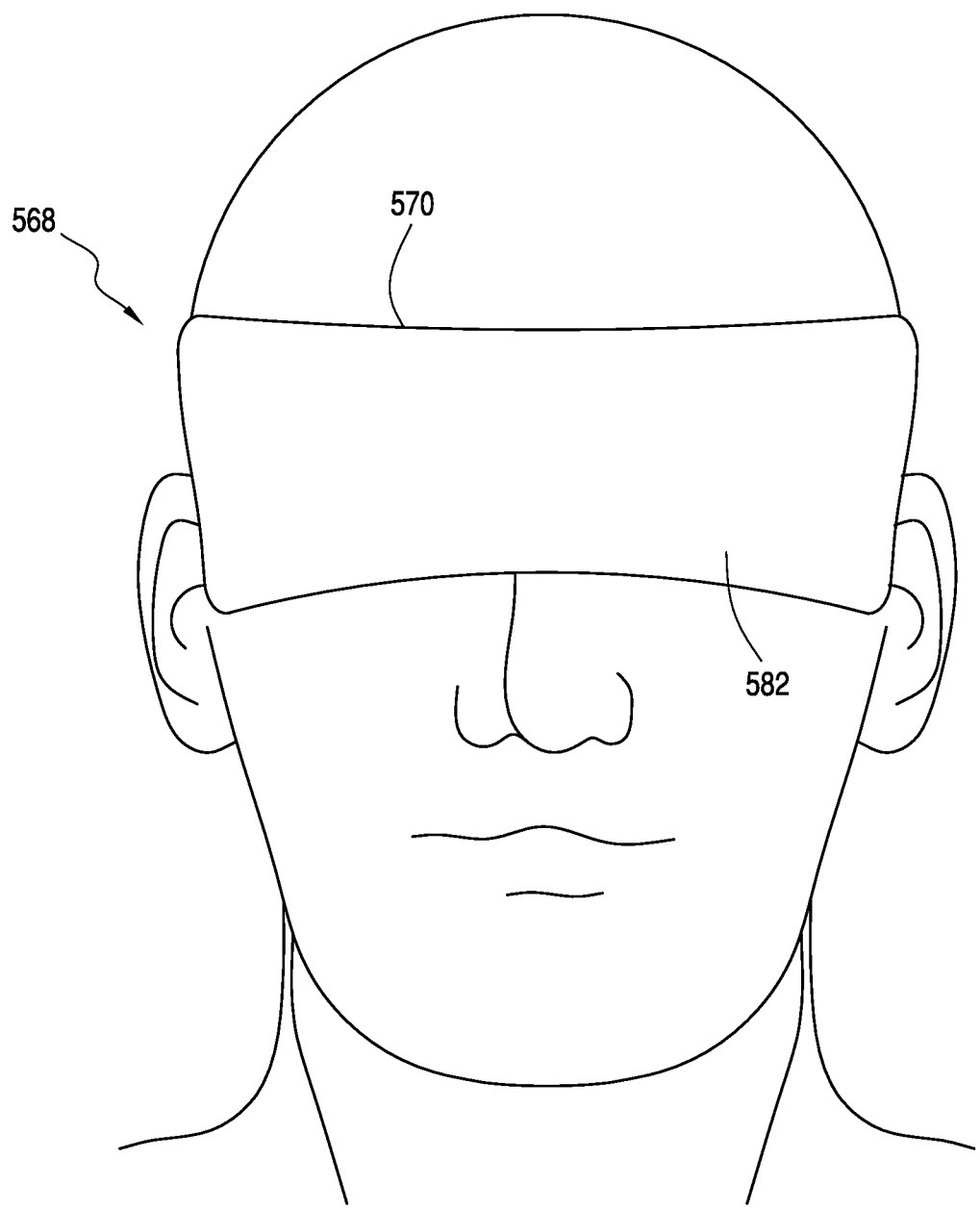

FIG. 122 is a view of a person wearing the thermal pack and the thermally retentive soft cloth of FIGS. 119-121, with the user's eyes covered by the thermally retentive soft cloth.

Figure 123:
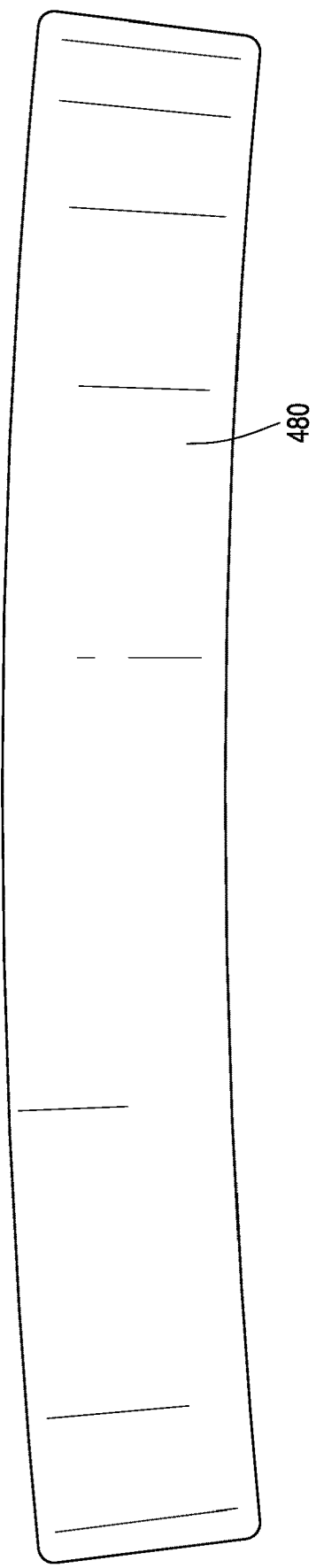

FIG. 123 is a view of a headband, in accordance with an exemplary embodiment of the present disclosure.

Figure 124:
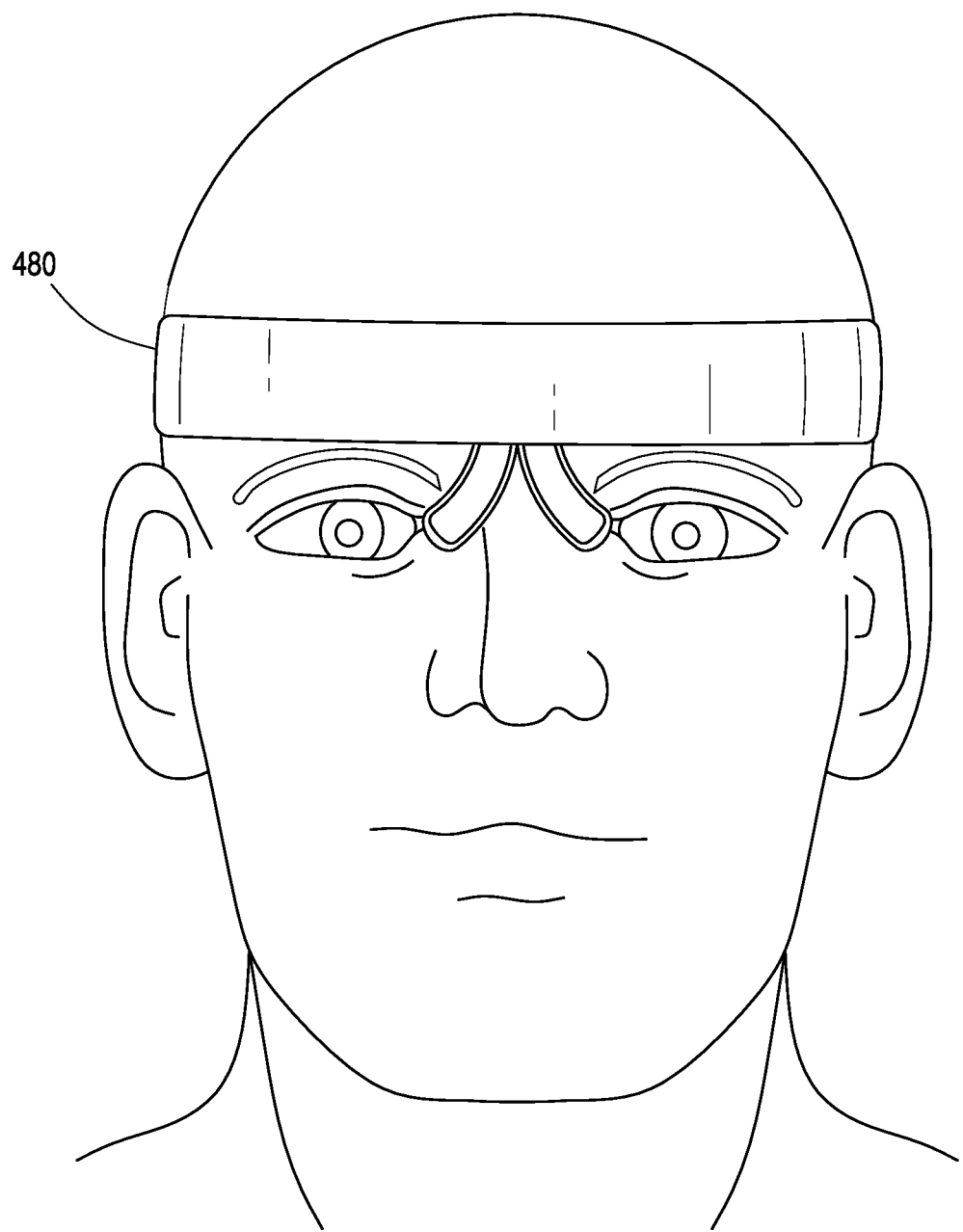

FIG. 124 is a view of a person wearing the thermal pack device of FIG. 122 and the headband of FIG. 121.

FIG. 125 is a front view of the clip nodes of FIG. 122.

FIG. 125A is a view of a node in accordance with an exemplary embodiment of the present disclosure.

FIG. 126 is a side view of the folded clip nodes of FIGS. 122 and 125.

FIG. 127 is a view of a side profile of a person wearing the nodes of FIGS. 125 and 126 by clipping them to the person's nose bridge.

Figure 128:
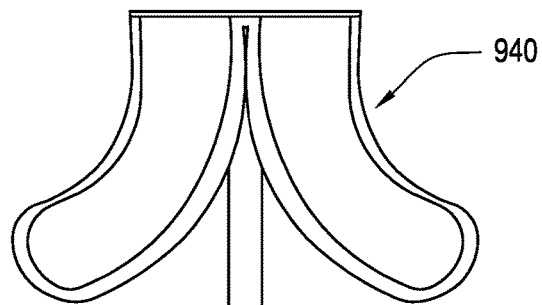

FIG. 128 is a front view of the nodes of FIGS. 125 and 126 attached to a handheld stick, in accordance with an exemplary embodiment of the present disclosure.

Figure 129:
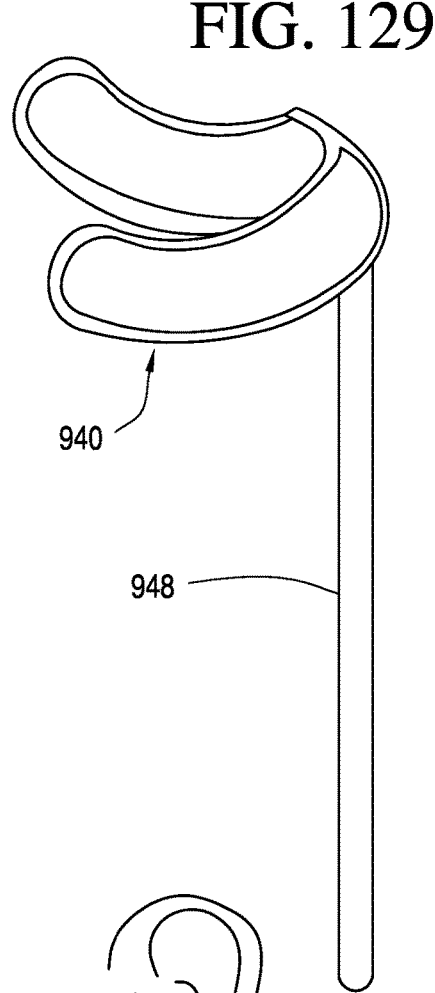

FIG. 129 is a side view of the folded nodes of FIG. 126 attached to a handheld stick, in accordance with an exemplary embodiment of the present disclosure.

Figure 130:
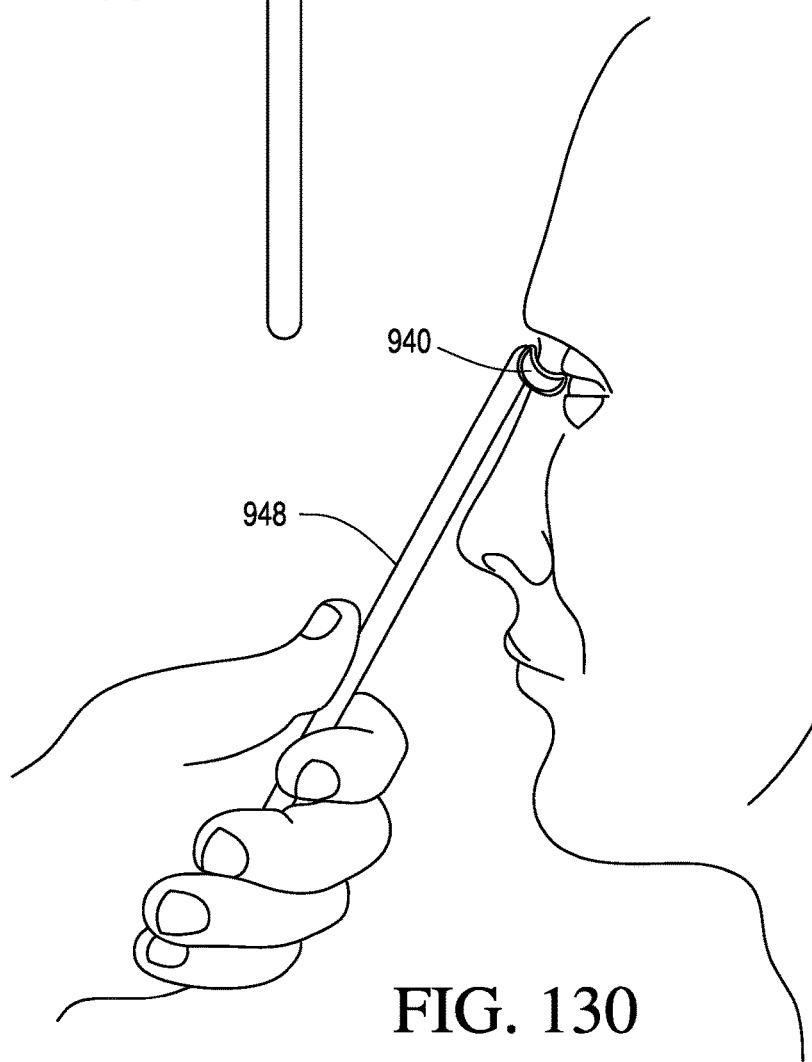

FIG. 130 is a view of a person using the embodiment of FIGS. 128 and 129, in accordance with an exemplary embodiment of the present disclosure.

DETAILED DESCRIPTION

In view of the dangers associated with heating and cooling a body using conventional techniques, Applicant recognized that the ability to accurately measure, monitor, and affect the brain's temperature would be advantageous for the diagnosis and treatment of many conditions, since changing the temperature of the body's peripheral receptors, as described hereinabove, may negate the effectiveness of other known treatments. Applicant further recognized that the brain's temperature is the only vital sign that cannot be artificially changed by emotional states, or affected by environmental temperature.

Apparatus and methods for detecting the brain's temperature accurately and quickly have been described in U.S. Pat. Nos. 7,187,960, 8,172,459, 8,328,420, 8,721,562, and 8,849,379, incorporated by reference herein in their entirety, which describe measuring the brain's temperature through the Abreu brain thermal tunnel (ABTT), previously called the Abreu brain temperature tunnel or the brain temperature tunnel. The tunnel includes a direct and undisturbed connection between the source of functions or signals within the brain and an external point at the end of the tunnel that is located on the skin. Applicant recognized through studies and analysis that the ABTT is an anatomic path that conveys undisturbed physiologic signals from the brain, and extending between the hypothalamus region of the brain to the skin in the only location in the human body absent of insulating fat. The point on the skin that is on, over, or adjacent to the ABTT may be described as the ABTT terminus. As identified and demonstrated by Applicant in pending U.S. patent application Ser. No. 14/512,421, filed Oct. 11, 2014, incorporated by reference herein in its entirety, the skin at the ABTT terminus is absent or without fat, and that undisturbed thermal signals or signatures are conveyed rapidly and accurately from the brain by the ABTT to the ABTT terminus. The ABTT is a physiologic tunnel that conveys continuous and integral data on the physiology of the body. Because the majority of brain tissue is water, the removal or application of heat necessary to cool or heat the brain can be precisely calculated. Applicant has determined that an undisturbed signal from within the brain is delivered to an external point at the end of the tunnel, and that thermal signals applied to the ABTT terminus can be delivered to the brain.

Applicant recognized that the characteristics of the ABTT presented a unique opportunity to directly cool or heat a body through a small area of skin without appreciably altering the temperature of the body's peripheral receptors.

Ongoing studies by Applicant has shown that methodologies and apparatus by Applicant can effectively treat conditions, which were not possible with the prior art for the reasons described hereinabove, including, but not limited to multiple sclerosis, fever, coma, stroke, cancer, Parkinson's disease, migraine, Alzheimer's disease, Huntington's disease, Amyotrophic Lateral Sclerosis, epilepsy, reproductive disorders, thyroid disorders, sleep disorders, depression, seasonal affective disorder, mood disorders, dehydration, and hormonal imbalances.

In describing embodiments of the present disclosure, specific terminology will be used for the sake of clarity. However, the disclosure is not intended to be limited to the specific terms selected, and it should be understood that each specific term includes all technical equivalents which operate in a similar manner to accomplish a similar purpose.

Throughout this specification, various apparatus, mechanisms, and devices are described that provide heat and cooling to the ABTT terminus. Each of these apparatuses, mechanisms, and devices may be described in a variety of terms. A combination of each component of each embodiment and a combination of embodiments is within the scope of the invention. By way of illustration, but not of limitation, a component such as an electrical heater of one embodiment can be integrated into a passive cooling device of another embodiment. Another combination includes any of the embodiments shown for animals that can be used in embodiments for humans and vice versa.

Anatomically and physiologically speaking, the ABTT includes a continuous, direct, and undisturbed connection between a thermal energy source within the brain, and an external point at the end of the tunnel, i.e., the ABTT terminus. The physical and physiological events at one end of the tunnel are reproduced at the opposite end. The ABTT enables integral and direct thermal energy transfer through the tunnel without interference by heat absorbing elements; i.e., elements that can absorb infrared radiation transmitted as heat by blood within the brain. The facial end of the ABTT, herein referred to as a "target area" or terminus on the skin, measures about 11 mm in diameter measured from the medial corner of the eye at the medial canthal tendon and the tear puctum (tear drainage point), and extends superiorly for about 6 mm and then extends into the upper eyelid in a horn like projection for another 22 mm.

The ABTT is located in a crowded anatomic area and thus the positioning of any apparatus in direct contact therewith requires special geometry for optimal thermal transfer to the skin overlying the end or terminus of the tunnel. The clinical usefulness of the tunnel can only be achieved with precise positioning of a therapeutic or measurement apparatus in relation to anatomic landmarks. The tunnel is located in a unique position with distinctive anatomic landmarks that help define the external geometry and location of the end or terminus of the tunnel.

Dissection of cadavers was undertaken as a part of understanding the unique characteristics of the ABTT. Cadaver dissection delineated anatomy, which may be seen in FIG. 19, showing the convergence of four veins at ABTT target area or terminus 20: frontal 12, superior palpebral 14, supraorbital 16, angular 18, and facial 19, which is an extension of angular vein 18. This area is unique, and is the only such area in the head, as recognized by Applicant, in which a vein, the superior ophthalmic vein in ABTT 22, courses transversally into the center of the brain with the opposite end terminating on the skin which is free of fat. Briefly, the blood from veins under the surface of a face 10 flows into ABTT 22, and also as recognized and tested by Applicant, there is bidirectional flow of blood in ABTT 22. Having converged at ABTT terminus 20, the blood from these four veins primarily flows into the brain from ABTT terminus 20, into ABTT 22, and then into the center of the brain, at the cavernous sinus (not shown), which Applicant identified as a thermal storage area, and which is adjacent to the thermoregulatory center of the brain. From the thermal storage area, thermal energy in the form of hot or cold blood is distributed throughout tissues of the brain, and by transmitting warm or cool blood to and from this region through ABTT 22, Applicant has realized that by regulating the temperature of the brain via ABTT 22, thermal disturbances may be treated or prevented, such as hyperthermia and hypothermia, or a variety of diseases may be treated.

Additionally, ABTT target area 20 is extremely vascularized and is the only skin area in which a direct branch of the cerebral vasculature is located and covered by a thin skin without a fat layer. The main trunk of the terminal branch of the ophthalmic vein is located right at ABTT target area 20, just above the medial canthal tendon supplied by the medial palpebral artery and medial orbital vein. ABTT target area or terminus 20 on the skin, supplied by a terminal and superficial blood vessel ending in a particular area without fat and void of thermoregulatory arteriovenous shunts, provides a superficial source of undisturbed biological signals including brain temperature, metabolic function, physical signals, and body chemistry such as glucose level, and the like.

Applicant has determined through experiment that since the thermal flow from ABTT terminus 20 of face 10 to the thermal storage area of the brain is bidirectional, the heating or cooling of the blood in frontal vein 12, superior palpebral vein 14, supraorbital vein 16, and angular vein 18 results in a cooling or heating of the thermal storage area in the brain, and, as a result, the entire brain and the body are cooled or heated. Thus, ABTT 22 allows for manipulation of the body's core temperature non-invasively and locally, through the cooling and heating of near-surface blood vessels in the face, without stimulating peripheral thermal receptors that lead to an opposite response from the brain. Furthermore, as seen in the histology of ABTT terminus 20, the skin at ABTT terminus 20 is void of fat, thereby allowing thermal energy transmission through the skin at ABTT terminus 20 and into the blood vessel directly under the dermis of ABTT terminus 20. Thus, the undesirable stimulation of peripheral receptors and the insulating presence of fat are eliminated with the apparatus and methods of the present disclosure.

The approximate locations of the veins 12, 14, 16, and 18 are shown in FIG. 19 with respect to other facial features. Angular vein 18 runs up alongside nose 24, superior palpebral vein 14 runs along eyebrow 26, and frontal vein 12 and supraorbital vein 16 run in the forehead 28. Applicant has determined that manipulating the body's core temperature or brain temperature by removing or adding heat through ABTT 22, according to the present disclosure, is best accomplished by concentrating application of heat or cold in the areas nearest these veins and over ABTT 22 to avoid stimulation of peripheral thermal receptors. It should also be understood that arterial blood also runs in parallel in some areas, but said arterial blood does not go toward the center of the brain as the venous blood does. Thus, it is preferred to apply heat or cold to the areas near and adjacent to veins 12, 14, 16, and 18.

For the purposes of disclosure, terminology referring to relevant facial areas or veins herein will be described as one or more of above-referenced veins 12, 14, 16, and 18, and ABTT target area 20. It should be understood that the present disclosure also includes the application or removal of thermal energy from other areas that may lie outside of these areas including, but not limited to, the under-eye area, behind the ears, the upper forehead, neck, trunk, extremities, etc. While these are less preferred areas of thermal application or removal, these areas can provide additional thermal benefits to core body temperature and are, as such, included in the scope of the disclosure. The reduction of stimulation of peripheral receptors in those areas is accomplished by a device or apparatus structure that follows the exact pattern of the associated blood vessel, as described further herein. Thus, minimal skin area is stimulated while the area covering a blood vessel is stimulated, which causes a change in the temperature of the blood of an affected vein, and this temperature change is reflected by a corresponding temperature change in the brain.

As discussed above, conventional methods of heating or cooling a body stimulate peripheral thermal receptors in order to treat thermal disturbance-related and other conditions. The heating or cooling of, for example, the body's extremities, activates peripheral sensors, which signal the brain to behave in the opposite manner, thus causing the core temperature to further rise or fall, ending in dangerous and often irreversible or fatal outcome.

Figure 54:
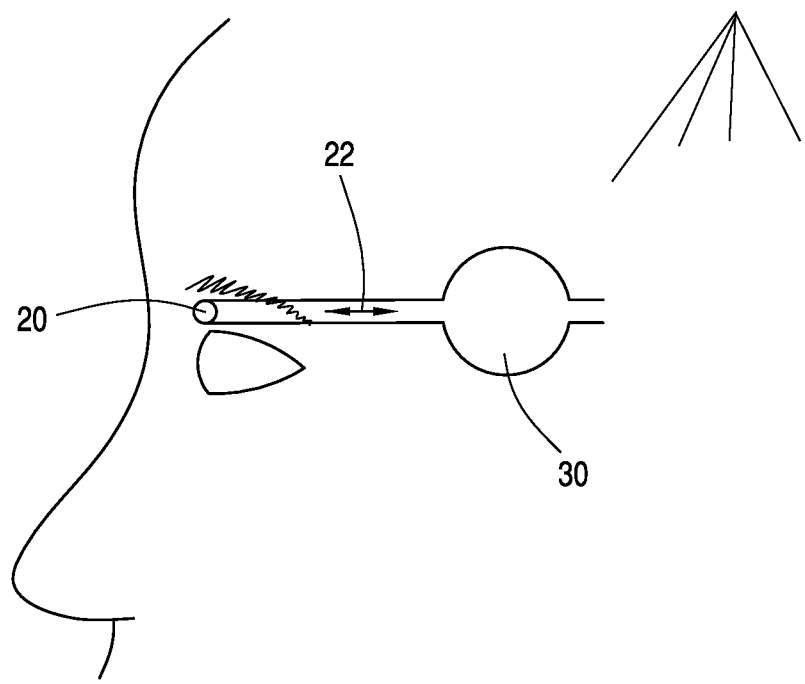
FIG. 54 is a stylized representation of the flow of thermal energy into and out from a brain core.

The present disclosure avoids the undesirable effects of conventional heating and cooling apparatus and methods by disclosing a method and apparatus for applying heat to or removing heat from the body by using a thermal transfer that occurs directly with the high thermoconductive skin having k=0.00004 Kcal/(s·N·C) in contact with at least one of ABTT target area 20 and veins 12, 14, 16, and 18 that converge into ABTT target area 20. The temperature change that occurs at ABTT terminus 20 and veins 12, 14, 16, and 18 is also carried to the thermal storage area of the brain through ABTT 22, and then to the rest of the brain. FIG. 54 provides a schematic view of heat flow from ABTT terminus 20 into and out from brain core 30, with the thin skin of ABTT target area 20 serving as the only barrier between tunnel 22 and the outside environment. Because only veins 12, 14, 16, and 18 receive the cooling or heating effects and no peripheral receptors are activated, the body's core temperature and brain temperature may be directly altered in proportion to heat applied or removed.

In experiments performed using a device configured only for cooling of ABTT terminus 20 and associated veins 12, 14, 16, and 18, shivering or changes in blood pressure were not elicited while reducing the temperature of the brain. In contrast, the same cold temperature stimulus applied to the torso, the limbs, or the head elicited shivering and changes in blood pressure with no immediate change in brain temperature, but after a time delay brain temperature increased in contrast to the desired decrease.

The present disclosure describes methods including altering a core temperature of a body by affecting the temperature of the skin directly in contact with at least one of frontal vein 12, superior palpebral vein 14, supraorbital vein 16, and angular vein 18, and superomedial orbit 20, which corresponds to ABTT terminus 20; or the upper eyelid region, which corresponds to superior palpebral vein 14. The present disclosure also describes apparatus including a thermally retentive material configured to allow for optimal thermal transfer with the skin directly in contact with at least one of frontal vein 12, superior palpebral vein 14, supraorbital vein 16, and angular vein 18, and superomedial orbit 20 or upper eyelid 14.

Exemplary brain cooling and heating devices of the present invention include both passive and active thermal transfer devices. Both types are described in detail in the present disclosure. A conventional thermal transfer substance used in passive thermal transfer apparatus is a thermally retentive gel-like substance such as, for example, a mixture of water and propylene glycol. In addition to gel substances, other passive thermal transfer methods include evaporative cooling, in which a structure is adapted to absorb water, thus providing cooling effects as the water evaporates, and phase change materials that demonstrate latent heat storage properties.

Figure 58A:
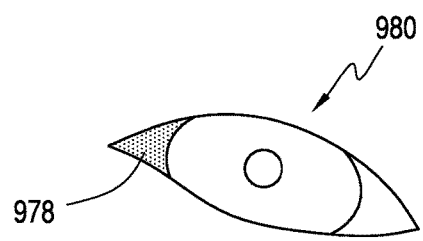
FIG. 58A is a view of an eye of the animal of FIG. 57.
Figure 57:
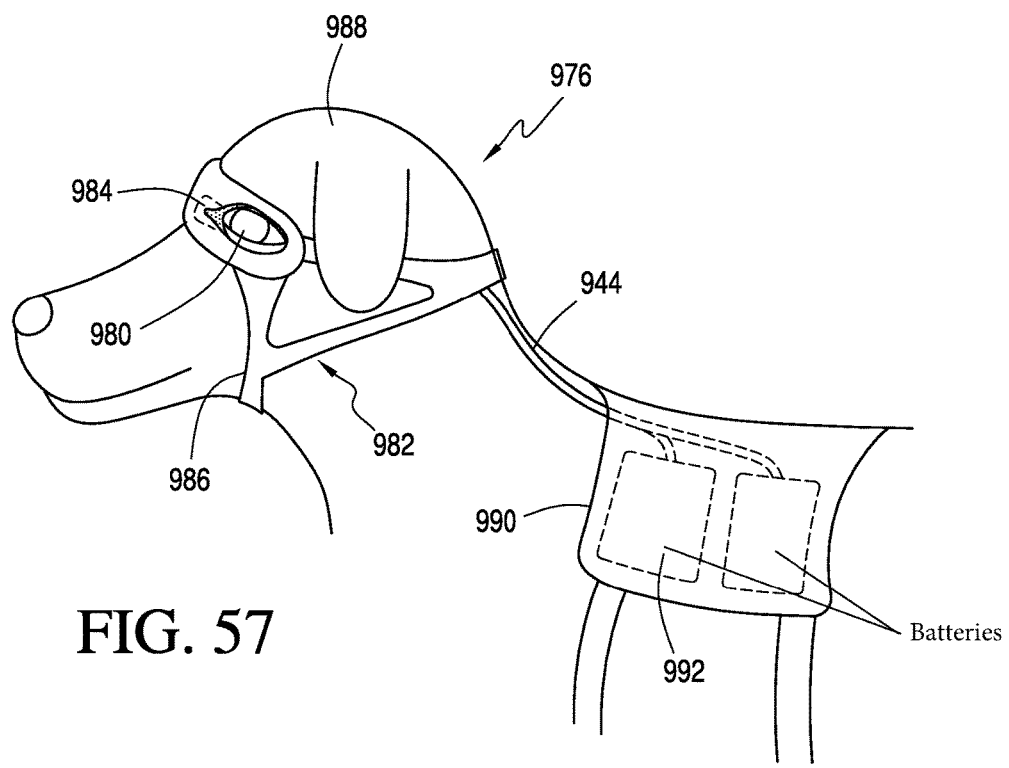
FIG. 57 is a view of an animal wearing a brain temperature modification device, in accordance with an exemplary embodiment of the present disclosure.

While the present disclosure is focused on the human ABTT, animals have a similar, though less effective, passage between the brain and the surface that is described as an intracranial thermal path (ITP). For example, FIG. 57 shows an animal, such as a dog 976. Dog 976 includes an ITP (not shown) that extends from the dog's brain to an ITP terminus 978 positioned adjacent to an eye 980 of dog 976, as shown in FIG. 58A. As the disclosed embodiments presented herein benefit humans, modifications of the devices presented herein can be modified to interface with ITP terminus 978 for benefit to animals. For example, FIG. 57 shows a heat exchange device in accordance with an exemplary embodiment of the present disclosure and indicated generally at 982.

Animals may have fur that reduces thermal conductivity, shifting the position of the equivalent of ABTT terminus 20 in animals to ITP terminus 978, which is represented by an area of transition skin-mucosa located in the corner of the eye, frequently adjacent to the tear duct and caruncle or conjunctival surface and referred to herein as the transition area. In some species, such as canines, felines and other predators, the transition area or ITP terminus 978 is located in the anterior or medial portion of the corner of the eye; in swine, ITP terminus 978 tends to be located in the posterior or lateral corner of the eye; in ovine, bovine and equines, ITP terminus 978 tends to be located in the anterior corner of the eye; and in primates such as chimpanzees, ITP terminus 978 tends to be located in both the medial corner and the lateral corner of the eye.

In the exemplary embodiment of FIG. 57, heat exchange device 982 includes a heat exchange apparatus 984 that may be, for example, a thermally retentive substance that can be heated or cooled prior to placing on animal 976, a thermoelectric cooling device, chemicals that can provide an endothermic or exothermic reaction, and the like. Typically, because animals frequently object to the presence of objects near their eyes, heat exchange device 982 includes a harness 986 for attachment of heat exchange device 982 to head 988 of animal 976. Harness 986 is configured to position heat exchange apparatus 984 over ITP terminus 978. If heat exchange apparatus 984 is a thermoelectric device, in an exemplary embodiment, a pack 990 configured to be positioned, attached, secured, or mounted on animal 976 is included in heat exchange device 982 to provide a location for one or more batteries 992. Batteries 992 are then connected to heat exchange apparatus 984 by, for example, wires or a cable 994 extending between batteries 992 and heat exchange apparatus 984.

Figure 58B:
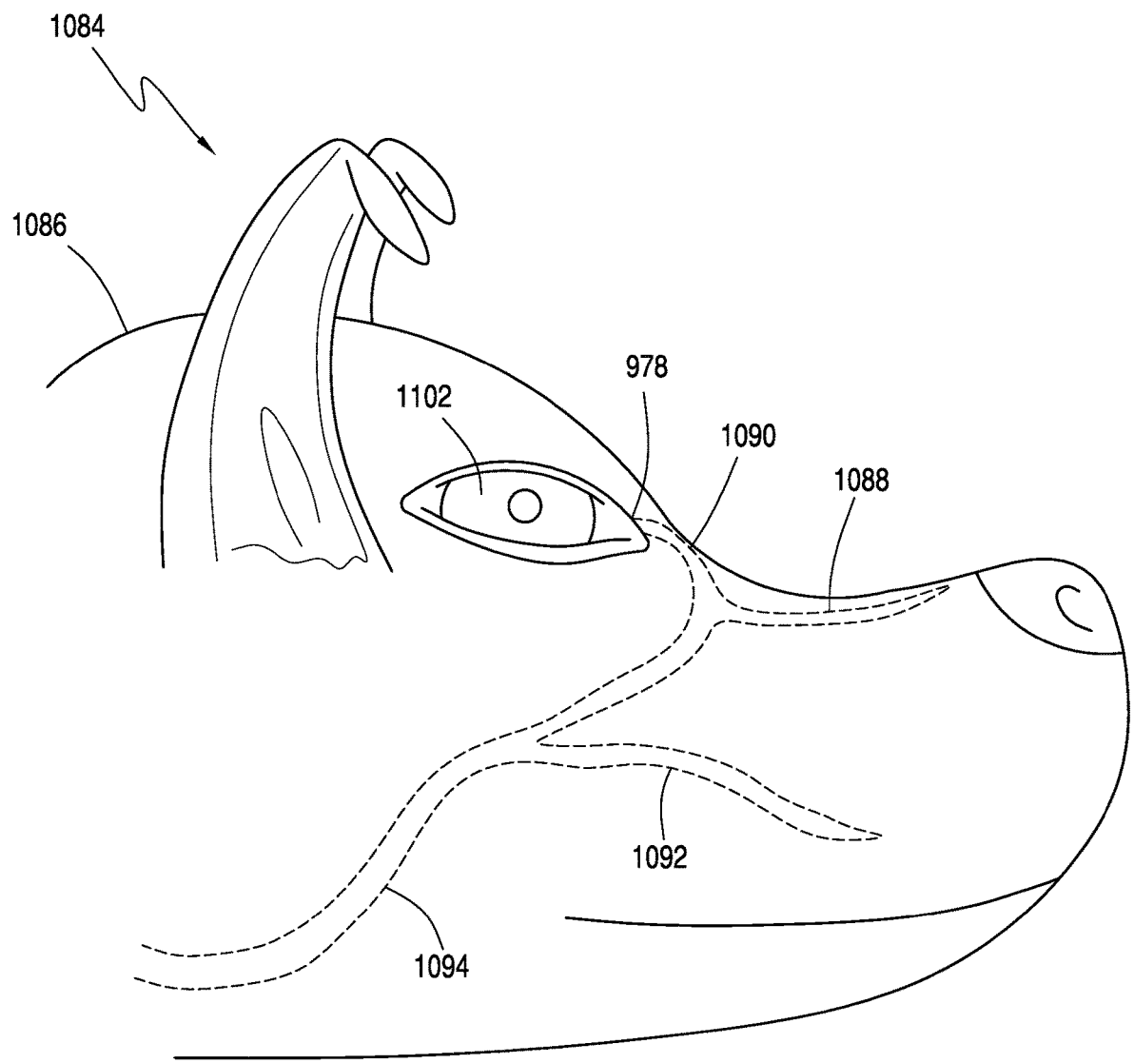
FIG. 58B is a view of an animal showing various features of the animal.

FIG. 58B is a view of a head 1086 of an animal 1084. As shown by Applicant, various blood vessels provide cooling or warming blood flow to the brain of animal 1084 via ITP 978. Such blood vessels can include, for example, nasal dorsal vein 1088, angular vein 1090, linguofacial vein 1092, and facial vein 1094, which extend along the surface of the skin of animal 1084. Automatic functions of the brain may operate to keep the brain of animal 1084 warm or cool by controlling the flow of blood from at least veins 1088, 1090, 1092, and 1094 to ITP 978. Exemplary embodiments of heat exchange devices disclosed herein, such as heat exchange device 982, assist an animal in keeping cool or warm by providing cool or warm area to at least one of the veins 1088, 1090, 1092, and 1094 and/or the transition area 978, which then flows to the brain of animal 1084.

Figure 58C:
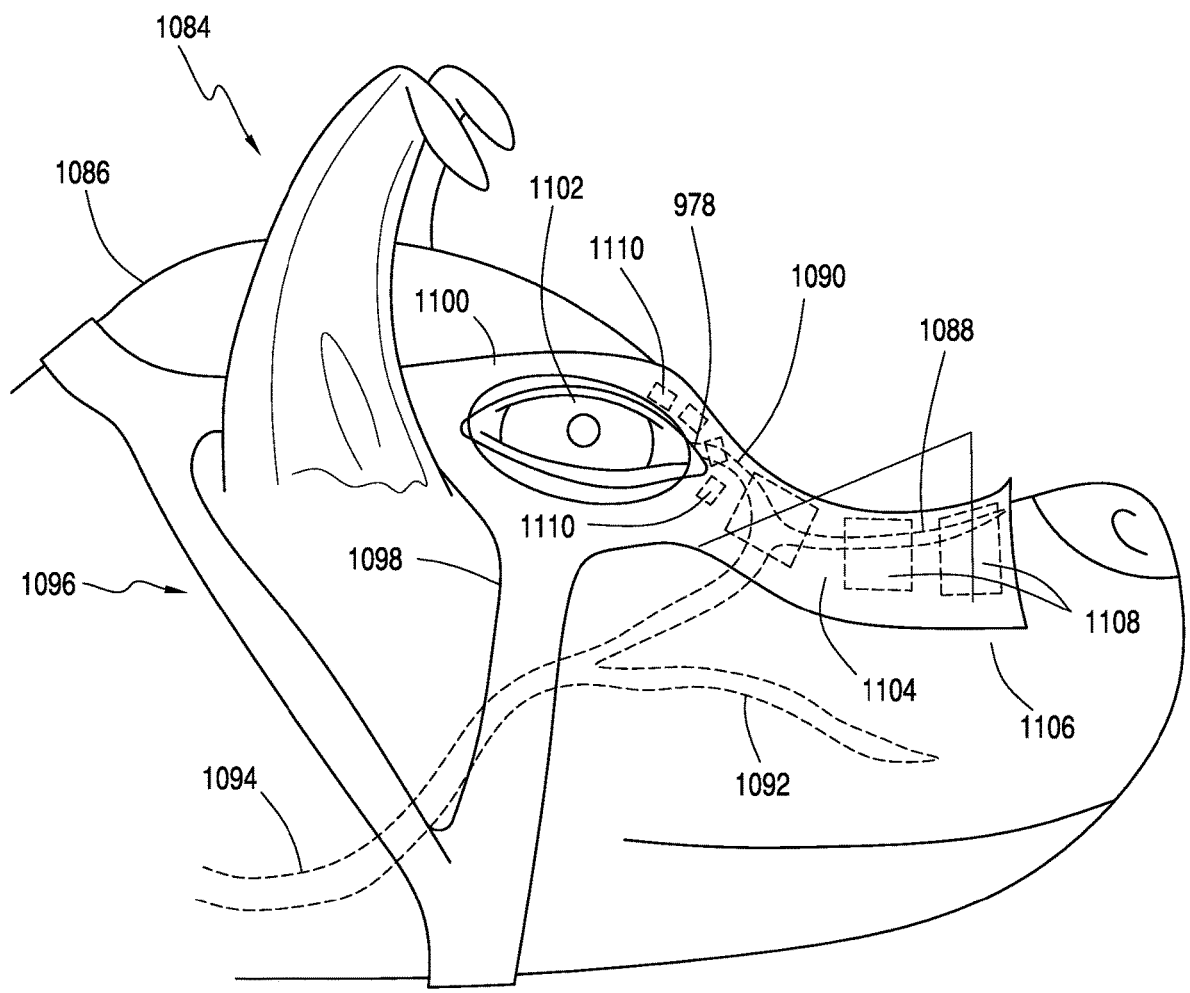
FIG. 58C is a view of an animal wearing a heat exchange device in accordance with an exemplary embodiment of the present disclosure.

FIG. 58C shows another heat exchange device configured to be positioned on and secured to animal 1084, indicated generally at 1096. Device 1096 includes a support apparatus 1098, which in an exemplary embodiment may be leather, cloth, plastic, or other materials suitable for anticipated environments. Support apparatus 1098 includes an annular ocular portion 1100 that extends around an eye 1102 of animal 1084, and a longitudinally extending muzzle portion 1104 that extends along a muzzle 1106 of animal 1084 and over at least a portion of nasal dorsal vein 1088. Device 1096 includes a plurality of heating or cooling apparatuses, such as thermoelectric devices 1108 and 1110, positioned to provide cooling and/or heating to at least a portion of angular vein 1090, and in the exemplary embodiment of FIG. 58C, nasal dorsal vein 1088. Device 1096 can be powered by, for example, pack 990 as shown in FIG. 57, which can be carried by animal 1084. Device 1096 provides more cooling or heating than device 982 shown in FIG. 57, and is configured to enable animal 1084 to operate or survive a greater ambient temperature range than device 982 is configured to enable.

Figure 58D:
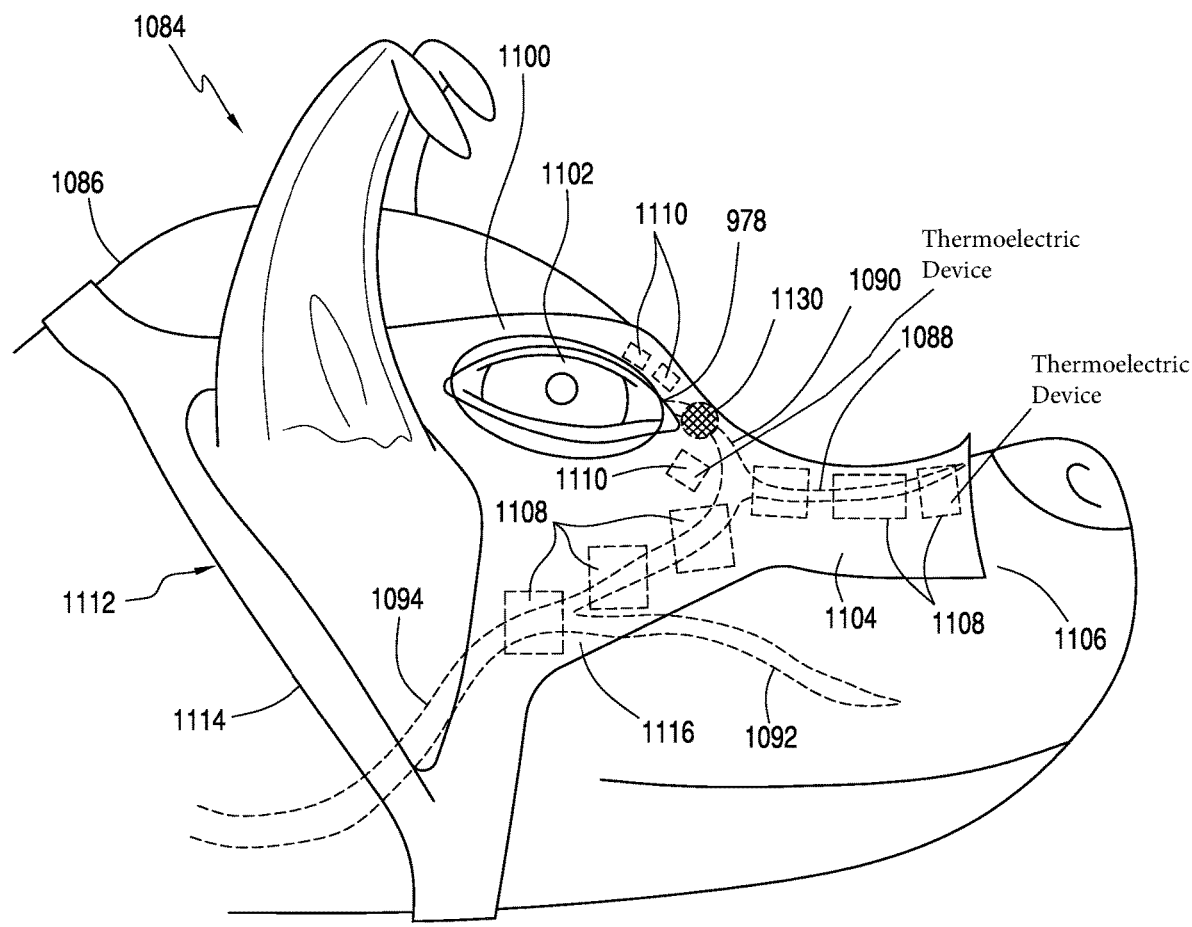
FIG. 58D is a view of an animal wearing another heat exchange device in accordance with an exemplary embodiment of the present disclosure.

FIG. 58D shows another heat exchange device configured to be positioned on and secured to animal 1084, indicated generally at 1112. Device 1112 includes a support apparatus 1114, which in an exemplary embodiment may be leather, cloth, plastic, or other materials suitable for anticipated environments. Support apparatus 1114 includes annular ocular portion 1100 that extends around eye 1102 of animal 1084, longitudinally extending muzzle portion 1104 that extends along muzzle 1106 of animal 1084 and over at least a portion of nasal dorsal vein 1088, and an upper side facial portion 1116 that extends along facial vein 1094. Device 1112 includes a plurality of heating or cooling apparatuses, such as thermoelectric devices 1108 and 1110, positioned to provide cooling and/or heating to at least a portion of angular vein 1090, at least a portion of nasal dorsal vein 1088, and at least a portion of facial vein 1094. Device 1112 can be powered by, for example, pack 990 as shown in FIG. 57, which can be carried by animal 1084. Device 1112 provides more cooling or heating than device 982 shown in FIG. 57 and device 1096 shown in FIG. 58C, and is configured to enable animal 1084 to operate or survive a greater ambient temperature range than device 982 or device 1096 are configured to enable. Device 1112 further includes a temperature sensor 1130 configured to measure the temperature of ITP 978. It should be understood that any of the embodiments that provide direct or indirect cooling or heating of ITP 978 may include a temperature sensor. Device 1112 may use the output of temperature sensor 1130 to provide precise control of the output of the heating/cooling devices, such as devices 1108 and 1110, to reduce power consumption and optimize the internal temperature of animal 1084. Temperature information from sensor 1130 may also be provided to a separate electronic device, such as a cell phone, watch, laptop, tablet, etc., such that a user may monitor the temperature of animal 1084.

Figure 58E:
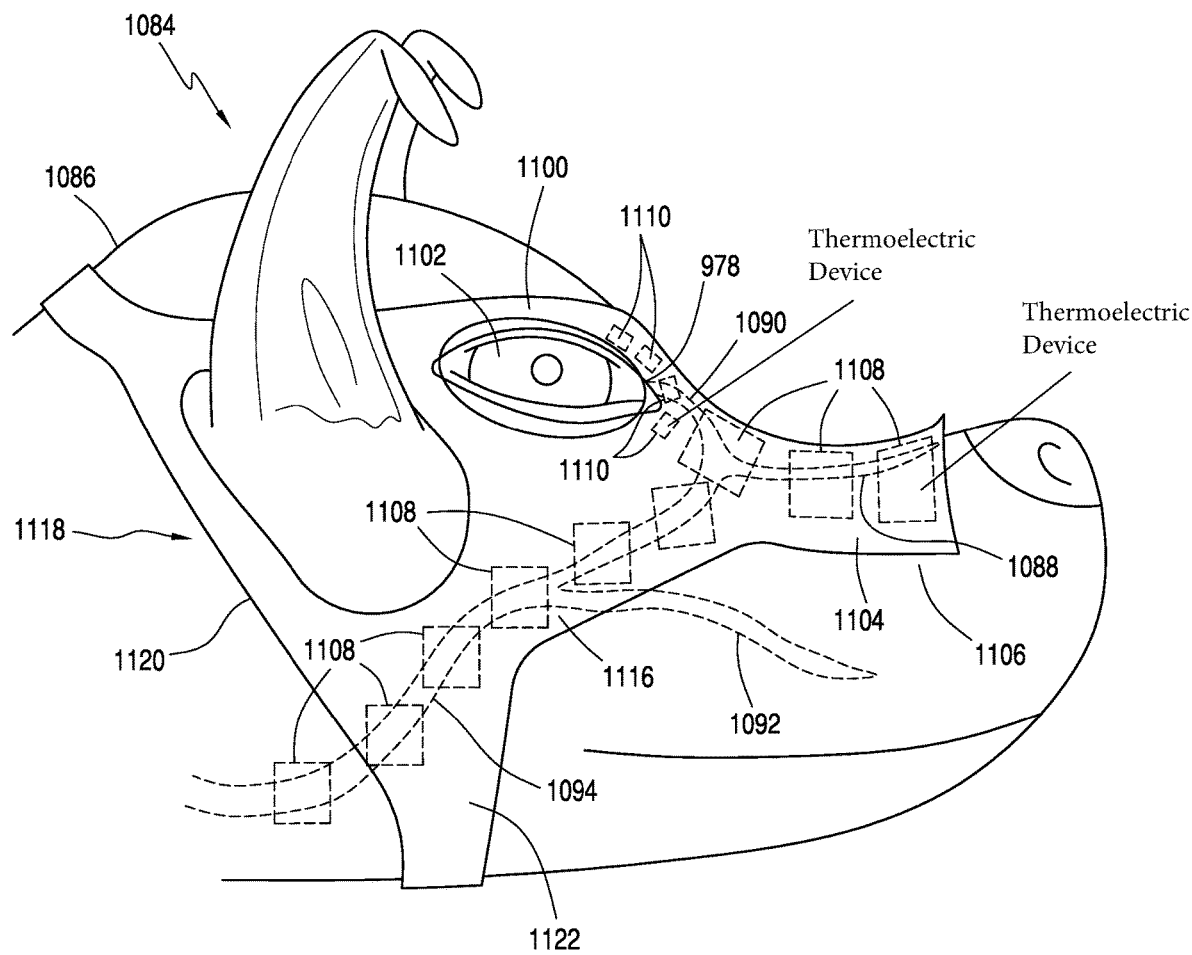
FIG. 58E is a view of an animal wearing a further heat exchange device in accordance with an exemplary embodiment of the present disclosure.

FIG. 58E shows another heat exchange device configured to be positioned on and secured to animal 1084, indicated generally at 1118. Device 1118 includes a support apparatus 1120, which in an exemplary embodiment may be leather, cloth, plastic, or other materials suitable for anticipated environments. Support apparatus 1120 includes annular ocular portion 1100 that extends around eye 1102 of animal 1084, longitudinally extending muzzle portion 1104 that extends along muzzle 1106 of animal 1084 and over at least a portion of nasal dorsal vein 1088, upper side facial portion 1116 that extends along facial vein 1094, and a lower side facial portion 1122 that extends further along facial vein 1094 from upper side facial portion 1116. Device 1118 includes a plurality of heating or cooling apparatuses, such as thermoelectric devices 1108 and 1110, positioned to provide cooling and/or heating to at least a portion of angular vein 1090, at least a portion of nasal dorsal vein 1088, and a greater portion of facial vein 1094 than device 1112. Device 1118 can be powered by, for example, pack 990 as shown in FIG. 57, which can be carried by animal 1084. Device 1118 provides more cooling or heating than device 982 shown in FIG. 57, device 1096 shown in FIG. 58C, and device 1112 shown in FIG. 58D, and is configured to enable animal 1084 to operate or survive a greater ambient temperature range than device 982, device 1096, and device 1112 are configured to enable.

Figure 58F:
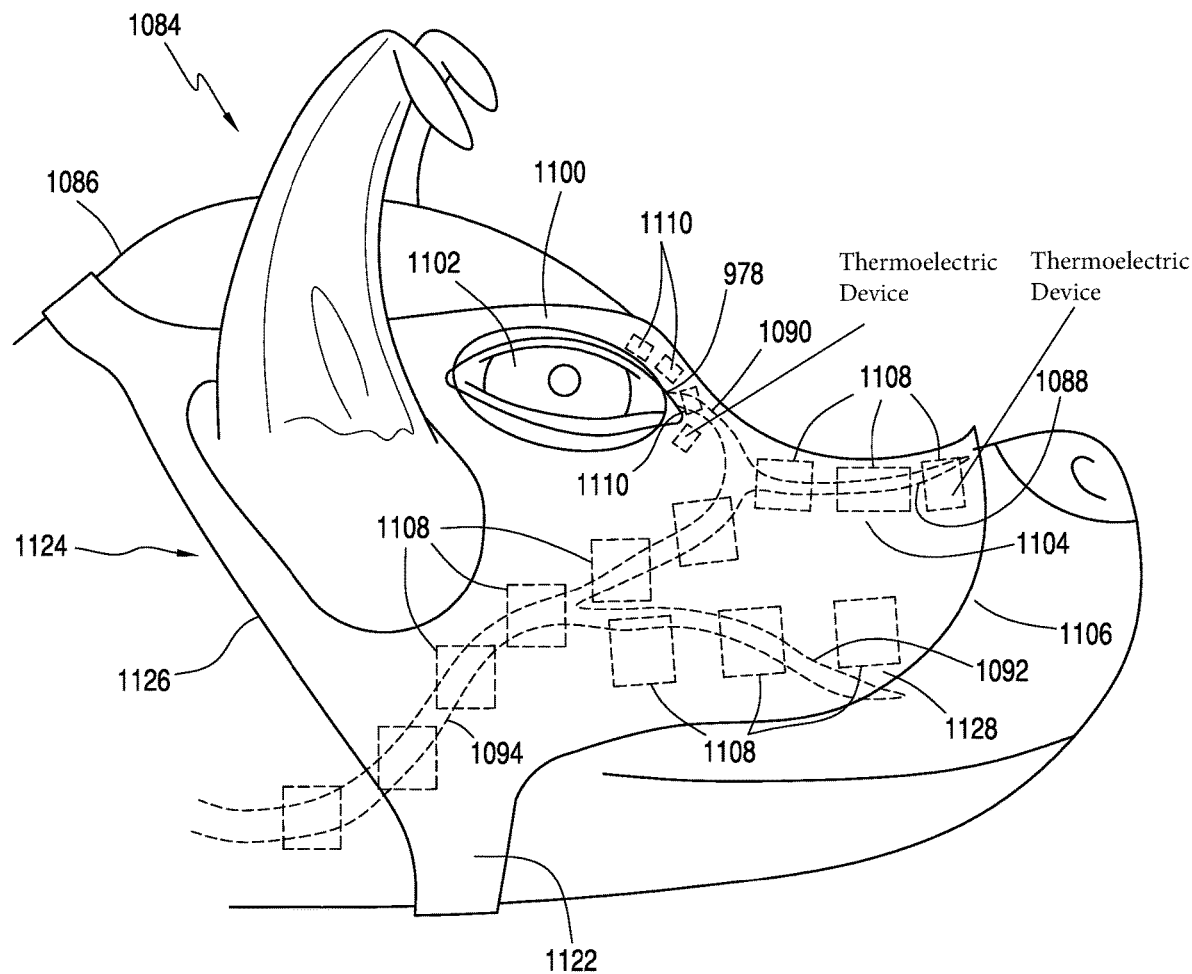
FIG. 58F is a view of an animal wearing yet another heat exchange device in accordance with an exemplary embodiment of the present disclosure.

FIG. 58F shows another heat exchange device configured to be positioned on and secured to animal 1084, indicated generally at 1124. Device 1124 includes a support apparatus 1126, which in an exemplary embodiment may be leather, cloth, plastic, or other materials suitable for anticipated environments. Support apparatus 1126 includes annular ocular portion 1100 that extends around eye 1102 of animal 1084, longitudinally extending muzzle portion 1104 that extends along muzzle 1106 of animal 1084 and over at least a portion of nasal dorsal vein 1088, upper side facial portion 1116 that extends along facial vein 1094, lower side facial portion 1122 that extends further along facial vein 1094 from upper side facial portion 1116, and a lower muzzle portion 1128 that extends along linguofacial vein 1092. Device 1124 includes a plurality of heating or cooling apparatuses, such as thermoelectric devices 1108 and 1110, positioned to provide cooling and/or heating to at least a portion of angular vein 1090, at least a portion of nasal dorsal vein 1088, at least a portion of facial vein 1094, and at least a portion of linguofacial vein 1092. Device 1124 can be powered by, for example, pack 990 as shown in FIG. 57, which can be carried by animal 1084. Device 1124 provides more cooling or heating than device 982 shown in FIG. 57, device 1096 shown in FIG. 58C, device 1112 shown in FIG. 58D, and device 1118 shown in FIG. 58E, and is configured to enable animal 1084 to operate or survive a greater ambient temperature range than device 982, device 1096, device 1112, and device 1118 are configured to enable.

Figure 58G:
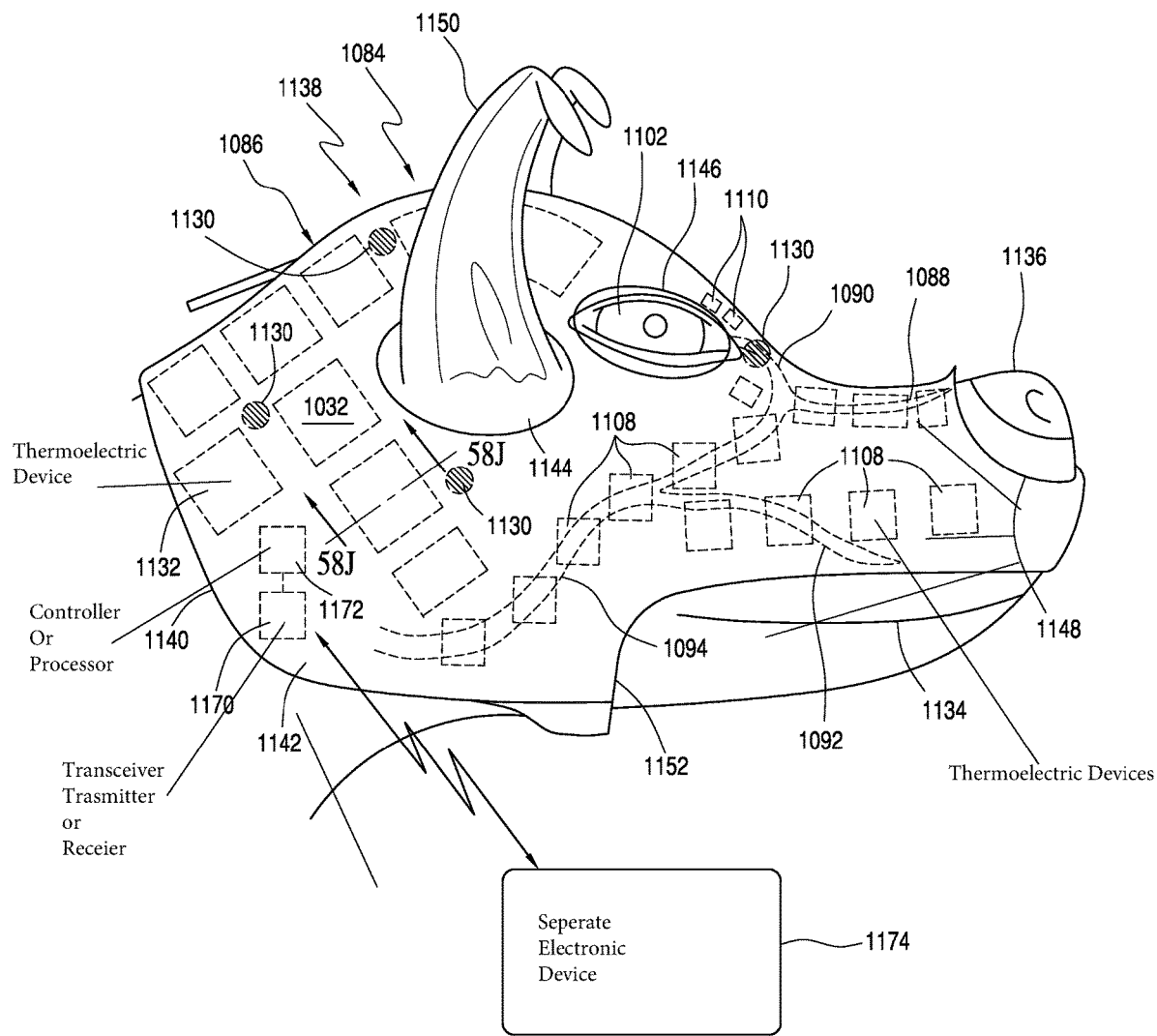
FIG. 58G is a view of an animal wearing an even further heat exchange device in accordance with an exemplary embodiment of the present disclosure.

FIG. 58G shows another heat exchange device configured to be positioned on and secured to animal 1084, indicated generally at 1138. Device 1138 includes a support apparatus or structure 1140, which in an exemplary embodiment may include an outer covering 1142 that may be leather, cloth, plastic, or other materials suitable for anticipated environments. Support apparatus 1140 covers most of head 1086 of animal 1084, though in the exemplary embodiment of FIG. 58G, support apparatus 1140 includes openings 1144, 1146, 1148, and 1152 for ears 1150, eyes 1102, nose 1136, and a mouth 1134. By covering most of head 1086, a significant portion of veins 1088, 1090, 1092, and 1094 are covered. Device 1124 includes a plurality of heating or cooling apparatuses, such as thermoelectric devices 1108, 1110, and 1132 positioned to provide cooling and/or heating to at least a portion of angular vein 1090, at least a portion of nasal dorsal vein 1088, at least a portion of facial vein 1094, and at least a portion of linguofacial vein 1092. Device 1138 can be powered by, for example, pack 990 as shown in FIG. 57, which can be carried by animal 1084. In an exemplary embodiment, device 1138 includes a plurality of temperature sensors 1130 to provide temperature at various locations on head 1086, which may be used to control the output of individual thermoelectric devices 1108, 1110, and 1132, as well as providing some redundancy in the event of failure of any one temperature sensor 1130.

In addition to providing heating or cooling to animal 1084, device 1138 is configured to protect head 1086 of animal 1084 from environmental hazards, including shrapnel, branches, etc. As such, device 1138, as shown in FIG. 58J, includes one or more structural elements 1154 and 1156, which in an exemplary embodiment are a para-aramid synthetic fiber, of which one brand name is KEVLAR. Because structural elements 1154 and 1156 reduce the ability of thermoelectric devices to reject heat, device 1138 is configured to include a thermally conductive heat spreader 1158 that extends from, for example, thermoelectric device 1132 to a side of device 1138 that is opposite the side that faces animal 1084. Thus, in a cooling mode, thermoelectric device 1132 rejects heat through heat spreader 1158, and in a heating mode, thermoelectric device 1132 absorbs heat or cools heat spreader 1158. It should be understood that outer covering 1142 may cover thermoelectric device 1132 to help in spreading heat or cold over a larger area of animal 1084, as well as assuring that any sharp edges or corners on thermoelectric device 1132 are covered to keep such edges or corners from irritating animal 1084.

As shown in FIG. 58J, thermoelectric device 1132 protrudes a spaced distance away from a lower surface 1160 of device 1138. Furthermore, in the exemplary embodiment of FIGS. 58J and 58K, support apparatus 1140 includes edges or borders 1162 that also protrude a spaced distance from lower surface 1160. The benefit of this configuration is that insulated pockets, spaces, or channels 1164 are formed and positioned between device 1138 and animal 1084, which improves the ability to heat and cool animal 1084 while providing protection of animal 1084 because of the presence of armor in device 1138. FIG. 58K shows an exemplary support apparatus 1140 comprised of a flexible material including plastic, leather, fabric, and the like for conforming to the body of the user (animal or human) and including a plurality of thermoelectric devices 1132 spaced apart to create an air pocket 1164 bounded by the skin 1084 and lower surface 1160. At least two thermoelectric devices are preferably housed in the exemplary embodiment, represented by support apparatus 1140. The preferred distance between each thermoelectric device 1132 in support apparatus 1140 is equal to or less than 15 mm, and preferably equal to or less than 10 mm, and more preferably equal to or less than 5 mm, and most preferably equal to or less than 2.5 mm, and even most preferably equal to or less than 1.5 mm. The preferred range for the distance between thermoelectric devices 1132 range from 1.5 mm to 15 mm The various embodiments of heat exchange devices that include temperature sensor 1130 may configure sensor 1130 to protrude from an associated support structure, such as support structure 1140 as shown in FIG. 58I. The benefit of this configuration is that temperature sensor 1130 is configured to be placed in closer contact with a vein, such as angular vein 1090, than might be possible without the existence of a protrusion 1166 including temperature sensor 1130. Protrusion 1166 may further include an opening 1168 for temperature sensor 1130 to measure air captured between a support device and animal 1084. In another exemplary embodiment, temperature sensor 1130 is flush with a bottom surface of support structure 1140 to permit the closest contact with the skin of animal 1084 as possible.

It should also be understood that device 1138 can be configured to include a plurality of electronic elements or devices, such as a controller or processor 1172, a transceiver, transmitter, or receiver 1170 for communication with a separate electronic device 1174, which can include a cell phone, laptop, tablet, etc., and other electronic devices.

Figure 58H:
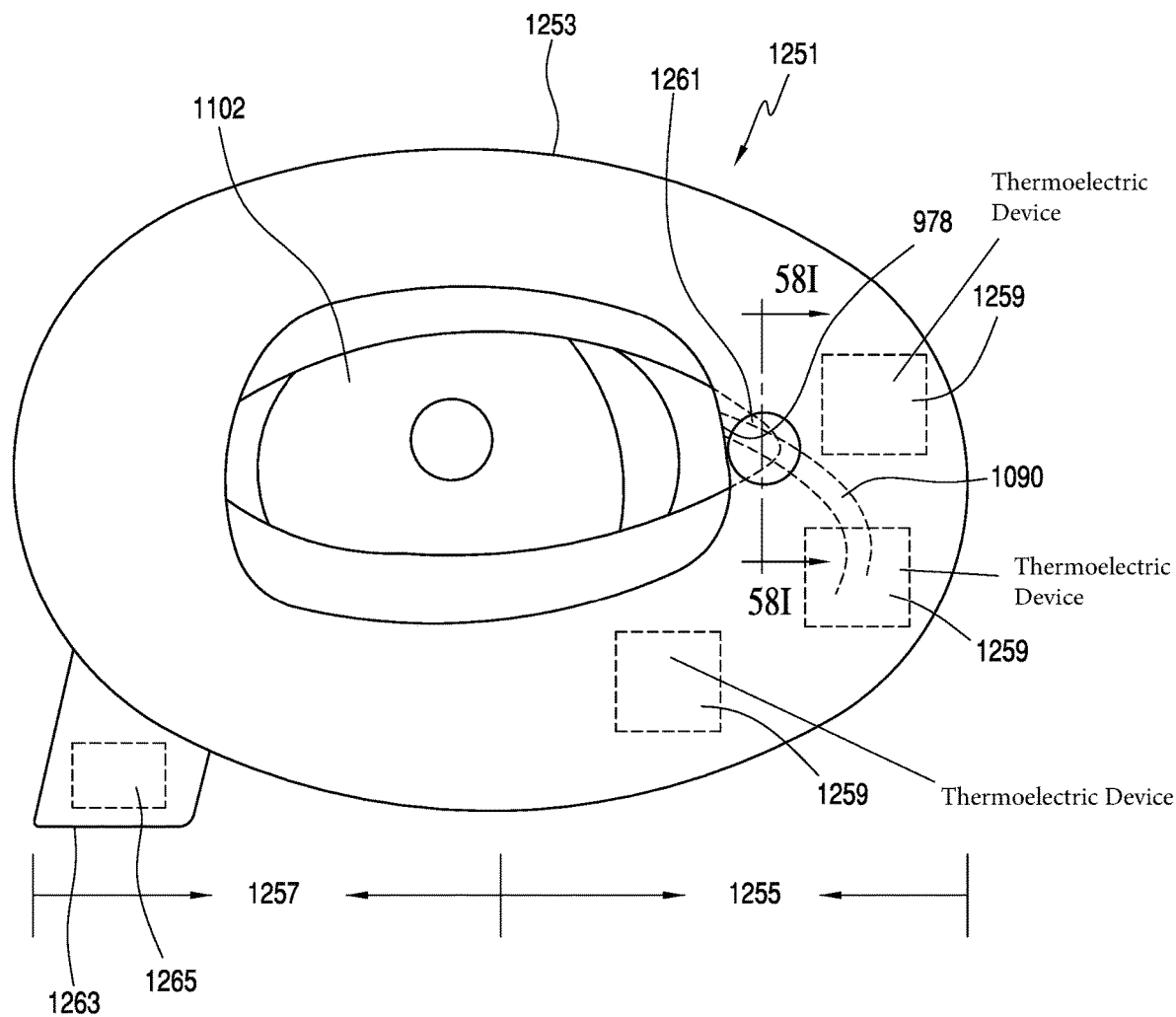
FIG. 58H is a view of a brain temperature modification device, in accordance with an exemplary embodiment of the present disclosure.
Figure 58I:
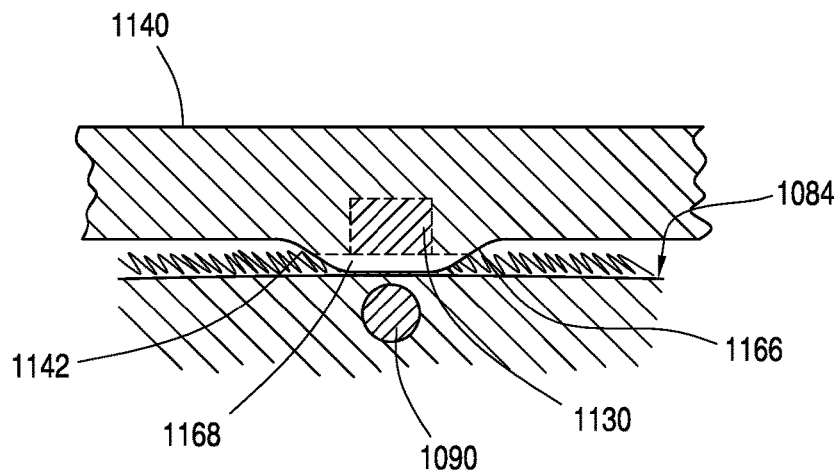
FIG. 58I is a cross-sectional view of the brain temperature modification device of FIG. 58H, along the line 58I-58I.
Figure 58J:
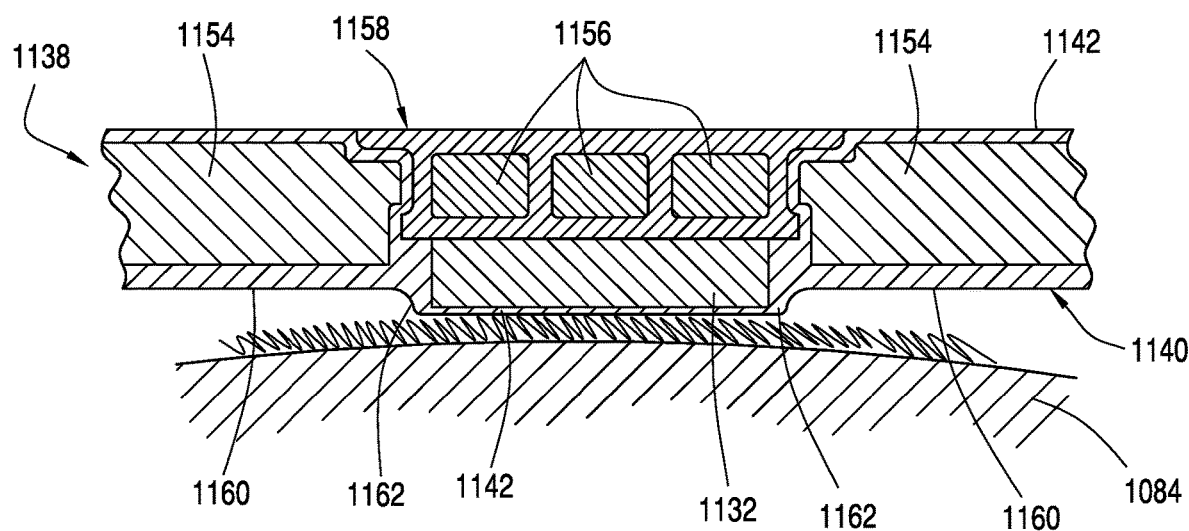
FIG. 58J is a cross-sectional view of the brain temperature modification device of FIG. 58G, along the line 58J-58J.
Figure 58K:
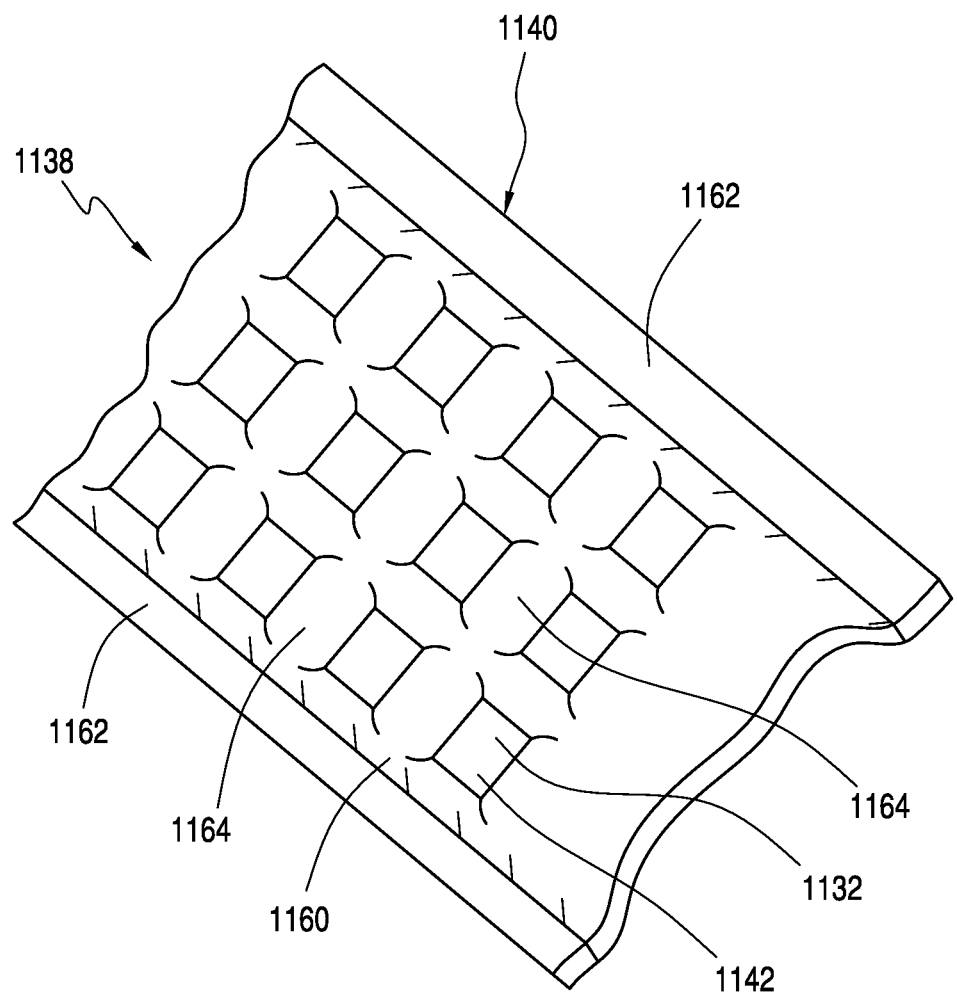
FIG. 58K is a view of a portion of the brain temperature modification device of FIG. 58G.

FIG. 58H shows an exemplary ring 1253 of a thermal exchange device 1251. In an exemplary embodiment, ring 1253 is divided in two equal halves comprised of two sections, anterior 1255 and posterior 1257. Anterior section 1257 includes a plurality of thermoelectric devices 1259 overlying transition area 978 and angular vein 1090, and a sensor 1261. Posterior section 1257 includes an extension 1263 in a lower half that houses a thermoelectric device 1265 that overlies the area of the ophthalmic plexus (not shown), to augment thermal effect to the brain.

Figure 95A:
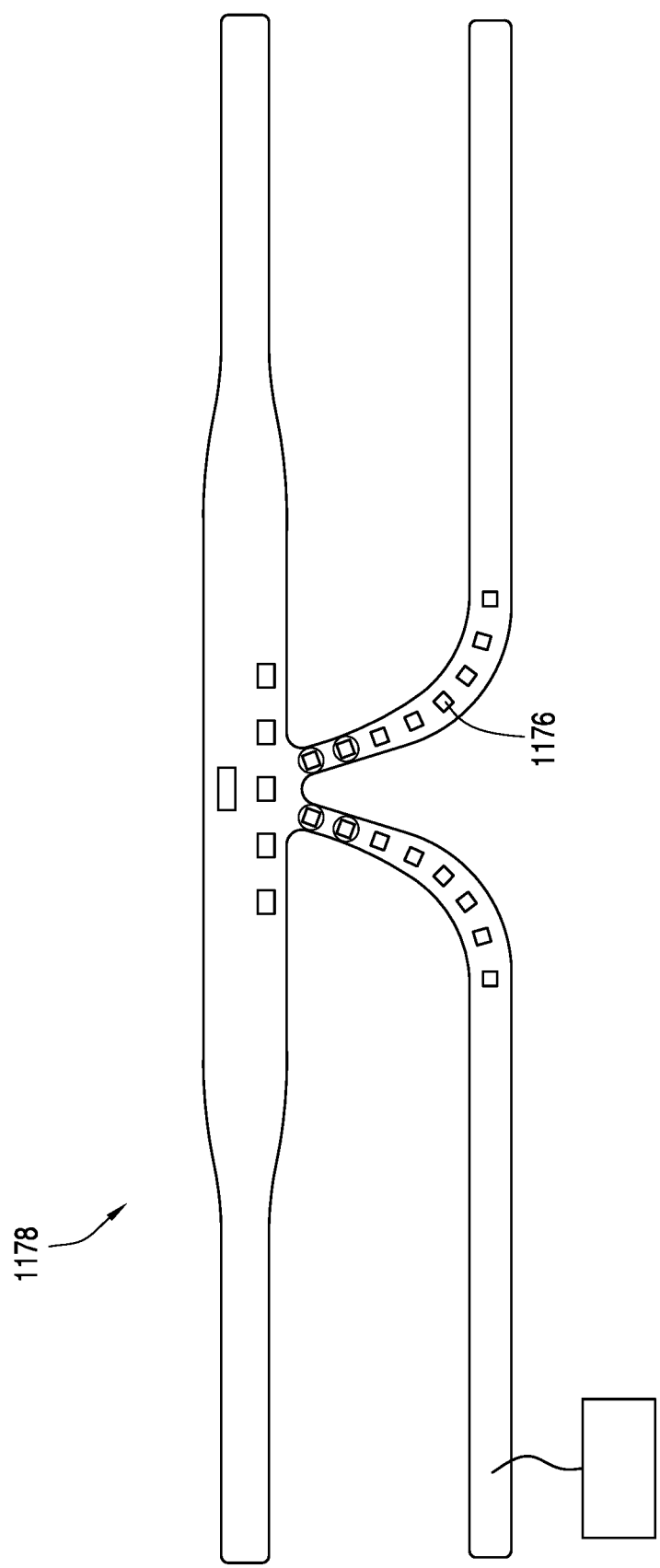
FIG. 95A is a view of an active thermal exchange system, in accordance with an exemplary embodiment of the present disclosure.

It should be apparent that the configuration of FIGS. 58G and 58K is also adaptable for use with a human patient or subject, either with or without the presence of structural elements 1154 and 1156. It should also be apparent that any of the configurations of masks, headbands, supports, etc., that show either passive or active elements can be configured to include thermoelectric devices, such as thermoelectric devices 1176 shown on support structure 1178 in FIG. 95A.

It should be understood that this same configuration used in animals as shown in FIGS. 57-58J, can be used in any of the embodiments of this disclosure for human use including but not limited to, eyeglasses, frames, facial bands, forehead bands goggles, adhesives, patches, clips, and the like, in which at least one of ABTT terminus 20, and veins 12, 14, 16, 18 and 19 are covered by thermoelectric devices spaced from the skin to create air pockets and increase the thermal effect.

Heat exchange apparatus 984 is beneficial in extreme environments faced by working animals, such as desert environments, where many working dogs suffer during intense heat, and artic environments where working dogs suffer during intense cold. Similarly, high value animals, such as breeding bulls, race horses, etc., can benefit from heating or cooling of the ITP by way of ITP terminus 978.

A configuration or structure that provides cooling to ABTT terminus 20 and veins 12, 14, 16, and 18 is the ABVTP. A thermal transfer material within the ABVTP of the present disclosure may be of an active type including, for example, an electric heating or cooling element connected to a power source, a serpentine device with a pumping or sucking mechanism in which heated or cooled fluid flows through a series of tubes adapted to deliver or remove thermal energy from the relevant areas, or any other active thermal transfer method. Such active thermal transfer methods may also comprise a temperature control unit and controller or processor for regulating temperature automatically.

Figure 55:
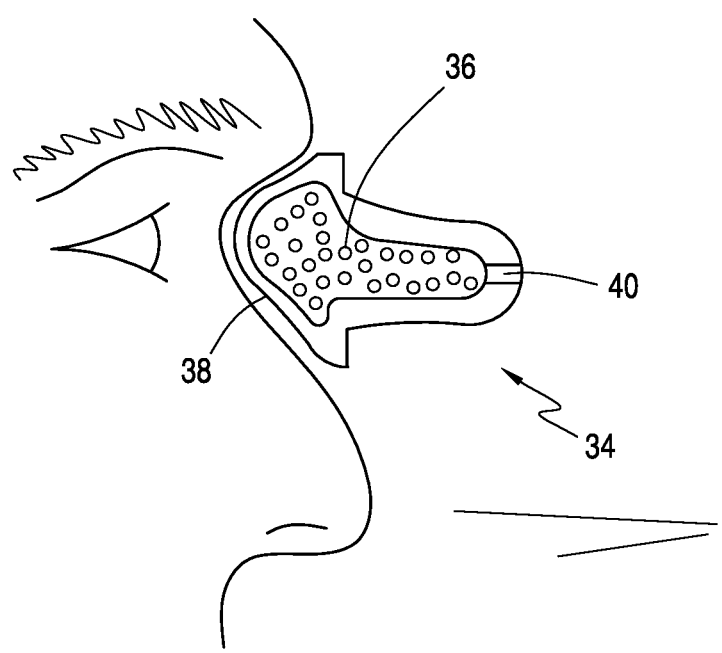
FIG. 55 is a view of a heat exchange device for manual placement on the ABTT terminus, in accordance with an exemplary embodiment of the present disclosure.

An exemplary passive-type brain cooling or heating device includes a thermal transfer hot and cold pad or pack. The ABVTP is a structure adapted to fit the special geometry of ABTT target area 20, and relevant veins 12, 14, 16, and 18 of the face converging in ABTT target area 20. The ABVTP includes a preferably flexible and sealed pouch 34, and a thermally retentive substance 36 within pouch 34, as shown in FIG. 55. Thermally retentive substance 36 may include water or a mixture of water and a freezing point depressant such as, but not limited to, propylene glycol, glycerin, and mixtures thereof associated with other compounds such as sodium polyacrylate, benzoate of soda, hydoxibenzoate, and mixtures thereof, and a thickening agent. Any other chemical compounds and gels may be used which may add or remove thermal energy to the applied area, including a combination of ammonium nitrate and water, or iron powder, water, activated carbon, vermiculite, salt and Purge natural mineral powder.

The ABVTP containing the thermal substance may be manually heated, as in a microwave or submersion in hot water, or cooled, by submersion in ice water or storage in a refrigerator or freezer, and as such, may be used to both heat and cool the body depending on the condition being treated. In an exemplary embodiment, such as pouch 34 of FIG. 55, the ABVTP preferably comprises a tough, flexible envelope 38 of a compliant material, such as a plastic, which is sealed in a conventional fashion.

Thermally retentive material 36 within the ABVTP may be a gel that maintains its gel-like consistency over a wide range of temperatures, and thermally retentive substance 36 will fill pouch 34 such that most of pouch 34 will contain thermally retentive substance 36 in areas intended for contact with ABTT terminus 20. However, preferably the interior of pouch 34 should not be filled with a thermally retentive substance 36 to the point where pouch 34 becomes inflexible. In an exemplary embodiment, thermally retentive substance 36 may be contained freely in pouch 34 or, in another exemplary embodiment, thermally retentive substance 36 may be in a particulate form as beads contained in pouch 34 to conform more readily to the shape of anatomical features of ABTT terminus 20, or an article of manufacturing having at least one convex surface for apposition to ABTT terminus 20. Thermally retentive substance 36 may be sealed within pouch 34 during manufacturing, or it may be added by way of a valve 40 by way of a fill needle (not shown).

Figure 51:
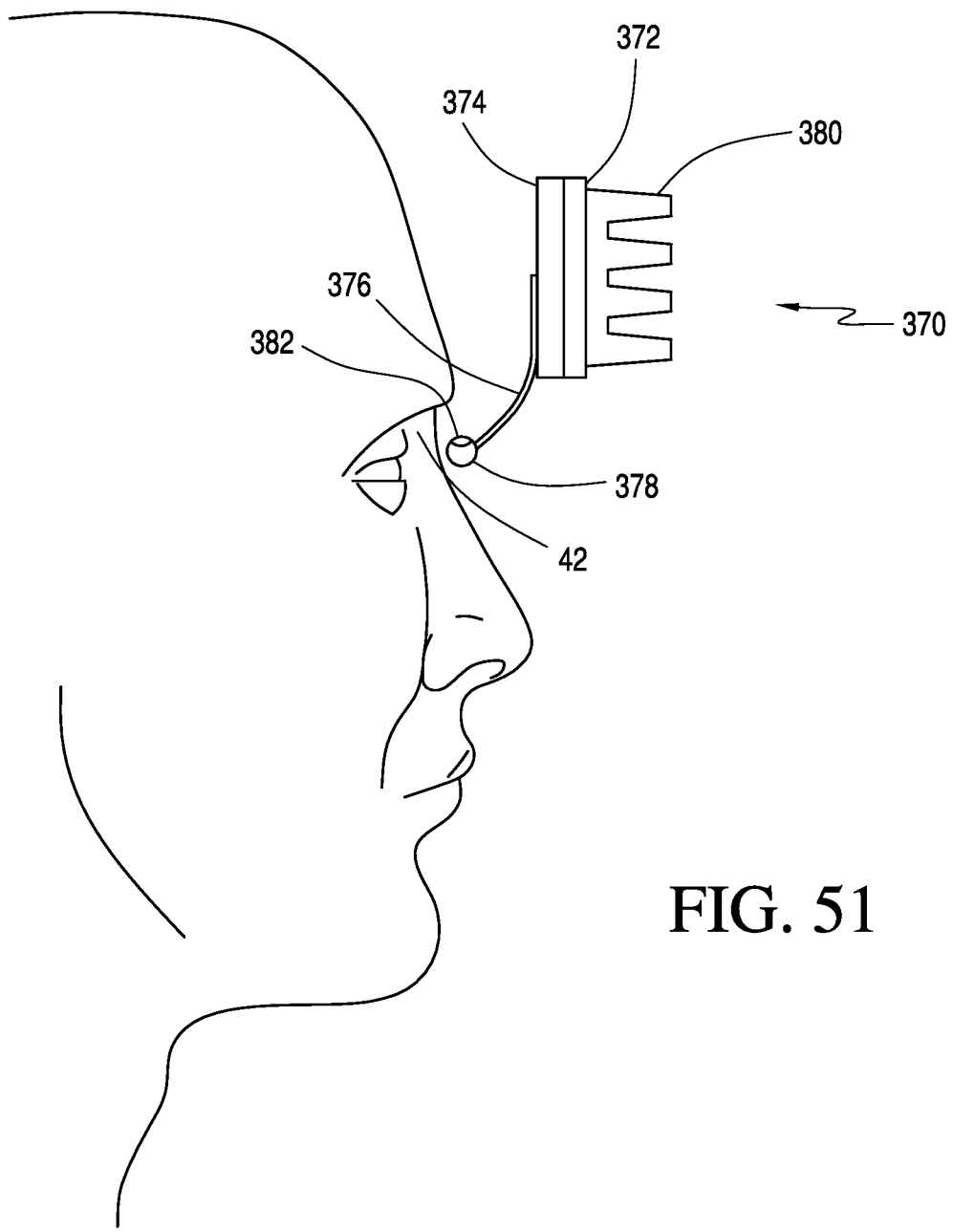
FIG. 51 is a view of an alternative embodiment of the apparatus of FIG. 38, in accordance with an exemplary embodiment of the present disclosure.

Although flexible plastic is described as an exemplary embodiment for containing thermally retentive substance 36, it should be understood that any material or fabric can be used, including vinyl, cotton, rayon, rubber, thermoplastic, synthetic polymers, mixtures of materials, and the like, which may be adapted to fit the special anatomy of a recess 42 between the eye and nose, as shown, for example, in FIG. 51, and for matching the special geometry of the entrance of the ABTT and associated veins 12, 14, 16, and 18. In an exemplary embodiment, pouch 34 is created from materials that are moldable, deformable, and otherwise pliable or flexible for temperatures in the range of −10 degrees Celsius to +50 degrees Celsius.

Another exemplary embodiment headband and thermal pack device configuration is shown in FIGS. 21-24 and indicated at 490. Device 490 includes similarities to the configuration of FIGS. 104 and 105. Device 490 includes an insulating headband 492, a thermal pack 494, and a temperature sensor 496 connected by wires 498 to a preferably detachable module 500. However, module 500 can be permanently affixed to thermal pack 494. Thermal pack 494 is insulated from the front by headband 492. Any appropriate insulating material may be used for headband 492, on its own or in combination, including, but not limited to polytetrafluoroethylene film containing minute pores (GORE-TEX), MYLAR, silicone, neoprene, SCAPA, cotton, and other materials with low thermal conductivity. Insulating headband 492 in this embodiment includes one or more extensions or protrusions 502 that dip down from the bottom center of insulating headband 492 to cover a corresponding node 504 included as part of thermal pack 494. In an exemplary embodiment, nodes 504 include a metal covering 506 or any other material such as plastic, or other insulating material. Connected to metal covering 506 may be adjustable arms 508 that extend upwardly into thermal pack 494. Adjustable arms 508 can include any flexible material such as a wire, said wire terminating in covering 506. Adjustable arms 508 in combination with metal covering 506 permit the adjustment of nodes 504 better contact with ABTT terminus 20. In the exemplary embodiment of FIGS. 21 and 23, headband 492 and thermal pack 494 are permanently attached to each other.

Further, this embodiment may include, but are not limited to, displaying relevant input or data output information on a display visually or orally reporting input and data output information. This embodiment includes temperature sensor 496 that is placed between headband 492 and thermal pack 494 for accurate temperature reading of thermal pack 494. Temperature sensor 496 allows the user to know when the device 490 is ready for use. In an exemplary embodiment, a light emitting diode (LED) 510 is positioned on or adjacent to a headband node 504. In an exemplary embodiment, LED 510 may emit a green light to indicate that node 504 is at optimal temperatures and a red light to indicate when optimal temperatures yet to be reached or have been surpassed. Other display or reporting devices may comprise an alarm, indicator light, and other electronics configured to alert a user when the temperature is above or below a threshold temperature. It should be understood that the alert or alarm may be visual, auditory, or vibrational.

In an exemplary embodiment, detachable module 500 serves as an energy source for temperature sensor 496 and LED 132. In an exemplary embodiment, detachable module 500 includes a speaker 512 to indicate various conditions of device 490, including readiness for use. Additionally, detachable module 500 may be configured to collect data for analysis, to analyze processed data, and to store processed thermal energy data. Once LED 510 indicates that optimal temperatures have been surpassed, the user can remove detachable module 500 from a connector 514, which is included as a part of device 490, and attach module 500 to a computer.

Detachable module 500 of the present disclosure may also comprise a communications interface 501 adapted to transmit data captured by module 500 to a computer system 503 including a tablet, cell phone, watch, and the like. In an exemplary embodiment, said communication interface 502 includes a wireless transmitter and wireless receiver adapted to transmit and receive signals from a remote device such as a computer, cell phone, tablet, watch, and the like. In this embodiment, the communications interface selected may be any suitable interface, including, but not limited to, a serial, parallel, universal serial bus (USB), FireWire, Ethernet, fiber optic, co-axial, and twisted pair cables. The data received by the computer processor from detachable module 500 may be stored in non-transitory memory as a database, and sorted into predetermined fields, and the database may be capable of graphical representations of the downloaded data.

Figure 104:
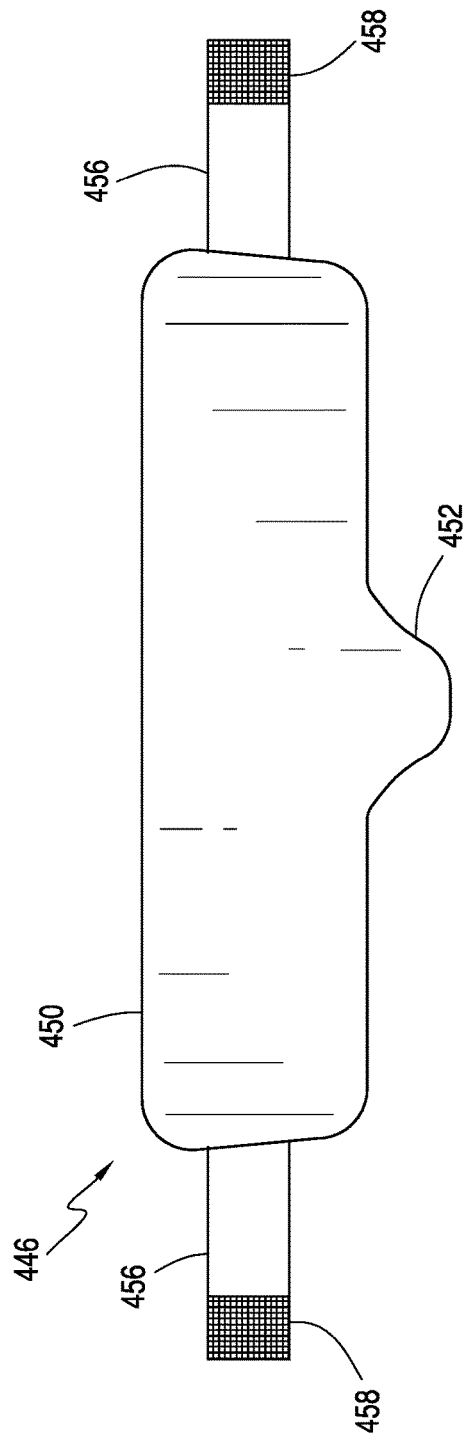
Figure 109:
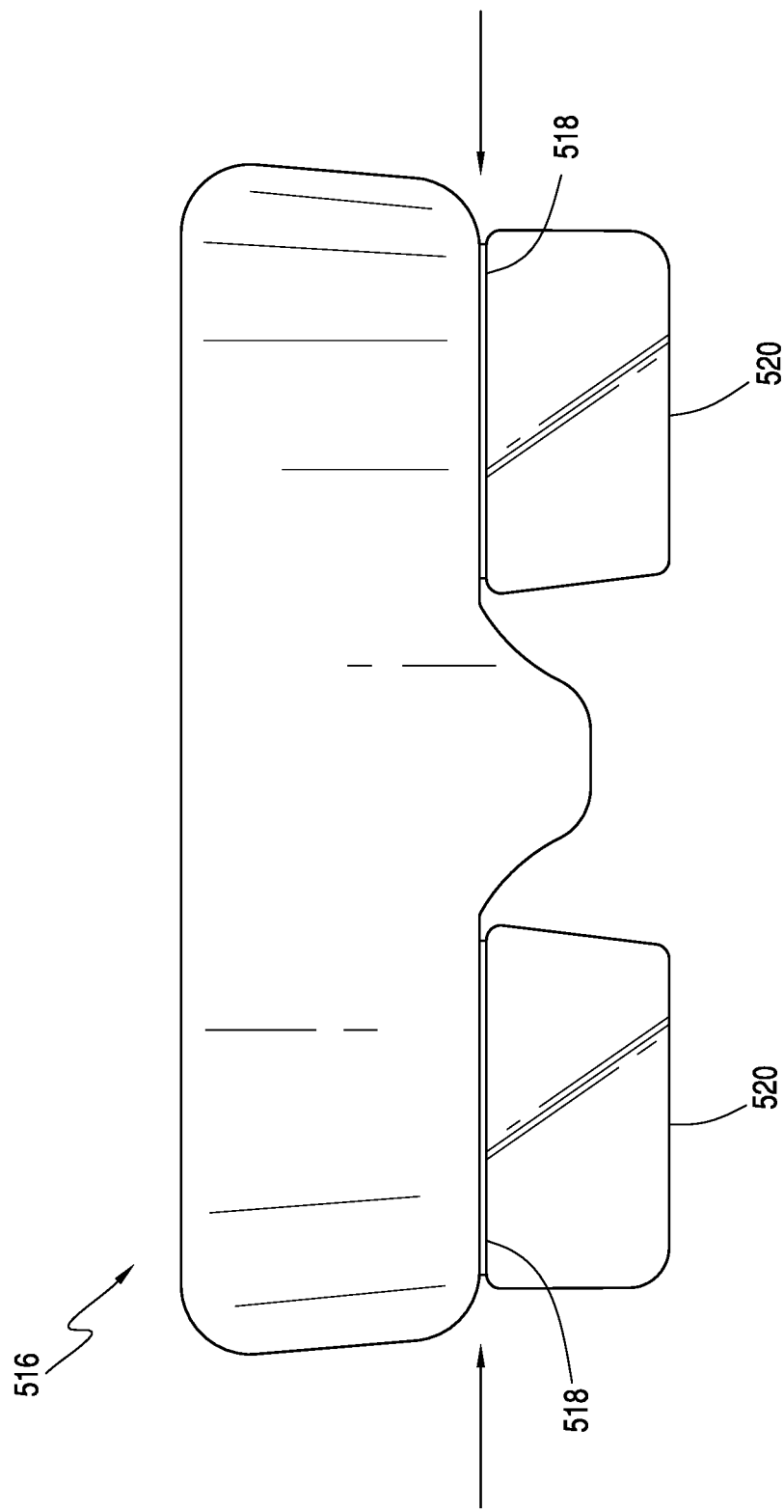

In another exemplary embodiment shown in FIG. 109, a headband, shown generally at 516, and which may be similar to headband 446 shown in FIG. 104, includes slots or grooves 518, or other supporting mechanisms, which allow a user to easily slide or attach sunglass or eyeglass lenses 520 to headband 516.

Figure 110:
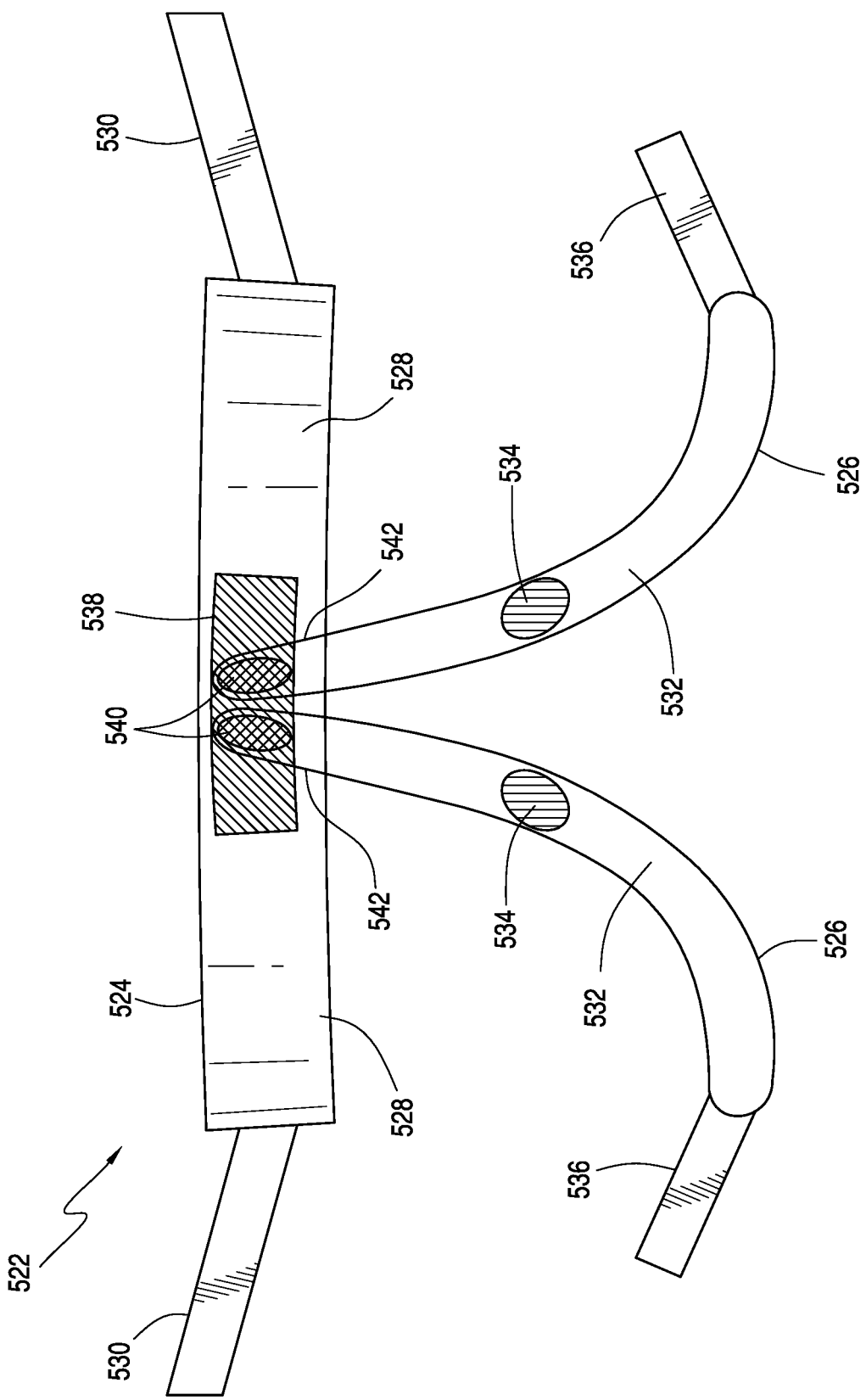
Figure 111:
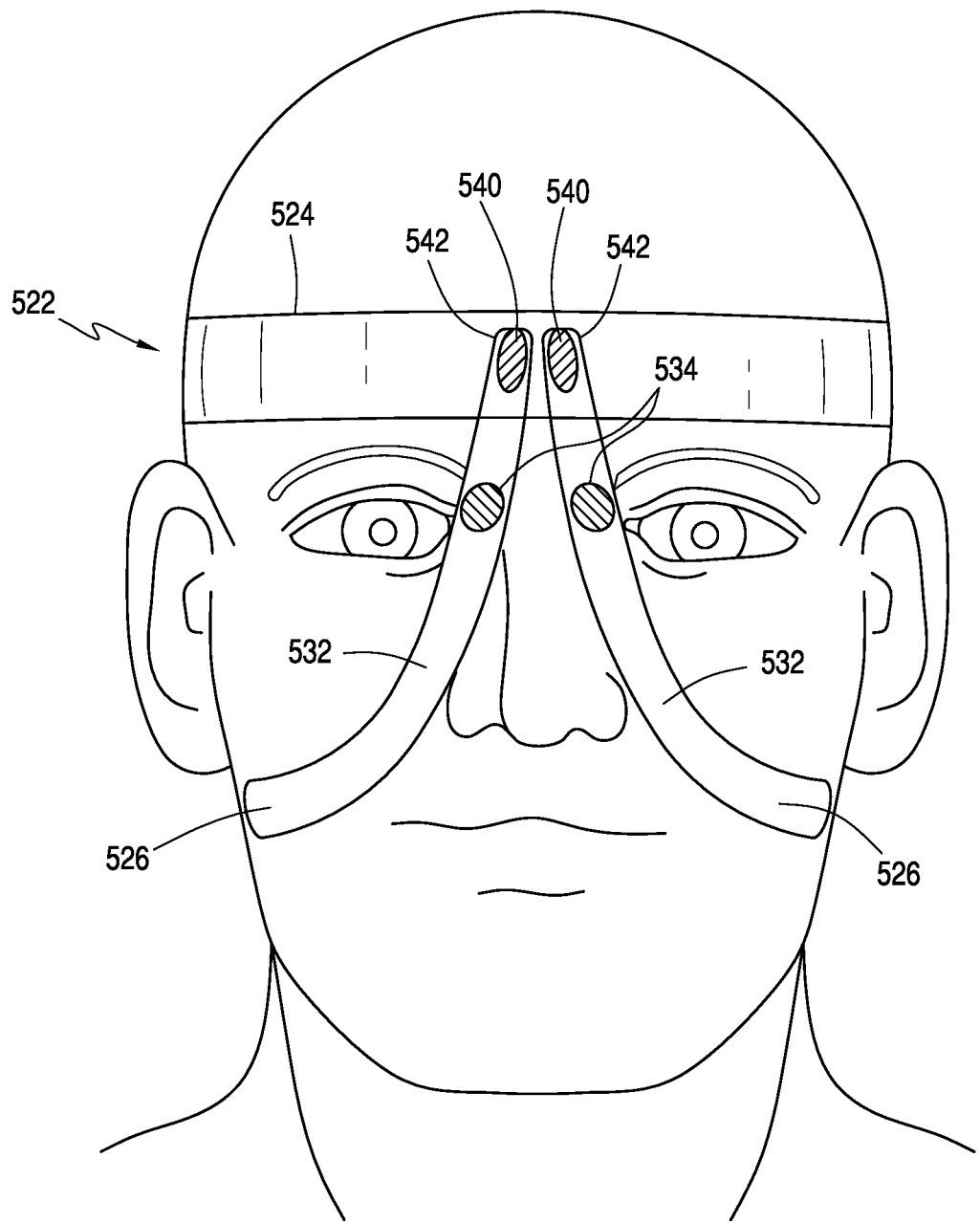

FIG. 110 shows another headband and thermal pack device in accordance with an exemplary embodiment of the present disclosure and indicated generally at 522. Device 522 includes a headband support 524, and one or more face extensions 526. Headband support 524 is configured to contain a thermally retentive substance along a forehead area 528 that, when headband support 524 is attached to a forehead, is in contact with portions of frontal vein 12 and supraorbital vein 16, and, depending on the size and configuration of headband support 524, possibly the superior palpebral vein 14. Headband support 524 includes a strap 530 configured to encircle a head, thus securing headband support 524 to a head. Face extensions 526 are configured to contain a thermally retentive substance or element in zones, regions, or portions 532 that extend down the sides of the nose and onto the cheek area, thus covering a portion of angular vein 18 and extending into the region of facial vein 19, as shown in FIG. 111. Face extensions 526 comprise preferably convex or comma, boomerang or banana shape configuration with nodes 534 that will allow the nodes 534 to conform closely to the special topography of ABTT target area and associated veins. Face extensions 526 contain thermally retentive materials and is configured to fit precisely in the medial canthal area adjacent to the medial corner of the eye in the superomedial orbit, where ABTT target area and the convergence of four veins 12, 14, 16, and 18 is located. In an exemplary embodiment, each face extension 526 can include a strap 536 that extends beyond the facial/angular vein thermal transfer portions to wrap around the head below the ears to fit each facial extension 526 securely to the face. For both headband support 524 and face extensions 526 of device 522, the opposite ends of respective straps 530 and 536 are configured to be fastened to one another to form a secure fit. In an exemplary embodiment, straps 530 and 536 may be fastened using a hook and loop arrangement, but may also use snaps, buttons, ties, hooks, adhesive, or other fastening mechanism, device, or apparatus. Headband support 524 includes a strip of a fastening arrangement 538, which in an exemplary embodiment is a hook and loop arrangement, located in a region at the center of the headband support 524. When worn by a user, fastening arrangement 538 will be located on the forehead directly between the eyebrows. Face extensions 526 include a mating fastening arrangement 540 located on an upper end 542 that, when positioned on the face of a user, is located above the bridge of the nose. Fastening arrangement 540 of face extension 526 is configured to mate and attach to fastening arrangement 538 of headband support 524. Once face extensions 526 are attached to headband support 524, the assembly forms headband and thermal pack device 522, which is one mask-like structure to cover vital areas related to ABTT 22. Fastening arrangement 540 of face extension 526 is smaller than fastening arrangement 538 of headband support 524. This size differential allows each face extension 526 to be adjusted by moving face extensions 526 left or right, or up and down the face. This adjustable configuration allows device or mask 522 to adapt to fit many different face types and shapes. For example, some people have longer faces or broader noses. With an adjustable fastening arrangement such as hook and loop, and two separate portions, i.e., headband support 524 and face extensions 526, mask or device 522 may be suitable for any number of wearers that have innumerable anatomical differences. It should be understood that device 522 may include thermoelectric devices instead of or in addition to thermally retentive material.

FIG. 114 shows yet another support device in accordance with an exemplary embodiment of the present disclosure and generally indicated at 544. Support device 544 includes a cooling visor cap top, hat, or baseball cap 546 that is configured to support a set of detachable nodes 548, shown in more detail in FIG. 115. In an exemplary embodiment, nodes 548 are attached to cap 546 by way of a fastening arrangement 550 included as a part of nodes 548. Cap 546 includes a mating fastening arrangement 552 positioned on a front inner lining 554 of cap 546 configured to mate and secure node fastening arrangement 550 located on the back of detachable nodes 548. Detachable nodes 548 further include a flexible metal piece 556 with position memory to change the position of detachable nodes 548 for better contact with ABTT target area 20. Nodes 548 are filled with thermally retentive gels or other thermally retentive materials that are manually heated or cooled prior to use. It should be understood that nodes 548 may comprise thermoelectric devices, as disclosed herein in other embodiments.

FIG. 116 shows yet another support device in accordance with an exemplary embodiment of the present disclosure and indicated generally at 558. Support device 558 is configured as a cooling or heating cap designed to fit over a user's scalp 560, like a swimmer's cap. In this embodiment, support device 558 includes two nodes 562 configured to have constant contact with ABTT target area 20. Set of nodes 562 is detachable through the use of node fastening arrangement 550 and cap fastening arrangement 552 located in a front inner lining 564 of support device 558. Nodes 562 cover the bridge of the nose and include an adjustable plate 566 with position memory to change the position of nodes 562 and for better contact with ABTT target area 20. Nodes 562 include a thermally retentive gel or other thermally retentive materials that are manually heated or cooled prior to use. It should be understood that nodes 548 may comprise thermoelectric devices.

FIGS. 125-127 show details of an adjustable plate and associated nodes used in various embodiments disclosed herein, with the adjustable plate indicated generally at 940 and the nodes indicated at 942. One or more flexible metal strips, plates, or springs 944 are positioned on adjustable plate 940, and are configured to form or shape adjustable plate 940 to interface with at least one ABTT terminus 20 and a user's nose. Adjustable plate 940 may include an a spring-like mechanism for anchoring to a user's nose, or an adhesive for retention on a user's nose, or may be attached along an edge 946 to a support structure, such as a hat, headband, etc. Flexible plate 944 may be formed of a material with sufficient grip that adjustable plate 940 is secured to a user's nose by frictional force or the grip of adjustable plate 940, in the manner of a nose clip, as shown in FIG. 127. In an exemplary embodiment, as shown in FIG. 125A, each node 538 (or any node of any embodiment disclosed herein for human use) is configured to be in a region of the face that extends in a range of 1 mm to 36 mm vertically from the medial corner of the eye 943 toward the eyebrow 945, represented herein as dashed line 947, and in a range of 1 mm to 31 mm transversely away from the medial corner of the eye 943 toward the nose, represented herein by dashed line 955. The node region may de defined by eyebrow 945 as the upper limit (considering a human standing), the medial limit by the nose 953, the lateral limit 947, and lower limit 955. The range disclosed herein encompasses the dimensions for different sizes of noses, heads, eyes and height of a subject.

Adjustable plate 940 of FIGS. 125-127 may be configured with a handle 948, as shown in FIGS. 128-130. Handle 948 is configured to be held by a subject or patient, or may be held by another person. In an exemplary embodiment, handle 948 is of a material sufficient rigid to secure adjustable plate 940 against at least one ABTT terminus 20.

FIG. 119 shows yet another exemplary headband support in accordance with an exemplary embodiment of the present disclosure and indicated generally at 568. Headband support includes a headband 570 configured with an inner lining mesh 572 on a back 580 of headband 570, which reduces the rate of heat transfer from a thermal pack body 574 to skin of the forehead. Thermal pack body 574 in this embodiment does not contain any gel-disks or water-disks, such as those disclosed elsewhere herein. Such disks increase or decrease the temperature of thermal pack body 574. Without the gel-disks or water-disks, this embodiment can regulate the temperature of thermal pack body 574 without thermal pack body 574 getting too cold or too warm. Inner lining mesh 572 acts as a pouch for thermal pack body 574 and a barrier to direct contact with skin, as shown in FIGS. 119-121. Headband 570 includes insulation and serves as an outer lining that faces the environment. In an exemplary embodiment, a plurality of fastening arrangements 576 configured as a hook and loop are placed on a top opening 578 of inner lining mesh 572. Fastening arrangements 576 are used to secure thermal pack body 574 once it is placed in the pouch formed by inner lining mesh 572. A thermally retentive soft cloth 582 covers headband 570 on a front 584 of headband 570, shown in FIG. 121, while inner lining mesh 572 covers at least a portion of back 580. In an exemplary embodiment, opposite ends 586 of soft cloth 582 are configured to be fastened to each other with a fastening arrangement 588, which may be a hook and loop configuration, to form a secure fit when worn around the head.

A user's eyes may also be covered by thermally retentive soft cloth 582 because this embodiment is useful for persons who suffer sleep disorders. As described herein, sleeping requires the release of melatonin. The cause of sleep disorders for many people is the deficiency of melatonin. Applying cold to ABTT terminus 20 may aid in the increase of melatonin production in the pineal gland. However, a pineal gland that is overstimulated by cold temperature does not release melatonin. Therefore, the rate of cold applied to ABTT terminus 20 must be regulated. Inner lining mesh 572 in this embodiment slows down the rate of thermal energy transfer. Regulating the transfer of cold temperature to ABTT terminus 20 will increase the production of melatonin that could result in improved sleep.

FIGS. 117 and 118 shown a thermal transfer device in accordance with an exemplary embodiment of the present disclosure and indicated generally at 590. Active transfer device 590 may include, but is not limited to, a plurality of serpentine tubes 592 that carry heated or cooled fluid to apply or remove thermal energy to or from ABTT terminus 20. Active thermal transfer device 590 further includes a power source, pumping mechanism, and reservoir for storing the heated or cooled liquid, which may be combined in a single device base unit 594. In the exemplary embodiment of FIGS. 117 and 118, serpentine tubes 592 are worn across the forehead and down to ABTT target area 20, and then crosses below the cheekbones towards the neck. Serpentine tubes 592 then continue to run down and along the neck down and down to an inlet 596 of device base unit 594. It should be understood that tubes 592 are preferably covered with an insulating material to preserve the thermal energy within said tubes.

As described herein, device base unit 594 includes a pump to force fluid through serpentine tubes 592 to ABTT terminus 20, and may be routed along one or more veins 12, 14, 16, and 18 as well. Device base unit 594 also includes a heating and cooling unit to modify the temperature of the fluid flowing through serpentine tubes 592. Device base unit 594 also includes a reservoir to hold or store a quantity of fluid to assure proper prime of the pump integral to device base unit 594. The fluid may be in various forms, including water-based fluids, gels, and the like suitable for conducting heat and suitable for pumping through serpentine tubes 592. Although one serpentine tube can be used, with fluid moving from the right to the left and back to device 594, preferably two serpentine tubes 591 and 593 are used for independent right and left flow. Heat exchange node 600 in one side may be replaced by a thermal sensor. In this alternative embodiment, as shown in FIG. 118A, tube 611 has a thermal exchange node 609 and the opposite tube 603 has a sensor 605 covered by insulating surface 607, which insulates sensor 605 against the fluid present in tube 603. This embodiment allows monitoring temperature at the ABTT terminus 20 while at the same adding or removing heat via serpentine tubes 611 and 603.

Once the fluid is heated or cooled, the pump in device base unit 594 pumps the fluid or gel from an outlet 598 into serpentine tubes 592. Serpentine tubes 592 are routed up along the neck towards and around the ears, then running across the forehead. Active thermal transfer device 590 includes one or more thermal transfer nodes 600 that are attached to serpentine tubes 592 in an area where serpentine tubes 592 cross ABTT target area 20. In an exemplary embodiment, thermal transfer nodes 600 are connected to an adjustable plate or spring 602 with position memory to change the position of thermal transfer nodes 600 for better contact with ABTT target area 20. This adjustable spring or plate 602 also maintains the positions of serpentine tubes 592 as they pass by ABTT target area 20. The configuration of this embodiment may be optimally used when a patient or subject is lying down, but may be used when the patient is upright. In some situations, serpentine tubes 592 may need to be secured by adhesive, a mask, or other devices, apparatus, or mechanism. It should be understood that direction of flow can go from device 594 towards the tubes 592 on the face along the nose, then reaching nodes 600, and moving toward the forehead and then behind the ears and down the neck towards device 594. Tube 592 preferably includes a retroauricular node 599 for thermal exchange behind the ear.

Device base unit 594 may include one or more controls. For example, device base unit 594 may include a temperature control 604. Device base unit 594 may also include other features, such as a wireless transmitter and a display to show the temperature at ABTT terminus 20, the temperature of fluid or gel flowing in or out from device base unit 594, a speaker or other display to alert to various conditions, such as suitability for operation and error conditions, etc.

FIG. 112 shows an active thermal transfer device in accordance with an exemplary embodiment of the present disclosure and shown generally at 606. Active thermal transfer device 606 includes a headband 608 that incorporates an integral thermoelectric cooling and heating apparatus. Active thermal transfer device 606 further includes one or more thermal exchange nodes 610 that are attached to headband 608. Thermal exchange nodes 610 are configured to have constant contact with ABTT target area 20. Active thermal transfer device 606 further includes an adjustable spring or plate 612 with position memory to change the position of thermal exchange nodes 610 and to aid in keeping thermally retentive nodes 610 in contact with ABTT target area 20. Thermal exchange nodes 610 are cooled or heated by the thermoelectric features of headband 608.

FIG. 113 shows yet active thermal device in accordance with an exemplary embodiment of the present disclosure and indicated generally at 614. Active thermal device 614 includes a thermoelectric cool/heating headband 616, face extensions 618, and thermal transfer nodes 620. Face extensions 618 may be attached using a fastening arrangement, as described in other exemplary embodiments, or may be integral with headband 616. Thermal transfer nodes 620 are positioned on face extensions 618 and located to be in contact with ABTT terminus 20, and receive thermal energy from or transfer thermal energy to headband 616.

FIGS. 92 and 93 show a two-piece support structure in accordance with an exemplary embodiment of the present disclosure and indicated generally at 44. Support structure 44 includes a first, headband structure 46, and a second face structure 48. Support structure 44 is designed to lie directly over the skin in contact with at least one of frontal vein 12, superior palpebral vein 14, supraorbital vein 16, and angular vein 18, as well as ABTT terminus 20 where all veins 12, 14, 16, and 18 converge. Thus, support structure 44 covers portions of the eyebrow, eyelid, and forehead regions, and along the sides of the nose, the regions where veins 12, 14, 16, and 18 are located. Thermal contact with as many of veins 12, 14, 16, and 18 as possible allows for the most effective thermal treatment of the brain through ABTT 22. However, it should be understood that embodiments of the present disclosure may be employed in contact with only one or any combination of veins 12, 14, 16, and 18, and ABTT terminus 20. For example, the apparatus of FIGS. 58 and 59, discussed in more detail herein, are designed to contact principally ABTT target area 20 and not veins 12, 14, 16, and 18. It should be apparent from FIGS. 19, 58, and 59 that apparatus configured to contact ABTT terminus 20 may also contact a small portion of one or more veins 12, 14, 16, and 18.

Headband portion 46 is configured to contain a thermally retentive substance in a pocket or pouch 50 that extends along the forehead area in contact with the portions of frontal vein 12 and supraorbital vein 16, and possibly superior palpebral vein 14. In the exemplary embodiment, headband portion 46 further includes a strap 52 configured to encircle the head. Strap 52 further includes a securing mechanism 54, which in an exemplary embodiment is a hook and loop arrangement, that permits securing each portion of strap 52 to itself, which also secures headband portion 46 to a head, and thus, the face, of a patient or subject.

Face structure 48 is configured to contain a thermally retentive substance or element in curvilinear portions 56 that extend down the sides of the nose and onto the cheek area, thus covering angular vein 18 and extending into the region of facial veins. In the exemplary embodiment, face structure 48 includes two small pouches 58 that contain a thermally retentive substance that are configured to fit precisely in the medial canthal area adjacent to the medial corner of the eye, where ABTT target area 20 and the convergence of four veins 12, 14, 16, and 18 is located. In an exemplary embodiment, small pouches 58 located on curvilinear portions 56 may be a generally convex or comma, boomerang, or banana shape associated with a convex and preferably spherical-like cross-sectional configuration, such as is shown in FIG. 55, which will allow each pouch 58 to closely conform to the topography of ABTT terminus 20.

Figure 66:
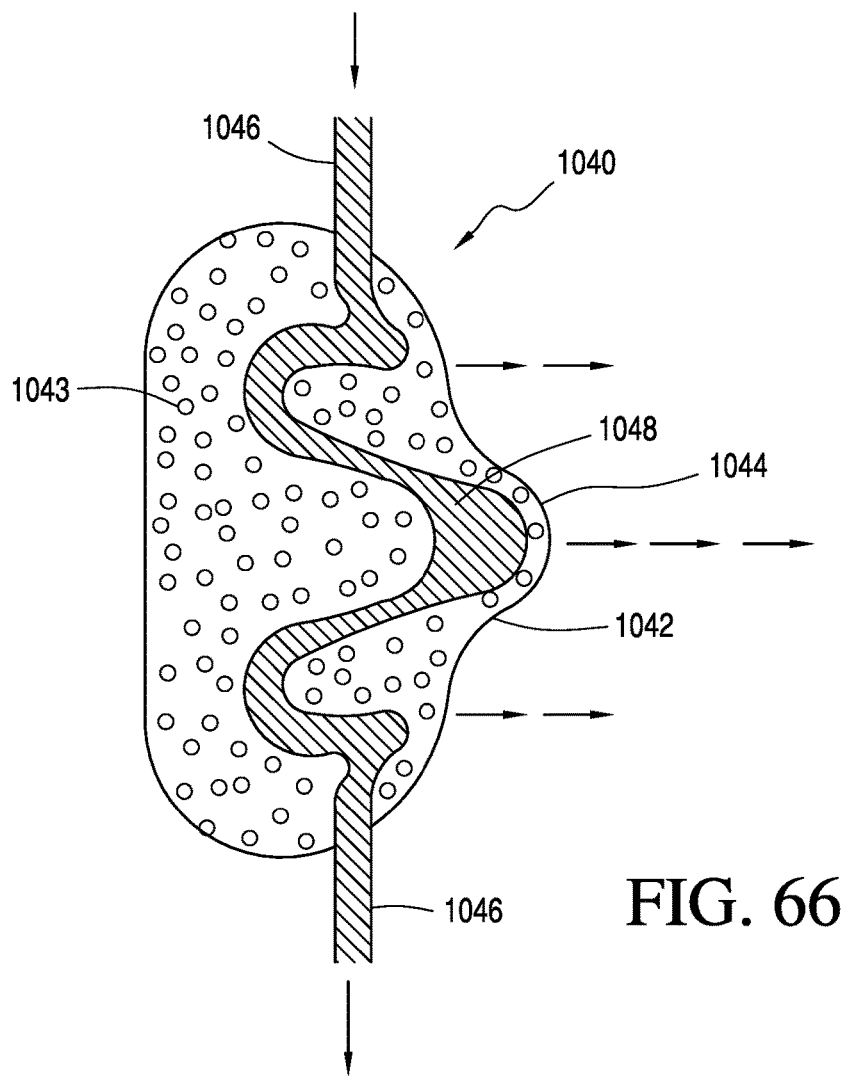
FIG. 66 is a view of an active heat exchange device, in accordance with an exemplary embodiment of the present disclosure.

FIG. 66 shows another active heat exchange device in accordance with an exemplary embodiment of the present disclosure, indicated generally at 1040. Device 1040 includes a housing 1042 having a convex surface 1044 for contact with ABTT terminus 20. Housing 1042 is configured to be connected to fluid tubes, hoses, lines, etc. 1046 to a remote heat exchanger for cooling or heating a fluid that flows through lines 1046 to housing 1042. Housing 1042 further includes one or more fluid passages 1048 internal to housing 1042 to permit heated or cooled fluid to flow through housing 1042 to heat or cool housing 1042, which consequently heats or cools ABTT terminus 20. Housing 1042 may be fabricated of a thermally conductive material to permit heat to be spread over a greater area or to permit heat from an ABTT 20 to be conducted into a greater area of housing 1042 for heating or cooling. Housing 1042 contains thermally retentive material 1043, such as a gel, to increase the heat exchange with tube 1042 further, and fluid passages 1048, besides spreading the thermal effect to a larger area. In this embodiment, thermal exchange device includes a combination of thermally retentive material 1043 and at least one tube 1042 containing fluid.

Figure 67:
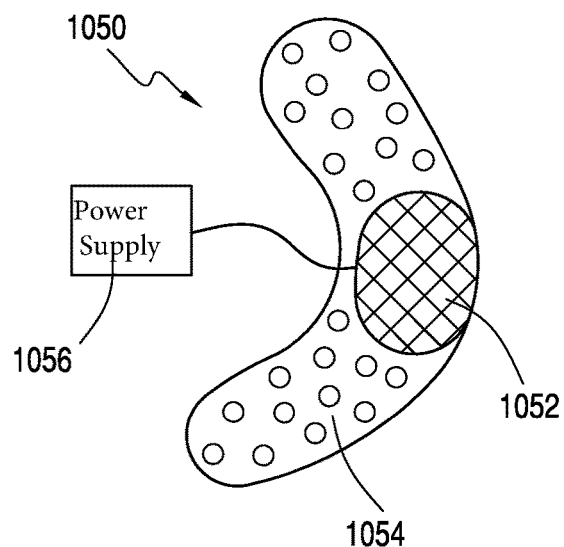
FIG. 67 is a view of an active heat exchange pad or patch in accordance with an exemplary embodiment of the present disclosure.

FIG. 67 shows yet a further active thermal exchange device in accordance with an exemplary embodiment of the present disclosure, indicated generally at 1050. Device 1050 includes an electrically operated heat exchange apparatus 1052, which has an essentially convex surface, and a thermally conductive material 1054, such as a gel, for spreading heat or cooling of ABTT terminus 20. Device 1050 is connected to a power supply 1056 that can be positioned in a plurality of locations, such as a wearable item, separately, etc.

Face structure 48 can also include a strap 66 that extends beyond curvilinear portion 56 to wrap around the head below the ears. In the exemplary embodiment of FIG. 93, face structure 48 includes a securing apparatus or arrangement 68, which may be, for example, a hook and loop configuration, to secure face structure 48 to the head of a patient or subject, which thus secures face structure 48 to the face of the patient or subject. In other embodiments, securing apparatuses or arrangements 54 and 58 may include snaps, buttons, ties, hooks, adhesive, or other fastening devices, mechanisms, configurations, apparatus, or arrangements.

In the exemplary embodiment of FIG. 92, headband structure 46 includes a securing mechanism 70 near the center of headband structure 46. When worn by a user, subject, or patient, securing mechanism 70 will be located on the forehead directly in between the eyebrows. In the exemplary embodiment of FIG. 93, face structure 48 includes a complementary securing mechanism 72 located on an upper end 74, which is configured to extend above the bridge of the nose. Securing mechanism 72 is configured to be attached, affixed, or engaged to securing mechanism 70 positioned on headband structure 46. Thus, face structure 48 is connected to headband structure 46 in a location that corresponds to the forehead between the eyebrows, thus forming a combined, mask-like structure to cover the areas related to ABTT cooling or heating. In the exemplary embodiment of FIG. 93, securing mechanism 72 is smaller than securing mechanism 70, which allows face structure 48 to be adjusted by moving upper end 74 of face structure 48 to the left or right, or up and down with respect to headband structure 46 as well as with respect to ABTT terminus 20. The adjustable configuration allows support structure 44 to adapt to fit many different face types as and shapes. For example, some people have longer faces or broader noses. With an adjustable fastener such as a hook and loop, and configuring support structure 44 as a headband structure 46 and a face structure 48, support structure 44, which may also be described as mask 44, may be suitable for any number of wearers having innumerable anatomical differences.

Figure 97:
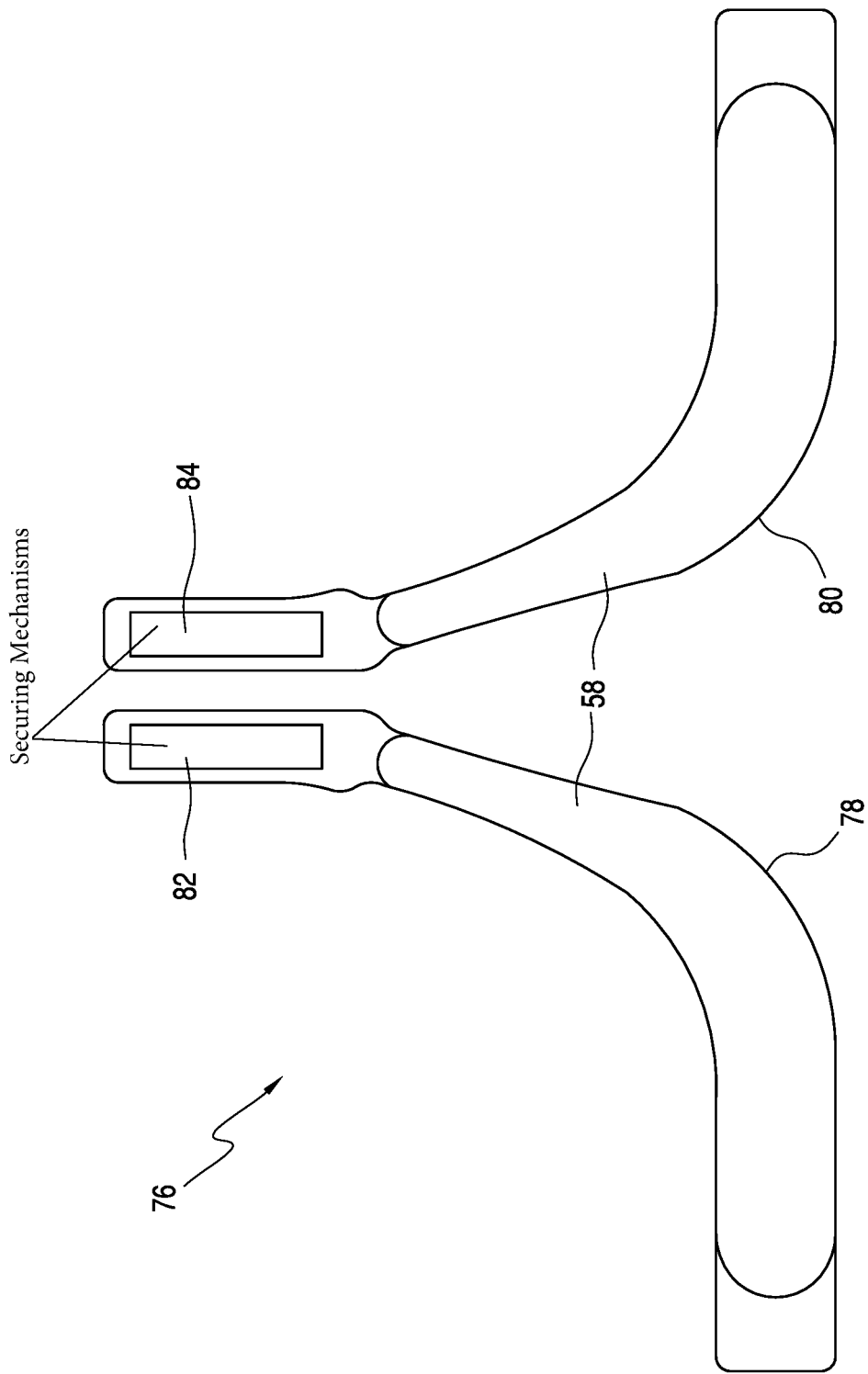
FIG. 97 is a passive thermal transfer system configured to be positioned on the support structure of FIG. 93, in accordance with an exemplary embodiment of the present disclosure.

In another exemplary embodiment, shown in FIG. 97, a face structure 76 may be split into two separate pieces 78 and 80, each of which preferably has its securing mechanism 82 and 84, respectively. The configuration of face structure 76 allows for further adjustability, as face structure 76 may be moved to a narrower or wider position to suit the anatomy of a wearer comfortably. Face structure 76 includes pouch 58 that corresponds to ABTT target area 20. As with other embodiments described herein, the shape of pouch 58 is configured in an exemplary embodiment with a convex cross-section on the side that contacts ABTT target area 20, because ABTT target area or terminus 20 is characterized by a concave surface.

Figure 98:
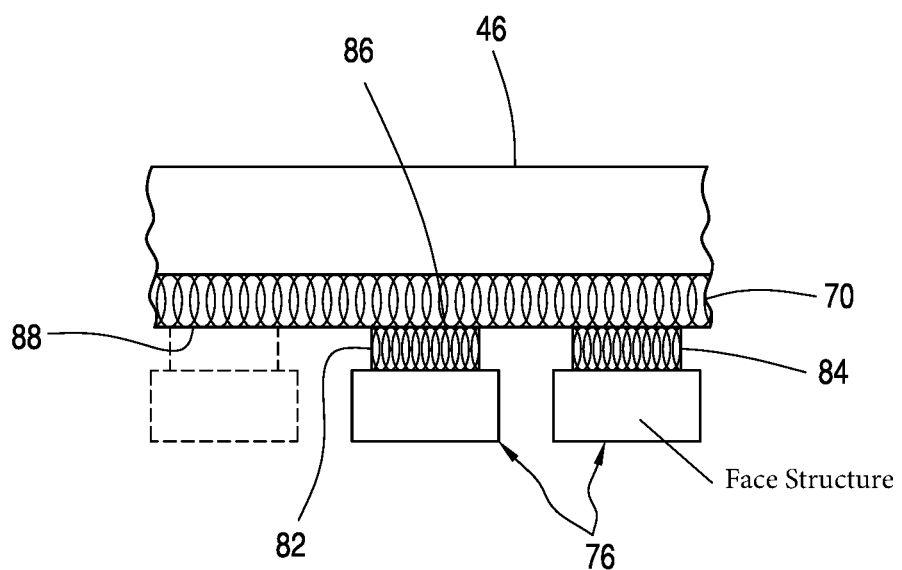
FIG. 98 is a view of a portion of the thermal transfer system of FIG. 97 connected to the support structure of FIG. 92.

FIG. 98 is an end or side view of the thermal transfer system of FIG. 97 connected to the support structure of FIG. 92. In the exemplary embodiment of FIGS. 92, 97, and 98, securing mechanism 70 on headband structure 46 is larger in cross-sectional area than the cross-sectional area of securing mechanism 82 and 84 positioned on face structure 76. This configuration permits face structure 76 to be adjustable to fit wearers with differing face shapes and sizes comfortably.

Because of the configuration of securing mechanism 70 and securing mechanisms 82 and 84, the location of attachment of face structure 76 to headband structure 46 can be adjusted. As shown in FIG. 98, the left portion of face structure 76 is in a first location 86. Each portion of face structure 76 shown in FIG. 98 may be positioned in a plurality of locations, such as second location 88 shown in FIG. 98, which helps to accommodate different sizes of noses while assuring the apposition of the thermally retentive substance in pouches 58 ABTT adjacent terminus 20 and any of veins 12, 14, 16, and 18 that pouches 58 may be adjacent.

In the exemplary embodiment of FIG. 93, securing mechanism 68 on left securing strap 66 is shorter than securing mechanism 68 on right securing strap 68. Thus, smaller securing mechanism 68 may readily be positioned in a plurality of locations on larger securing mechanism 68, allowing fastened strap 66 to have a larger or smaller diameter to meet the anatomical needs of the wearer. A securely fitting support structure 44 allows for optimum delivery of heat to or removal of heat from ABTT 20 and/or veins 12, 14, 16, and 18 that provide blood flow to or from ABTT 20, thus allowing for optimized cooling or heating of the brain's core temperature, and thus the body's core temperature. Having apparatus 44 securely fastened to the subject or patient's head will also enable the wearer to experience the cooling or heating effects of the pouches 58 during physical activity.

Figure 105:
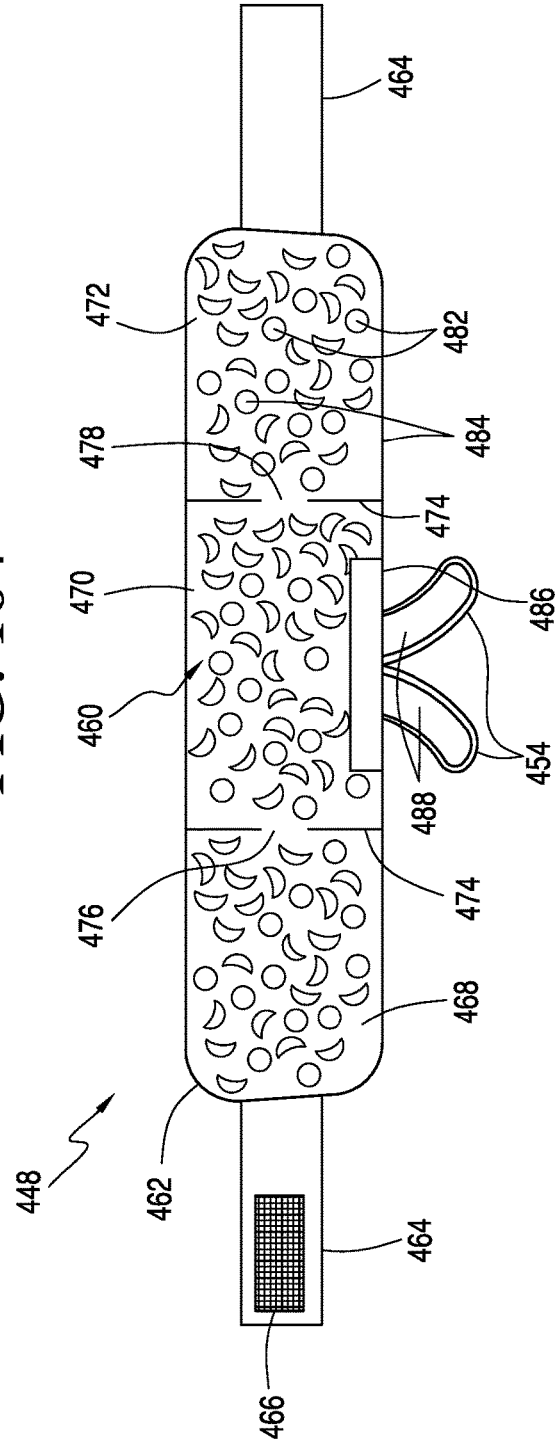

FIGS. 104 and 105 shown another support apparatus and thermal pack configured as a headband in accordance with an exemplary embodiment of the present disclosure, which includes two portions that can be detachable or permanently attached. The support apparatus of FIGS. 104 and 105 includes a headband 446 and a thermal pack device 448. Headband 446 is comprised of material that is configured to insulate thermal pack device 448 when device 448 is attached to headband 446 and positioned on the head of a patient or subject. In order to prevent excess thermal transfer with the environment, i.e. losing heat to or gaining heat from the surroundings, headband 446 includes a thermally insulating layer 450. In the exemplary embodiment of FIG. 104, insulating layer 450 is configured to cover only the portion of thermal pack device 448 that is exposed to the surroundings, thus preventing thermal loss to the environment, but allowing maximum thermal transfer, as shown in FIGS. 106, 122, and 124. Headband 446 includes a headband protrusion or extension 452 configured to cover nodes or thermal pack extensions 454 of thermal pack device 448. Headband protrusion 452 dips down in an exemplary embodiment from about 58 mm, in another exemplary embodiment to about 50 mm, and in yet another exemplary embodiment to cover the bridge of the nose. The opposite ends of headband 446 include straps 456 that are configured to be fastened to each other with a fastening apparatus, device, or mechanism 458, which in an exemplary embodiment may be a hook and loop configuration, to form a secure fit when worn around the head.

Users will wear headband 446 and thermal pack device 448, secured with fastening apparatus 458 around the forehead, with nodes 454 positioned to contact ABTT terminus 20. Thermal pack device 448 is configured to contain a thermally retentive substance or material 460. It should be understood a plurality of materials may be used to contain thermally retentive substance or material 460, including flexible plastic, cloth, leather, metalized fabric, vinyl, cotton, rayon, rubber, thermoplastic synthetic polymers, and mixtures of materials are among the many possible alternative materials. It should also be understood that another thermally retentive covering, such as a bandana 480 shown in FIGS. 123 and 124, is a possible substitute for headband 446.

In an exemplary embodiment, thermal pack device 448 is smaller than headband 446. Thermal pack device 448 includes a body 462, previously described nodes 454, and thermal pack straps 464. The length of thermal pack body 462 in an exemplary embodiment is about 56 cm, in another exemplary embodiment is about 54 cm, and in another exemplary embodiment is about 52 cm, preferably ranging from about 52 cm to about 57 cm. The width of thermal pack body 462 in exemplary embodiments is about 5.6 cm, about 5.5 cm, or about 53.8 mm, preferably ranging from 3.0 cm to 6.0 cm. In an exemplary embodiment, opposite ends of thermal pack device 448 includes straps 464 that are configured to be attached to one another with a fastening arrangement 466, which in an exemplary embodiment is a hook and loop arrangement, to form a secure fit when worn around the head. Thermal pack device 448 may have its own fastening arrangement in order to allow the user to wear thermal pack device 448 prior to covering thermal pack device 448 with insulating headband 446. The user can then adjust nodes 454 to be positioned on ABTT target area 20. After the adjustment, the user can then put on thermally retentive headband cover 446. Prior to placing thermal pack device 448 against the user's forehead, thermal pack device 448 should be cooled or warmed to a predetermined temperature.

In an exemplary embodiment, thermal pack body 462 is divided by walls 474 into three sections 468, 470, and 472 that communicate with each other through a first opening 476 positioned between first section 468 and second section 470, and a second opening 478 that is positioned between second section 470 and third section 472. Thermal pack body 462 and the exterior portions of thermal pack 448 in an exemplary embodiment are formed of a tough and flexible plastic material. Thermally retentive material or substance 460 within thermal pack device 448 is moldable, pliable, or flexible. Thermally retentive substance 460 can be manually heated or cooled to a temperature range between −10° C. to 50° C. Thermally retentive substance 460 in thermal pack body 462 may be comprised of, but not limited to, any chemical compounds or gels that add or remove thermal energy to the applied area. Gel-disks 482 and water-disks 484 may be added to thermal pack body 462. The proportion of gel-disks and water-disks may change depending on the desired effect of thermal pack 448. For colder temperatures, a higher proportion of water-disks are preferable.

Figure 107:
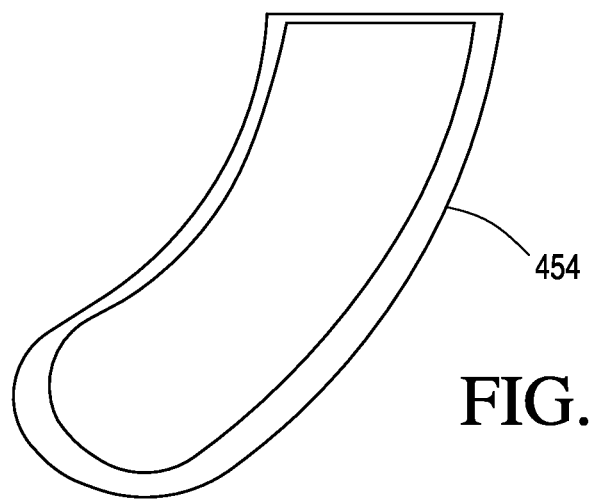
Figure 108:
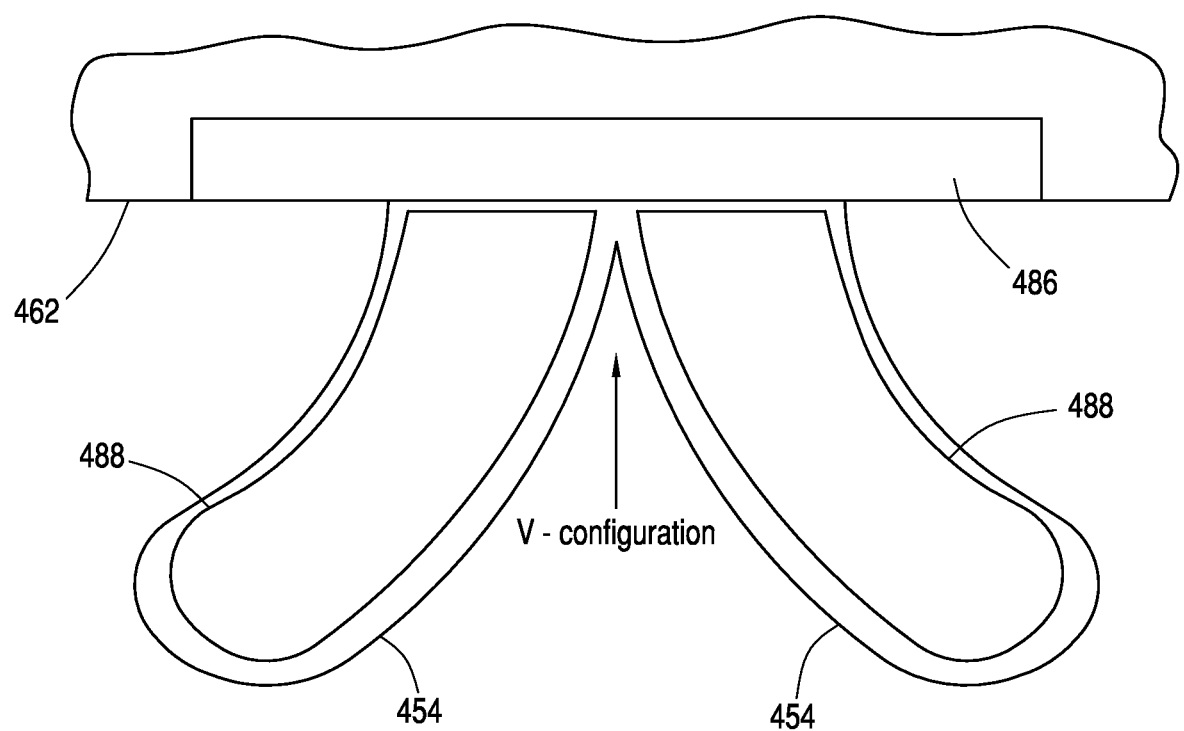

In the exemplary embodiment of FIG. 105, thermal pack device 448 includes a flexible metal strip 486 positioned along the bottom center of thermal pack body 462 that is deformable to assist with the adjustment of the nodes 454. From the bottom center of the body, at least one node 454 extends downwardly toward the bridge of the nose in V-shape formation that is approximately perpendicular to a longitudinal or long dimension of thermal pack body 462. Nodes 454 are attached to thermal pack body 462. Nodes 454 in the exemplary embodiment of FIG. 105 are kidney shaped or tear-drop shaped nodes and are configured to have constant contact with the medial canthal area of ABTT target area 20. Each node 454 may include a node flexible metal 488 that, in combination with flexible metal strip 486, configures nodes 454 to be adjustable, as shown in FIGS. 107 and 108. This adjustable configuration allows nodes 454 to adapt to fit many different face types and shapes. For example, some people have longer faces and broader noses while others have rounder faces and narrow noses. Just like thermal pack body 462, thermally retentive substance 460 in nodes 454 may be comprised of, but not limited to, any chemical compounds and gels that add or remove thermal energy to the applied area or a thermoelectric device.

It should be understood that such dimensions presented hereinabove for headband 446 and thermal pack device 448 are for human adults and that different dimensions are needed for younger children or other animals.

Figure 94:
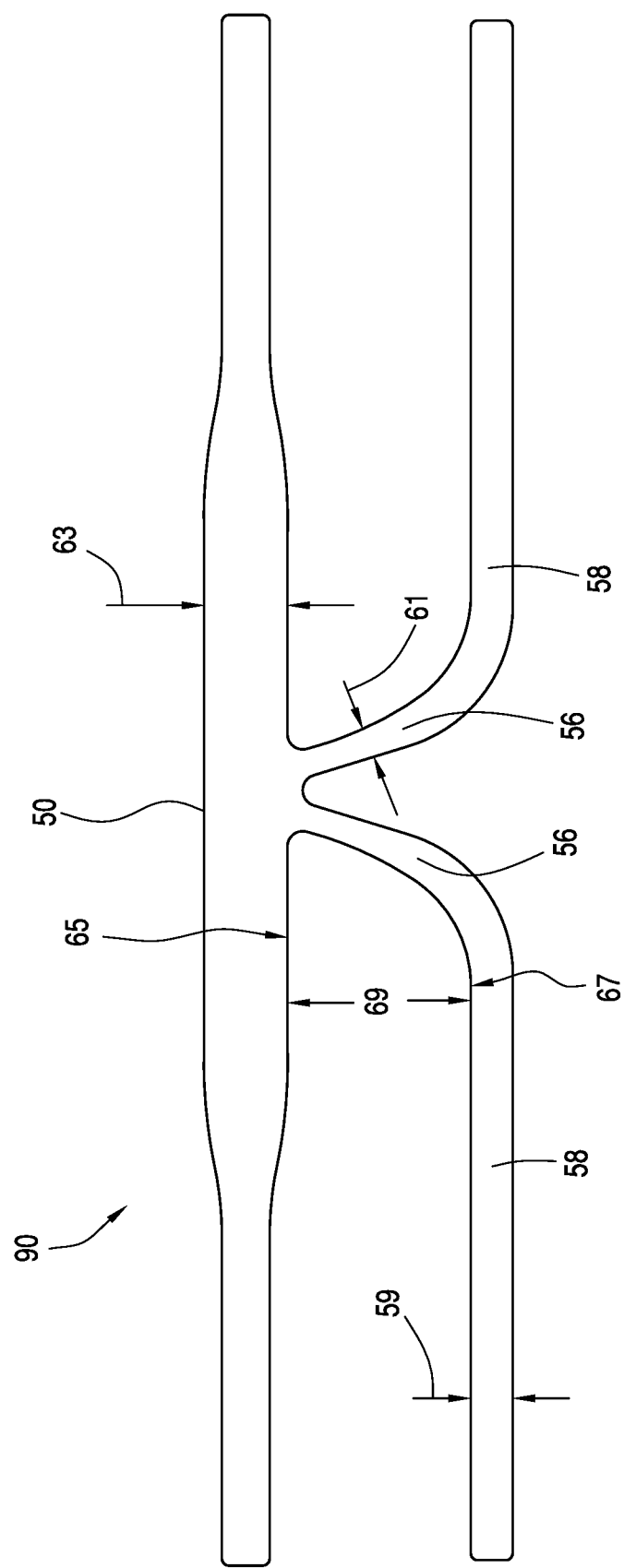
FIG. 94 is an integrated headband support structure and a thermal exchange system, in accordance with an exemplary embodiment of the present disclosure.

FIG. 94 shows another exemplary embodiment of the present disclosure. In this embodiment, an ABVTP mask 90 is made of one piece, rather than having separate headband and face portions. In this embodiment, the mask is not as easily adjustable for size, but the cooling and heating effects can be obtained by a wearer, as the mask still covers at least one of the key venous areas. In this embodiment, three to four different sizes are used to cover a whole range of different head sizes. An exemplary set of dimensions for ABVTP mask 90 is shown in the FIG. 94, and are such that ABTVP mask 90 properly positioned heat transfer apparatus to fit with ABTT terminus 20 and veins 12, 14, 16, and 18.

Dimensions, such as width of the bands covering the veins are important, otherwise peripheral thermal receptors outside the vein area can be activated that can impact the thermal effect, as explained elsewhere herein. Specialized preferred dimension of face portion 58, shown by arrows 59, is 4.5 cm or less, and preferably 3.5 cm or less, and most preferably 2.5 cm or less, and yet most preferably 1.5 cm or less, and even most preferably 1 cm or less. Specialized preferred dimension of nose portion 56, shown by arrows 61, is 3.7 cm or less, and preferably 2.7 cm or less, and most preferably 1.7 cm or less, and yet most preferably 1.2 cm or less, and even most preferably 1 cm or less. Specialized preferred dimension of forehead portion 50, shown by arrows 63, is cm or less, and preferably 4.5 cm or less, and most preferably 3.5 cm or less, and yet most preferably 2.5 cm or less, and even most preferably 2.0 cm or less. Specialized preferred distance between the lower edge 65 of forehead portion 50 and upper edge 67 of facial portion 58, shown by arrows 69, is 10.5 cm or less, and preferably 9.5 cm or less, and most preferably 8.5 cm or less, and yet most preferably 7.5 cm or less, and even most preferably 6.0 cm or less. Specialized preferred length of forehead portion 50, shown by arrows 73, is 17 cm or less, and preferably 14 cm or less, and most preferably 12 cm or less, and yet most preferably 10.5 cm or less, and even most preferably 9.5 cm or less.

FIGS. 95 and 96 show details of an ABVTP mask 96 that are similar to the mask of FIG. 94, including exemplary dimensions. FIG. 95 shows the side of ABVTP mask 96 that is in contact with the body. Pouches or blisters 92 include a thermally retentive substance that may be heated or cooled. Blisters 92 include a convex surface 94 that faces toward the skin of the subject or patient. FIG. 96 shows a side of ABVTP mask 96 that faces away from the wearer, which includes an insulated lining 96 to keep thermal energy directed to the skin or to prevent the loss of cooling capability.

Figure 99:
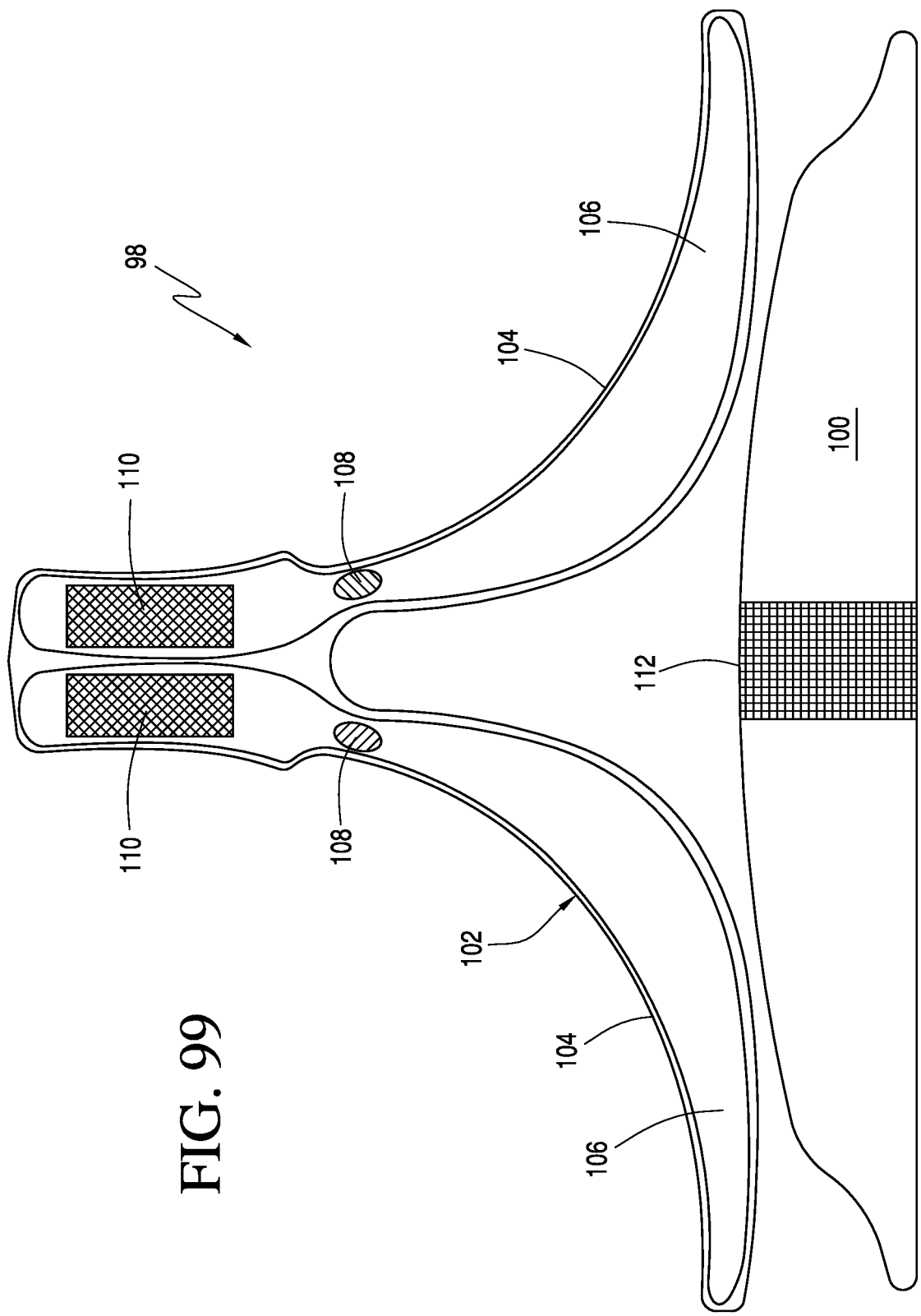
FIG. 99 is thermal transfer system, in accordance with an exemplary embodiment of the present disclosure.

FIG. 99 shows yet another exemplary embodiment ABVTP mask 98. ABVTP mask 98 includes a headband structure 100 and a face structure 102. In this embodiment, face structure 102 includes extensions or arms 104 that includes an adhesive surface 106, heating or cooling nodes or pouches 108 configured to contact ABTT terminus 20, and securing apparatus 110. Headband structure 100 includes a mating securing apparatus 112 configured to mate with and secure face structure 102 by way securing apparatus 110. Face structure 102 does not include a strap for securing face structure 102 to the head of a user, which may be preferable for a wearer who may use the apparatus while lying in a prone position. In this embodiment, adhesive surface 106 can be used for securing extensions or arms 104 to the skin of a user or wearer. In addition, optimal cooling or heating can still be obtained with ABVTP mask 98 because headband 100 is adjustable by way of securing apparatus (not shown) that may be similar to securing arrangement 54 of FIG. 92, and face structure 102 is positionable with respect to headband structure 100 by the ability to obtain a plurality of attachments locations of securing apparatus 110 on securing apparatus 112.

Figure 100:
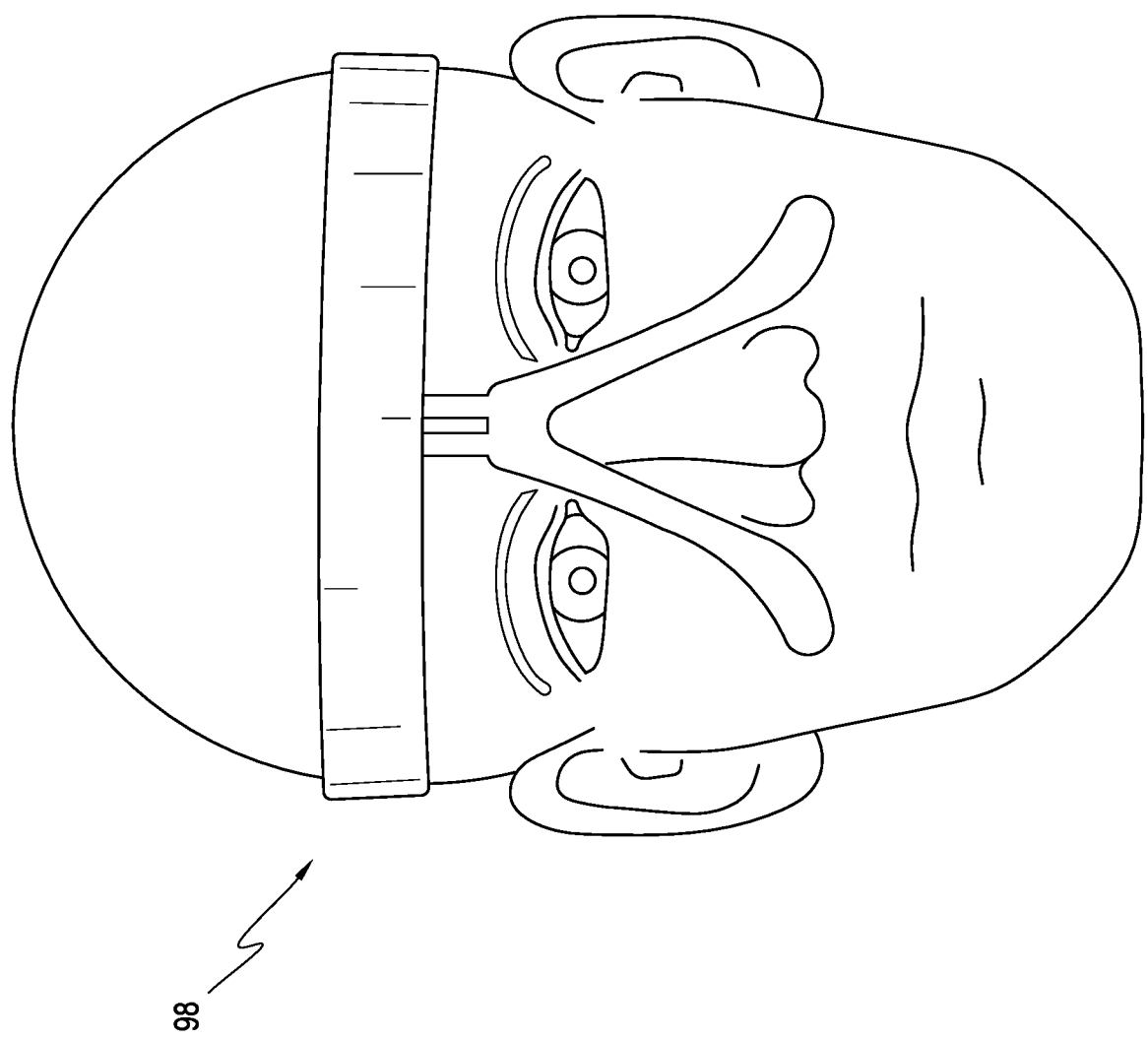

FIG. 100 shows ABVTP mask 98 being worn by a user.

Figure 101:
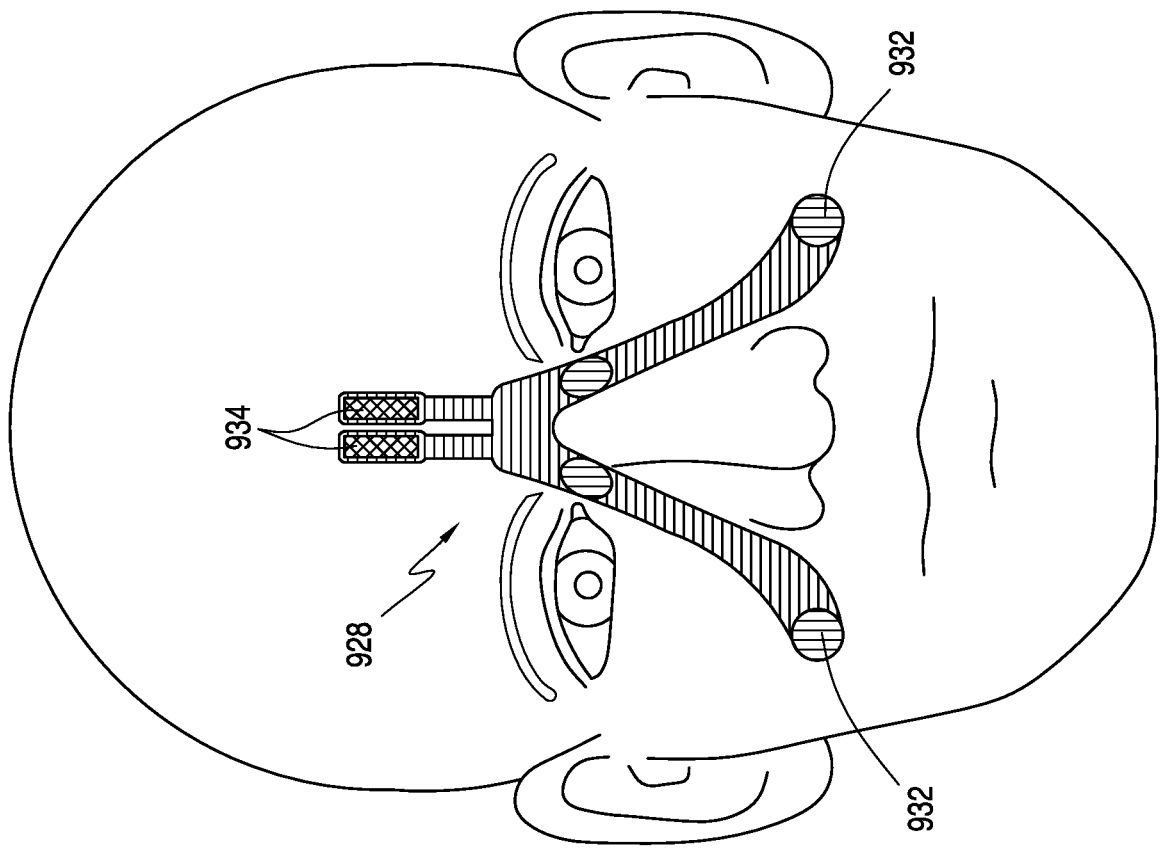
Figure 102:
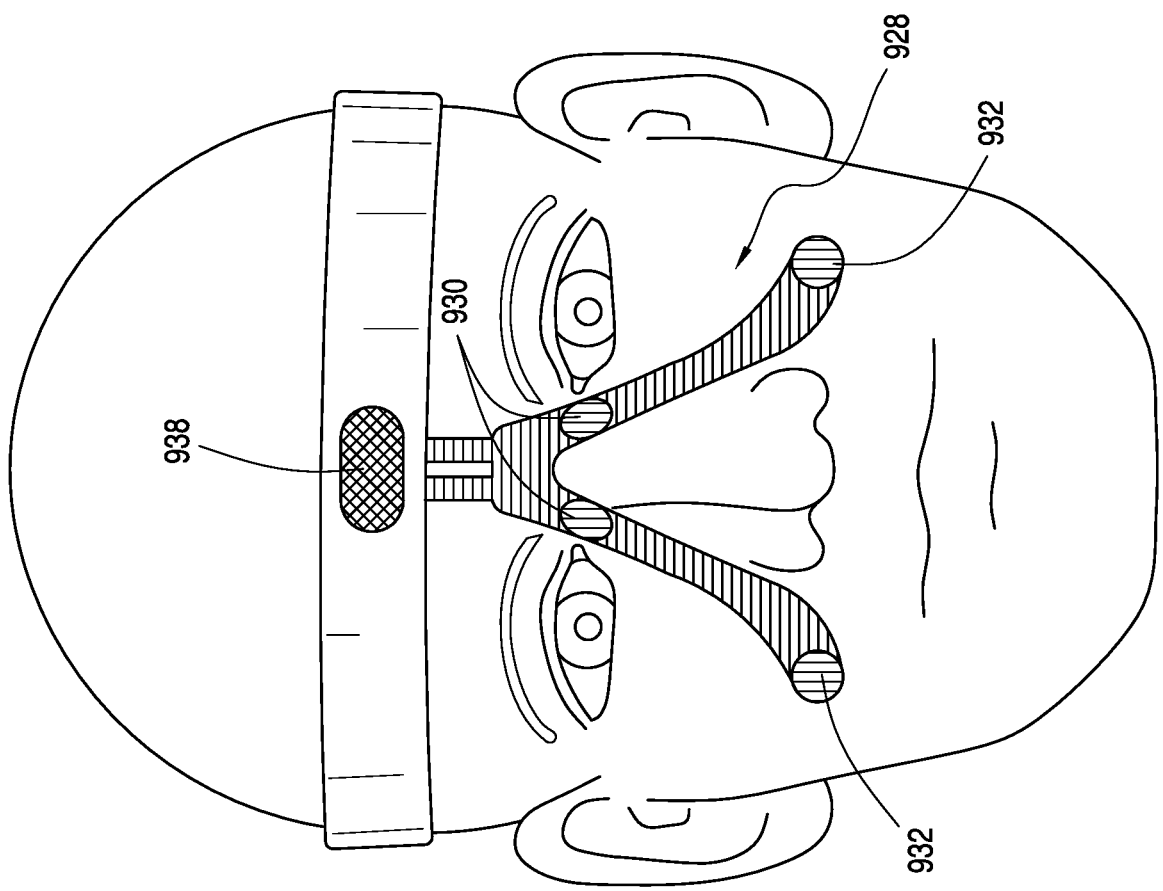
Figure 103:
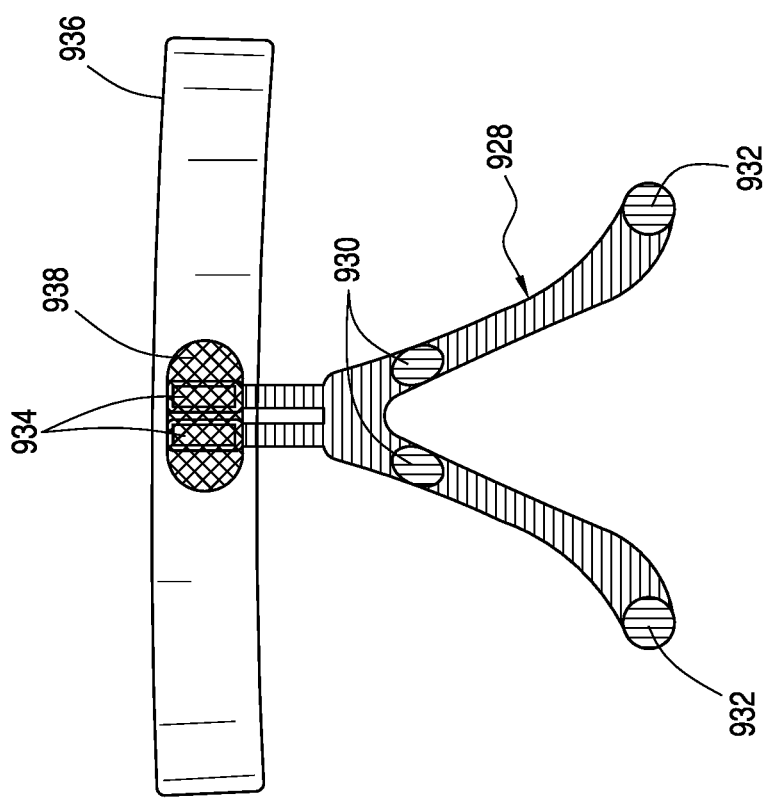

FIGS. 101-103 show another ABVTP mask in accordance with an exemplary embodiment of the present disclosure and indicated generally at 928. ABVTP mask 928 includes thermal pouches 930 to interact with ABTT terminus adhesive patches 932 to secure ABVTP mask 928 to a subject or patient's face, and hook and loop fasteners 934 to attach ABVTP mask to a support apparatus, such as a headband 936 shown in FIGS. 102 and 103, or a hat, cap, etc. Headband 936 includes a mating hook and loop fastener 938 for connection or attachment to hook and loop fasteners 934.

Figure 1:
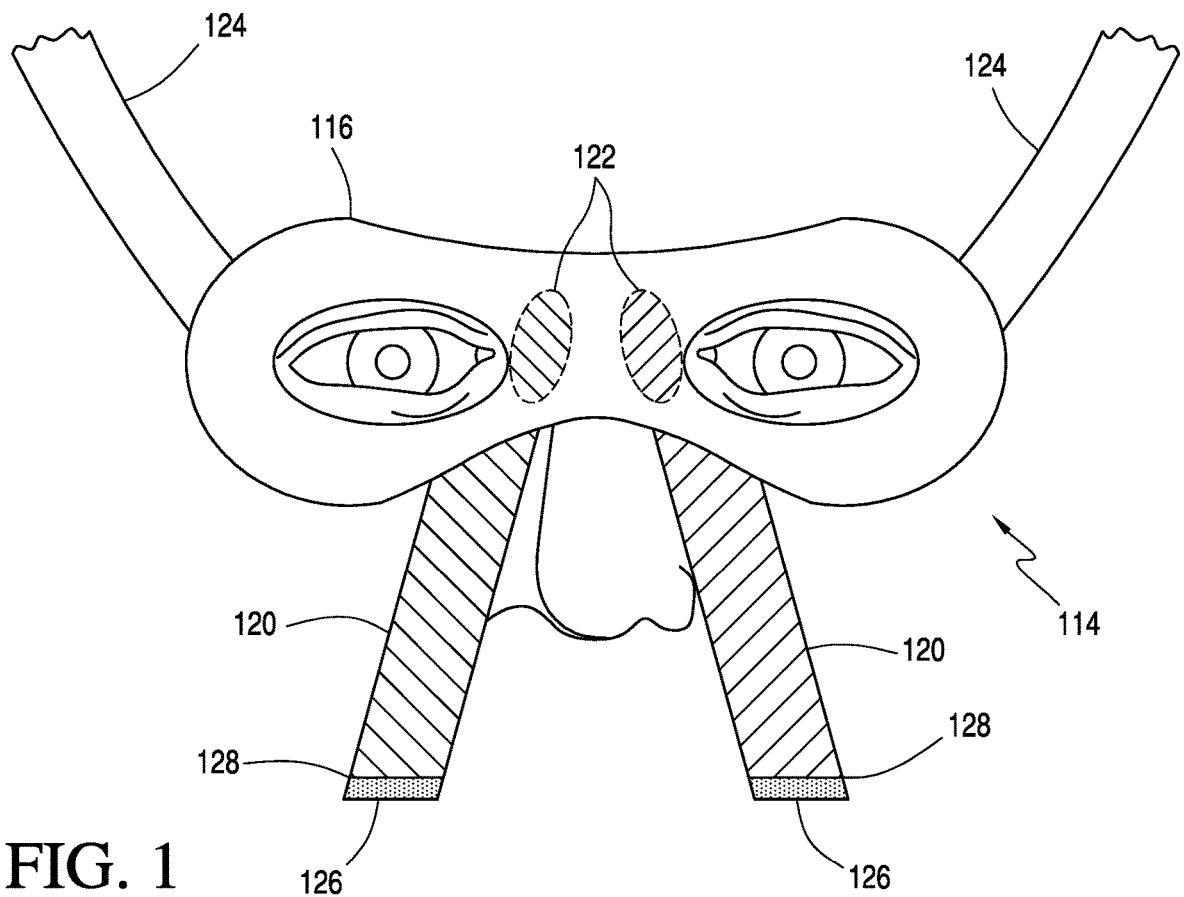
FIG. 1 is a view of a mask in accordance with an exemplary embodiment of the present disclosure.

Another exemplary ABVTP mask is shown in FIG. 1 and indicated generally at 114. In this embodiment, the thermally retentive substance is located throughout ABVTP mask 114. The thermally retentive substance may be any one of the materials or components described herein for transferring thermal energy between the skin of ABTT terminus 20 or over veins 12, 14, 16, 18, and 20 and the thermally retentive substance, either for cooling or for heating of the brain core. ABVTP mask 114 of FIG. 1 includes an ocular structure 116 with openings 118 encircling the eyes. Thus, ocular structure 116 covers superior palpebral vein 14 on the brow line and small portions of the supraorbital vein 16 and frontal vein 12. ABVTP mask 114 also includes extensions 120 for placement along both sides of the nose, in order to cover facial vein 18 and at least a portion of angular vein 19. The apparatus also includes one or more pouches 122, shown in hidden lines in FIG. 1, configured to cover the portion of the eye socket between the eyebrow and the bridge of the nose, thus effectively covering ABTT target area 20 and the convergence of veins 12, 14, 16, and 18 carrying blood into the brain near ABTT 22.

The apparatus as shown in FIG. 1 is designed to be fastened to the head using a strap 124 that is fastened on both sides to ocular structure 116 at a location that is near the outer corner of each eye, thus allowing a user to securely fasten ABVTP mask 114 to his or her head. In an exemplary embodiment, strap 124 may be made of an elastic material in a closed configuration without free ends. Strap 124 may also be of a non-elastic material having open ends that employ a fastener such as a hook and loop configuration, snaps, buttons, ties, adhesive, or the like for securing the mask to the head. In an alternate embodiment, strap 124 may be omitted when the mask is configured for use when a person is lying in a prone position, or the mask could be fastened to the face using an adhesive. In a further embodiment, the apparatus may be configured to be supported by any number of head-worn structures including, but not limited to, goggles, masks, helmets, hard-hats, headbands, for use in many different applications such as sports, firefighting, military, or hospital settings. Extensions 120 and pouches 122 may constitute a thermal pack that may be secured using adhesive, by hand, or used without any type of structure anchored to the head or face.

One aspect of the disclosed embodiment of FIG. 1 provides for ends 128 of each extension 120 running along the sides of the nose to include a weight 126. Including weight 126 or other, heavier material near the end of each extension 120 provides for firmer, more constant contact between the apparatus and the skin, thus providing for more effective cooling or heating of blood vessels 12, 14, 16, and 18, and ABTT terminus 20. In an alternate embodiment, the ends of each facial/angular extension 120 may include an adhesive substance to allow a wearer to adhere each end 128 of each extension 120 to his or her skin, thus also providing for better contact with the skin. In an exemplary embodiment, extension 120 may extend down the face to the jawbone and loop around the head just underneath the ears. In an exemplary embodiment, the thermally retentive substance, e.g., a cooling gel, continuously wraps around the face and back of the neck, thus providing full thermal benefits to facial vein 19 and angular vein 18, as well as some additional thermal contact with the area underneath the ears and the back of the neck, described elsewhere herein. In this example, the ear could also serve as a support for the ABVTP structure including a retroauricular node. This embodiment, and any other exemplary embodiment, is configured to avoid stimulation of peripheral thermal receptors, and the structure is configured for apposition to blood vessels 12, 14, 16, and 18, as well as ABTT terminus 20, thereby avoiding brain stimulation.

In yet another alternate exemplary embodiment, the apparatus of FIG. 1 may be designed to include only the eyebrow/forehead portion of ocular structure 116, with facial extensions 120 and ABTT terminus pouches 122, while omitting the under-eye portion of ocular structure 116, thus resulting in a more headband-like structure instead of an eye mask. Removing the under-eye portion of ocular structure 116 does not decrease the effectiveness of thermal transfer to the brain.

Figure 7:
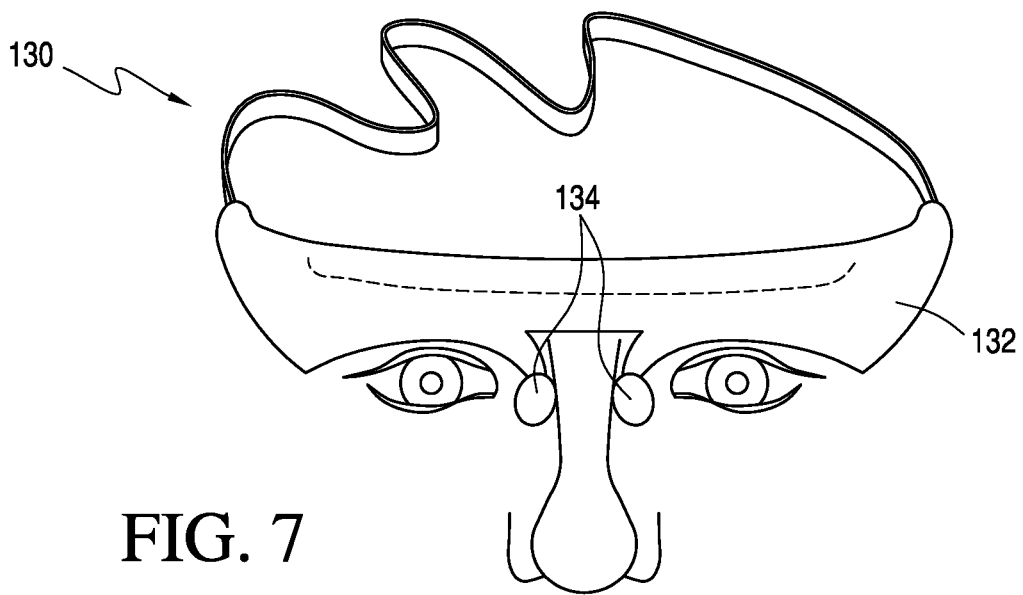
FIG. 7 is a view of a headband for cooling and heating the ABTT terminus, in accordance with an exemplary embodiment of the present disclosure.

Another exemplary ABVTP mask in accordance with the present disclosure is shown in FIG. 7 and generally indicted at 130. ABVTP mask 130 may include only a headband structure 132 and one or more ABTT nodes or pouches 134, while omitting both the under-eye portion and the facial extensions of FIG. 1. ABVTP mask 130 apparatus according to this aspect of the disclosed embodiments remains effective for treating thermal conditions, as it may still rest in constant direct contact with the skin of ABTT target area 20 and the brow/forehead area. ABVTP mask 130 is also ideal for activities such as sporting events, competitions, outdoor activities, and exercise.

Figure 8:
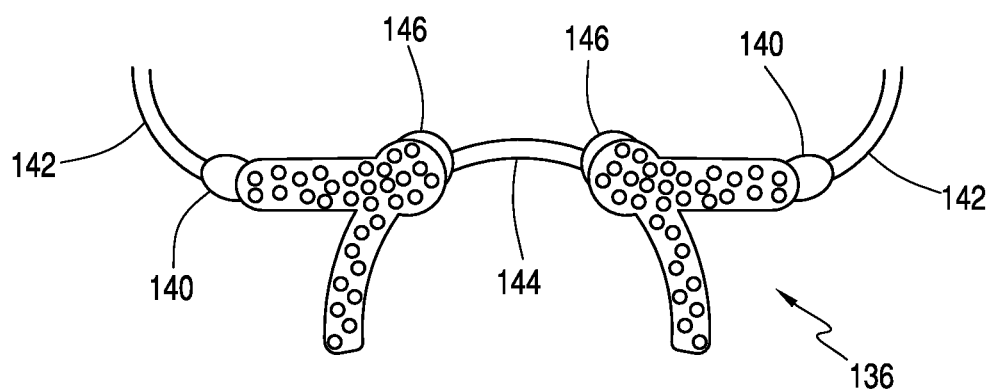
FIG. 8 is a view of a thermal pack for cooling and heating the ABTT terminus, in accordance with an exemplary embodiment of the present disclosure.

A further exemplary embodiment ABVTP mask or thermal pack 136 is shown in FIG. 8 and generally indicated at 136. In this embodiment, ABVTP mask 136 includes a headband support structure 138 to which are attached hooks 140 at opposite ends thereof for fastening an elastic strap or band 142 to headband support structure of ABVTP mask 136. Elastic strap 142 allows ABVTP mask or thermal pack 136 to be used by wearers with different head and face sizes, as the elastic stretches as needed. Hook 140, or other fastening device, would allow a wearer to secure thermal pack 136 to their face by hooking elastic band 142 instead of sliding the entire ABVTP mask 136 apparatus over his or her head. This configuration is ideal for wearers who, for example, may have pear-shaped faces that are bigger around the crown of the head than they are around the eye level of the face. Another aspect of this embodiment is a similarly configured elastic nose bridge 144 that may be secured to the head band portion on either side either in a fixed fashion, or with hooks 146 that may be similar or identical to hooks 140. Elastic nose bridge 144 across the bridge of the nose, or an adjustable clip (not shown) provides further adjustability for a variety of face widths and nose sizes, and one or more hook fasteners 146 would allow a wearer to easily put on and remove the pack.

In the exemplary embodiment of FIG. 8, both head strap 142 and nose bridge strap 144 may have fasteners, e.g. hooks 140. In alternate embodiments, the fasteners may be used for only one of straps 142 and 144, or both straps may be fixed to thermal pack 136. It should also be understood that the hook configuration could be used with a non-elastic strap. In an alternate embodiment, when a non-elastic strap is employed, the fastener may be adjustable or the size varied to provide some level of personal adjustability even in the absence of elastic.

Figure 9:
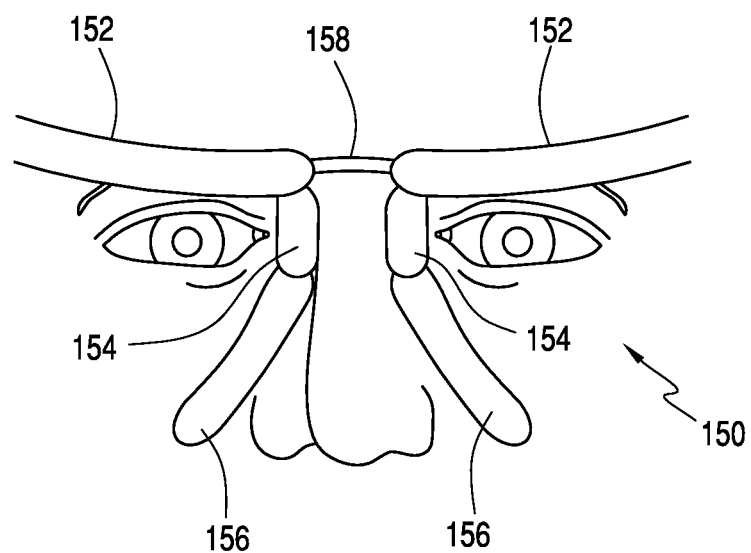
FIG. 9 is a view of a frame similar to eyeglass frames, including an adjustment mechanism over the bridge of the nose, in accordance with an exemplary embodiment of the present disclosure.

A further exemplary embodiment ABVTP mask or thermal pack is shown in FIG. 9 and generally indicated at 150. ABVTP mask 150 includes a rigid headband structure 152, which includes the frame of eyeglasses without the portion for the lenses. According to aspects of this embodiment, rigid headband structure 152 could be formed of a rigid material that may contain the thermally retentive substance and also which allows for sufficient thermal transfer between the ABVTP mask 150 apparatus and the skin. The rigid material headband structure 152, which can be configured as a frame of eyeglasses, may be filled with the thermally retentive substance in the form of a thermal transfer gel or liquid. The thermally retentive substance may also be in the form of a Phase Change Material. Alternatively, rigid headband structure 152 may contain an electric cooling or heating element or other active thermal transfer apparatus. Rigid headband structure 152 may also comprise a rigid material on an outer portion, with a non-rigid material on the inside to contain the thermally retentive substance, thus providing both adequate thermal transfer with the skin, while also creating rigid support for ABVTP mask 150. ABVTP mask 150 may also include pouches or nodes 154 to cover ABTT target area 20, and may also include facial extensions 156, but facial extensions 156 are not necessary, as rigid headband structure 152 will provide some cooling benefits to the brow/forehead area even without those portions. ABTT pouches or nodes 154 may also be comprised of a rigid exterior material, thus allowing ABTT pouches or nodes 154 to serve the function of a nose piece for supporting rigid headband structure 152, if a securing head strap is used or not.

The apparatus of FIG. 9 also comprises an adjustable piece 158 located over the bridge of the nose to allow a wearer to adjust the width of rigid headband structure 152 to comfortably fit different face and nose sizes. Adjustable piece 158 may be able to be inserted and removed from the inside of rigid headband structure 152 or it may be configured to collapse in on itself in a telescopic fashion. Alternately, adjustable piece 158 may be comprised of an elastic material so that rigid headband structure 152 automatically adjusts to a wearer with a wider face or nose, as described elsewhere herein.

Figure 10:
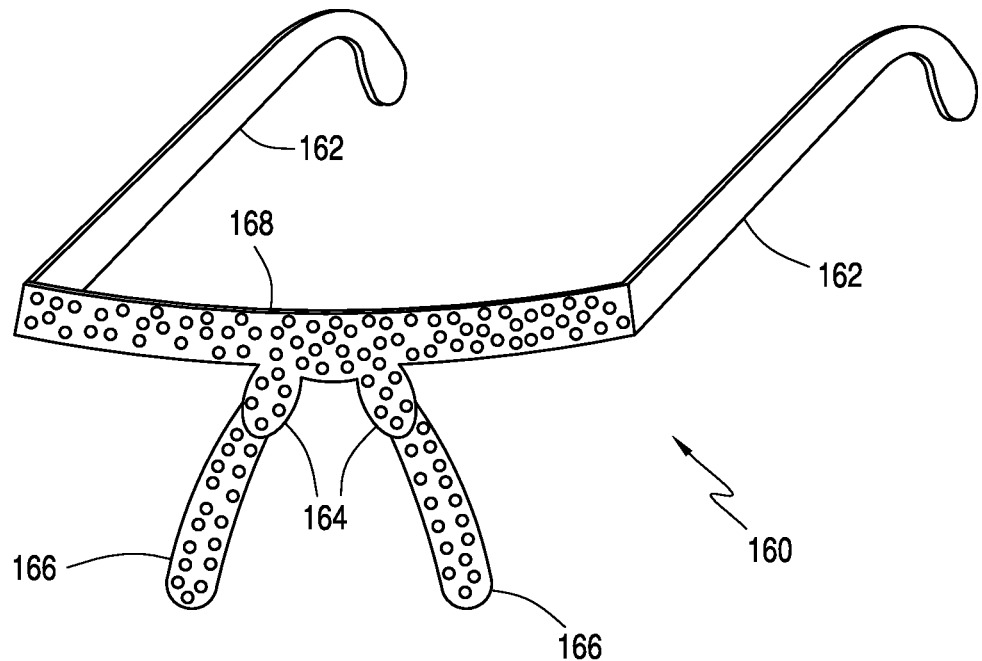
FIG. 10 is a view of a heating or cooling mechanism configured to be positioned under eyeglasses, in accordance with an exemplary embodiment of the present disclosure.

In another exemplary embodiment presented in FIG. 10, an ABVTP mask or thermal pack 160 may include temple frames 162 of the same rigid material that forms ABVTP mask 160. Temple frames 162 extend past the temples on a face and are curved at the free end to secure ABVTP mask 160 to the face by hooking behind the ears. Such a configuration allows rigid thermal retention pack 160 to be used similar to a pair of eyeglasses. In fact, the design of ABVTP mask 160 allows the ABVTP mask 160 to be worn on top of, or in conjunction with, a pair of glasses. Thus, the configuration of ABVTP mask 160 is beneficial for wearers who must also wear prescription eyeglasses, or for out-of-doors use where a wearer may prefer to wear sunglasses also. This arrangement is most ideal for use in sporting events or other activities where the user may be moving around. This arrangement is also beneficial for use during activities that require the wearer to wear a helmet, cap, hard hat, or other head covering also, which may interfere with the placement of a strap that completely encircles the head.

Also presented in FIG. 10, as an alternate embodiment, ABVTP mask or thermal pack 160 includes ABTT nodes or pouches 164 and extension portions 166. ABTT nodes or pouches 164 and extension portions 166 of ABVTP mask or thermal pack 160 may comprise a material with shape memory so that these components may be shaped or bent to fit anatomical variations comfortably. The flexible structure of ABTT nodes or pouches 164 and extension portions 166 is also ideal for ensuring that sufficient pressure is created between ABVTP mask or thermal pack 160 and the skin underneath, which is important for thermal transfer to the veins of the face. In an alternate embodiment, the ABVTP mask or thermal pack 160 may include a front frame structure 168, and instead of comprising a flexible material, ABTT nodes or pouches 164 and extension portions 166 may be connected to front frame portion 168 using a hinge mechanism or be spring-loaded to allow for changing position and pressure on the skin.

Figure 11:
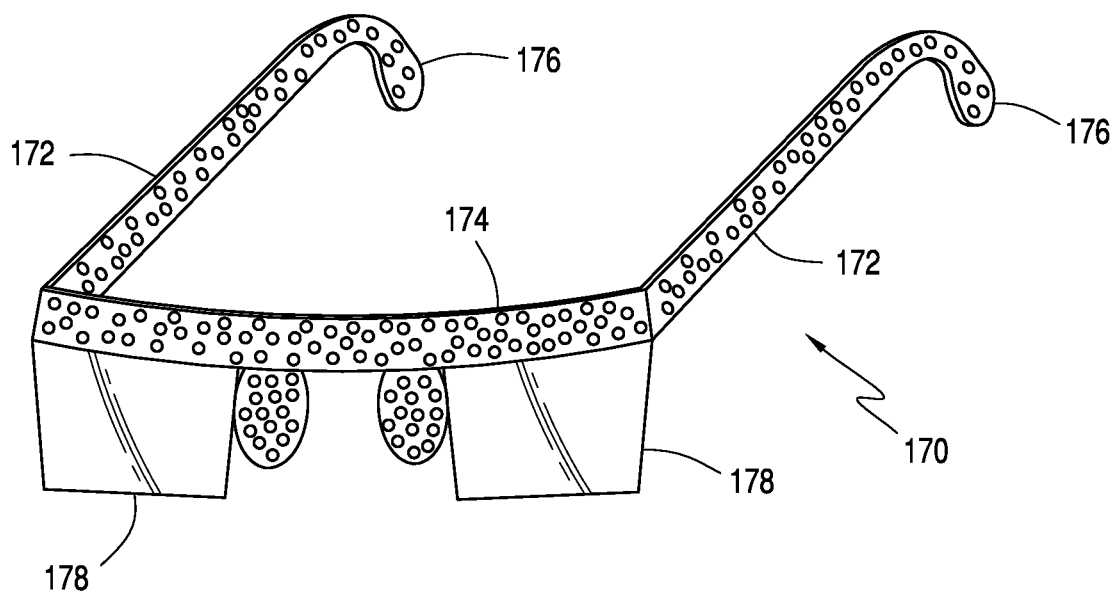
FIG. 11 is a view of a heating or cooling mechanism configured to be integral with an eyeglass frame that includes lenses, in accordance with an exemplary embodiment of the present disclosure.

Another exemplary embodiment ABVTP mask or thermal pack is shown in FIG. 11 and indicated generally at 170. ABVTP mask or thermal pack 170 includes temple frames 172 and front frame structure 174 that may be filled with thermally retentive substance or a thermal element. This configuration allows the temples of the head to be cooled or heated and eliminates the need for separating the front frame structure 174 and temple frames 172, as they may be comprised of the same materials. In yet another embodiment, temple frames 162 containing thermally retentive substance may comprise a bulge or pouch 176 at the free end so that additional heating or cooling benefits may be applied to veins that are located behind the ears. Although it is preferred for a cooling or heating apparatus to cover ABTT target area 20 and frontal vein 12, superior palpebral vein 14, supraorbital vein 16, facial vein 18, and angular vein 19, it should be understood that cooling effects may be applied to other vascular systems, though equal benefits may not be produced. For optimal brain cooling effects, an ABVTP mask or thermal pack must treat ABTT target area 20 and/or relevant facial veins 12, 14, 16, and 18. However, an ABVTP mask or thermal pack may be adapted to cover other vascular areas as well, as long as peripheral receptors that would cause an undesirable temperature reaction from the brain are not stimulated.

In yet another exemplary embodiment of the present disclosure, ABVTP mask or thermal pack 170 may be used as a support for lenses 178. In this configuration, ABVTP mask or thermal pack 170 may support prescription lenses, colored lenses, and tinted UV protection lenses for sunglasses. As such, ABVTP mask or thermal pack 170 would replace conventional plastic or metal frames for eyeglasses and sunglasses. In yet another alternative exemplary embodiment, temples frames 172 and front frame structure 174 may be similarly employed as a support for masks and goggles for professional, sports, and personal use applications.

Figure 13:
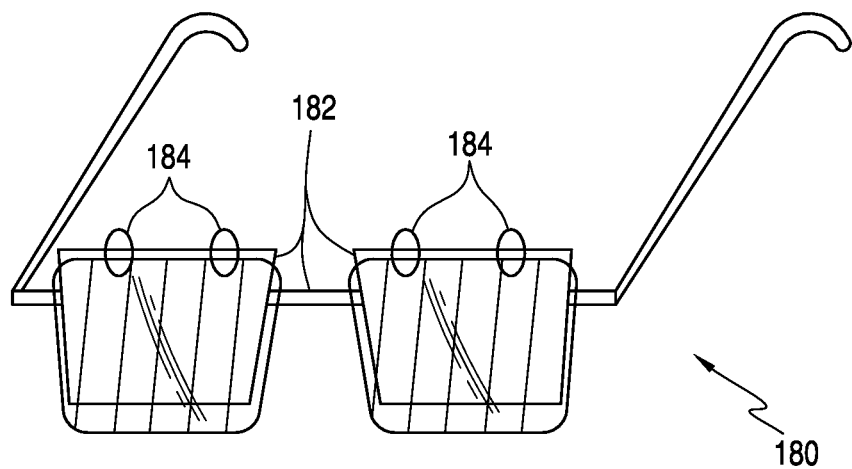
FIG. 13 is a view of yet another heating or cooling mechanism configured to be integral with an eyeglass frame that includes lenses, in accordance with an exemplary embodiment of the present disclosure.

Yet another exemplary embodiment ABVTP mask or thermal pack is shown in FIG. 13 and indicated generally at 180. ABVTP mask or thermal pack 180 includes a front frame structure 182. Front frame structure 182 may include anchors or hooks 184 for attaching lenses 178, as well as sliding areas or grooves so lenses 178 may be interchangeable.

Figure 12:
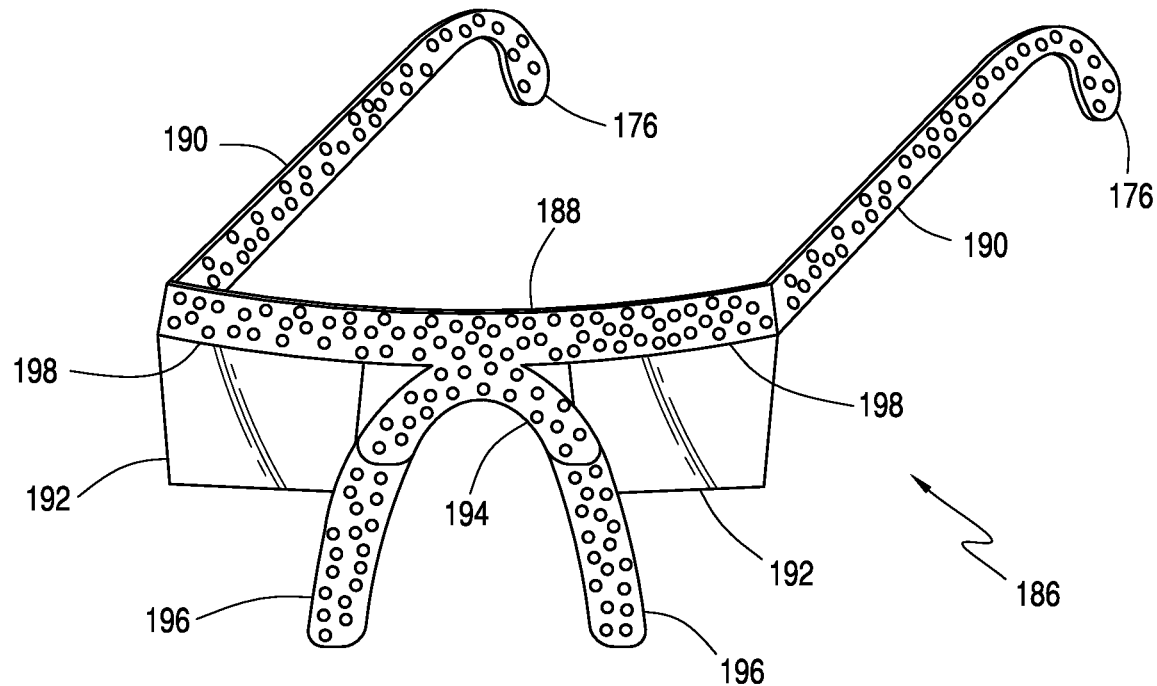
FIG. 12 is a view of another heating or cooling mechanism configured to be integral with an eyeglass frame that includes lenses, in accordance with an exemplary embodiment of the present disclosure.

A further embodiment ABVTP mask or thermal pack is presented in FIG. 12 and indicated generally at 186. ABVTP mask or thermal pack 186 includes a front frame 188, temple frames 190 that are attached to and extend from front frame 188, lenses 192, nose pads 194, and extensions 196. Nose pads 194 can include thermal transfer devices or the thermally retentive substance for delivering or removing heat from ABTT target area 20. Thus, nose pads 194 also include an ABTT node thermal transfer portion and the combined ABTT node thermal transfer and nose pad portion serves as a support for ABVTP mask or thermal pack 186. In an exemplary embodiment, nose pads 194 may be adjustable, comprising a material with position memory, a hinge, or spring.

In FIG. 12, according to the principles of this disclosure, a thermal eyeglasses frame is disclosed. The thermal eyeglasses frame, similar to other embodiments, includes front frame structure 188, nose pads 194, and extensions 196 of nose pads 194, all of which have thermal transmission capability. In an exemplary embodiment, this thermal transmission capability includes thermal retentive materials or substances, but can also include any material, element, system, thermoelectric devices, such as a Peltier cooler, and the like that have a thermal surface disposed within the frame of the eyeglasses, for example, front frame structure 188, nose pads 194, and extensions 196 of nose pads 194. These surfaces may include metals that can be cooled or warmed, and that are configured to rest directly on the skin. Once activated, such surfaces warm or cool blood vessels 12, 14, 16, and 18 lying underneath the skin.

Front frame structure 188 has thermal transfer capability, which may include thermally retentive materials, electric cooling/warming systems, warming and cooling chemical systems, and the like. In the exemplary embodiment, front frame structure 188 includes grooves 198 in a thermally transmissive area of front frame structure 188. Grooves 198 are configured to receive lenses 192. In an exemplary embodiment, grooves 198 may mate with lenses 192, and lenses 192 may be retained by an adhesive. In yet another exemplary embodiment, grooves 198 and lenses 192 may include complimentary sliding means to permit lenses 192 to slide into grooves 198, with retention provided by an adhesive or mechanical mechanism. Temple frames 190 in this embodiment include conventional eyeglass temple frames.

Alternately, though less preferred, ABVTP mask or thermal pack 186 may comprise conventional nose pads 200 with no thermal transfer properties, as presented in FIG. 14. FIG. 14 shows an exemplary ABVTP mask or thermal pack in accordance with an exemplary embodiment of the present disclosure and indicated generally at 202. ABVTP mask 202 includes temple frames 204 in addition to nose pads 200. In the exemplary embodiments of FIGS. 12 and 14, temple frames 190 and 204 of ABVTP mask 186 and 202, respectively, thermal transmission surfaces follow temporal and auricular blood vessels, including behind the ear. Temple frames 190 and 204 further include bulges 176 for apposition and thermal transmission to the auricular blood vessels.

FIGS. 15 and 16 show a portion of an ABVTP mask or thermal pack in accordance with an exemplary embodiment of the present disclosure and indicated generally at 206. ABVTP mask 206 includes a front frame structure 208 and a temple frame 210. Temple frame 210 is shaped such that interior walls or surfaces 214 of temple frame 210 form a hollow cavity 212. Hollow cavity 212 is configured to receive a thermal transfer device, such as a gel pack or serpentine device, but which may be worn with or without the thermal transfer device in place. The structure of hollow cavity 212 alleviates the need for multiple frames for prescription lenses, sunglasses, goggles, or the like by allowing a user to adapt ABVTP mask 206 for use in specific situations. As such, a user may wear ABVTP mask 206 as it is, or perhaps in the case of an outdoor activity, may insert a thermal transfer device into hollow cavity 212. FIG. 16 presents a cross-sectional view of temple frame 210 showing an exemplary hollow cavity 212 configured to receive a thermal transfer device. Hollow cavity 212 may be a simple cut-out or may employ the use of snaps, grooves, or other mechanisms for securing the thermal gel pack or a thermal transfer device. In FIG. 15, temple frame 210 includes a thermal transfer device positioned therein.

Figure 17:
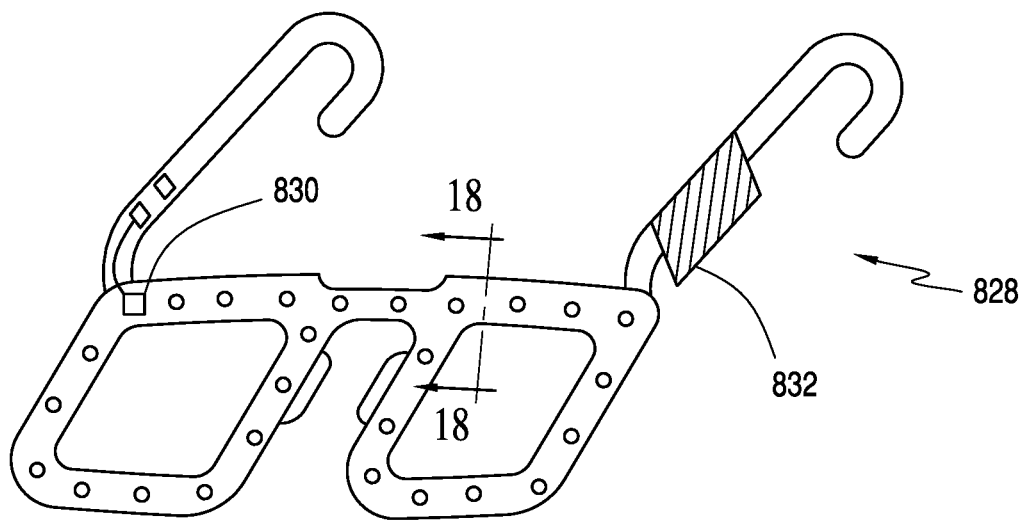
FIG. 17 is a view of an eyeglass frame containing a thermal transfer material and compatible with a face mask, such as is worn by a firefighter, a gas mask, or other type of mask, in accordance with an exemplary embodiment of the present disclosure.
Figure 18:
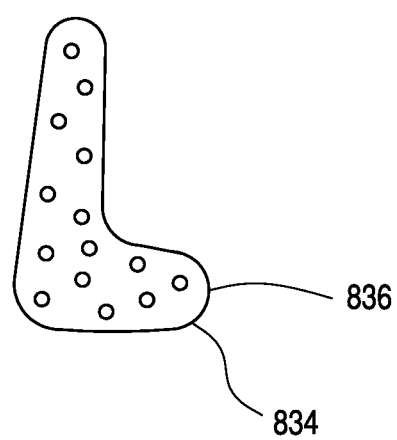
FIG. 18 is a view of a portion of the eyeglass frame of FIG. 17 along the line 18-18.
Figure 21:
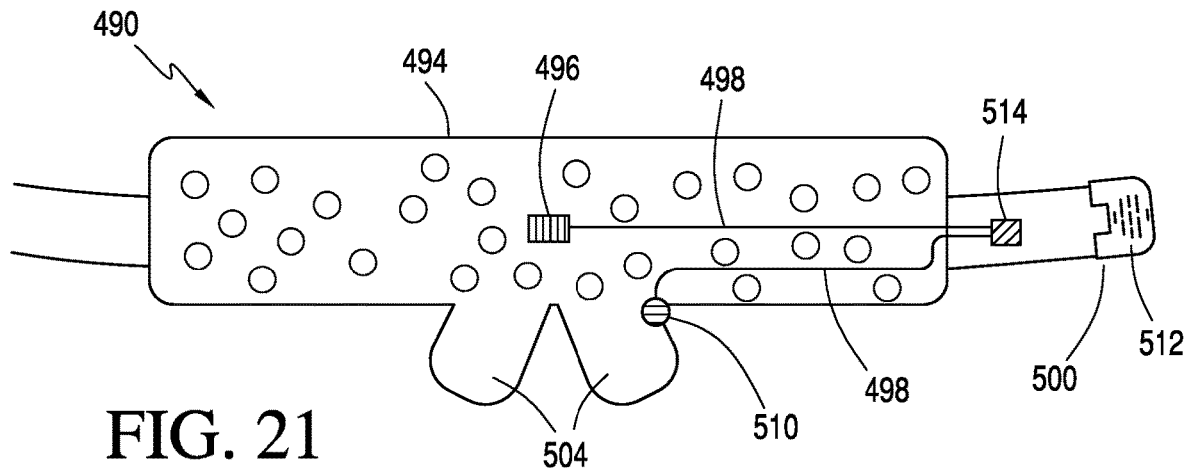
FIG. 21 is a view of another thermal pack including thermal sensors and an alarm, in accordance with an exemplary embodiment of the present disclosure.
Figure 22:
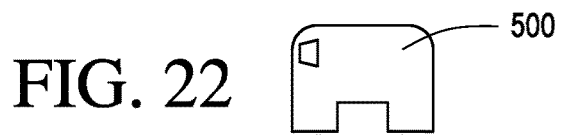
FIG. 22 is a view of an energy module of FIG. 21.
Figure 23:
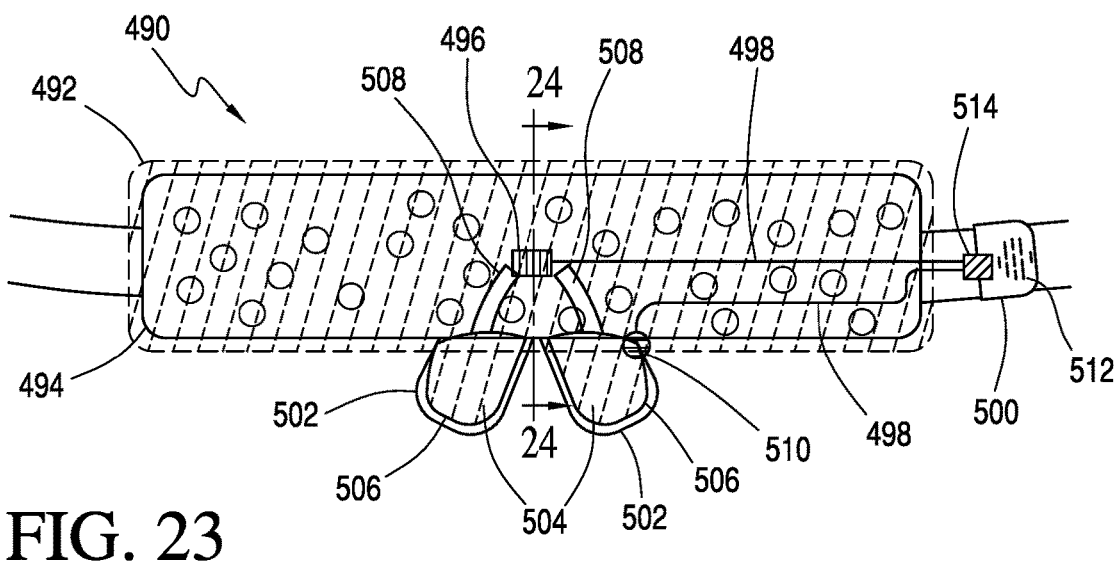
FIG. 23 is a view of another thermal pack similar to the thermal pack of FIG. 21, with an insulating headband, in accordance with an exemplary embodiment of the present disclosure.
Figure 24:
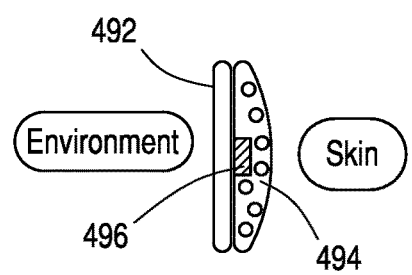
FIG. 24 is a stylized cross-sectional view of the thermal pack of FIG. 23 along the line 24-24.

In some cases, an eyeglass frame, either with or without lenses, may be used with other headgear, such as helmets, masks, etc. FIGS. 17 and 18 show an eyeglass frame in accordance with an exemplary embodiment of the present disclosure and indicated generally at 828. Eyeglass frame 828 may include a thermally retentive substance or material located throughout to provide a predetermined heat capacity, for removing heat from or providing heat to ABTT terminus 20. It should be apparent from the teachings provided herein that various electronic components may be provided in eyeglass frame 828, such as a temperature sensor 830, one or more controllers or processors, a transmitter, receiver, or transceiver, screens, cameras, speakers, headphones, etc. Eyeglass frame 828 may include a frame housing 832 in which at least a portion of the electronics are located, though the electronics may be distributed throughout eyeglass frame 828, and connect by wires or through other apparatus.

As shown in FIG. 18, eyeglass frame 828 includes a protrusion or extension for interfacing with ABTT terminus 20, indicated generally at 834. Protrusion 834 includes a curvilinear surface 836 configured with a geometry that approximately mimics or reflects the unique geometry of ABTT terminus 20 such that the contact between curvilinear surface 836 provides as much contact with ABTT terminus 20 as possible for thermal transfer to or from ABTT 22. Protrusion 834 may contain a conductive material to transfer thermal energy between eyeglass frame 828 and ABTT 22, such as copper or a high thermal conductivity plastic. Protrusion 834 may also include a thermally retentive material to help provide heat or cold storage, as well as thermal conductivity to transfer heat to and from ABTT terminus 20.

Figure 25:
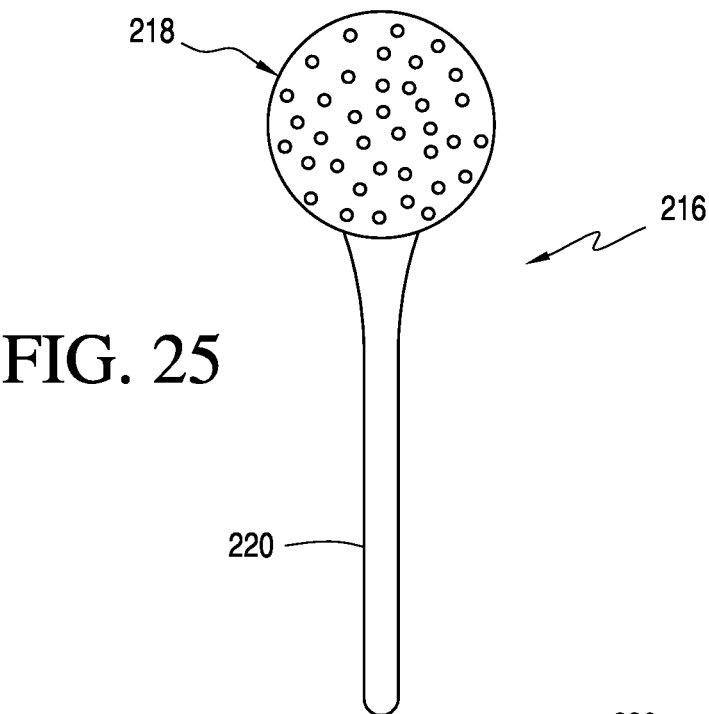
FIG. 25 is a view of a stick mounted thermal pack, in accordance with an exemplary embodiment of the present disclosure.

Support structures for a thermal transfer pack may also include a longitudinally extending support, such as a rod, or stick. A thermal transfer pack in accordance with an exemplary embodiment of the present disclosure is shown in FIG. 25 and indicated generally at 216. Thermal transfer pack 216 includes a pouch 218 containing a thermally retentive substance, and a longitudinally extending support 220. Longitudinally extending support 220 can be held by hand and manually placed on ABTT terminus 20. In one embodiment, longitudinally extending support 220, which acts as a handle, may be formed of a rigid material such as, for example, plastic, and may be a simple stick configuration or may be designed to have finger grips or other comfort features. For example, a player may position thermal transfer pack 216 on his or her ABTT terminus 20 during a break in a sporting event to reduce the temperature in the brain, or to increase the temperature of the brain when participating in a cold weather activity. Pouch 218 may comprise a generally round, or spherical shape, as presented in FIG. 25, or, in an alternative embodiment, may comprise a convex kidney, comma, or banana shape in order to rest in intimate contact with ABTT terminus 20. It should be apparent that any passive thermal transfer-type devices described herein may be handheld rather than supported by a strap or other apparatus. It should be understood that a conductive metal rod having an insulating portion for the handle is within the scope of the invention, such conductive metals including, but not limited to, gold, silver, copper, and aluminum, said rods can be cooled, such as by refrigeration, and stored in a kit disclosed herein.

A handheld thermal pack, such as thermal transfer pack 216, may be manually heated or chilled as described herein, or a thermal transfer pack may comprise a device for self-heating or cooling the gel or liquid inside the thermal transfer pack. Such a device may comprise a power source and/or an electrical heating apparatus. In an exemplary embodiment, a handheld thermal transfer pack comprises two compartments for containing water and nitrogen that mix when a seal is broken, thus freezing and causing the thermal transfer device to freeze. A similar configuration may be employed for heating a thermal transfer pack, using appropriate substances to generate an exothermic reaction.

Figure 26:
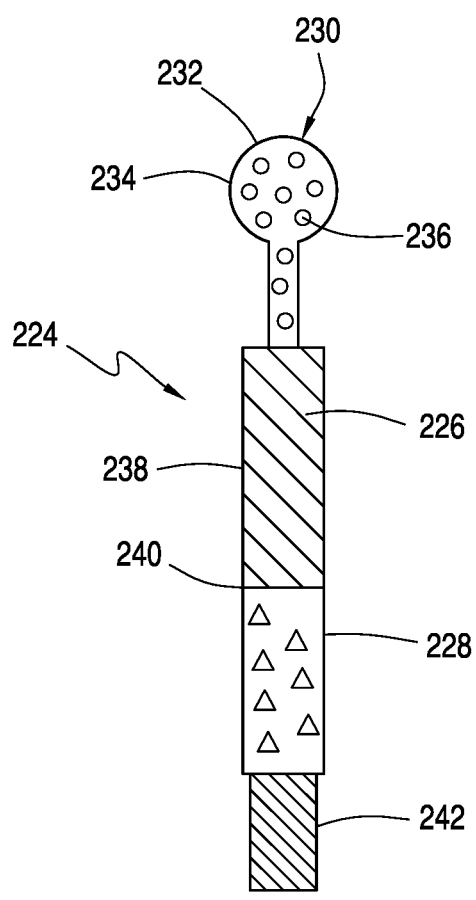
FIG. 26 is a schematic view of a hand held thermal transfer device, in accordance with an exemplary embodiment of the present disclosure.
Figure 27:
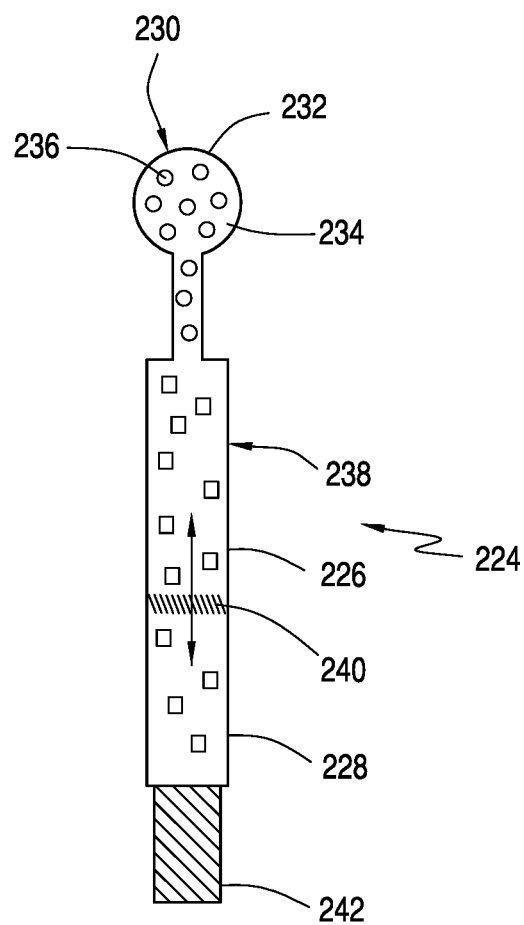
FIG. 27 is a schematic view of the hand held thermal transfer device of FIG. 26 with a breakable or adjustable seal broken, in accordance with an exemplary embodiment of the present disclosure.

FIGS. 26 and 27 show an exemplary handheld self-cooling device in accordance with the present disclosure and indicated generally at 224. Handheld self-cooling device 224 includes a first compartment 226, which in an exemplary embodiment contains water, and a second compartment 228, which in an exemplary embodiment contains nitrogen. In the exemplary embodiment of FIGS. 26 and 27, first compartment 226 and second compartment 228 are arranged side-by-side or adjacent to each other, and each compartment 226 and 228 extends longitudinally. When handheld self-cooling device 224 is oriented vertically, first compartment 226 and second compartment 228 are in vertical alignment, i.e., they overlap each other, along with being in vertical alignment with the other elements of handheld self-cooling device 224.

Handheld self-cooling device 224 also includes a housing 230 with a convex surface 232. Convex surface 232 is configured to mate with the geometry of ABTT terminus 20. Housing 230 extends longitudinally away from at least one of first compartment 226 and second compartment 228. First compartment 226 and second compartment 228 form a handle 238. Housing 230 includes an interior portion 234 in which is located or positioned a thermally retentive substance 236.

In the exemplary embodiment of FIGS. 26 and 27, first compartment 226 and second compartment 228 are separated by a breakable or adjustable seal 240 that can be compromised to permit the water and the nitrogen to mix. The compromise may include breaking seal 240, or opening seal 240, which may be accomplished by bending handle 238. After seal 240 is compromised, a cold reaction is generated in first compartment 226 and second compartment 228, which draws heat from housing 230, thereby cooling housing 230. Convex surface 232 may be positioned in contact with ABTT terminus 20 or veins 12, 14, 16, and/or 18 that drain into ABTT 22, cooling the blood of the aforementioned veins and ABTT 22.

In an exemplary embodiment, a handle extension 242 is connected or attached to handle 238 that is insulated from first compartment 226 and second compartment 228 so the user does not have to hold the cold water and nitrogen mixture. Thus, handheld self-cooling device 224 may be applied by the user more comfortably. In another exemplary embodiment shown in FIGS. 28 and 29, a handheld self-cooling device is shown and generally indicated at 246. In this embodiment, handle 238 may include an insulating sleeve 244, and insulating sleeve 244 may be removable as well as adjustable so that insulating sleeve 244 may be removed while the user is compromising or breaking seal 240, as shown in FIG. 29. Once the liquid mixture is cooled, insulating sleeve 244 can be replaced, as shown in FIG. 28.

FIGS. 30 and 31 show another handheld self-cooling device in accordance with an exemplary embodiment of the present disclosure and indicated generally at 248. Handheld self-cooling device 248 includes features similar to handheld self-cooling device 246, but instead of insulating sleeve 244, device 248 includes thermal insulation 250 that covers the entirety of device 246 except housing 230. Thermal insulation 250, shown closed in FIG. 31, may be opened to reveal handle 238 and to permit compromise of seal 240. Once seal 240 is compromised, thermal insulation 250 is closed, as shown in FIG. 31, exposing only housing 230 so that housing 230 may be placed on ABTT terminus 20.

Figure 32:
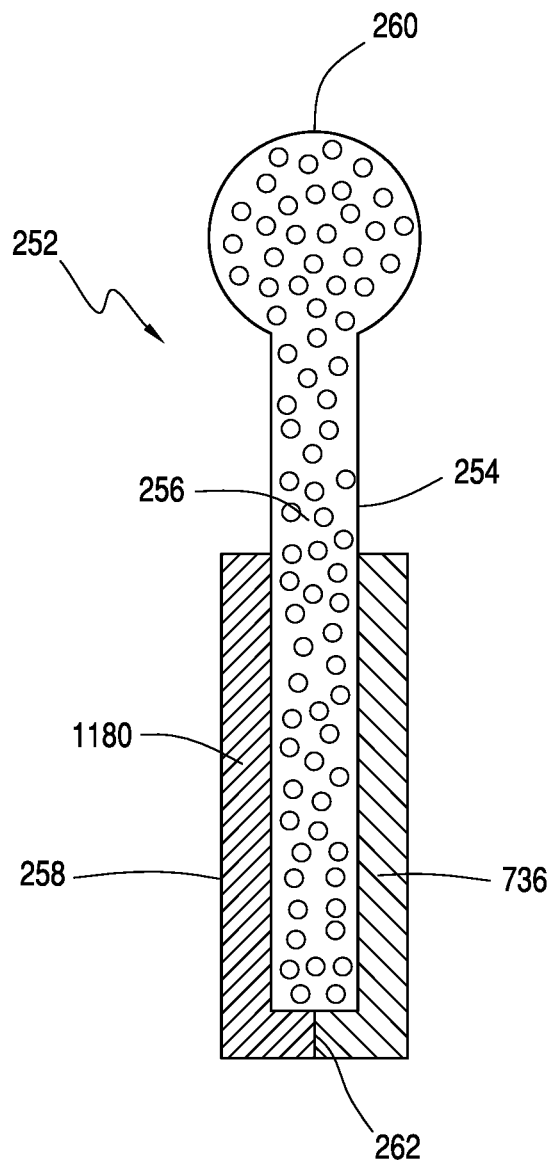
FIG. 32 is a schematic view of another alternative embodiment hand held thermal transfer device, in accordance with an exemplary embodiment of the present disclosure.
Figure 33:
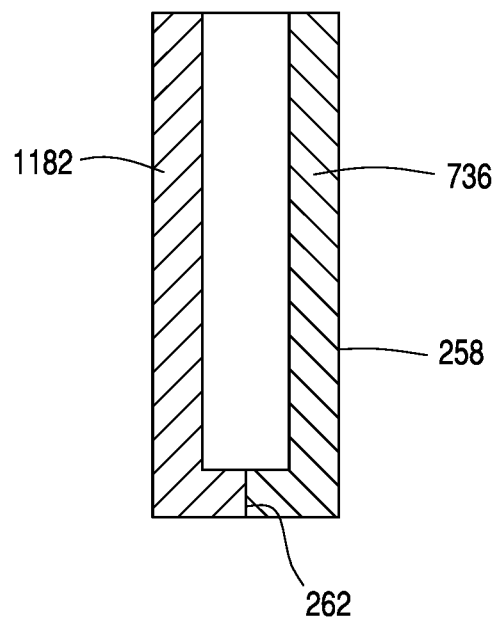
FIG. 33 is an insulating self-cooling apparatus of the hand held thermal transfer device of FIG. 32.

Yet another exemplary handheld self-cooling device is shown in FIG. 32 and indicated generally at 252. In this embodiment, handheld self-cooling device 252 includes a handle 254, and a housing 260 located at one end of handle 254. Handle 254 includes a thermally retentive material 256 enclosed within a substantial portion of the length of handle 254. Handheld self-cooling device 252 further includes an insulated self-cooling apparatus 258, shown in FIG. 33, that is positioned adjacent to and longitudinally along handle 254, and self-cooling apparatus 258 is configured to encircle handle 254. Self-cooling apparatus 258 is a separate element or component so that once the self-cooling process has been accomplished, self-cooling apparatus 258 may be sterilized and recharged or discarded while handle 254 and housing 260 may be reusable.

Self-cooling apparatus 258 includes a first portion 1180, a second portion 1182, and a seal 262 disposed between first portion 1180 and second portion 1182 to keep the contents of each portion separated. In an exemplary embodiment, first portion 1180 is configured to contain water, and second portion 1182 is configured to contain ammonium nitrate. When seal 262 is broken, which can be accomplished, for example, by bending self-cooling apparatus 258, the water and ammonium nitrate mix, creating an endothermic reaction and cooling handle 254. It should be understood that seal 262 can be positioned in a plurality of locations, depending on how the chemicals used to generate an exothermic or endothermic reaction are disposed. The cooling (or heating) compounds of self-cooling (or heating) apparatus 258 are disposed around handle 254, and is detachable, so as to allow self-cooling apparatus 258 to be replaced by a new self-cooling apparatus 258 once the temperature of self-cooling apparatus 258 is insufficient to heat or cool ABTT 22.

It should also be understood that besides the hand held embodiments described, a body supported thermal system are within the scope the disclosure. By way of illustration, a clip having a surrounding housing with cooling compounds and a breakable seal can be used. In this embodiment, the clip has a spherical shape nose pad resting between the eye and eyebrow, more particularly in the supero-medial orbital region. The bridge of the nose pad is fitted with compartments with a breakable seal. Once the seal is broken, the cold thermal energy is transferred to the nose pads, which contain thermal retentive material.

It should be understood that besides the handheld embodiment described, a body supported thermal system are within the scope the disclosure. By way of illustration, a clip having a surrounding housing with cooling compounds and a breakable seal can be used. In this embodiment, the clip has a spherical nose pad resting between the eye and eyebrow, more particularly in the superior-medial orbital region. The bridge of the nose pad is fitted with compartments with a breakable seal. Once seal 262 is broken, cold thermal energy is transferred to the nose pads, which contain thermal retentive material.

Figure 34:
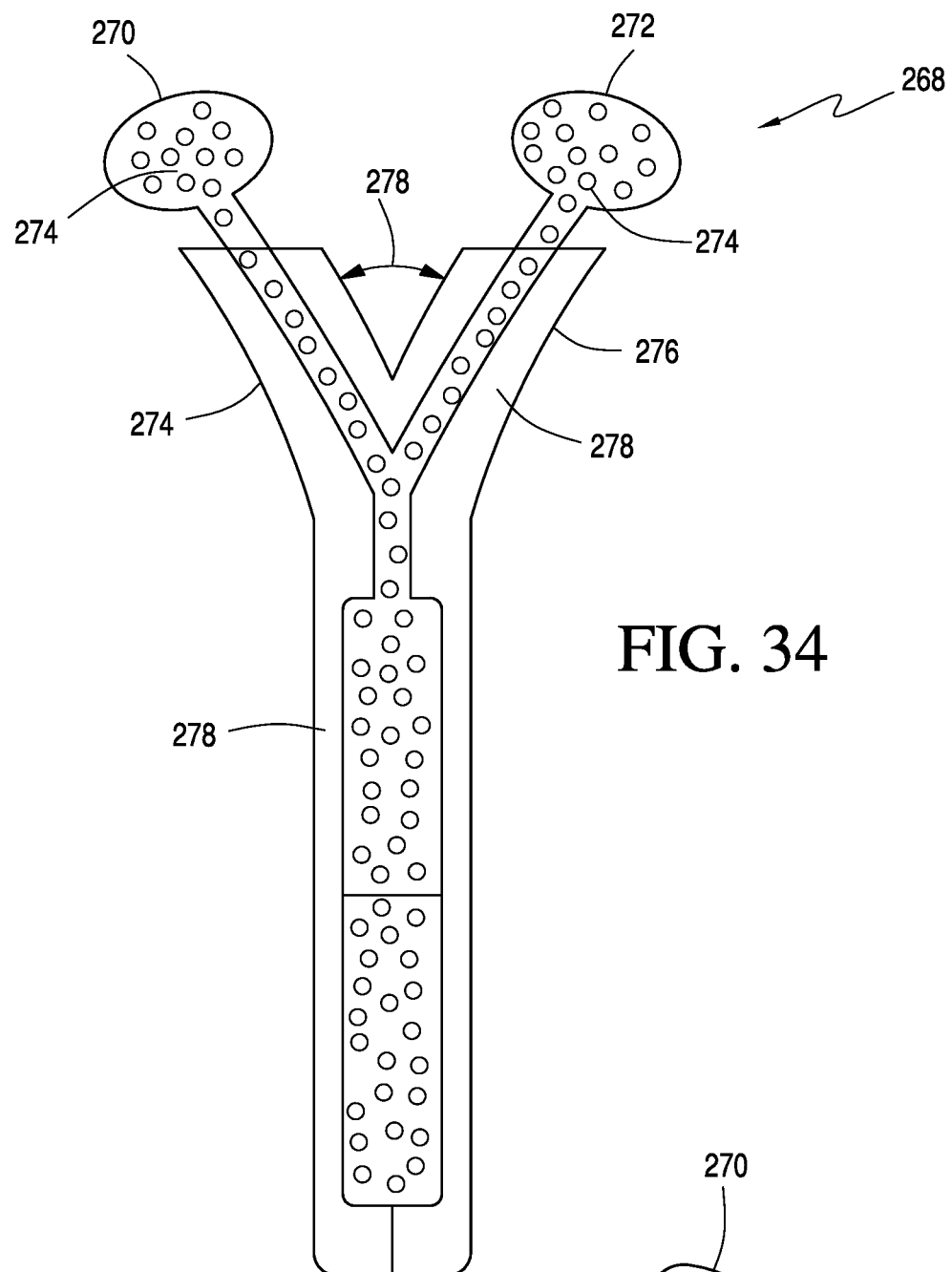
FIG. 34 is a schematic view of a further embodiment of a hand held thermal transfer device, in accordance with an exemplary embodiment of the present disclosure.

FIG. 34 shows another handheld self-cooling device in accordance with an exemplary embodiment of the present disclosure and indicated generally at 268. Handheld self-cooling device 268 includes a first branch 274 from which a first ABTT contact housing 270 extends, and a second branch 276 from which a second ABTT contact housing 272 extends. Each of first ABTT contact housing 270 and second ABTT contact housing 272 includes a thermally conductive and retentive material 274. First ABTT contact housing 270 and second ABTT contact housing 272 are configured to apply heat or to remove heat to ABTT terminuses 20 on both sides of the nose. First branch 274 and second branch 276 may be repositionable or bendable that an angle 278 may be adjusted to position first ABTT contact housing 270 and second ABTT contact housing 272 more precisely on ABTT terminus 20 positioned on each side of a subject or patient's nose, thus enabling handheld self-cooling device 268 to be customized to fit individual anatomies. Handheld self-cooling device 268 may also include insulation 278 on any portion of the device, excluding the tips of first ABTT contact housing 270 and second ABTT contact housing 272 in the locations where they are to be placed against the skin of ABTT terminus 20 BIT area, to avoid excess thermal transfer with the environment that, in turn, enables maximum thermal transfer between handheld self-cooling device 268 and the skin.

Figure 35:
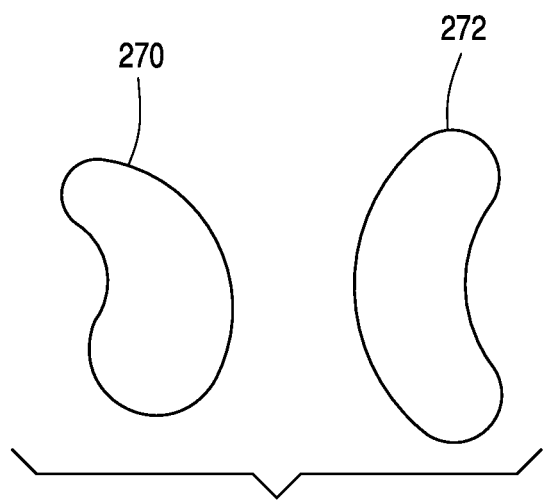
FIG. 35 is a view of an end of a hand held thermal transfer device for contact with the skin of a subject or patient, in accordance with an exemplary embodiment of the present disclosure.

While FIG. 34 shows first ABTT contact housing 270 and second ABTT contact housing 272 as having an elliptical shape, housings 270 and 272 may have other shapes to conform with ABTT terminus 20. For example, FIG. 35 illustrates an exemplary shape of housings 270 and 272 that may be described as bean, kidney or banana shaped. The shape of housings 270 and 272 is configured to provide the best chance of contacting ABTT terminus 20 and transferring heat either to or from ABTT terminus 20.

Another handheld self-cooling device is presented in FIGS. 37 and 38 and generally indicated at 280. Handheld self-cooling device 280 may include an insulated case 282 that covers the entirety of the device and which may be split open to reveal a thermal transfer tip 284 for placing in contact with the skin. Handheld self-cooling device 280 is similar to self-cooling apparatus 258 and includes a seal 1184 that is broken to cause an endothermic reaction in device 280. Once the reaction is initiated, a narrow, reduced diameter, or neck portion 1186 included as a part of device 280 is positioned in a mating feature in case 282 that positions tip 284 outside case 282 to permit contact ABTT terminus 20.

Figure 2:
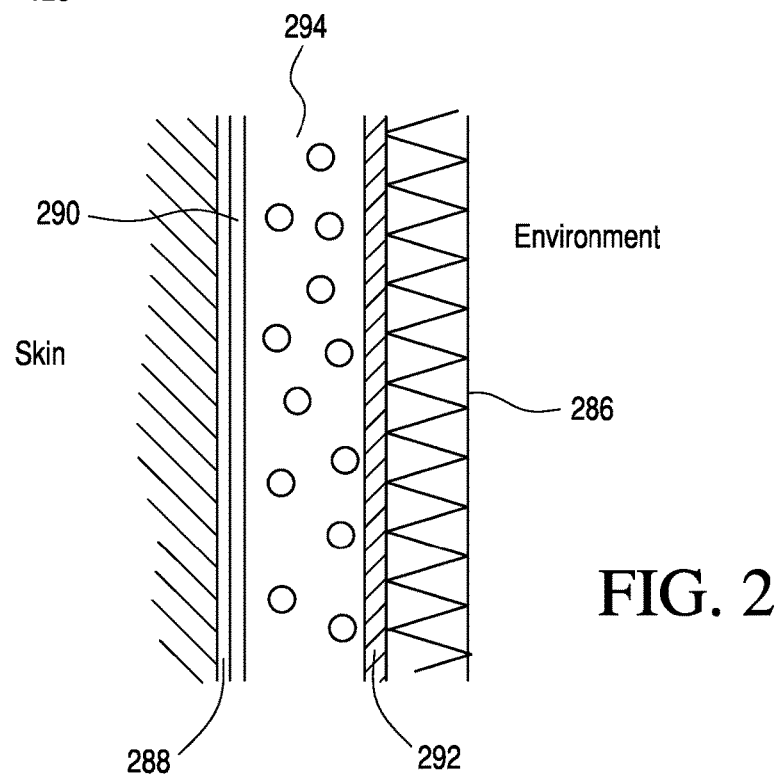
FIG. 2 is a cross-sectional view of a portion of a flexible thermal pack that may be included in the mask of FIG. 1, in accordance with an exemplary embodiment of the present disclosure.

In order to prevent excessive thermal exchange or transfer with the environment, i.e., losing heat to or gaining heat from the surroundings, the thermal transfer pack preferably includes an insulating layer. As shown in FIG. 2, an insulating layer 286 covers portions of the various thermal transfer pack embodiments described herein that are exposed to the surroundings, thus preventing thermal loss to the environment, but allowing maximum thermal transfer to a subject or patient's skin 288. Any appropriate conventional insulating material may be used, as disclosed herein. In addition to insulating layer 286, the thermal packs described herein may include a high thermal conductivity inner lining 290 that is configured to rest on or contact skin 290 and one or more of blood vessels 12, 14, 16, and 18, and an opposite, low thermal conductivity outer lining 292 with insulating properties. Positioned between inner lining 290 and outer lining 292 is a volume containing a thermally retentive material or substance 294.

Figure 3:
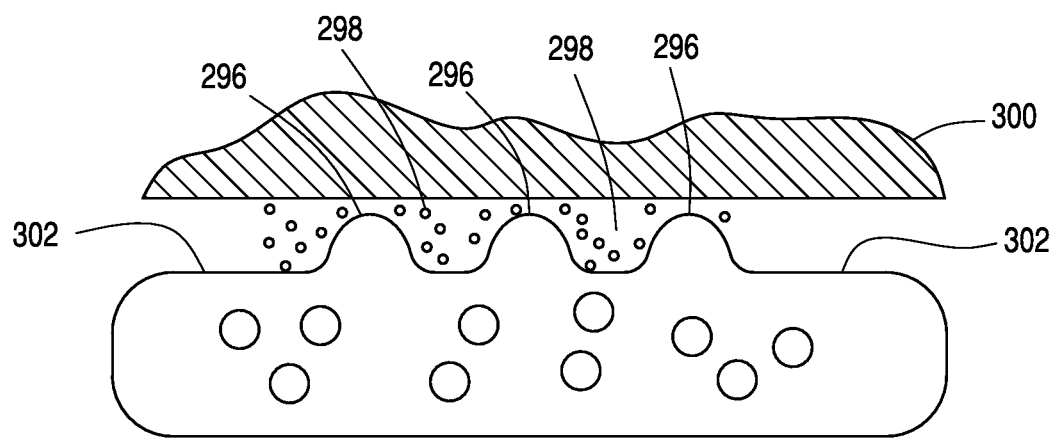
FIG. 3 is a cross-sectional view of a flexible thermal pack in accordance with an alternative embodiment of the present disclosure.

As shown in FIG. 3, the structure of the gel pack or thermal transfer device may also include raised portions 296, thus creating air pockets 298 between an insulating material 300 and a lining material 302 on the side of the thermal pack that is not in contact with skin. Air pockets 298 provide insulation benefits for retaining or keeping out heat. Adequate insulation is especially necessary in applications where the environmental temperatures are extremely high or low where there is a risk that the benefits of the heating or cooling of ABTT 22 may be lost too quickly to provide proper benefits to the user.

In another embodiment, in addition to the outer insulation, the portion of the thermal pack in contact with the skin may comprise a lining of a material that will allow only gradual thermal transfer with the skin. Such a lining may be a mesh or fenestrated tissue or material. Such a material still allows for adequate thermal transfer with the skin and associated blood vessels, but slows the thermal transfer, thus further extending the length of time a thermal pack may be used. The mesh lining also prevents excessive thermal transfer with the skin, which may cause pain or local vessel constriction.

Figure 4:
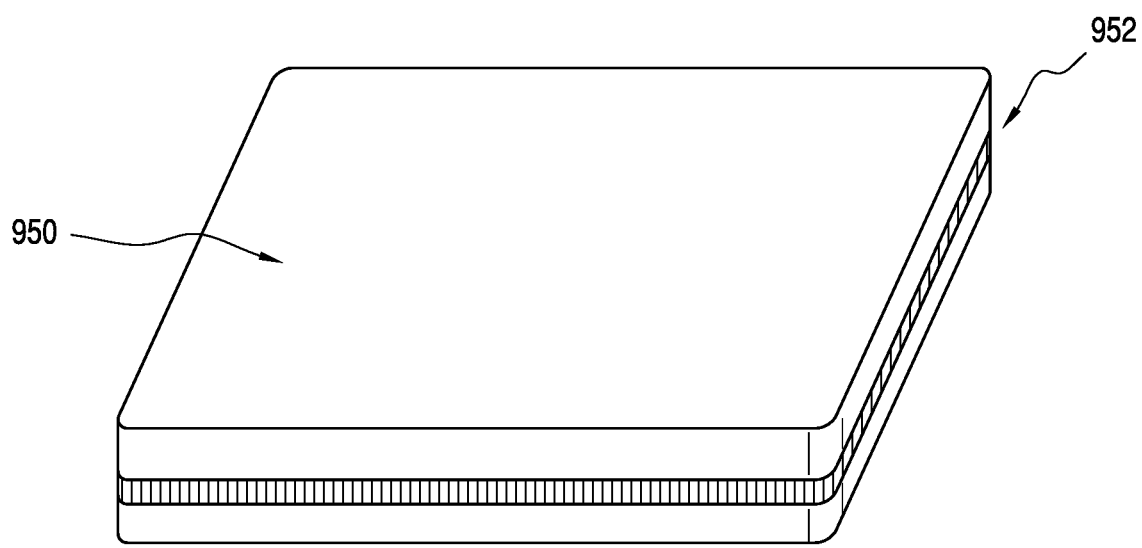
FIG. 4 is a perspective view of a thermal pack kit or bag, in accordance with an exemplary embodiment of the present disclosure.
Figure 5:
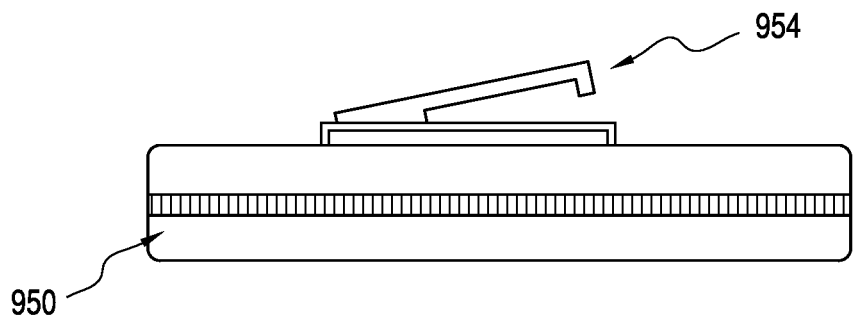
FIG. 5 is a side view of the thermal pack kit of FIG. 4.

FIG. 4 shows a kit in accordance with an exemplary embodiment of the present disclosure and indicated generally at 304. Kit 304 includes an ABVTP characterized by the presence of a thermally retentive material and a housing having a power source for heating and cooling the devices inside said housing using for example a Peltier device. FIG. 5 shows a kit that includes a cooling pack.

Another exemplary brain heating/cooling device is an active-type thermal transfer device which may include but is not limited to a serpentine comprising a series of tubes or hoses for carrying heated or cooled fluid to apply or remove thermal energy from the relevant veins and ABTT area. The serpentine structure comprises also a power source, pumping mechanism and device for storing the heated or cooled liquid and may also comprise a device for heating or cooling the liquid therein. The liquid to be used may also be manually heated or cooled by the user before placing in the storage container or device. The device may also comprise, instead of hoses or tubes, one or more flexible fluid transfer spaces designed for passing temperature control fluid there through while remaining in close conformity to the anatomy of the body, in particular close apposition to the ABTT and veins in accordance of the principles of this disclosure. Such fluid transfer spaces may also comprise a spacer adapted to keep the inner and outer lining walls from collapsing on one another. For example, a mask adapted to fit with the anatomy of the BIT including pouches and tubes disposed as an inverted V shape may be configured to allow cooled fluid to fill the entire pouch created by the inner and outer walls, the cooled fluid being pumped from a source to carry heat away from the ABTT area and facial veins.

Alternatively, the active thermal transfer device may comprise an internal heat or cold producing capability such as, for example, a Peltier thermoelectric heat pump device that uses electrical energy to transfer heat from one side of the device to another across a temperature gradient. Peltier devices may be employed to heat or cool either liquids or air for adding or removing thermal energy to the ABTT area and/or the veins draining into the brain. Other devices that utilize power source, resistors, thermistors, and other electronics to create thermal effects (e.g., resistors generating heat) and control temperature may also be employed.

In one aspect of the disclosed embodiments, active thermal transfer devices may be used in conjunction with gel-pack devices described herein, for example, in a fluid-filled pack that also contains a resistive heating element. Active thermal transfer devices may not necessarily be surrounded by a gel-like substance, but may be instead simply enclosed in a flexible pack-like support structure made of a material that will allow for sufficient thermal exchange with skin. Active thermal devices may be fashioned so that they appear similar to the flexible thermal pack similar to those in FIGS. 1, and 6 through 8, with features that allow the thermal pack to come into intimate contact with ABTT terminus 20 and skin overlying one or more facial veins 12, 14, 16, and 18. Active thermal transfer devices may also be used in eyeglasses-type support structures similar to those in FIGS. 10 through 17. Additionally, these active thermal transfer devices may be incorporated into any of the support structures described herein, or in conventional support structures that may be worn on the head and face including, but not limited to, a mask, eyeglasses, goggles, helmet, patch, headband, clip, cap, or they may be configured to be held by a user and manually placed in direct contact with ABTT terminus 20 and/or veins 12, 14, 16, and 18, or may be attached to ABTT terminus 20 and/or veins 12, 14, 16, and 18, or other facial areas using an adhesive patch or strip. The portion of the thermal pack device which comes in contact with the skin of the face may be comprised of a material that is foam, rubber, MYLAR or other material to provide additional comfort. Active thermal transfer devices, when used in conjunction with one of the herein described support structures may also comprise an insulating layer on the outer wall as described in detail above for gel pack-type devices. Active thermal transfer devices may also employ the use of a mesh lining on the interior wall of the device to slow thermal transfer if needed. However, a lining may not be necessary, as an active-type or thermoelectric device may allow a user to control thermal transfer adequately without the use of a lining.

Active thermal transfer methods provide additional benefits to the thermal transfer pack. While a fluid pack may be more suitable for consumer or home use, the time of use may be limited to the thermal retention time of the particular substance contained within the pack. There will also not always be a convenient way to heat or cool the device before use. Active thermal transfer devices that may be powered by a portable power source such as a battery or solar panel can have many applications for cooling or heating the brain in remote settings such as military operations or some outdoor activities such as mountaineering, ice climbing, hiking, boating, and the like. Active thermal transfer devices connected to a power source may also be more practical for hospital uses such as surgeries, where the pack must be used for an extended period of time without interruptions for re-heating or cooling the pack. Active thermal transfer methods also allow for the temperature to be more accurately and consistently controlled, so that a specific, determined temperature may be applied.

The aspects of the disclosed embodiments may also comprise a display, such as an alphanumeric display, including, but not limited to, a liquid crystal display (LCD), a plasma display panel (PDP), and a field emission display (FED). In an alternate embodiment, the apparatus comprises an audio output that may be provided with an audio source comprising recorded audio clips, speech synthesizers, and voice emulation algorithms to report user settings and current brain temperature audibly. Other display or reporting apparatus, devices or mechanisms may include an alarm, indicator light, and other electronics configured to alert a user when a temperature is above or below a predetermined threshold temperature. It should be understood that the alert or alarm may be visual, auditory, or vibrational.

The apparatus of this disclosure may also comprise a communications interface adapted to transmit data captured by the apparatus to a computer system. In such embodiments, the communications interface selected may be any suitable interface, including, but not limited to, a serial, parallel, universal serial bus (USB), FireWire, Ethernet, fiber optic, co-axial, and twisted pair cables. In a further embodiment, the device may also comprise a transmitter adapted to transmit temperature measurement data to a remote computer processor or user. A remote computer processor may be a cellular or wireless handheld device, personal computer, internet database, or the like. In such embodiments, remote users may be physicians, research institutes, specialists, nurses, hospice service providers, insurance carriers, and health care providers.

The support structure may comprise a simple system that provides consistent thermal energy, where the temperature may not be adjusted, but more preferably, the structure will comprise a control unit with an input device that may be, for example, hard or soft keys, dials, knobs, or touch screens, for customizing the temperature threshold and alarm settings. Regulatory electronics may also be automatically controlled by threshold sensors and regulators designed to adjust settings based on information obtained from current measurements rather than user input. For example, in a glasses frame-type structure, the right nose pad of the eyeglasses may have a temperature sensor while the left side is adapted with the cooling/heating device to apply or remove heat from ABTT terminus 20 and veins 12, 14, 16, and 18 according to temperature measurements obtained on the opposite side.

Figure 6:
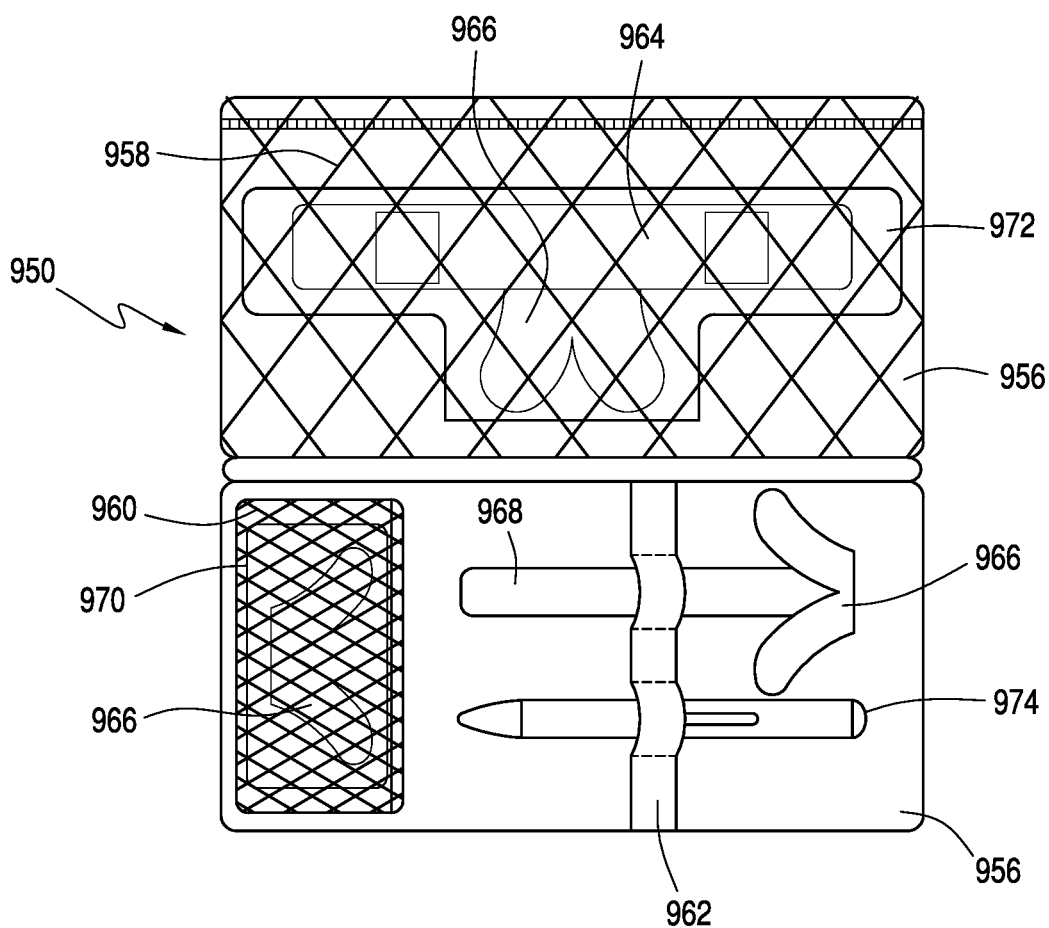
FIG. 6 is a top view of the thermal pack kit of FIGS. 4 and 5, when the thermal pack kit is open.

Any and all of the separate pieces or components of the structures and devices may be stored together in a kit or storage compartment, such as a thermal pack bag shown in FIGS. 4-6 and indicated generally at 950. Thermal pack bag 950 may be closed or secured by, for example, a zipper 952. Thermal pack bag 950 may also include a fastening mechanism, apparatus, or arrangement 954 for securing thermal pack bag 950 to a belt, backpack, equipment rack, etc. Such a storage compartment may comprise a power source and an electric or solar heating element or cooling element or resistors for heating or cooling the thermal transfer substance in the gel pack, thus allowing the device to be easily transported to and used in remote areas where the device may not be easily heated or cooled using conventional methods such as heated water, microwave, or freezer.

Such a storage compartment may also comprise a thermally retentive material for maintaining the temperature of the thermal pack and preventing thermal transfer to the environment, e.g., insulation 956. The interior of thermal pack bag 950 may include retention features such as meshes 958 and 960 and strap 962. Various components, such as a headband 964, either with or without adjustable plate and nodes 966, separate adjustable plate and nodes 966, and adjustable plate and nodes 966 configured with a handle 968 may be located inside thermal pack bag 950. Some elements of thermal pack bag 950 may be included in recesses 970 and 972 sized and dimensioned for the respectively stored elements. In an exemplary embodiment, the kit includes a thermometer 974 for measuring the thermal pack temperature prior to it being used. A thermal pack that is too cold can cause nerve damage. Ideally, prior to use, the thermal pack is at 5 degrees Celsius. The kit also allows one or more thermal transfer devices to be easily transported to and used in remote areas where the device may not be easily heated or cooled using conventional methods such as heated water, microwave, or freezer. Another object of the portable kit is to provide an interior that is thermally retentive for thermal pack 950.

Figure 39:
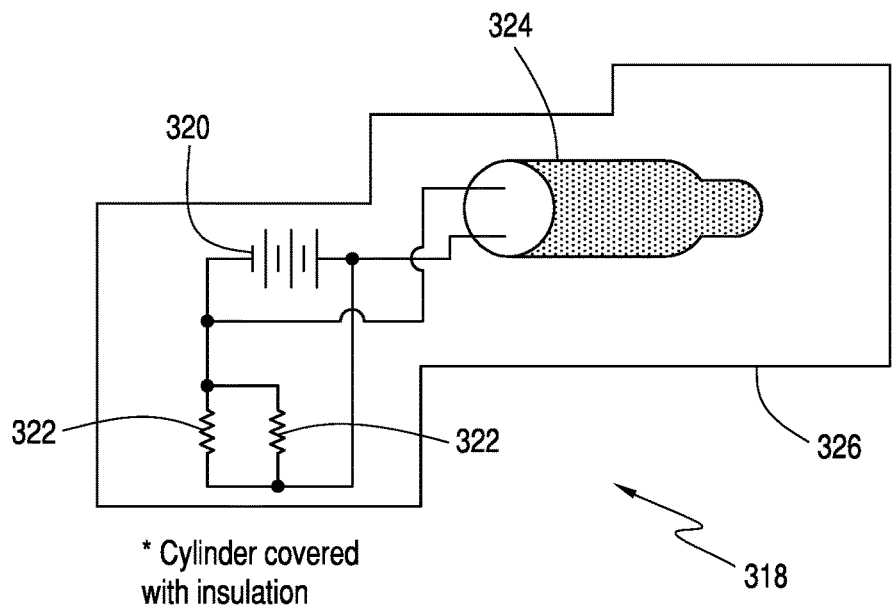
FIG. 39 is a simplified schematic of an electronics portion of an active thermal transfer device with a manual temperature control, in accordance with an exemplary embodiment of the present disclosure.
Figure 40:
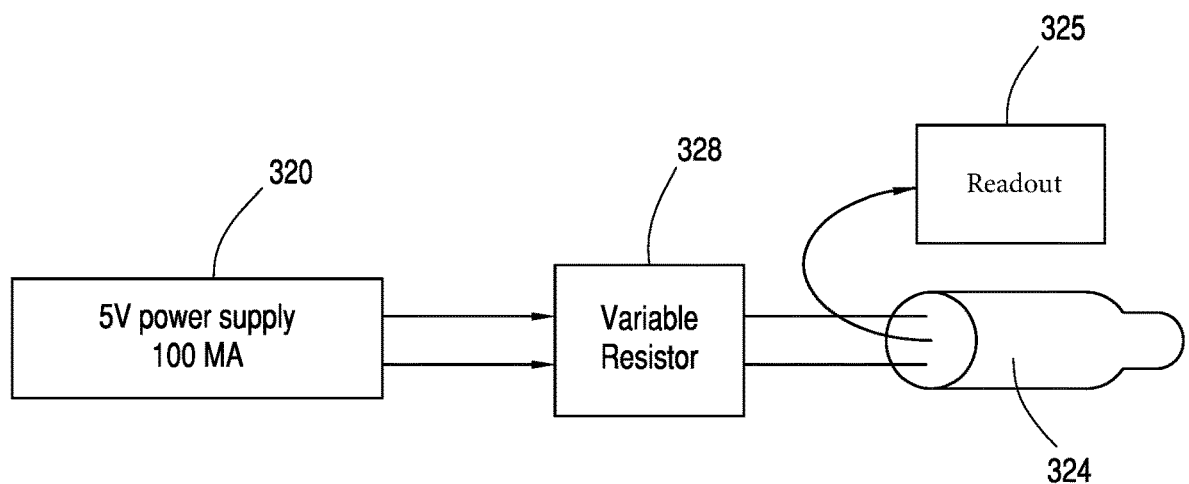
FIG. 40 is a block diagram of an ABTT heat transfer system, in accordance with an exemplary embodiment of the present disclosure.

FIGS. 39 and 40 show a schematic and block diagram, respectively, for a non-limiting example of an electronics portion for an active thermal transfer device with a manual temperature control function for heating the brain. As shown in FIG. 39, a control circuit 318 may include a power source 320, which in an exemplary embodiment may generate 5 VDC, two resistors 322 connected in parallel, which in an exemplary embodiment may be 100 ohm resistors, a thermistor 324 that in an exemplary embodiment may be 10 K ohm, a readout 325 and a potentiometer 328 to control temperature. These components may be positioned or located in cylinder 326.

In this particular example, with potentiometer 328 set to 0 ohms, the temperature of a probe or a contact portion of a thermal exchange device is greater than 45 degrees Celsius and with the potentiometer adjusted to 50 ohms the temperature of the probe stays consistently around 39 to 40 degrees Celsius while in contact with ABTT target area 20. In this embodiment, a setting chosen by a user will provide continuous thermal energy according to the settings until the user either alters the desired temperature setting or turns the active thermal transfer device off. In alternate embodiments, the active thermal transfer device may also include a timer for automatically turning the active thermal transfer device off after a predetermined threshold for time elapsed has been exceeded or temperature has achieved a predetermined threshold.

It is understood that the foregoing description of an active thermal transfer device is a specific example and that any combination of one or more resistors, thermistors, and potentiometers may be adequate for controlling applied temperature to ABTT terminus 20 and one or more blood vessels 12, 14, 16, and 18. It should also be understood that the above-described electronics portion may also comprise display units and control units such as a screen, indicator lights, and hard or soft keys that are required for a user to set the desired temperature level. In the previously described exemplary embodiment, the heating element and thermistor are located inside an aluminum cylinder and are covered with insulation to prevent the cylinder portion from becoming excessively hot to the touch and to prevent heat loss to the surrounding environment. It should be understood that the heating element may also be contained in a fluid-filled sack or pouch or covered with a material having low thermal conductivity as long as the heat element does not come in direct contact with the skin. The cylinder is configured with dimensions that fit the ABTT area and/or the veins draining to the brain.

Figure 41:
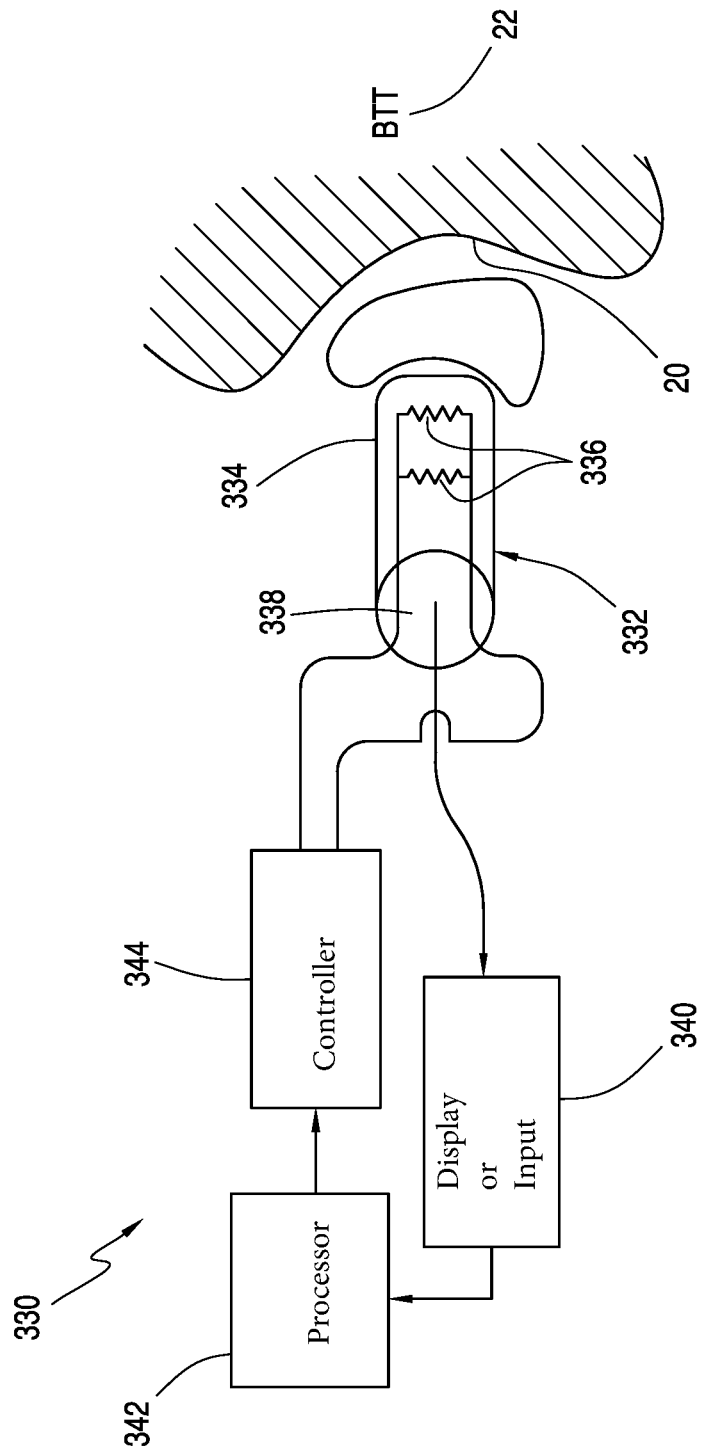
FIG. 41 is a simplified representation of an active heating or cooling device, in accordance with an exemplary embodiment of the present disclosure.

An alternate embodiment of an active heating or cooling device in accordance with an exemplary embodiment of the present disclosure is presented in FIG. 41 and indicated generally at 330. Active device 330 is configured as an automatic active thermal transfer device designed to self-regulate thermal transfer to or from relevant facial areas and ABTT terminus 20. It should be understood that active device 330 may include fewer or additional components than what is presented in FIG. 41, as described in detail herein. Active device 330 of FIG. 41 includes a heating or cooling element 332 encased in a cylinder or probe 334 configured to lie in intimate contact with the skin of ABTT terminus 20 and/or veins 12, 14, 16, and 18 similar to the configurations of the manual devices disclosed herein. An interface 335 to prevent direct contact with skin of ABTT 20 can be used with active device 330.

In an exemplary example of a heating device, element 332 may comprise resistors 336. In addition to the heating/cooling element, an exemplary active device 330 includes a thermistor 338, display or input 340, a CPU or processor 342, and a controller 344. When a desired temperature setting is input by a user, the controller 344 regulates the amount of thermal energy to be generated by heating/cooling element 332 in order to achieve the proper thermal transfer with ABTT terminus 20 and/or veins 12, 14, 16, and 18. Thermistor 338 obtains constant thermal data from ABTT terminus 20, which may also be displayed on a readout or display 340 of active device 330. CPU or processor 342 is configured to analyze the data captured thermistor 338 as compared to a temperature set point entered into CPU 342, which may be done through display/input 340 or with other conventional apparatus. By comparing the output of thermistor 338 to an established set point, and adjusts controller 344 as needed, the temperature of heating or cooling element 332 may be regulated more consistently and accurately.

The configuration of FIG. 41 is preferred for situations such as, for example, treatments where it is desired that the brain remain at a constant temperature for an extended period of time. A doctor or nurse, for example, could input the desired brain temperature, i.e., the set point, to be achieved. Over time, an equilibrium between thermal energy applied by active device 330 and the temperature of the brain will be achieved. Rather than having to manually change the temperature setting of active device 330, as would be the case with a manually controlled device, CPU or processor 342 in combination with thermistor 338 and controller 344 will either increase or decrease thermal exchange so that the desired brain temperature will be attained. Such an automatic device is the preferred embodiment for use in conjunction with support structures that are anchored to the face using an adhesive, a headband, eyeglasses, or a structure similar to that of FIG. 42, which allows for intimate and continuous contact with the skin for maximum thermal transfer. It should be understood that the automatic thermal transfer device of this embodiment may also be used in a handheld device or in conjunction with any of the mask, helmet, clip, cap, or other support structures mentioned herein.

FIGS. 42-48 show another active heating or cooling device in accordance with an exemplary embodiment of the present disclosure and indicated generally at 346. Active device 346 is a thermoelectric heater/cooler, for example, a Peltier effect module, which is used to generate thermal energy for transfer with the skin of ABTT terminus 20. It should be understood that this Peltier module may also be used interchangeably with any of the support structures mentioned in the above disclosure and that the patch support structure is merely a preferred example and is not intended to be limiting. The use of a Peltier junction allows the device to provide both heat and cold to ABTT terminus 20, or to both apply to and remove thermal energy from the brain. The resistive heating element in the previous example is limited to heating, and similarly, a cooling element would be limited to cooling. A device employing the use of a Peltier module may provide benefits of heating and cooling to the brain using a single device.

Figure 42:
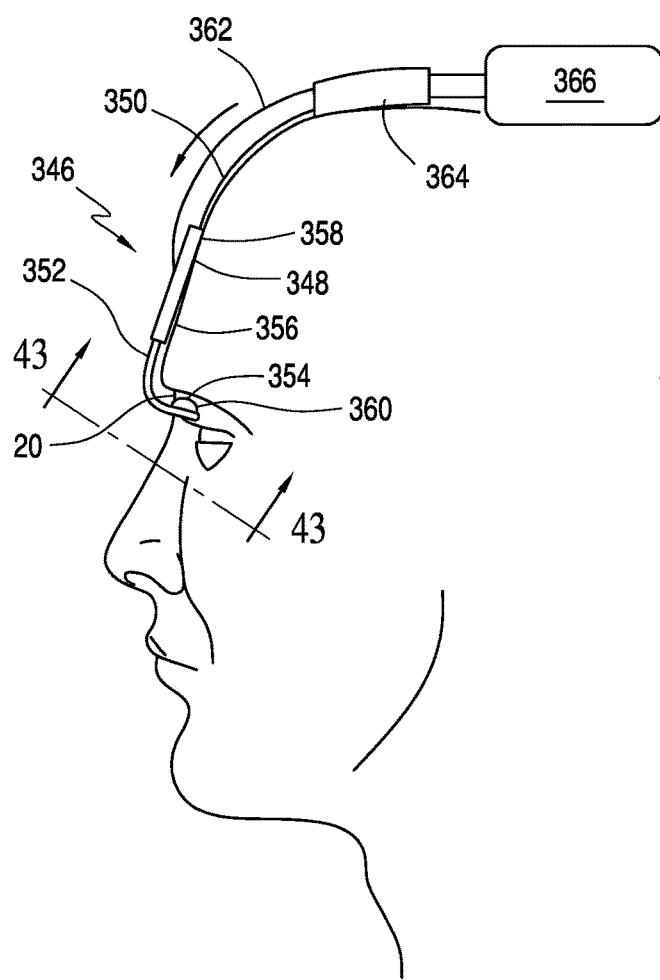
FIG. 42 is a view of a device for automatically regulating the temperature of the ABTT terminus positioned on a subject or patient, in accordance with an exemplary embodiment of the present disclosure.
Figure 46:
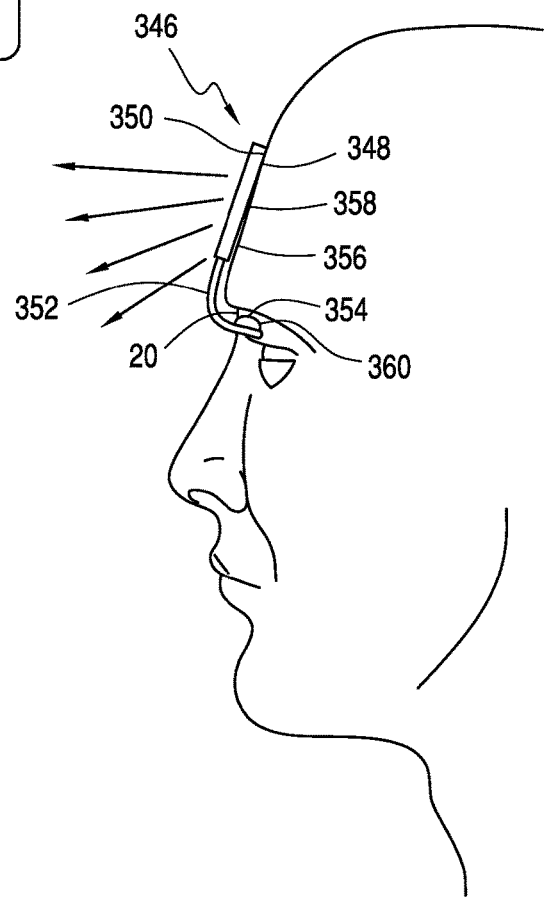
FIG. 46 is a view similar to FIG. 42, with an alternative embodiment of the device shown in FIG. 42, in accordance with an exemplary embodiment of the present disclosure.

The device of FIGS. 42 and 46 includes a patch 348 for securing at least a portion of active device 346 to forehead 350, a flexible arm 352 that extends across the brow bone into the eye area, and a thermopile/Peltier junction 354 that is configured to be placed in direct contact with ABTT terminus 20. In order to secure active device 346 to forehead 350, patch 348 includes an adhesive strip 356 and may also comprise an insulating material 358 between adhesive 356 and active device 346 to protect forehead 350 from any excess heat that may dissipate from active device 346. In an exemplary embodiment, flexible arm 352 is formed of a flexible metal and is curved or arched so that when patch 348 is adhered to forehead 350, thermoelectric device 354 will contact ABTT terminus 20. In an alternate embodiment, flexible arm 352 may be made of any material that can be configured to take on the same particular shape such as, for example, a flexible plastic. Thermoelectric device 354 also includes a Peltier junction and may also comprise a fluid-filled sack, pouch, or a rounded piece of foam or rubber material 360 for comfort when the active device 346 comes in contact with the skin of ABTT terminus 20. The Peltier junction is configured to either supply or remove thermal energy to or from ABTT terminus 20 and/or veins 12, 14, 16, and 18 based on desired temperatures settings which may either remain fixed or may be adjusted by a user.

As the heat removed from the brain using a Peltier module must be dissipated, the present embodiment includes a heat sink. Active device 346 of FIG. 46 simply utilizes patch 348 as the heat sink. As such, the heat removed from the Peltier junction is conducted by the metal of patch 348 and heat is radiated into the surrounding environment. The head is protected from the excess heat by insulating material 358 on patch 348 portion of active device 346. This embodiment is less preferred, however, as an exterior surface of active device 346 will be very warm and possibly hot to the touch.

Figure 47:
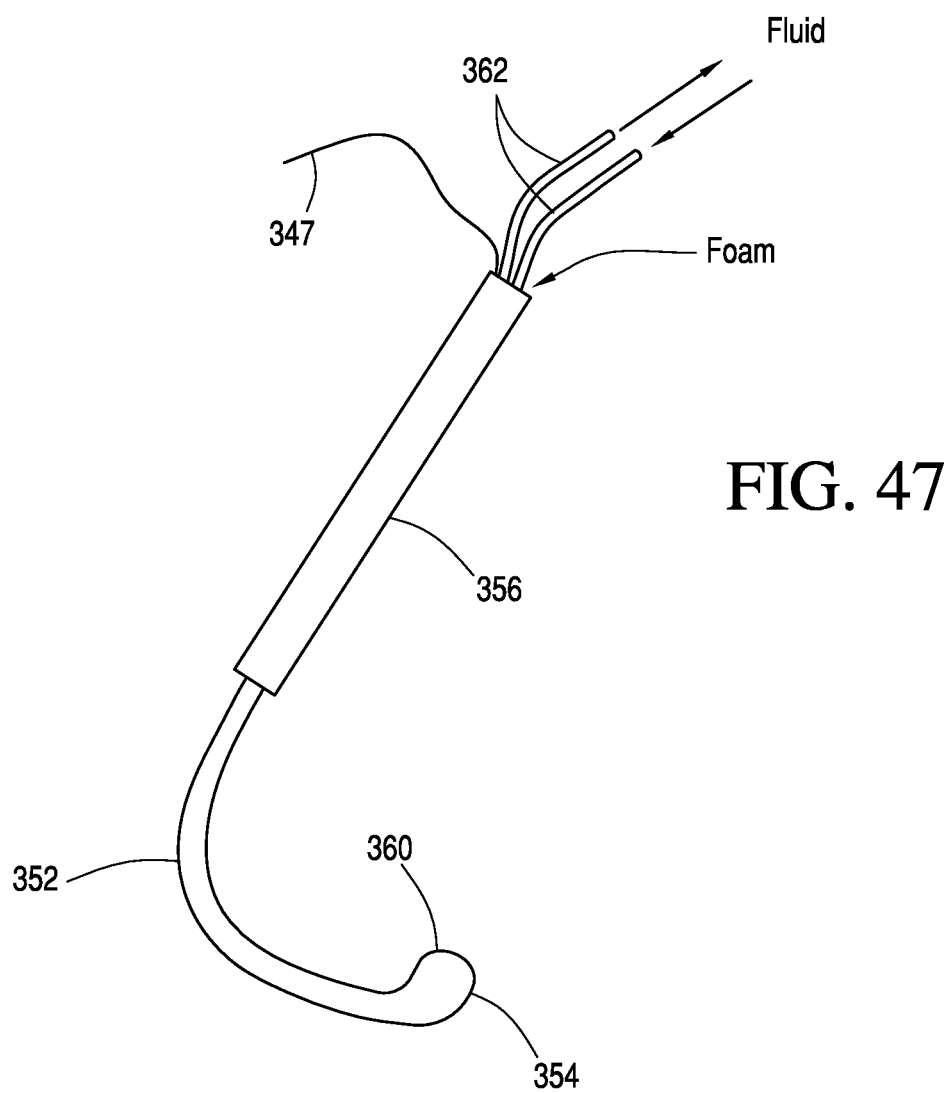
FIG. 47 is a side view of the device of FIG. 42.
Figure 48:
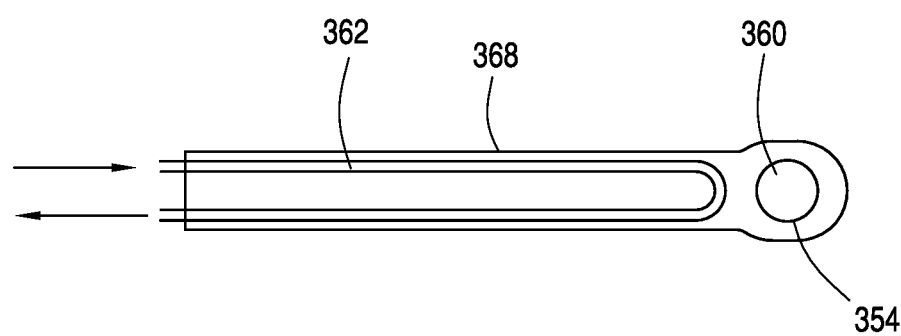
FIG. 48 is a view similar to FIG. 43, showing additional details of the features of FIG. 43.

The configuration of active device 346 as shown in FIGS. 42, 47 and 48 is a more preferred embodiment, in which a series of tubes or hoses 362 runs from a pump 364 through patch 348 and flexible arm 352 of active device 346 and to the Peltier junction 354, looping back to a reservoir 366 that is exposed to air so heat can escape into the environment. In this exemplary example, the heat is carried away by water or other thermally retentive fluid, which is pumped through tubes 362 to and from reservoir 366. As a result, heat is no longer radiated directly from patch 348 of active device 346, thus eliminating the discomfort of having the heat radiating portion lying close to forehead 350. Active device 346 may further include wires 347 to a controller (not shown) for readout of temperature.

Figure 43:
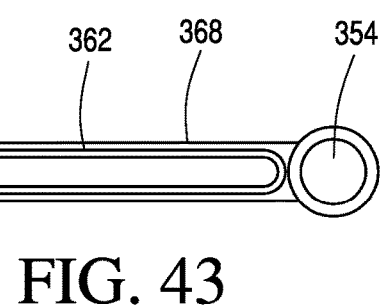
FIG. 43 is a cross-sectional view of a portion of the device of FIG. 42, along the line 43-43 in FIG. 42.
Figure 44:
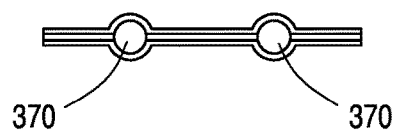
FIG. 44 is an end view of the portion shown in FIG. 43, along the line 44-44 in FIG. 43.
Figure 45:
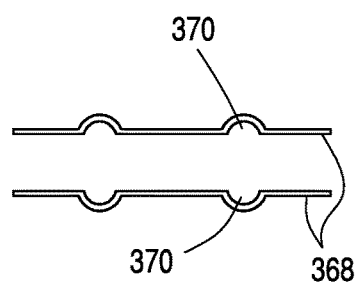
FIG. 45 is a view of the portion shown in FIG. 44, in accordance with an exemplary embodiment of the present disclosure.

In this exemplary example and shown in more detail in FIGS. 43-45, patch 348 may be comprised of two sheets of stamped metal 368, which include grooves 370 adapted to hold tubes 362, welded together. Tubes 362 may be comprised of plastic or another material that is suitable for carrying flowing liquid. Active device 346 also includes a power source for driving pump 364. The Peltier junction 354 is close to ABTT target area 20 so that minimal heat loss occurs between the junction 354 and ABTT terminus 20. Hoses or tubes 362 simply act as a heat sink, not as pathways for thermal energy delivery. In a less preferred embodiment, however, it is understood that the Peltier junction can be placed at any point on the device and thermal energy may be delivered using flowing fluid through hoses, though more energy is wasted using this method.

Figure 52:
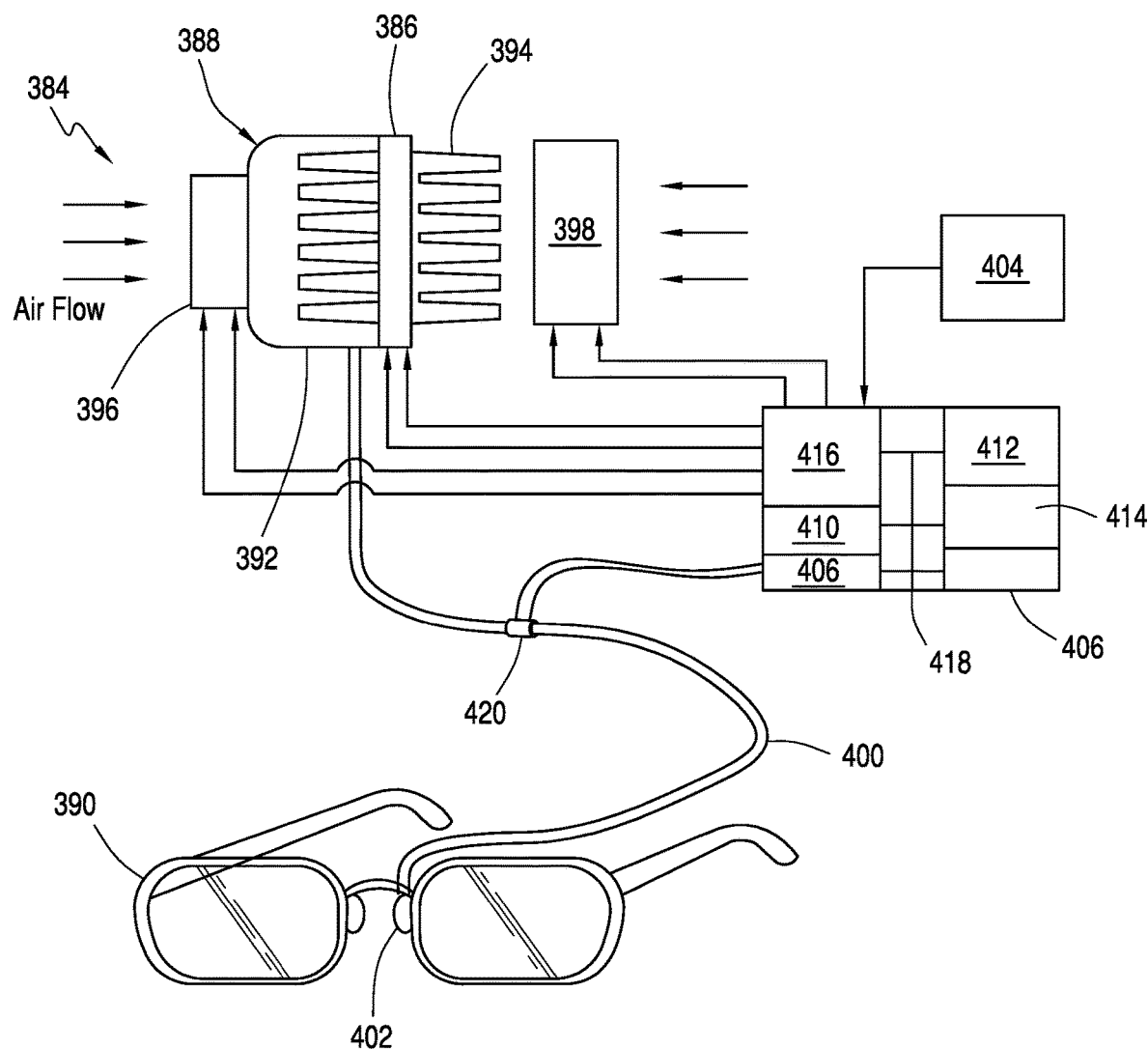
FIG. 52 is a view of an active heating and cooling apparatus for delivering heat or cooling to the ABTT terminus, in accordance with an exemplary embodiment of the present disclosure.

FIG. 51 shows a head mounted thermoelectric cooling and heating system in accordance with an exemplary embodiment of the present disclosure and indicated generally at 370. In the exemplary embodiment, system 370 includes a Peltier junction 372, attached to a copper plate 374. System 370 further includes a copper wire 376, which in an exemplary embodiment is approximately 0.15 inches in diameter, directly attached to and mounted on copper plate 374. Wire 376 terminates in an ABTT contact 378, which is configured to fit the anatomy of the face of the subject and touch ABTT target area 20, thus enabling thermal transfer to efficiently occur with ABTT target area 20. Mounted on the opposite side of Peltier junction 372 from copper plate 374 is a heat sink 380. System 370 is configured to be supported by clipping onto a headband or a glasses frame structure, as shown in FIG. 52. Peltier junction 372 is configured to receive energy from a remote pulse wide modulation (PWM) control receiving its signal from a thermistor 382 mounted in conjunction with ABTT contact 378.

An alternate Peltier heating/cooling system using eyeglasses for a support is presented in FIG. 36 and indicated generally at 384. System 384 includes a Peltier junction 386 which heats or cools using air flow and which is positioned a spaced distance from ABTT target area 20. System 384 a heating/cooling unit 388 which is separate from a support structure 390 and which includes Peltier junction 386 and a first heat sink 392 positioned on a first side of Peltier junction 386, and a second heat sink 394 positioned on a second, opposite side of Peltier junction 386. Each heat sink is preferably in direct contact with Peltier junction 386. System 384 may also include a first fan 396 positioned to direct air onto first heat sink 392 and a second fan 398 positioned to direct air onto second heat sink 394. System 384 may also include an insulating cover (not shown).

Heating/cooling unit 388 is connected to support structure 390, which in the exemplary embodiment of FIG. 52 is an eyeglass frame, using a tube or hose 400 that is configured to carry heated or cooled air into a nose piece 402, which serves as a thermal transfer point with ABTT terminus 20. System 384 may also include a power source 404, and a control unit 406. Control unit 406 may include a PWM (Pulse Wide Modulation Control) 408, a CPU or microprocessor 410, an input unit 412, a display unit 414, a power distribution unit 416, and a bus 418 connected to each of the elements of control unit 406 to provide communication between the elements. System 384 may also include a temperature sensor to measure the temperature of the air flowing into heating/cooling unit 388 as well as a temperature sensor 420 and/or controller and processor for measuring and regulating the heated or cooled air flowing out of unit 388 through tube or hose 400. It should also be understood that although only one nosepiece is depicted in this example as having the thermal transfer point, the heated or cooled air hoses may also be configured to deliver heated or cooled air to any portion of support structure 390, and to both of nosepieces. In an alternate embodiment, system 384 can be configured to deliver or remove thermal energy using flowing water instead of air. In this alternate embodiment, system 384 would further comprise a water pump (not shown).

Figure 49:
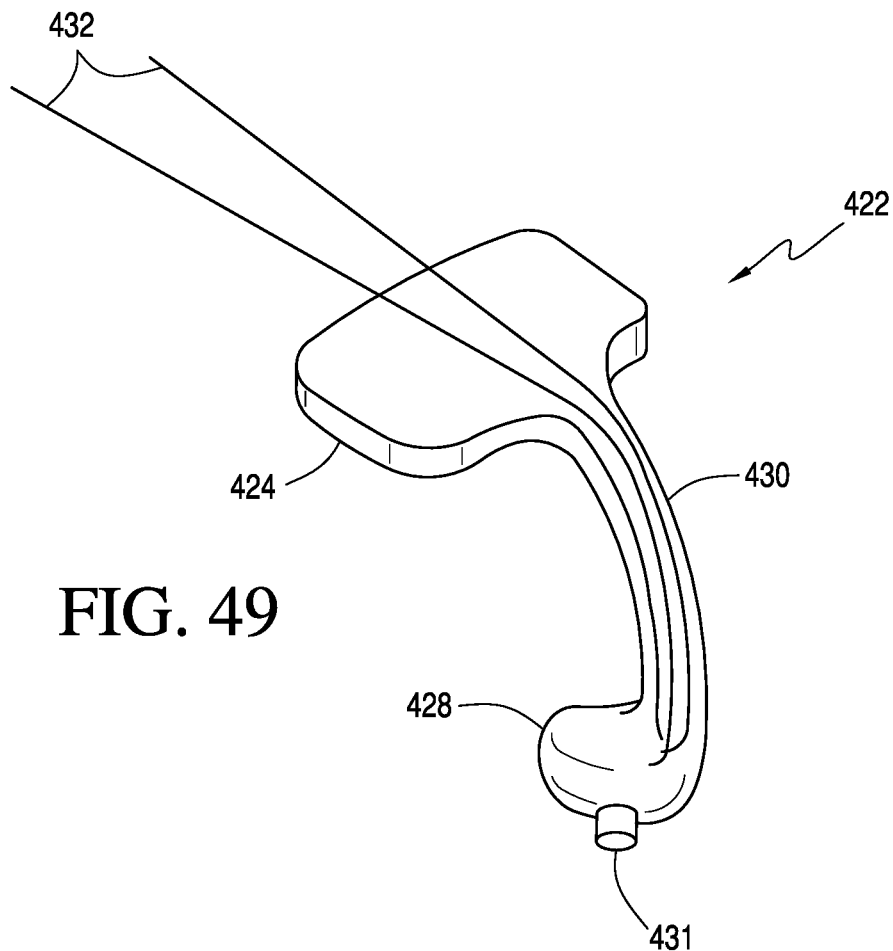
FIG. 49 is a view of another apparatus for cooling and heating the ABTT terminus, in accordance with an exemplary embodiment of the present disclosure.
Figure 50:
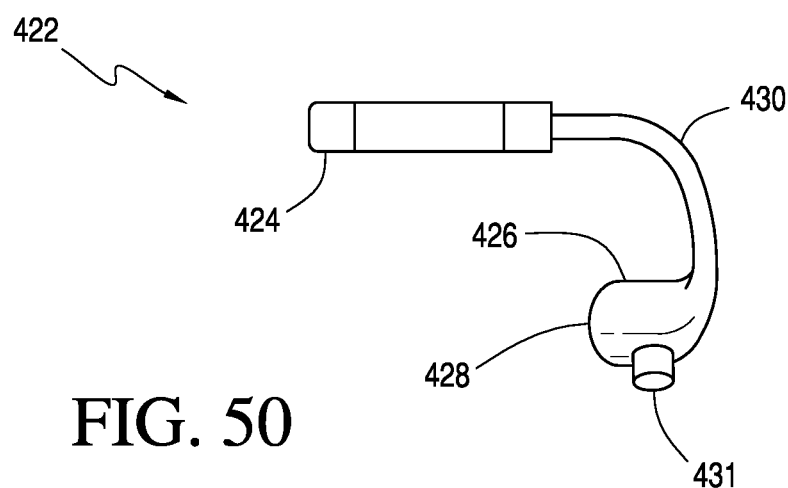
FIG. 50 is a side view of the apparatus of FIG. 49.

An active thermal transfer device in accordance with an exemplary embodiment of the present disclosure is shown in FIGS. 49 and 50, and indicated generally at 422. Active thermal transfer device 422 includes and adhesive layer 424, and is configured to be secured to a forehead or a brow area using adhesive layer 424, similar to other devices described herein. The exemplary active thermal transfer device 422 includes a multi-layer Peltier stack 426, which enables a higher temperature differential than a single Peltier junction. In this example, Peltier stack 426 is positioned or located on a tip of active thermal transfer device 422, and active thermal transfer device 422 is configured to position a contact surface 428 on the skin of ABTT target area 20. Active thermal transfer device 422 further includes a flexible arm 430, which is preferably comprised of metal to conduct heat away from Peltier stack 426 when Peltier stack is used for cooling. Such an arrangement allows the heating or cooling of the Peltier apparatus to be concentrated on the small portion of skin in contact with active thermal transfer device 422. Also shown schematically in FIG. 49 are wires 432 used to supply power to Peltier stack 428. In this embodiment, temperature applied or removed may be controlled using a thermistor mounted between the Peltier junction and the subject's skin. The temperature reading of a thermistor 431 is used to control the energy applied to the Peltier junction stack. Initially thermistor 431 measures the temperature of the skin, then thermal exchange device is activated and thermistor 431 measures the temperature of the thermoelectric device 422. After thermal effect is achieved and thermoelectric device is turned off, then thermistor 431 measures the post-operation temperature.

Figure 49A:
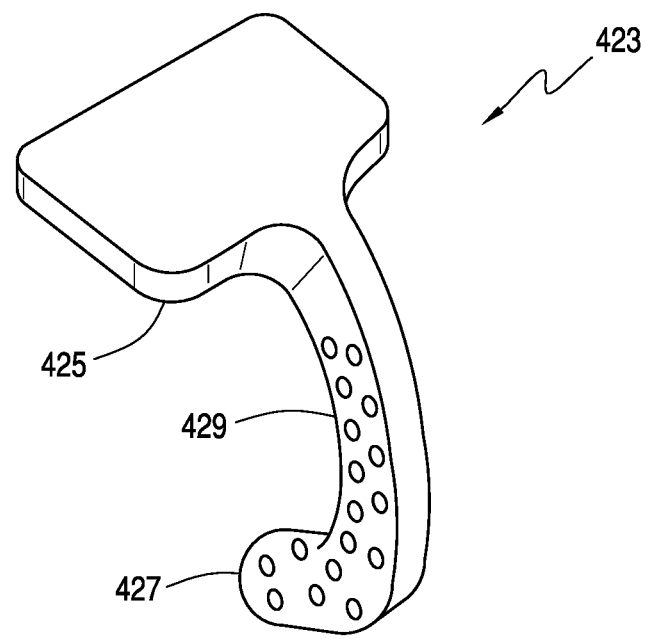
FIG. 49A is a view of an apparatus for cooling and heating the ABTT terminus similar to the apparatus of FIG. 49, using a thermally retentive material in place of active heating or cooling.

FIG. 49A shows a passive thermal transfer device in accordance with an exemplary embodiment of the present disclosure, indicated generally at 423. Passive thermal transfer device 423 includes an adhesive layer 425, and is configured to be secured to a forehead or a brow area using adhesive layer 425, similar to other devices described herein. The exemplary passive thermal transfer device 423 includes a node 427 configured to contain a thermally retentive material and an arm 429, which in an exemplary embodiment is configured to include thermally retentive material.

Figure 49B:
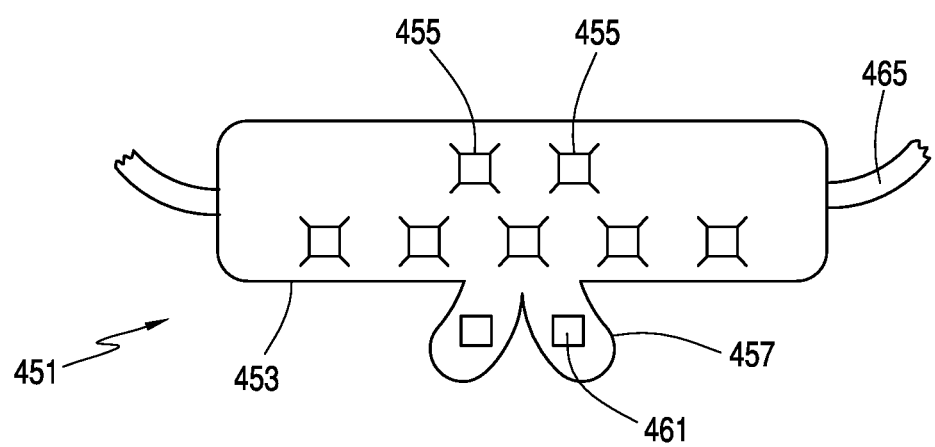
FIG. 49B is a view of an active apparatus for cooling and heating the ABTT terminus in accordance with an exemplary embodiment of the present disclosure.

FIG. 49B is a view of an active thermal transfer device in accordance with an exemplary embodiment of the present disclosure, indicated generally at 451. Active thermal transfer device 451 includes an elongated body 453, and is configured to be secured to a forehead using fastener 465 and the like, similar to other devices described herein. Active thermal transfer device 451 includes a plurality of thermoelectric devices 455 in elongated body 453, and includes at least one node 457 configured to contact ABTT terminus when device 451 is positioned on a person's head. In the exemplary embodiment of FIG. 49B, each node 457 contains a thermoelectric device 461 configured to provide a thermal exchange with ABTT terminus 20.

Figure 53:
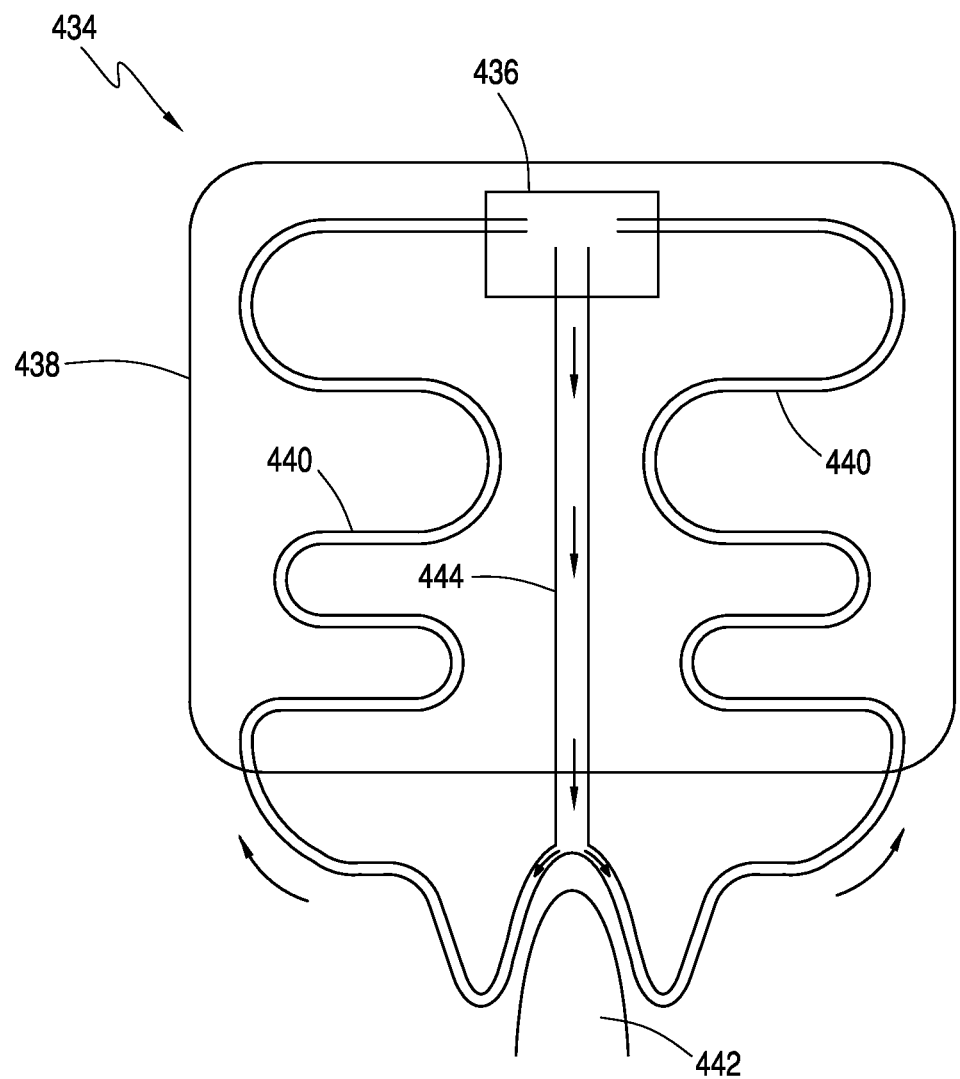
FIG. 53 is a schematic view of a heat exchange device mounted to the back of a helmet, in accordance with an exemplary embodiment of the present disclosure.

Yet another exemplary active thermal transfer device is shown in FIG. 53 and indicated generally at 434. Active thermal transfer device 434 includes a Peltier heat exchanger and pump assembly 436 mounted to a back of a helmet 438. Active thermal transfer device 434 also includes a flexible membrane with tubing 440 positioned therein to direct a flow of a heat exchange fluid. The heat exchange fluid can assist in the cooling or heating of a head. The thermal flow would be from Peltier heat exchanger and pump assembly 436 through a tube 444 going directly to a nose piece 442 attached to at least one ABTT terminus 20 of a subject or patient, represented by nodes 443 and 445. The return fluid will go through a series of serpentine tubing or hoses 440 over the patient's head and return to the temperature controlled fluid source in Peltier heat exchanger and pump assembly 436.

The aspects of the present disclosure provide methods for applying or removing thermal energy from ABTT target area 20 and, as a result, from the brain. The method of the present disclosure also discloses detecting brain temperature, displaying gathered data, processing data, and adjusting or controlling output temperature. The present disclosure also relates to treatments of various diseases and conditions through the use of thermal treatments applied to ABTT terminus 20 and one or more of veins 12, 14, 16, and 18. Examples of specific conditions and diseases that may be treated and the methods for treating each will be provided herein, which are designed to be non-limiting and for description purposes only.

A circadian rhythm is a 24-hour cycle in the biochemical and physiological functions of the human body. Understanding the circadian thermal cycle is vital to understanding many of the biochemical and physiological behaviors of the human body, and can also serve as a baseline for comparison across population groups. Currently, continuous measurement of core temperature relies on invasive methods, such as blood, bladder, rectal, and esophageal thermometry. Since temperature cannot be measured by conventional methods without breaks in measurement and for long periods of time (unless a patient is in the Intensive Care Unit for a long time), gaps exist in the thermal curves that result from this type of testing.

The present disclosure provides a non-invasive measurement of body temperature and, as a result, an effective non-invasive creation of thermal circadian profiles (thermal circadian signatures) by using the Abreu brain thermal tunnel (ABTT) as a window to the core of the brain that provides an accurate representation of the brain's temperature. The present disclosure also provides a method and device for diagnosing various diseases and conditions based on the comparison of these thermal circadian profiles with a database of predetermined profiles, or a library of baseline profiles.

Since the ABTT enables, for the first time, a continuous temperature measurement of a body's core and brain temperature, it allows for continuous and long term measurement and recording of thermal patterns in the human body, without the gaps in measurement that are often associated with other measurement means such as, for example, conventional measurements by oral or anal thermometers. In addition, by applying the teachings of the present disclosure, temperature patterns may be magnified for closer study and a more precise comparison of thermal curves and signatures. As a result, it is possible to obtain accurate and detailed thermal circadian profiles for use in the study of circadian rhythms and the comparison with abnormal cycle results.

An exemplary disease to be studied using comparisons of thermal circadian profiles is Alzheimer's disease. As shown in studies by the Applicant, human circadian thermal patterns show a peak in brain temperature during daytime hours and the lowest body temperature around 5 a.m. This pattern reveals an important relationship between brain temperature and sleep cycles that can be used to help identify problems and research potential solutions associated with Alzheimer's disease.

Alzheimer's disease is a progressive neurologic disease of the brain that leads to the irreversible loss of neurons and dementia. The lesions of Alzheimer's disease begin in the hippocampus, which is adjacent to the temperature control center of the brain, and the internal (intracranial) terminus of ABTT 22. Studying the thermal circadian patterns of Alzheimer's sufferers via the ABTT allowed identifying a link between the sleep dysfunction and the damage to the temperature control center of the brain and body.

A study by Applicant, in accordance with the present disclosure, was conducted to monitor the body temperature of Alzheimer's patients continuously, using a sensor placed at ABTT target area 20 in order to create a thermal circadian profile. The thermal circadian profiles of Alzheimer's patients revealed a large pattern shift from a normal rhythm so that the lowest temperature was seen in the range of around 9 a.m. and 10 a.m. to 1 p.m., which is about 5-6 hours later than the normal low point. Similarly, the highest temperatures were shifted into the nighttime hours, thus explaining the tendency of Alzheimer's patients to wake in the middle of the night. In addition, it was noted by Applicant that the extent of the shift in the brain thermal circadian profile of a given Alzheimer's patient is nearly proportional to the extent of lesions and the progression of the disease.

With the creation of a thermal circadian profile for diseases such as, for example, Alzheimer's, the continuous monitoring of thermal circadian rhythms of patients via ABTT 22 can be used to diagnose the onslaught of such diseases effectively. For example, a person who has a genetic history of Alzheimer's disease can begin monitoring his thermal circadian rhythms at an early age and, if a similar shift in the profile occurs, an earlier diagnosis of the disease can be made. Earlier detection of the shift, especially in younger people, may help to identify a predisposition to the disease and allow for earlier treatment that may, in turn, slow progression and control the effects of the disease. In addition, the thermal profile for Alzheimer's disease may enable physicians to better distinguish between Alzheimer's disease and normal or non-Alzheimer's dementia, as well as better judge the extent of the progression of the disease and the lesion in the brain. Since each person's thermal signature may vary slightly, it will also allow researchers and doctors to provide patients with personalized care and treatment based on each person's needs. The embodiments of the present disclosure can aid patients suffering from Alzheimer's by using a novel and noninvasive apparatus that applies thermal energy to the brain (to heat the brain) through ABTT target area 20 and associated vessels, as disclosed herein.

It should be understood that the apparatus of the present disclosure is not limited to the creation of thermal circadian profiles for Alzheimer's disease, and is applicable and may be used to create the thermal signatures for many different diseases and conditions. Non-limiting examples of other diseases and conditions that may also be diagnosed as well as treated using simple, non-invasive temperature measurements and thermal exchange devices disclosed herein, are hyperthermia, hypothermia, Multiple Sclerosis, breast cancer and other forms of cancer, sleep awareness, dehydration, migraine, pain, Parkinson's disease, Huntington's disease, stroke, Amyotrophic Lateral Sclerosis (ALS), epilepsy, reproductive issues, thyroid dysfunction, depression, seasonal affective disorder, fever, and hormonal dysfunction.

Traditional treatment for epilepsy consists primarily of seizure-preventing medications. If drugs are not effective, brain surgery is the alternative. The present disclosure can aid patients suffering from epilepsy by using a novel and noninvasive apparatus that applies thermal energy to cool the brain through ABTT target area 20.

Embodiments of the present disclosure can also help people suffering from insomnia or sleeping problems. Applying cold to ABTT terminus 20 increased melatonin production in the pineal gland. However, a pineal gland that is overstimulated by cold temperature does not release melatonin. Therefore, the rate of cold applied to ABTT terminus 20 must be regulated. The adequate control of ambient temperature that matches the needs of body temperature, such as during sleeping, has a key effect on metabolism causing improved efficiency of enzymatic reactions that leads to improved mental ability and improved immune response.

These diseases are mentioned as an example not as a limitation for the use of the present disclosure. The thermal pack can also be used by athletes or any person that needs to cool or warm their core temperature.

The method of the present disclosure is carried out by activating a thermal sensing device, positioning a sensing element adapted for sensing thermal energy on the skin of ABTT target area 20, processing thermal data collected by the sensing device into a format that is usable for analysis, analyzing processed data, and storing processed thermal energy data. Further embodiments of the present disclosure can include, but are not limited to, displaying relevant input or data output information on a display, transmitting collected data to a remote device, server, or other output or storage device, alerting a user when threshold temperatures have been surpassed, and communicating said data by wireless or wired means to remote locations including a cell phone, computer, and the like, including using the internet, or any computer network. A processor is configured to record and process the signal (e.g., temperature) received from an ABTT sensor for at least a 24 hour period.

Any device of the present disclosure may comprise a sensing portion preferably adapted to fit the anatomy of ABTT target area 20, a controller or processor, a resistor, connectors, a non-transitory memory that is operatively linked to the controller or processor, a communications interface adapted to receive and send data within the controller or processor, and a computer program stored in non-transitory memory that executes in the controller or processor. The components of this embodiment may further comprises a database, wherein data received by the controller or processor may be stored in non-transitory memory as a database, and sorted into predetermined fields, and the database may be capable of graphical representations of the downloaded data. The graphical representations of this embodiment may include, but are not limited to, column, line, bar, pie, XY scatter, area, radar, and surface graphs or charts.

The processor of the device of the present disclosure is preferably configured to continuously record temperature data gathered by the sensing portion. More preferably, the processor is configured to record a 2 millisecond measurement from the sensing portion every 1 to 2 seconds. The database of the computer processor is preferably configured to arrange the data points in an XY graphical representation for data analysis and storage, so that the data points represent a curve. In the illustrated example using Alzheimer's disease, the measured temperature (represented as a thermal profile and/or thermal curve) is compared to stored thermal profile and/or curve that characterizes the disease being diagnosed. In the case of attempts to diagnose Alzheimer's disease (AD), the processor compares the thermal profile of Alzheimer's (stored) with the measured profile (of the person being tested). In case there is a match based on predetermined characteristics, a variety of reporting are activated based on the information received, and may include: no Alzheimer's Disease (AD) pattern, low risk for AD, high risk for AD, and AD. The same can apply to any other disorder.

In addition to the diagnosis of diseases according to the pattern of various circadian thermal profiles in a digital library and identifying a shift in normal thermal circadian patterns, the present disclosure also discloses a method for treatment of diseases by applying energy to ABTT target area 20. In the examples of the present disclosure, thermal energy is often applied to ABTT terminus 20 for treatment of disease, however, it is understood that other forms of energy may also be effectively applied to ABTT terminus 20 for treatment such as, for example, light of any type within the electromagnetic spectrum (e.g., infrared, ultraviolet, visible including fluorescent, radio, gamma, and the like), sound waves, vibration, electrical (including electrical pulses), magnetic, pressure, and the like. Devices delivering such energy forms to ABTT terminus 20 preferably conform to the dimensions of ABTT terminus 20 for optimizing delivery. This focused method and apparatus disclosed in the present disclosure allows maximizing the benefits of therapy. This approach may also preserve other body areas not configured for receiving such energy therapy thereby reducing side-effects.

The present disclosure provides a device and method for counteracting the disturbance in sleep pattern caused by damage in the brain in AD by applying thermal energy to the brain through ABTT target area 20 at predetermined times to ensure sleep during the night and wakefulness during day time. The same can be applied to other sleep disorders to assure the user sleep at night and is awake during the day The method of the present disclosure provides for the treatment of sleep disturbances associated with Alzheimer's disease describes a pre-scheduled application of thermal energy to ABTT target area 20 to preserve a normal sleep/wake cycle so the patient remains asleep during nocturnal hours and awake during the daytime hours. Since the Alzheimer's thermal circadian profile has its lowest temperature point in the period ranging from 9 a.m. to 12 p.m., the present disclosure allows for the application of thermal energy or heat to the ABTT area to prevent this drop in temperature during this time, thus keeping the patient awake during daytime hours. Similarly, as the temperature rises in the middle of the night indicating a waking period, thermal energy is removed from the ABTT (cooling the body) in order to keep the patient asleep during normal nocturnal hours.

The method of the present disclosure includes positioning a thermal exchange device (such as a thermoelectric device) adapted for delivery of thermal energy to ABTT target area 20, applying thermal energy on the surface of the skin of ABTT target area 20 and creating a thermal change in the brain temperature tunnel and, as a result, changing the brain and body core temperature, said delivery of thermal energy including the step of applying heat to the ABTT to increase the temperature of the brain during the day and the step of removing heat (cooling) the ABTT during the night. The method includes a timing device such as clock operatively coupled to a controller to apply or remove heat in accordance with the period of the day. If an electronic device is used for the application/removal of thermal energy, the method further comprises the steps of activation of the device prior to application of thermal energy, sensing the temperature of an area to which thermal energy is applied, processing data gathered by the sensing portion, controlling amount of thermal energy applied to ABTT target area 20, storing data in a memory. The method includes a processor being adapted to activate the delivery of thermal energy to the ABTT in order to normalize the sleep/wake cycle. This same method and device can be used for treating jet-lag, depression, and sleep disorders.

In order to carry out the method of the present disclosure, both passive and active-type thermal transfer devices may be used. Examples of thermal transfer devices may include, but are not limited to, cold/hot packs which comprise two layers of material fused together containing therein a substance configured to hold thermal energy such as, for example, polypropylene glycol, ice, or other gels or liquid materials; phase change cooling or heating materials; evaporative cooling or heating materials; and the like. Active-type devices may include, but are not limited to those which directly convert electrical energy into thermal energy for direct application to the skin, or those which are configured to heat or cool air or liquid configured to flow through hoses which deliver and remove thermal energy to or from ABTT target area 20. It is understood that any acceptable thermal transfer device may be used for this method and for the methods of treating any of the other diseases disclosed herein. In addition, it is understood that a combination of active and passive type devices may be used in order to achieve optimal thermal transfer. Also, it is understood that in addition to ABTT target area 20, thermal transfer may be carried out with the skin that lies above at least one of any of veins 12, 14, 16, 18, and 19 that converge in the ABTT target area. It is understood that the device used to treat the sleep disturbance effects of Alzheimer's disease may also be used to carry out other methods described in the present disclosure and included in the scope of the present disclosure.

In an exemplary embodiment of the present disclosure, the controller or processor is coupled to a clock or a sensor. When the controller or processor of the device is coupled to the clock, the device is configured to apply or remove thermal energy to/from ABTT target area 20 based on pre-set or predetermined clock settings or a timer. For example, a device designed to keep a patient asleep during nighttime hours will include a controller or processor which is coupled to a clock. Such a device may, for example, be configured to remove thermal energy from the brain between the hours of 3 a.m. and 7 a.m. in order to keep the patient asleep when the patient would normally experience a rise in body temperature and waking. In this exemplary example, the predetermined time may be based on a circadian thermal profile that shows the hours of the night that the patient normally experiences sleep disturbance so that the treatment is customized to the personal thermal profile or curve of the patient. As such, the method and device of the present disclosure provides for a personalized treatment of the sleep disturbance pattern of Alzheimer's disease patients. A device of the present disclosure in which a controller or processor is coupled to a temperature sensor is configured to apply or remove thermal energy once a threshold has been surpassed. In this exemplary embodiment, when used, for example, to keep a patient awake during daytime hours, the controller or processor may be configured to communicate to a heating element to apply thermal energy to ABTT terminus 20 when the sensor provides information that a low-temperature threshold has been surpassed. In an exemplary embodiment, the device is designed to apply the appropriate amount of thermal energy once a sleep disturbance has been detected. It should be understood that the method and apparatus disclosed herein can be used with any other heating or cooling system and other means of measuring body temperature, by combining delivery of heat and cold to the body in accordance with the principles of the disclosure.

Alzheimer's patients suffer cognitive dysfunction, confusion, delirium, and rapid deterioration after being subject to general anesthesia, with symptoms sometimes lasting for months or years. The basis for pathologic changes causing Alzheimer's disease is a hyperphosphorylation of tau protein. The enzyme phosphatase A2 inhibits hyperphosphorylation of tau proteins. The use of anesthesia induced rapid hyperphosphorylation of tau protein, rapid and prolonged hypothermia, and inhibition of phosphatase A2. In studies by Applicant, reestablishing normal body temperature during anesthesia completely restored tau phosphorylation to normal levels, via heat delivery to ABTT terminus 20 per thermoelectric devices disclosed herein. The changes in the tau phosphorylation were not a result of anesthesia per se, but a consequence of anesthesia-induced hypothermia, which led to inhibition of phosphatase activity and subsequent hyperphosphorylation of tau protein. Also, because allowing the brain of Alzheimer's patients to lower to a critical level causes rapid deterioration, there is a need to monitor and regulate temperature, even in situations other than under general anesthesia.

Exemplary methods of the present disclosure provide a means of monitoring and controlling brain and body core temperature, thus greatly reducing and potentially eliminating the risk of hypothermia and further deterioration of Alzheimer's disease patients. Exemplary methods of the present disclosure includes the steps of positioning a heating element adapted to deliver heat to ABTT target area 20 and/or associated veins, as described herein, applying heat exclusively to the surface of the skin of ABTT target area 20, creating a thermal effect in ABTT 22, and, as a result, affecting or controlling brain (and body) temperature. A further step may include positioning heating device on or over at least one of the veins 12, 14, 16, 18, and 19. Exemplary methods may further comprise activating a heating element, providing input settings, sensing temperature of the area to which heat is applied, processing data stored by a sensor, communicating with a control center, regulating the heating element, storing information in a memory, and transmitting information.

ABTT 22 can also be used to diagnose and treat Epilepsy. Approximately one percent of the population of the industrialized world has epilepsy. Many of those afflicted with epilepsy do not respond to existing treatments, and must suffer through the constant threat of seizures. Clearly, a novel therapeutic measure to treat epilepsy would be beneficial.

The present disclosure provides a device and method for the treatment of epilepsy by cooling the brain through ABTT 22. In the present disclosure, any of the active or passive devices described herein may be used to apply cooling effects or remove thermal energy from ABTT terminus 20 or the vascular system veins 12, 14, 16, and 18 that flow into the brain via ABTT 22. Similar to the treatment of Alzheimer's disease, cooling may be applied in a manual fashion, applying the cooling of a specified temperature to ABTT terminus 20 for a specified period of time. In addition, treatment may also be automated using processors, controllers, and regulators, which may provide treatment at certain periods of the day, or based on sensor information gathered from ABTT target area 20.

Multiple Sclerosis (MS) is another disease that may be treated and diagnosed using ABTT target area 20. When the body temperature of MS patients rises, deterioration and increased inflammation occur. Currently, cooling vests are used to cool the patient's entire body. However, such conventional devices, may provide too much cooling to the body, leading to pain by causing the skin to be too cold, or may cause the periphery of the body to become too cold causing the brain to overheat as a result. Cooling the ABTT slows progression, treats symptoms, and prevents complications due to epilepsy.

The present disclosure involves a method of cooling the brain through the cooling of the skin of ABTT target area 20. Cooling ABTT 22 causes the brain and core temperature to be decreased by simply cooling a localized area, rather than the entire body. Application of heat or cold to ABTT terminus 20 eliminates the need for bulky vests and other clothing and also allows for more control of applied temperature and the length of treatment. Methods and apparatus of the present disclosure may employ any of the embodiments described herein designed to apply cooling effects or remove thermal energy to the brain.

The devices of the present disclosure for treatment of MS include a controller or processor that is designed to deliver modulated cooling treatment. The controller or processor may be coupled to a sensor and be adapted to detect a rise in temperature and to counteract the effects of the rise. In addition, the controller or processor may be on a timer, to begin cooling treatment when a patient wakes in the morning, which is when a spike in temperature occurs.

ABTT target area 20 may also be monitored using a sensing device, in order to monitor the progression of the disease and allow doctors to create a personalized and detailed plan of treatment.

Treatment through ABTT 22 may also be used to treat or prevent breast cancer by increasing melatonin production by the pineal gland via brain cooling. ABTT 22 may offer a new therapeutic tool for prevention and treatment of breast cancer by modulating melatonin production by acting on the sleep-wake cycle.

Application of various devices to the ABTT terminus 20 increases melatonin production by reducing light transmission through ABTT 22 or by reducing temperature (for prevention and therapy of breast cancer, and other cancers).

Exemplary apparatuses for application of thermal energy on ABTT terminus 20 are discussed herein. These embodiments are illustrations and do not in any way limit the scope of the disclosure.

Figure 56:
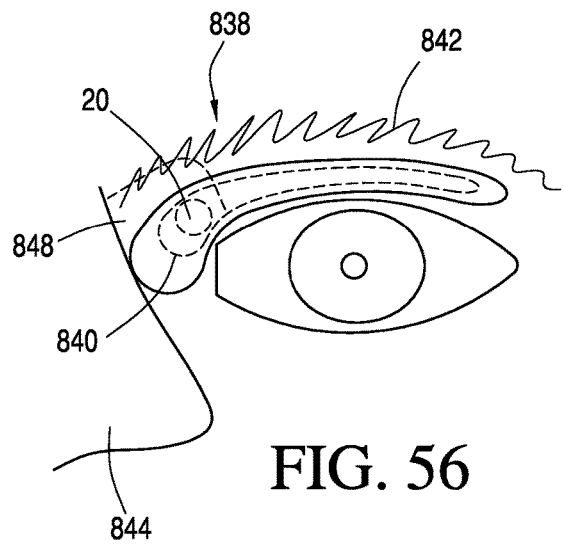
FIG. 56 is a view of a passive heat exchange device, in accordance with an exemplary embodiment of the present disclosure.
Figure 56A:
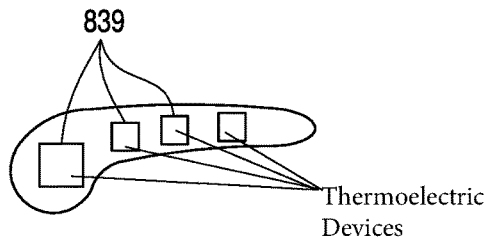
FIG. 56A is a view of an active heat exchange device, in accordance with an exemplary embodiment of the present disclosure.

FIG. 56 shows an exemplary passive adhesive heat exchange device in the form of a patch in accordance with an exemplary embodiment of the present disclosure, indicated generally at 838. Heat exchange device 838 includes a thermally retentive substance, such as substance 36, positioned to deliver heat to, or remove heat from, ABTT terminus 20. In the exemplary embodiment of FIG. 56, heat exchange device or patch 838 includes thermally retentive material in a region or portion 840 that extends for a distance over the location of superior palpebral vein 14, which is particularly beneficial in providing heat to ABTT terminus 20 or removing heat from ABTT terminus 20. Region 840 may, as shown in the exemplary embodiment of FIG. 56, be larger than ABTT terminus 20, but needs to be at least partially in a region 848 bounded by eyebrow 842, nose 844, and eye 846 where ABTT terminus 20 is located. Region or portion 840, though shown in phantom lines in FIG. 56 as an elongated kidney shape, can be other shapes, such as elliptical, polygonal, etc., as long as region 840 substantially overlaps ABTT terminus 20, and in the embodiment of FIG. 56, superior palpebral vein 14. In the context of this disclosure, an exemplary overlap of region 840 with ABTT terminus 20 is at least 80%, though an overlap as low as 50% can still provide a therapeutic heat transfer in some situations. The goal in every case should be 100% overlap of ABTT terminus 20. FIG. 56A shows a similar shape and configuration of device 838 of FIG. 56, but the thermally retentive material is replaced by a plurality of thermoelectric devices 839.

Figure 60:
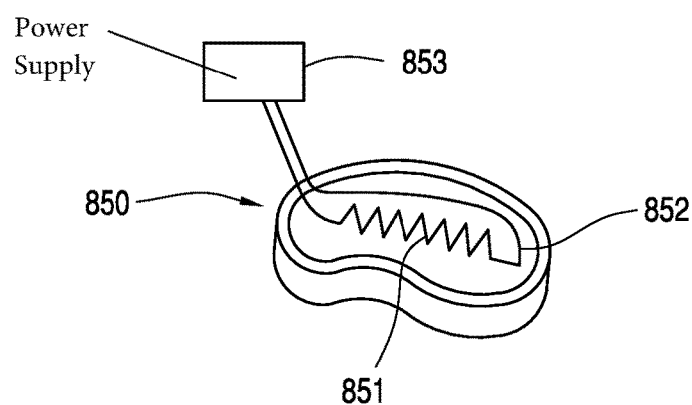
FIG. 60 is a view of an active heat exchange pad for contacting the ABTT terminus, in accordance with an exemplary embodiment of the present disclosure.

FIG. 60 shows another active thermal exchange device in in accordance with an exemplary embodiment of the present disclosure, and indicated generally at 850. Active thermal exchange device 850 includes a convex surface 852 configured to mate with ABTT terminus 20, which thus provides a preferable contact with ABTT terminus 20 for thermal exchange. Active thermal exchange device 850 further includes an electric or electronic heater 851, which is shown as a resistive heater in FIG. 60. Resistive heater 851 is connected to a power supply 853, which may be positioned in a plurality of locations, such as a wearable item, or as a standalone device connected to device 850.

Figure 61:
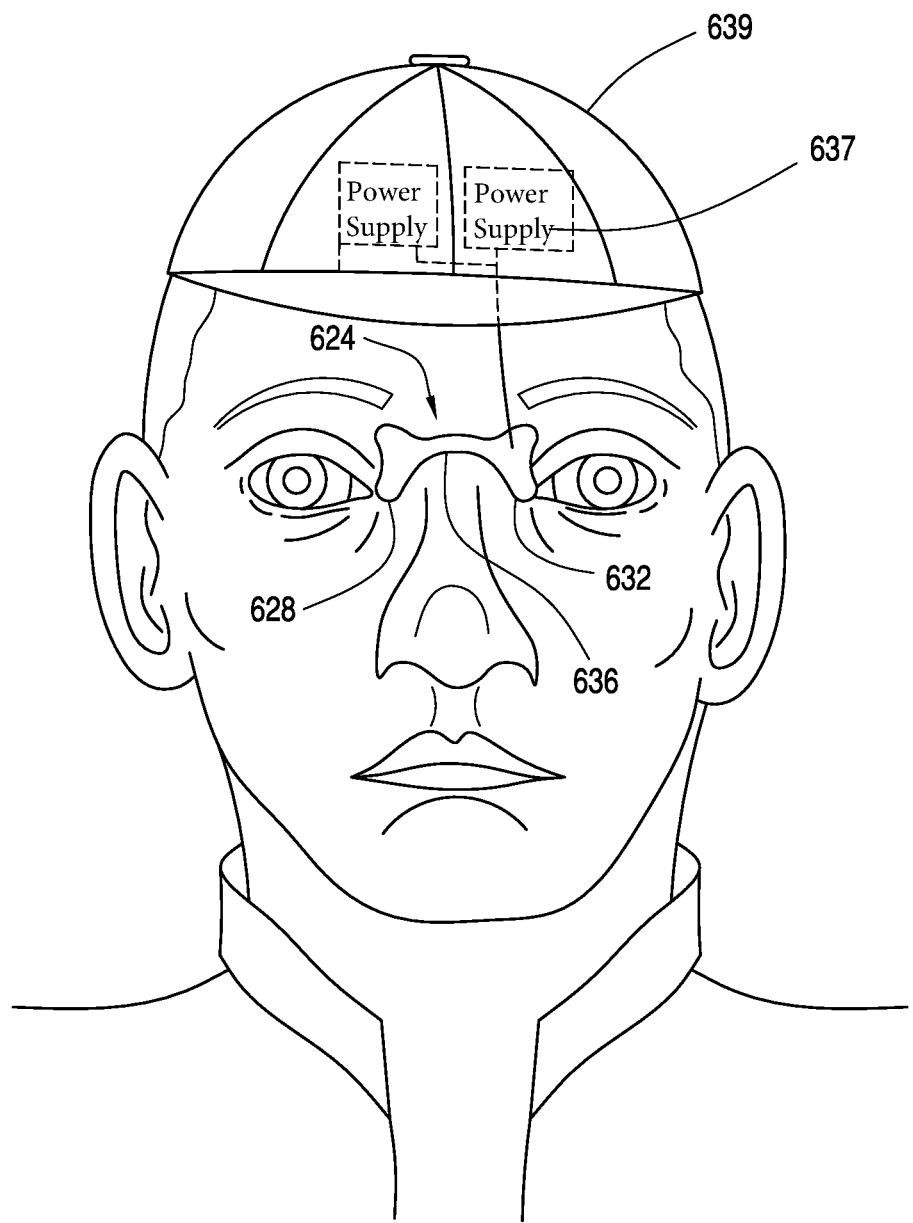
FIG. 61 is a view of another active heat exchange device, in accordance with an exemplary embodiment of the present disclosure.

FIG. 61 shows yet another active thermal exchange device in accordance with an exemplary embodiment of the present disclosure and indicated generally at 624. Thermal exchange device 624 includes features similar to heat exchange device 622 shown in FIG. 59, including a left portion 628, a right portion 632, and a strip of material 636 connecting left portion 628 and right portion 632. A heating or cooling apparatus located in thermal exchange device 624 is powered by a power supply 637 that may be, for example, batteries, which can be located in a plurality of locations, including a wearable item such as a hat 639 or any head gear or neck gear.

Figure 62:
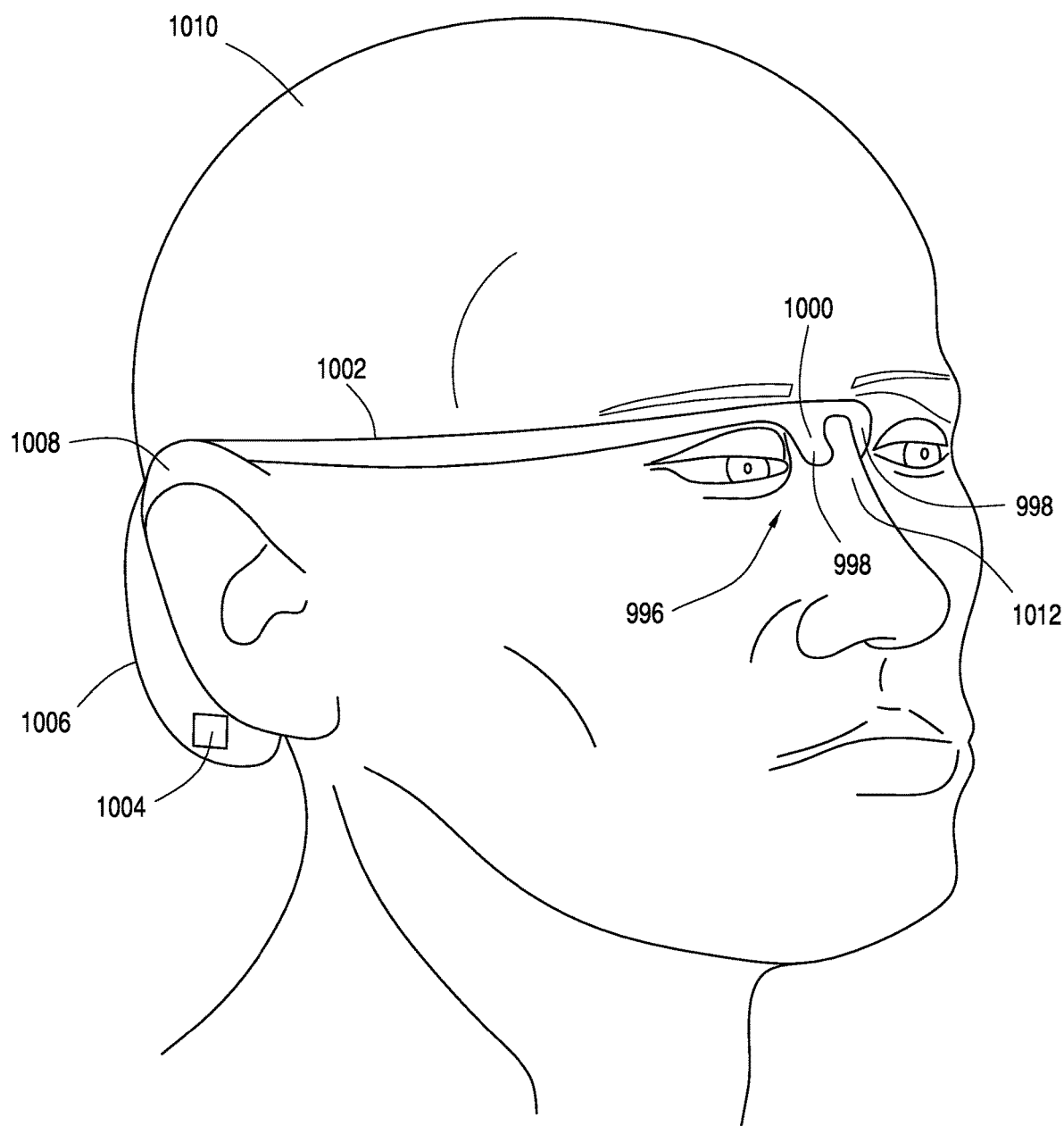
FIG. 62 is a view of yet another active heat exchange device, in accordance with an exemplary embodiment of the present disclosure.
Figure 63:
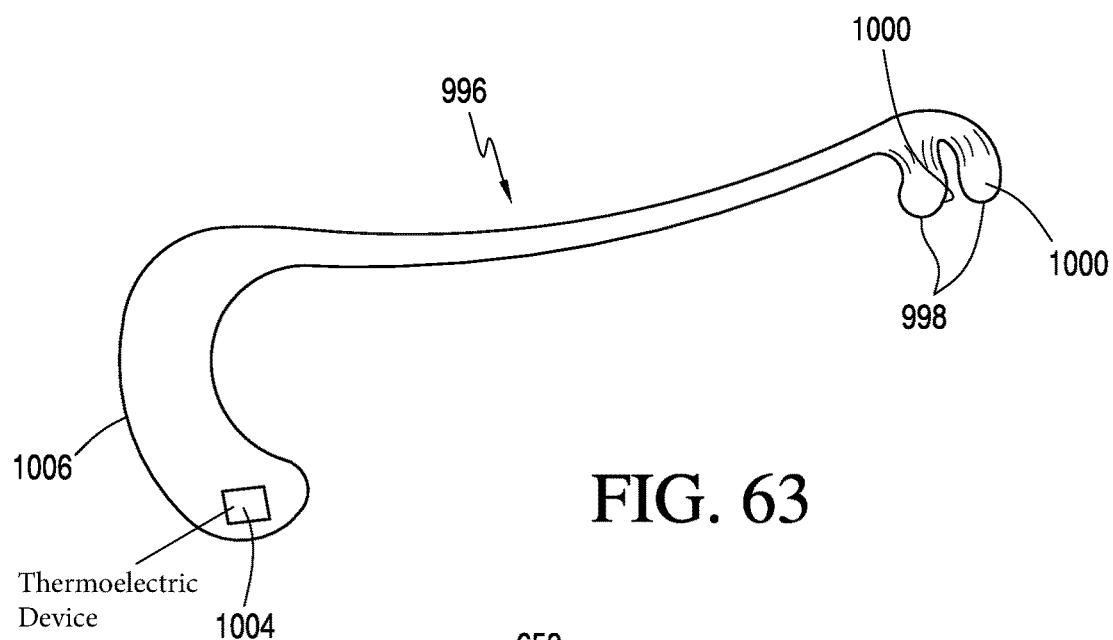
FIG. 63 is a view of the active heat exchange device of FIG. 62.

FIGS. 62 and 63 show another active thermal exchange device in accordance with an exemplary embodiment of the present disclosure, indicated generally at 996. Thermal exchange device 996 includes a housing 998 that includes a convex surface 1000 configured to follow the geometry of the skin of ABTT terminus 20, which provides the most effective contact for heat exchange with ABTT terminus 20, and may include any of the nodes containing thermoelectric device described elsewhere herein. Thermal exchange device 996 further includes two housings 998 for contact with both ABTT terminuses 20. Thermal exchange device 996 further includes a transceiver 1009 located in a curvilinear frame 1006 of a frame 1002 supporting curvilinear frame 1006 and housings 998. Frame 1002 is configured to be supported on a head 1010 by a single ear 1008 and a nose 1012. In this embodiment, thermal exchange device 996 has a dual support ear and nose. In another embodiment, frame 1002 extends to a second ear and frame 1002 is supported on both sides of head 1010. Active thermal exchange device 996 includes an electrically operated heating apparatus (not shown), operated by a power supply 1007 positioned in curvilinear frame portion 1006 or separate from active thermal exchange device 996. Active thermal exchange device 996 may further include a thermoelectric device 1004 in the end of the ear-wrapping portion for thermal exchange with vessels behind the ear.

Figure 69:
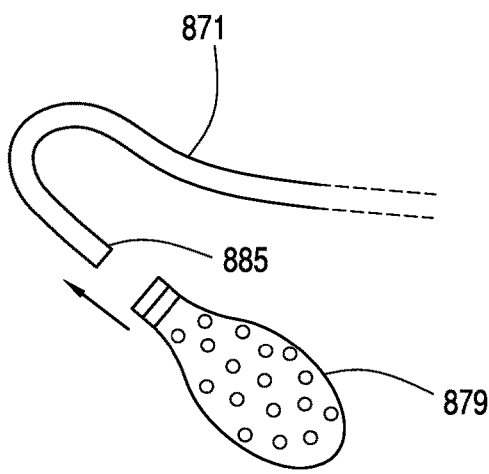
FIG. 69 is a view of a portion of the active and passive heat exchange device of FIG. 68.
Figure 68:
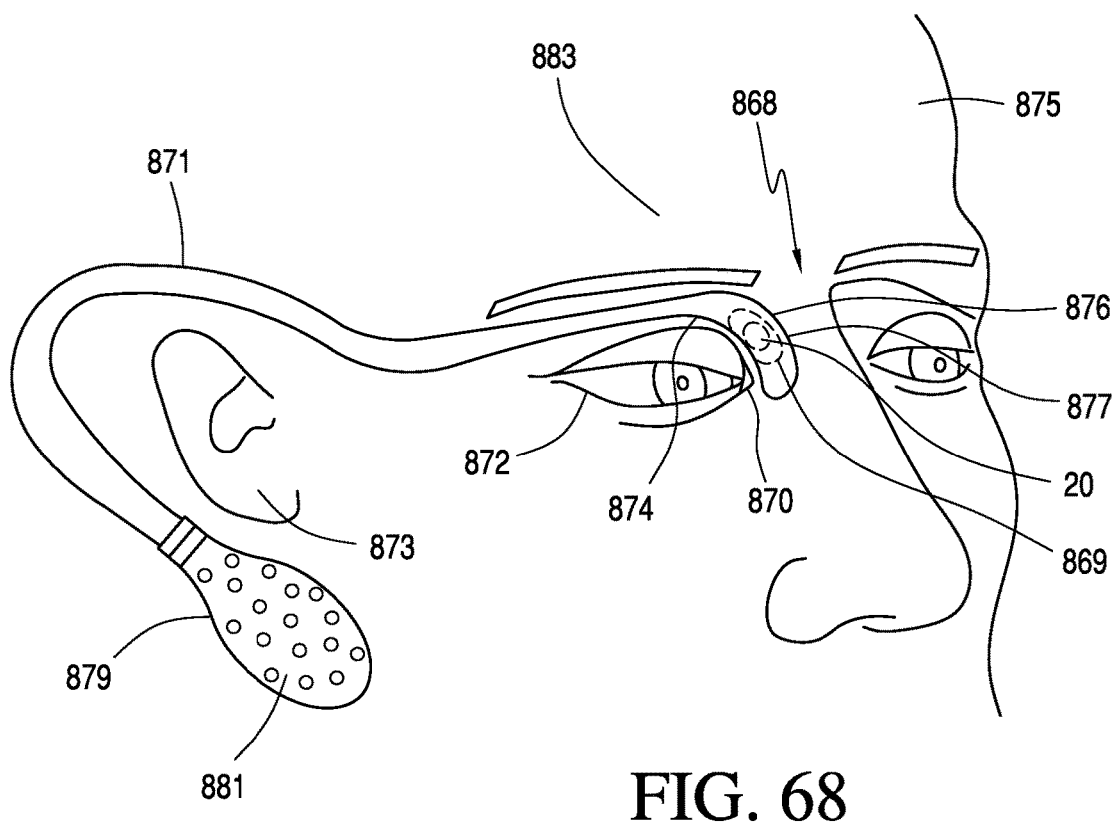
FIG. 68 is a view of a combination active and passive heat exchange device in accordance with an exemplary embodiment of the present disclosure.

FIGS. 68 and 69 show details of another active thermal exchange device in accordance with an exemplary embodiment of the present disclosure, indicated generally at 868. Device 868 includes an active cooling and/or heating apparatus 869 positioned to heat and/or cool ABTT terminus 20. Device 868 includes a frame 871 to support apparatus 869 and the other elements of device 868. Frame 871 is supported partially by an ear 873 of a subject 875. An end 877 of frame 871 is formed with a C-shaped geometry that approximately matches the unique geometry of the area around ABTT terminus 20. The C-shaped geometry or arrangement is configured to fit close to a corner 870 of an eye 872. The C-shape provides several benefits, including ease of properly locating device 868, clearance with corner 870 of eye 872, and a geometry that provides optimal contact with ABTT terminus 20. Though delivery device 868 may be formed overall in a C-shape, it should be noted that only one side or edge of delivery device 868, such as a side or edge 874 closer to eye 872 than a side or edge 876 further from eye 872, may be formed as a C-shape.

Device 868 includes a bulb 879 positioned at an end 885 of frame 871 that is opposite end 877. Bulb 879, which is easily removable from end 885 of frame 871, is configured to include a cooled or heated thermally retentive substance or material 881 for heating or cooling of the retroauricular blood vessels located behind ear 873, which, though insulated by fat, provides some thermal transfer to a head 883.

Figure 59:
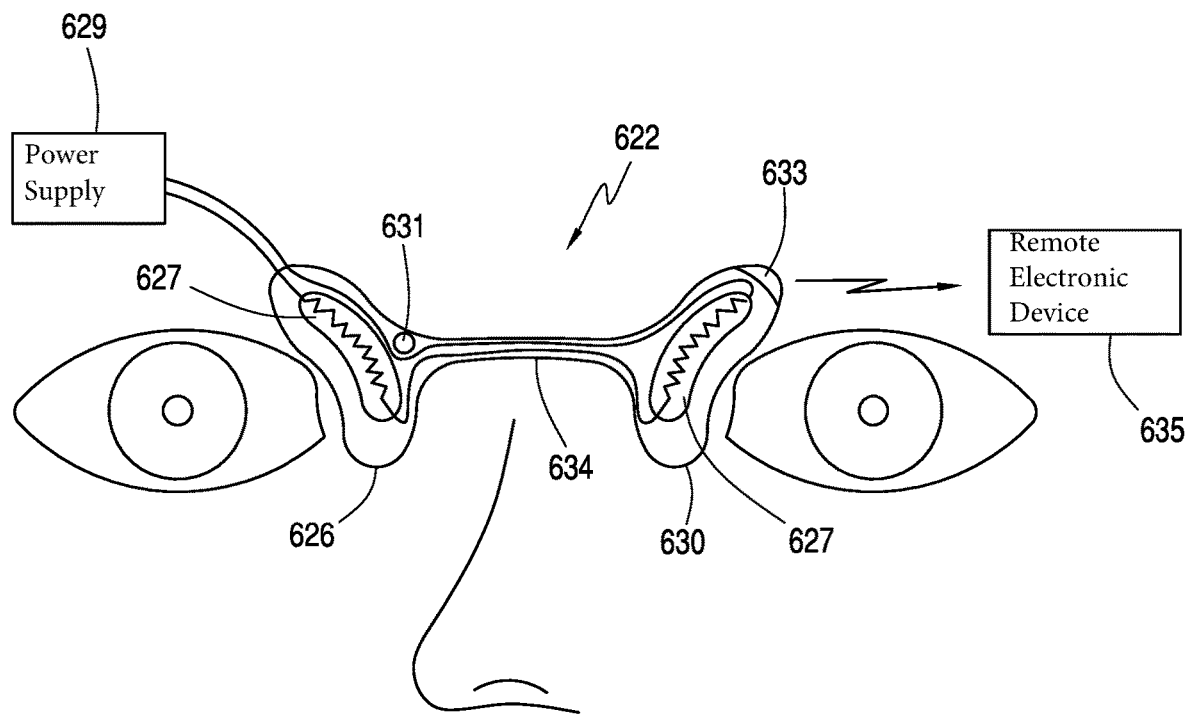
FIG. 59 is a view of an active heat exchange device or apparatus configured to contact both ABTT terminuses, in accordance with an exemplary embodiment of the present disclosure.

In the embodiment of FIG. 59, thermal exchange device 622 includes resistive heaters 627, which, in another embodiment, are thermoelectric devices, controlled by a power supply 629 and ambient temperature sensor 641. Thermal exchange device 622 also includes a sensor 631 for measuring the temperature of device 622, a controller 643, and a transmitter 633 for communicating with a separate or remote electronic device 635, such as a cell phone, tablet, laptop, computing device, etc. Ambient temperature sensor 641 transmit temperature data to controller 643 that is operatively coupled with the thermoelectric device to increase or decrease heating or cooling based on the ambient temperature.

Figure 64:
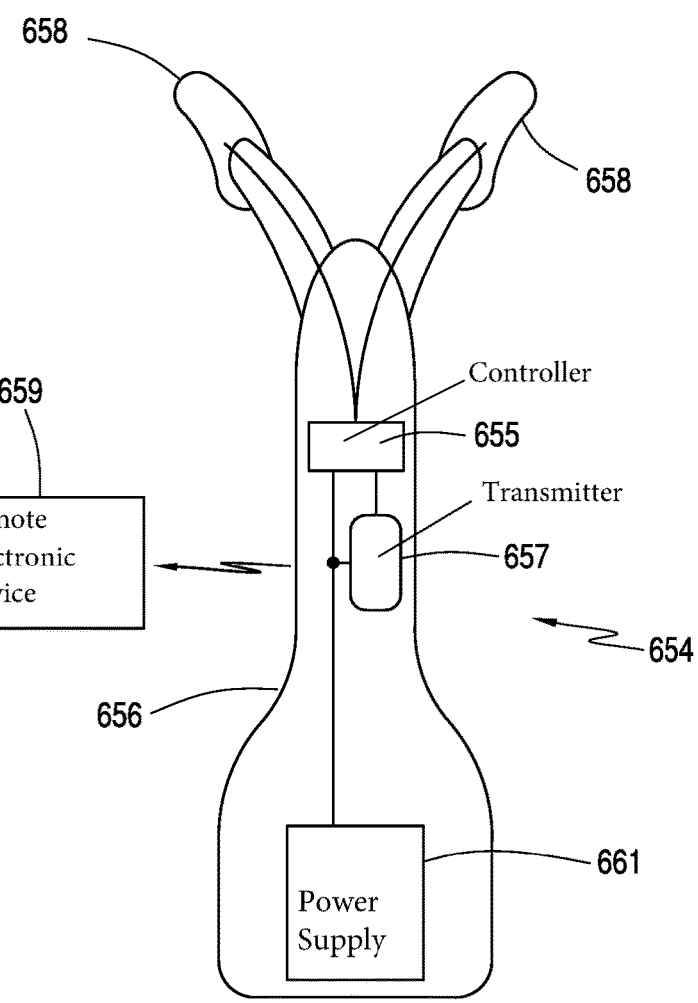
FIG. 64 is a view of a hand held active heat exchange device, in accordance with an exemplary embodiment of the present disclosure.

FIG. 64 shows an active thermal exchange device in accordance with an exemplary embodiment of the present disclosure and indicated generally at 654. Device 654 includes a handle 656 and thermal exchange pads 658 for contact with ABTT terminus 20. Device 654 further includes a controller 655 for operating thermal exchange device 654, a transmitter 657 for communicating with a remote electronic device 659, such as a cell phone, and a power supply 661, all of which are located in handle 656.

Figure 65:
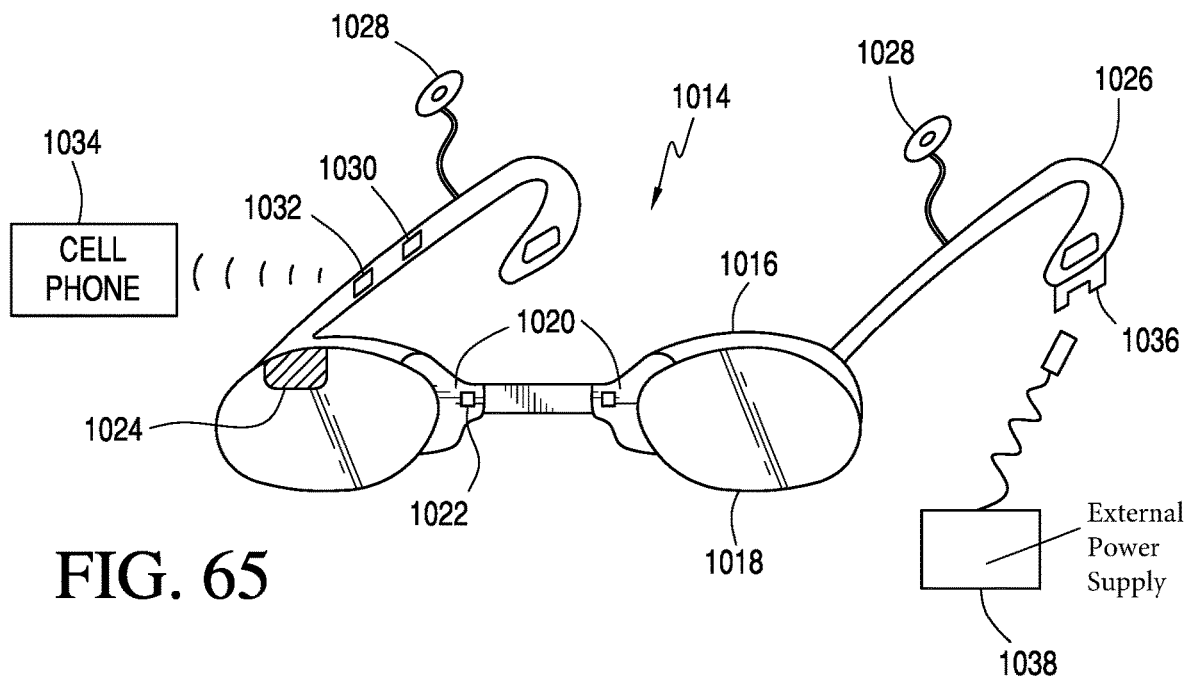
FIG. 65 is a view of an active heat exchange device, in accordance with an exemplary embodiment of the present disclosure.

FIG. 65 shows a further active thermal exchange device in accordance with an exemplary embodiment of the present disclosure, and indicated generally at 1014. Active thermal exchange device 1014 is configured as frames 1016 to support eyeglasses 1018. Device 1014 includes an electrically operated heat exchange device 1020, such as a thermoelectric device or resistive heater, a sensor 1022 configured to measure the temperature of heat exchange device 1020, a display 1024 for displaying information related to device 1014, a battery 1026 to operate the features of device 1014, ear phones 1028 for sound content related to display 1024 or other portions of device 1014, a processor or controller 1030, and a transmitter 1032 configured to communicate with a separate electronic device 1034, such as a cell phone, laptop, tablet, etc. Device 1014 may also include a connector 1036 to connect device 1014 to an external power supply 1038. Heat exchange device 1020 may include thermoelectric devices contained in the frame of eyeglasses and in the nose pads of eyeglasses.

FIG. 36 is a view of yet another active thermal exchange device in accordance with an exemplary embodiment of the present disclosure, indicated generally at 1188. Device 1188 includes a frame 1190, which further includes a plurality of upper lens rims 1053, a plurality of nose pads 1055 configured to contact a user's nose to support device 1138 on the user's face, and a nose bridge 1051 positioned, located, or elevated above upper lens rims 1053. Nose pads 1055 are each configured to include an extension 1057. Nose bridge portion 1051 includes a thermoelectric device 1059 that is in apposition with at least a portion of supraorbital veins 16 and frontal veins 12. Each extension 1057 includes a thermoelectric device 1061 that is in apposition with at least a portion of angular vein 18 and may also be in apposition with at least a portion of facial vein 19. Extension 1057 may be configured to include an apparatus, mechanism, or device to provide or maintain contact of extension of 1057 with the skin of a user or subject. For example, extension 1057 may include a material with memory configured to provide force against the user's skin.

It should be understood that all of the aspects of the disclosed embodiments and examples presented herein may comprise a sensor, a resistor, connectors, a thermistor, a controller or processor, a non-transitory memory that is operatively linked to the controller or processor, a communications interface adapted to receive and send data with at least the controller or processor, and a computer program stored in non-transitory memory that executes in the controller or processor. The controller or processor of this embodiment may further comprises a database, wherein data received by the controller or processor may be stored in non-transitory memory as a database, and sorted into predetermined fields, and the database may be capable of graphical representations of the downloaded data. The graphical representations of this embodiment may include, but are not limited to, column, line, bar, pie, XY scatter, area, radar, and surface.

The aspects of the disclosed embodiments may also comprise a display, such as an alphanumeric display, including, but not limited to, a liquid crystal display (LCD), a plasma display panel (PDP), and a field emission display (FED). In an alternate embodiment, the apparatus comprises an audio display that may be provided with an audio source comprising recorded audio clips, speech synthesizers, and voice emulation algorithms to report, for example, user settings and current brain temperature audibly. Other display or reporting apparatuses, devices, and mechanisms may comprise an alarm, an indicator light, and other electronics configured to alert a user when the temperature is above or below a threshold temperature. It should be understood that the alert or alarm may be visual, auditory, or vibrational.

The apparatus of the present disclosure may also comprise a communications interface adapted to transmit data captured by the apparatus to a separate or remove computer system. In such embodiments, the communications interface selected may be any suitable interface, including, but not limited to, a serial, parallel, universal serial bus (USB), FireWire, Ethernet, fiber optic, co-axial, and twisted pair cables. In a further embodiment, the apparatus, device, or mechanism may also comprise a transmitter adapted to transmit temperature measurement data to a remote computer processor or user. A remote computer processor may be a cellular or wireless handheld device, personal computer, internet database, or the like.

FIG. 70 shows another active thermal exchange device in accordance with an exemplary embodiment of the present disclosure and indicated generally at 708. Device 708 is configured to measure the temperature of one ABTT terminus 20 while applying heat to or removing heat from a second ABTT terminus 20 on the same subject or patient. Device 708 includes a support layer 716; a sensor 710 positioned on support layer 716 that is configured to be positioned to contact ABTT terminus 20 to measure the temperature of associated ABTT terminus 20; an adhesive layer 712 located under support layer 716 for securing device 708 to the region of the face near ABTT terminus 20; an electric cooling and/or heating device 714, which in an exemplary embodiment is a reversible thermoelectric cooler/heater; and circuitry 720. Circuitry 720 may include, for example, a controller or processor 721, a transmitter 723, and a power supply 725. Device 708 may be connected to a separate external power supply 727 by a cable or wire 729. FIG. 71 shows a device 708a that works as a clip, as compared to the adhesive-based device 708 of FIG. 70, and includes a spring-like means 731 and two arms 733 and 735, arm 733 includes a housing 737 that contains a sensor 739 and arm 735 includes a housing 741 that contains a thermoelectric device 753. Arm 733 further includes a module 743 that includes a transmitter and processor, operatively coupled to a remote device 755 such as a computer or cell phone. Arm 735 includes a power supply 745 and an LED 747. At the end of arm 733 and 735 are pads 749 and 751 for anchoring device 708a to a nose (not shown).

FIG. 71A shows another thermal exchange device in accordance with an exemplary embodiment of the present disclosure and indicated generally at 708b. Clip-based device 708b is similar to device 708a that includes spring mechanism 767, but also includes two adjustable arms 757 and 759 connected to a bridge portion 761 of device 708b, and a wire 769 connected to a power supply 771. Adjustable arm 757 allows positioning a sensor module 763 in ABTT target area 20, and adjustable arm 759 allows positioning thermoelectric device 765 in the opposite ABTT target area 20.

FIG. 72 shows a thermal exchange device in accordance with an exemplary embodiment of the present disclosure, indicated generally at 1056. Thermal exchange device 1056 includes a support structure 1060 on which the other elements of device 1056 are positioned. Support structure 1060 may be positioned on a head 1062 of a subject 1064 and retained on head 1062 by an adhesive, or an apparatus, device, or mechanism 1066, which may be, for example, a hat, a headband, a support device, fasteners, hook and loop, etc. Device 1056 includes heated or cooled pads 1058 positioned to contact one or both ABTT terminuses 20. Pads 1058 are heated or cooled prior to installation on device 1056. It should be understood that pads 1058 may include extensions as shown in FIG. 97 for apposition against angular vein 18 as well as thermally retentive material in support structure 1060 for apposition against frontal 12 and supraorbital vein 16. Device 1056 further includes an LED 1081 and temperature sensors 1068 positioned to measure the temperature of pads 1058. Support structure 1060 may include temperature sensors to measure temperature of the skin at ABTT terminus 20. In the exemplary embodiment of FIG. 72, device 1056 includes a plurality of electronics, for example a controller or processor 1083 and a transmitter 1070 configured to communicate with a device, either by wire or wirelessly, such as, for example, a first separate electronic device that may be a cell phone, and a second separate electronic device that may be an appropriately configured watch.

Thermal exchange device 1056 is configured to apply a specific predetermined temperature to each ABTT terminus 20, which may be either positive (hotter) or negative (colder) than the equilibrium temperature of ABTT terminus 20, which in an exemplary embodiment is the nominal "normal" temperature of ABTT terminus 20. The temperature is applied for a predetermined period, and then pads 1058 are allowed to cool or warm. By measuring the temperature rise or increase rate, or the temperature decay or decrease rate, a medical condition of subject 1064 can be determined. The length of time of measuring the rise rate or decay rate is dependent on the condition or conditions being diagnosed. For some conditions, the measurement time can be as short as seconds, for example 15 to 20 seconds to determine hypothermia or hyperthermia, to many minutes for other conditions. FIGS. 73 and 74 show exemplary temperature rise rate curves indicative of conditions of a subject. FIG. 73 indicates a nominal or statistically normal condition of a healthy patient. FIG. 74 is a temperature rise rate curve of a subject or patient with a non-normal medical condition indicative of a non-normal hyperthermic cerebral state. The patient of FIG. 74 would be considered to be in need of medical treatment on the basis of the temperature rise rate curve.

The power of device 1056 is greater when temperature rise and decay rates are measured over time, establishing an initial baseline and comparing subsequent measurements with the baseline. Such comparison measurements enable early detection of certain medical conditions that may take years or even decades to be manifest in a clinical examination or by conventional diagnostic techniques and apparatus.

Figure 75:
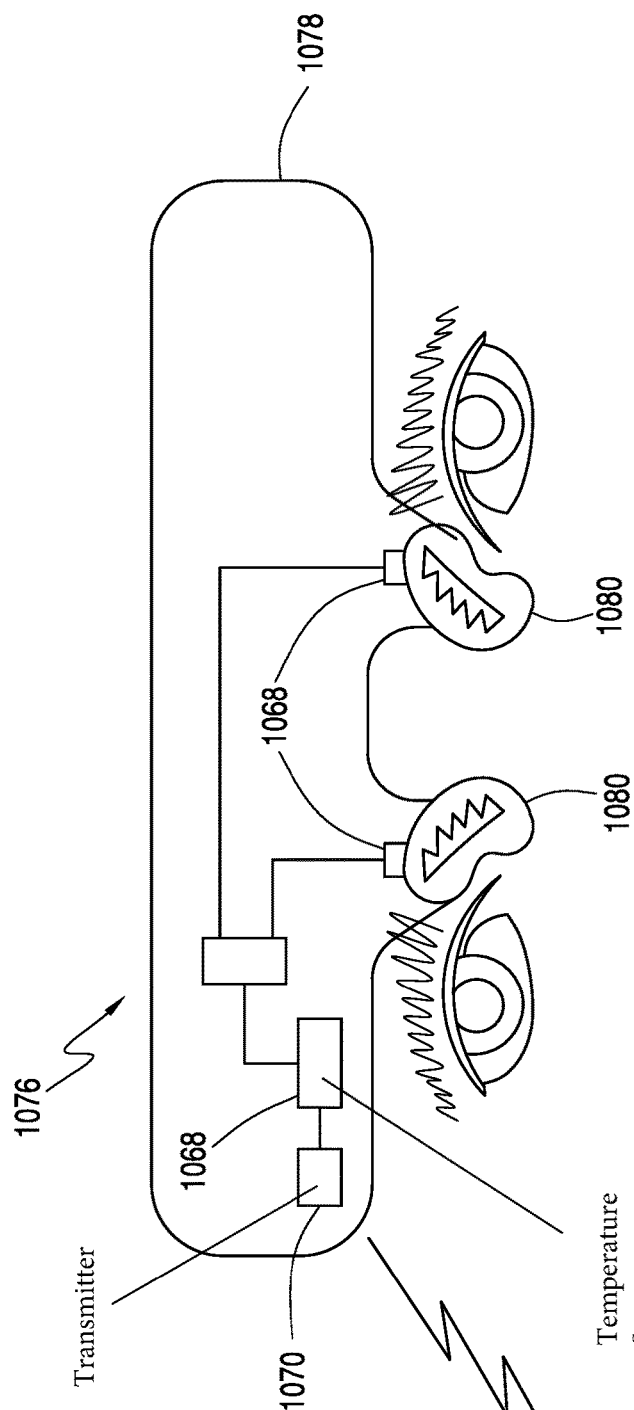
FIG. 75 is a view of an active thermal exchange device in accordance with an exemplary embodiment of the present disclosure.
Figure 76:
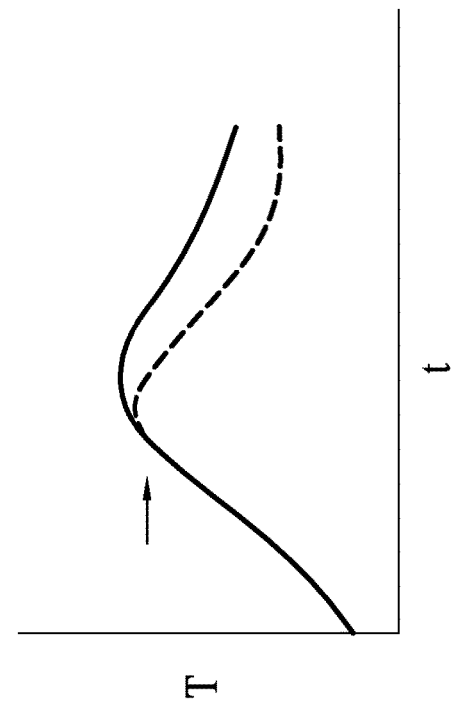
FIG. 76 is a graph of a temperature measurement provided by the active thermal exchange device of FIG. 75.

FIG. 75 shows an active thermal exchange device in accordance with an exemplary embodiment of the present disclosure and indicated generally at 1076. Device 1076 is similar to device 1056, except that the pads are actively heated or cooled. Device 1076 includes a support structure 1078 and actively heated or cooled pads 1080. It should be understood that actively heated or cooled pads 1080 may include extensions as shown in FIG. 97 containing thermoelectric devices for apposition against angular vein 18 as well as thermoelectric devices in support structure 1078 for apposition against frontal 12 and supraorbital vein 16. Device 1076 provides a capability similar in many ways to device 1056, except that the ability to vary the peak temperature with time to create different temperature "impulses" provides significant capability in measuring the response of ABTT 22, and ultimately, the brain, to positive or negative thermal stimuli. Such response provides an indication of a medical condition of the subject or patient. As one example, FIG. 76 shows a curve (a) that is nominally or statistically normal, and a curve (b) that is indicative of a potentially serious medical condition that would typically be considered to require medical treatment.

Thus, while the generic application of heat and cold to ABTT terminus 20 provides benefits from the perspective of treatment of various medical conditions, applying thermal impulses or applying a cold object to ABTT terminus 20 and measuring the resulting temperature curve of the device applying the heat or cold, provides a powerful, fast, non-invasive, diagnostic tool and apparatus for evaluating progression and severity of a medical condition. In addition, the effectiveness of drugs is measurable by using this apparatus.

FIG. 77 shows an active thermal exchange device in accordance with an exemplary embodiment of the present disclosure, indicated generally at 768. Device 768 includes a frame 770, which is configured similar to eyeglass frames. Frame 770 supports an active thermal device, mechanism, or apparatus 772, which in an exemplary embodiment is a resistive heater 774 surrounded by an insulating material 776. Active thermal apparatus 772 is positioned on frame 770 by a flexible support 778, which permits adjusting the position of resistive heater 774 to align with ABTT terminus 20. Device 768 further includes one or more electronic components, such as a power supply 780 to provide power to operate resistive heater 774, and a transmitter 782 for communicating wirelessly with a separate electronic device 784, such as a cell phone, watch, laptop, tablet, or the like, to provide control of device 768. Active thermal apparatus 773 has a body 797 connected to an adjustable arm 778, said body 797 having preferably a cylindrical configuration as shown in FIG. 78A and may include a thermoelectric device 775 instead of resistive heater to allow applying or removing heat from the ABTT 20. A preferred length 777 of body 797 of active thermal device 773 is equal to or less than 40 mm, and preferably equal to or less than 25 mm, and more preferably equal to or less than 15 mm, and most preferably equal to or less than 10 mm, and even most preferably equal to or less than 7 mm, including a range of 7 mm to 40 mm. A preferred diameter 779 of body 797 of active thermal device 773 is equal to or less than 20 mm, and preferably equal to or less than 15 mm, and more preferably equal to or less than mm, and most preferably equal to or less than 5 mm, and even most preferably equal to or less than 2.5 mm, including a range of 2.5 mm to 20 mm. A preferred length 795 of adjustable arm 778 is equal to or less than 50 mm, and preferably equal to or less than 40 mm, and more preferably equal to or less than mm, and most preferably equal to or less than 20 mm, and even most preferably equal to or less than 10 mm, including a range of 10 mm to 50 mm. It should be understood that preferred dimensions disclosed herein apply to any of the embodiments of present disclosure.

Figure 79:
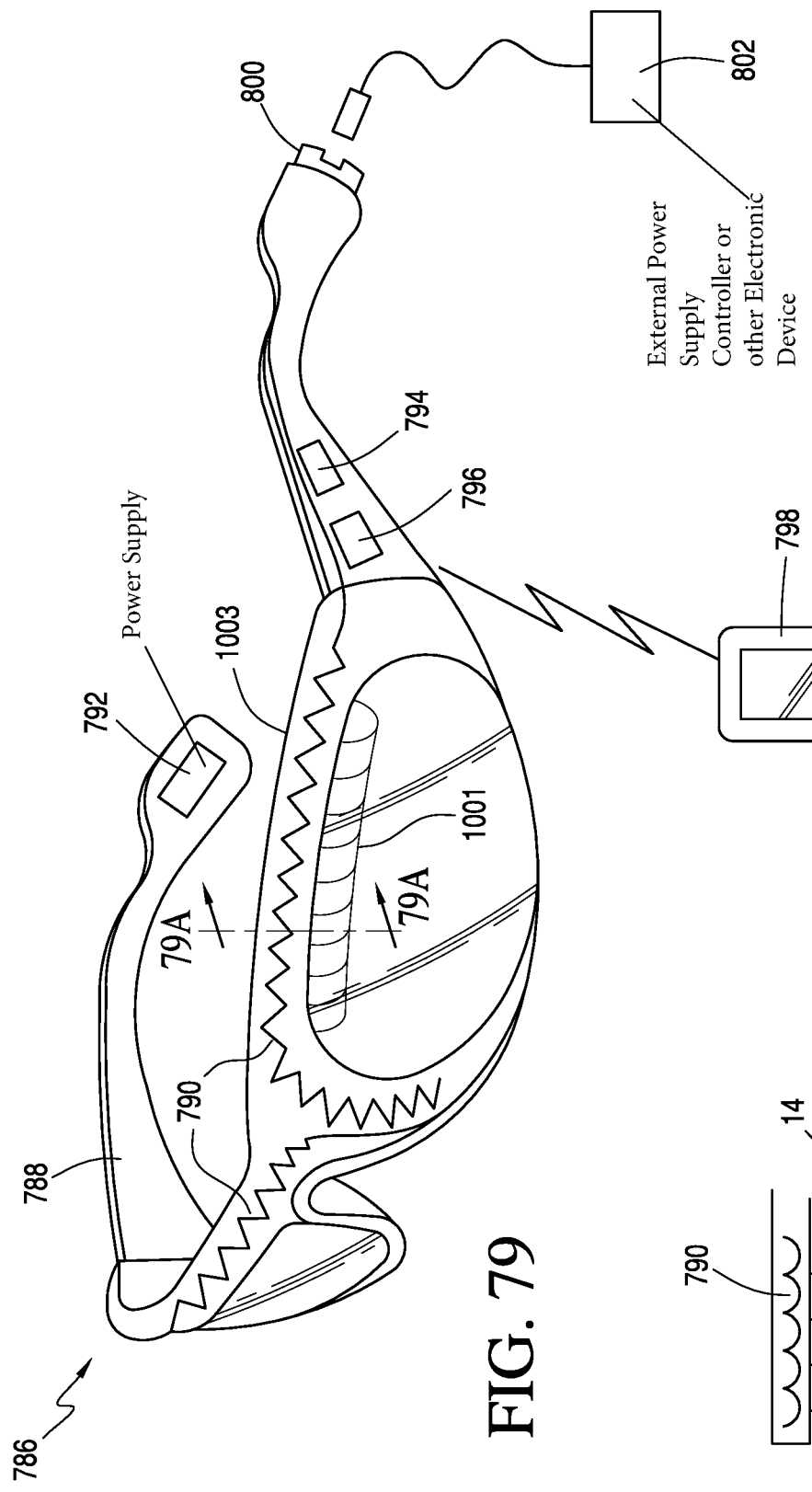
FIG. 79 is a view of an active thermal exchange device in accordance with an exemplary embodiment of the present disclosure.
Figure 79A:
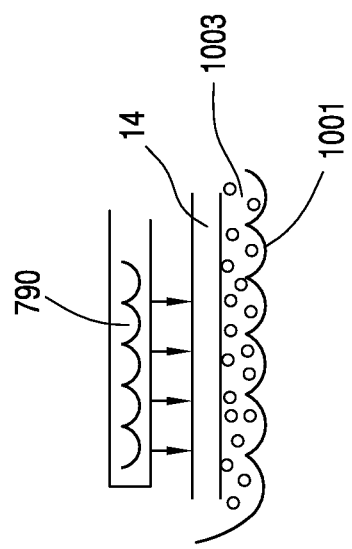
FIG. 79A is a view of the active thermal exchange device of FIG. 79 along the line 79A-79A.

FIG. 79 shows an active thermal exchange device in accordance with an exemplary embodiment of the present disclosure, indicated generally at 786. Device 786 includes a frame 788 in which is located one or more thermoelectric devices 790. It should be understood that that resistive heaters or any other active (or passive) thermal exchange device can be used instead of thermoelectric devices. Frame 788 is configured to include a plurality of electronic components, such as a power supply 792, a controller or processor 794, and a transmitter 796 for communication with a separate electronic device 798 such as a cell phone or computing device. Frame 788 further includes a connector 800 for connection to an external power supply, controller, or other electronic device 802. Device 786 is configured to radiate heat to the skin, or to remove heat over superior palpebral vein 14, shown in the stylized view of FIG. 1*t* should be understood that in another embodiment, thermoelectric devices can be positioned along frame 788 to cool the air adjacent to the skin over superior palpebral vein 14. Such an embodiment is particularly beneficial when using the embodiment in the presence of flowing air, such as when running and air is flowing onto the face of the runner. The cool air from frame 788 then flows toward the face of the runner, including superior palpebral vein 14 and ABTT terminus 20. Frame 788 may also include along the areas containing thermoelectric devices 790 a hood 1001 along the inferior edge of lens rim 1003 to keep cold or hot air in the region of the superior palpebral vein 14. FIG. 79A is a schematic view of hood 1001 creating air pockets 1003 showing thermoelectric device 790 applying heat to or removing heat from the vein 14, and forming a thermal environment bounded by hood 1001, thereby augmenting the thermal effect of device 790.

Figure 80:
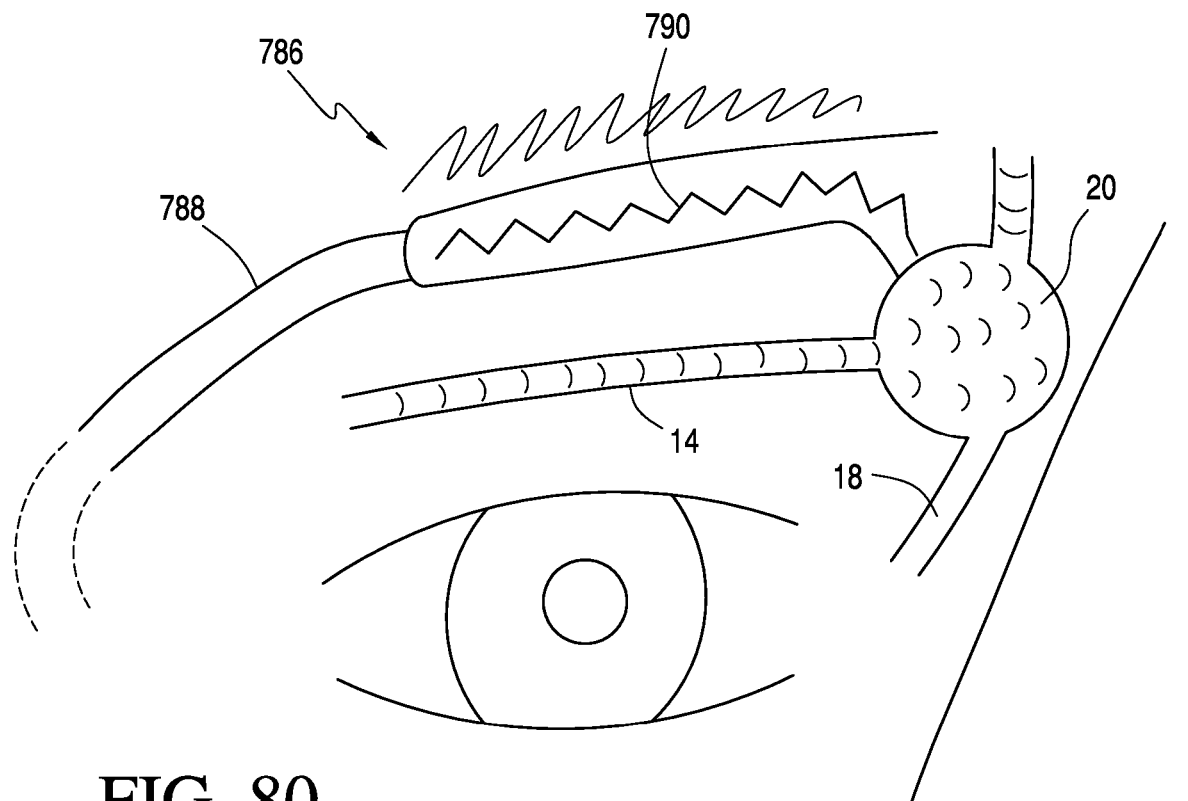
FIG. 80 is a stylized view of heat transfer from the active thermal exchange device of FIG. 79 to the superior palpebral vein and the ABTT terminus.
Figures 80A, 80B:
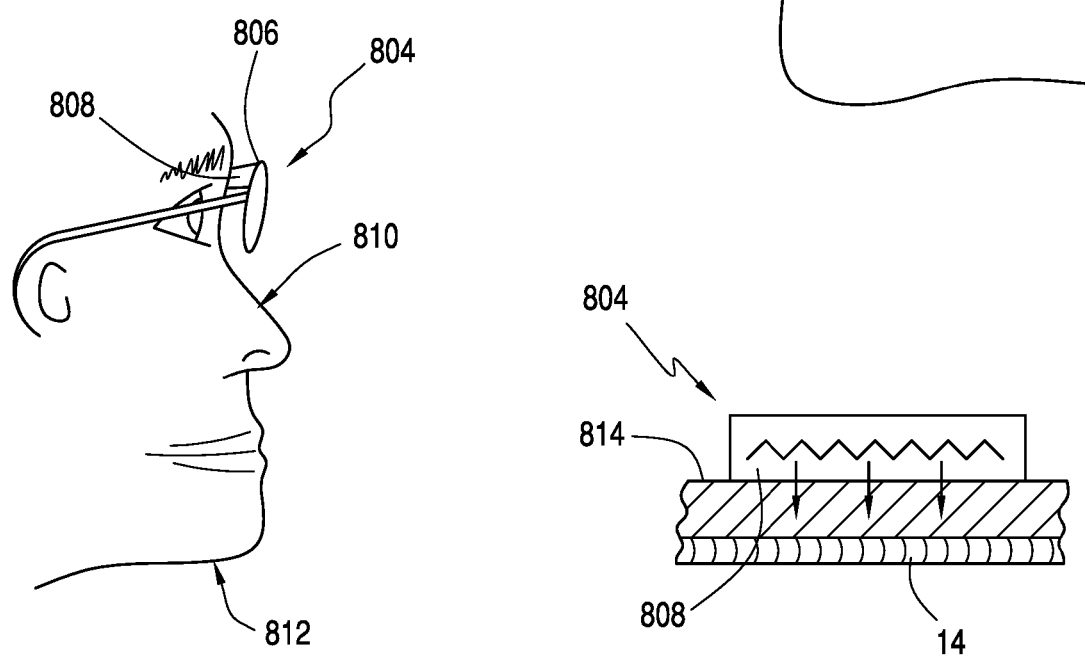
FIG. 80A is a view of an alternative embodiment of the active thermal exchange device of FIG. 80 in accordance with an exemplary embodiment of the present disclosure.
FIG. 80B is a stylized cross-sectional view of a front portion of the active thermal exchange device of FIG. 80A from a top or bottom direction of the active thermal exchange device.

FIGS. 80A and 80B show a thermal exchange device in accordance with another exemplary embodiment of the present disclosure, indicated generally at 804. Device 804 includes a frame 806 on which is positioned one or more thermoelectric devices 808. Thermoelectric devices 808 extend between frame 806 and a face 810 of a subject 812 to contact skin 814 over superior palpebral vein 14, providing cooling to vein 14. Thus, when the brain of subject 812 is warm, cooled blood will flow from vein 14 into ABTT 22, and then into the brain of subject 812, along with any additional cooling provided at ABTT terminus 20 by thermoelectric devices 808. It should be understood that frame 806 can include an extension (not shown) that positions thermoelectric device 808 above the eyebrow of subject 812 to contact the skin of the forehead over the supraorbital vein 16 and frontal vein 12, and/or an extension (not shown) that positions thermoelectric device 808 along the side of the nose of subject 812 to contact the skin over angular vein 18 and facial vein 19, to increase thermal effect to the brain. FIG. 80B shows device 804 in direct contact with skin 814 for optimal thermal effect via conduction for cooling the vessel underneath, illustrated herein as vein 14.

Figure 81:
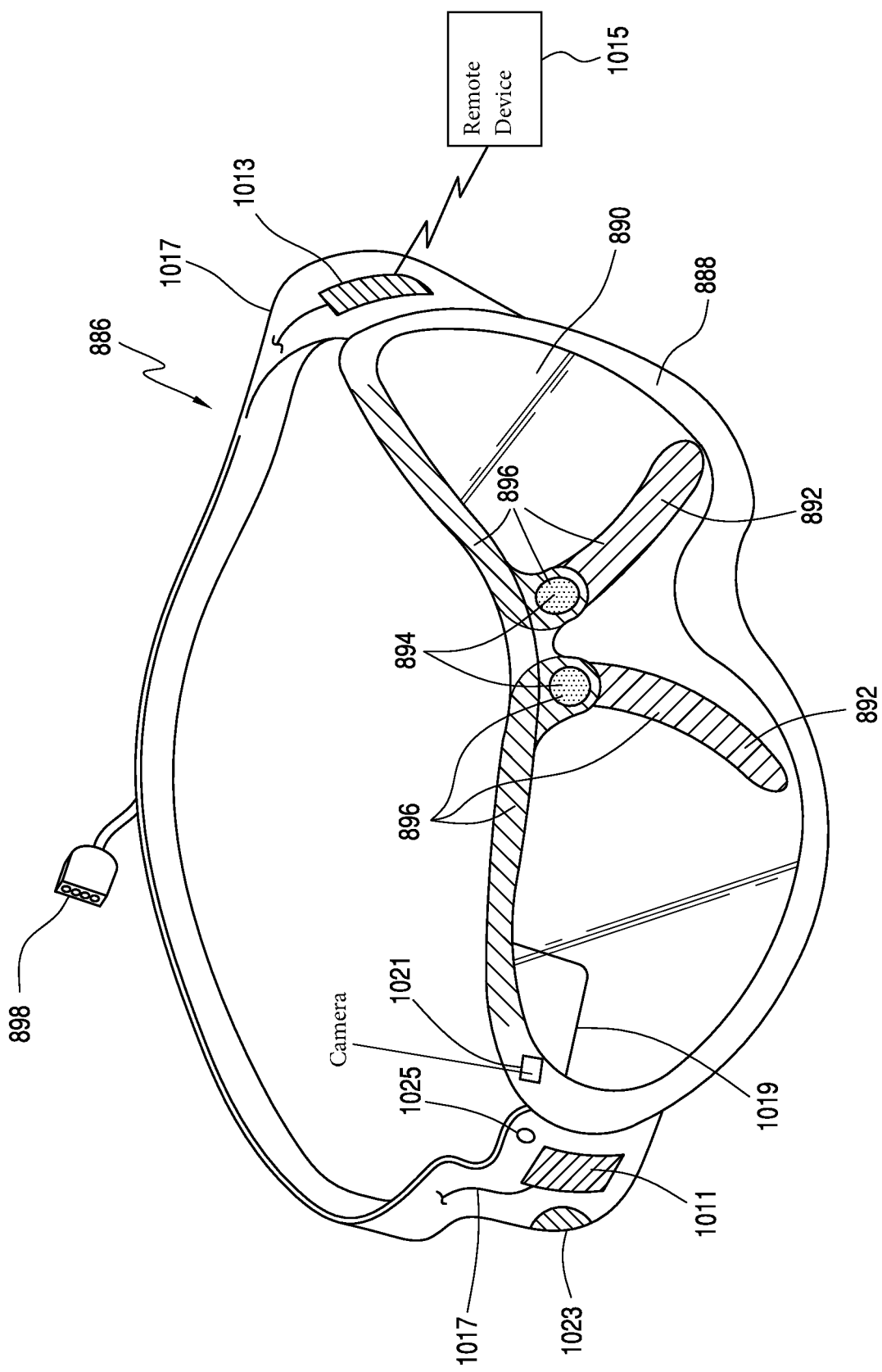
FIG. 81 is a view of an active thermal exchange device in accordance with an exemplary embodiment of the present disclosure.

FIG. 81 is a view of a further active thermal exchange device in accordance with an exemplary embodiment of the present disclosure, indicated at 886. Device 886 is configured as goggles that include a frame 888 and at least partially transparent plastic, glass, or the like 890, which may be configured as clear or tinted lenses. Device 886 further includes extensions 892 that are positioned to follow the path of angular veins 18 approximately, along with nodes or pads 894 for contacting ABTT terminus 20. Device 886 further includes a plurality of thermoelectric heaters/coolers 896 positioned in one or more locations along frame 88, which can include extensions 892 and nodes 894, for cooling or heating of superior palpebral veins 14, angular veins 18, and ABTT terminus 20. In addition, device 886 may also cool supraorbital veins 16 depending on the size of device 886, and can also cool a portion of frontal veins 12. Device 886 may also include an electronic module 1011 containing memory, processor, and circuitry connected by a wire 1017 that runs along a band 1019 to connect with a second module 1013, said module including a wireless transceiver to communicate with a remote device (including a computing device, cell phone, and the like). A transceiver in module 1013 is adapted to receive signals from a remote device 1015 and to transmit signals to remote device 1015. Remote device 1015 can include a cell phone, watch or any computing device containing instructions for adjusting the amount of heat applied or removed by a thermoelectric device. Device 886 may further include a display to show the temperature at ABTT terminus 20, the temperature of thermoelectric devices, or any other information or data, including data received from the internet or from remote device 1015. Device 886 may include a camera 1021 that is particularly useful by military or firefighters using device 886 to cool and that need to report visually ambient conditions to a remote station, and a microphone 1023 for oral commands of device 886 or for recording in a recorder (not shown). Device 886 further includes a speaker 1023, said speaker may include ear phones, or other display or means to alert to various conditions, such as suitability for operation and error conditions, etc. It should be understood that any of the components described for device 886 can be integrated in any and all of the embodiments of the present disclosure. While device 886 may include one or more power supplies, because device 886 is likely to be used for an extended period, device 886 includes a connector 898 for connecting the various electronic elements of device 886 to an external power supply (not shown).

Figure 82:
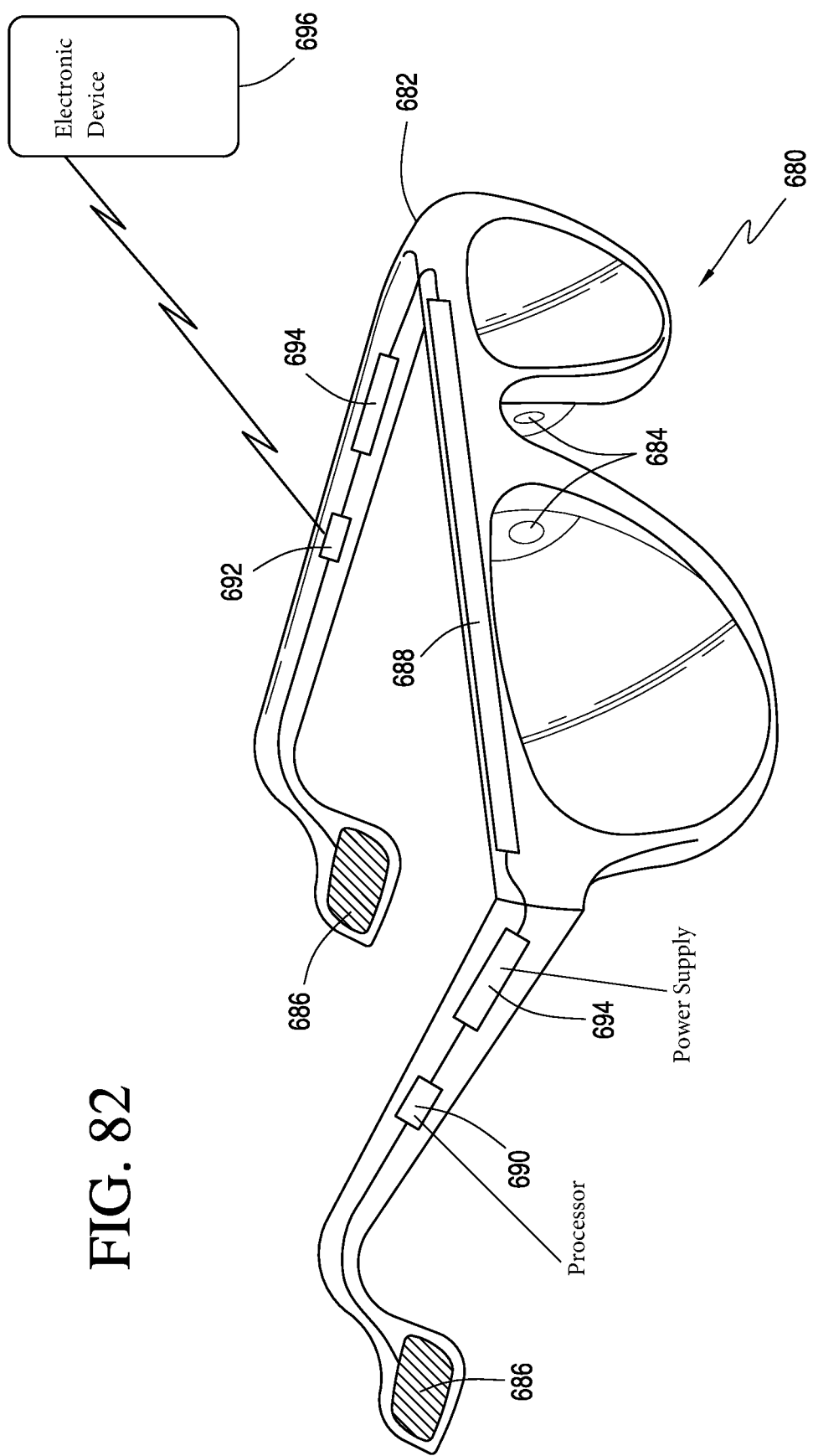
FIG. 82 is a view of an active thermal exchange device in accordance with an exemplary embodiment of the present disclosure.

FIG. 82 is a view of yet another active thermal exchange device in accordance with an exemplary embodiment of the present disclosure, indicated generally at 680. Device 680 includes a frame 682, in or on which are located one or more sensors 684. Sensors 684 are positioned to contact ABTT terminuses 20 for measurement of the temperature of ABTT 22. Device 680 further includes thermoelectric coolers/heaters 686 positioned in or on frame 682 and located or positioned to provide cooling to the retroauricular vein located behind the ear. Additionally, thermoelectric coolers/heaters 688 may be positioned along frame 682 to provide cooling/heating to superior palpebral vein 14, and some portions of supraorbital vein 16 and frontal vein 12. As with other embodiments, device 680 includes a plurality of electronic devices positioned on frame 682, such as a controller or processor 690, a transmitter 692 for communication with a separate electronic device 696, and one or more power supplies 694. As with other embodiments, device 680 may include a connector (not shown) to provide power and/or control by an external power supply and other electronic devices.

Figure 83:
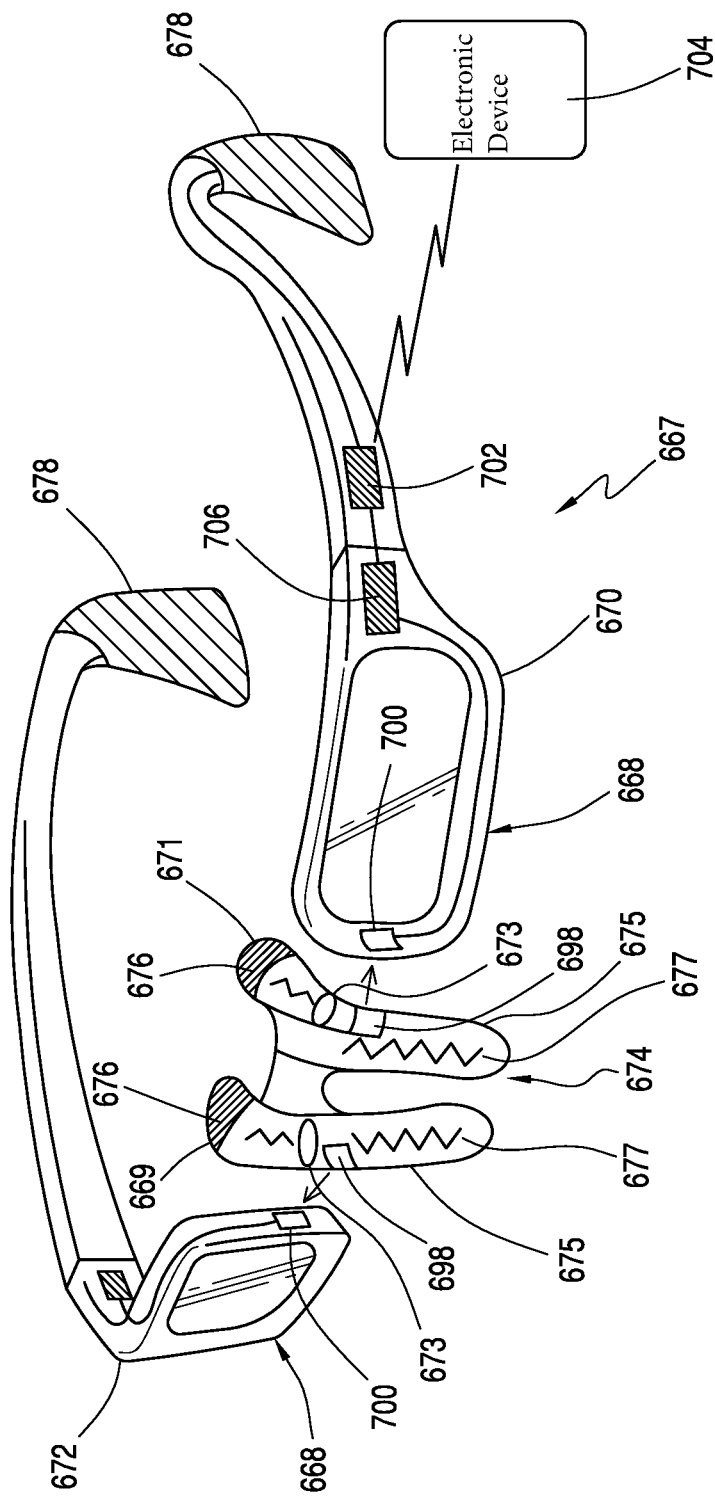
FIG. 83 is a view of an active thermal exchange device in accordance with an exemplary embodiment of the present disclosure.

FIG. 83 shows yet another active thermal exchange device in accordance with an exemplary embodiment of the present disclosure and indicated generally at 667. Delivery device 667 includes a pair of glasses 668 with a first or left side frame 670 and a second or right side frame 672, which are configured to connect to each other by way of a removable and exchangeable nose piece 674. Removable nose piece 674 has two horn-like projections 669 and 671 in the right and left side respectively, and includes an active heating and cooling device 676 configured in a location that places heating and cooling device 676 in contact with the skin between the eyebrows and about up to 5 mm above the upper edge of the eyebrow in order to overlie the region of frontal vein 12 and supraorbital vein 16. Removable nose piece 674 includes an active heating and cooling device 673 configured in a location that places heating and cooling device 673 in contact with ABTT terminus 20. Lower extensions 675 of removable nose piece 674 include an active heating and cooling device 677 configured to be positioned in a location that places heating and cooling device 677 in contact with the skin along to side of the nose in order to overlie a least a portion angular vein 18. Device 667 further includes active heating and cooling devices 678 at an end of frames 670 and 672 for cooling of the retroauricular vein behind the ear. Removable nose piece 674 is configured to connect left frame 672 to right frame 670 and to support left frame 672 and right frame 670 as an assembly, pair of glasses 668. Removable nose piece 674 further includes electrical connectors 698 for connection with mating connectors 700 located in left frame 672 and right frame 670. Device 667 further includes a plurality of electronics located in left frame 672 and right frame 670, such as a transmitter, transceiver, or receiver 702, which is configured to communicate with a separate electronic device 704, and a power supply 706, though power may be provided to device 667 by an external device through a wired or wireless connection (not shown). In another exemplary embodiment, nose piece 674 can be cooled or heated prior to installation in device 667, and thus device 667 an also be configured as a passive heating or cooling device. In yet another exemplary embodiment, nose piece 674 can be configured without any heating or cooling features, and thus eyeglasses 668 can include configurations with and without heating capabilities.

Figure 84:
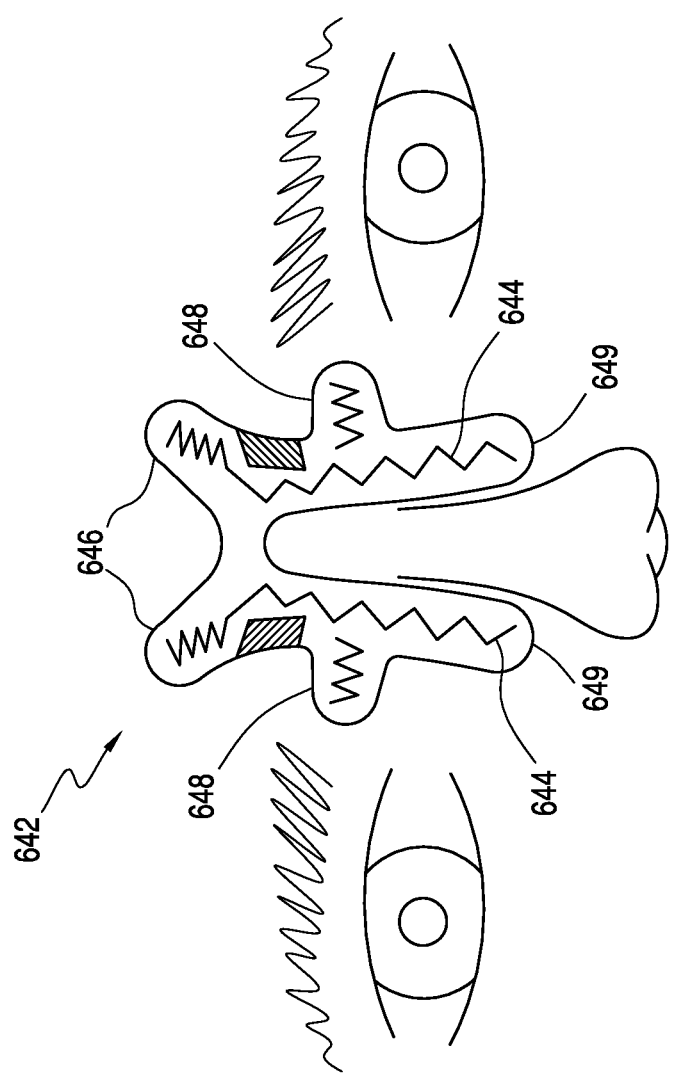
FIG. 84 is a view of an active thermal exchange device in accordance with an exemplary embodiment of the present disclosure.

FIG. 84 shows another active thermal exchange device in accordance with an exemplary embodiment of the present disclosure, indicated generally at 642. Device 642 incorporates one or more thermoelectric coolers/heaters or resistive heaters 644. Device 642 further includes a plurality of first longitudinal extension 646 for configured to provide cooling or heating to at least a portion of frontal vein 12 and supraorbital vein 16, a second transverse or horizontal extension 648 configured to provide cooling or heating to ABTT terminus 20, and a third longitudinal extension 649 configured to provide heating or cooling to angular vein 18.

Figure 85:
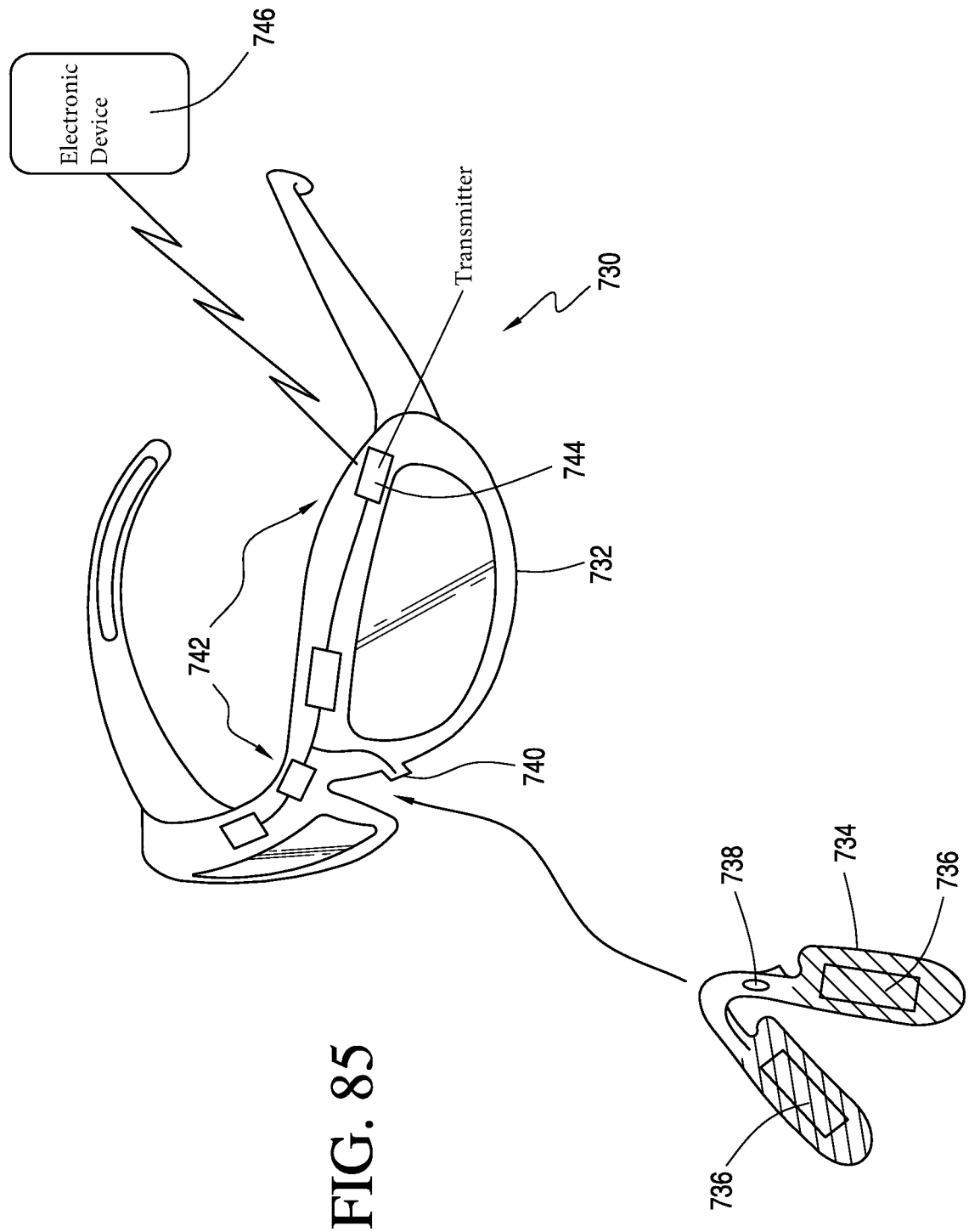
FIG. 85 is a view of an active thermal exchange device in accordance with an exemplary embodiment of the present disclosure.

FIG. 85 shows another active thermal exchange device in accordance with an exemplary embodiment of the present disclosure, indicated generally at 730. Device 730 includes a frame 732 and a separate nose piece 734 removably connectable to frame 732. Separate nose piece 734 includes one or more thermoelectric heating/cooling devices 736 positioned to provide cooling to ABTT terminus 20, along with a connector 738 for interfacing with a mating connector 740 positioned on frame 732. It should be understood that nose piece 734 may also be resistively heated, or heated or cooled prior to installation and may include passive heating or cooling using thermally retentive material such as a gel in pouches to fit the anatomy of the ABTT 20. Further, nose piece 734 may be replaced by a nose piece that provides no heating or cooling. As with other embodiments, device 730 includes a plurality of electronics 742, which can include a transmitter 744 for communication with a separate electronic device 746.

Figure 86:
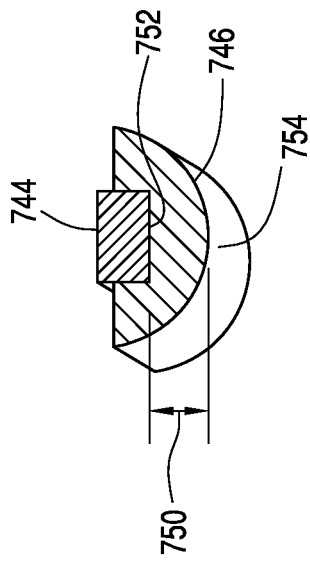
FIG. 86 is a view of an envelope for a thermoelectric device in accordance with an exemplary embodiment of the present disclosure.

Some of the various devices described herein include thermoelectric devices configured to heat or cool ABTT terminus 20. Such devices can be sized to be larger or smaller than ABTT terminus 20. Making such a device larger typically decreases positional sensitivity, but increases the power required to drive the cooler. Thus, there is a tradeoff between size of a thermoelectric devices and power. FIG. 86 is a view of an envelope 742 for exemplary thermoelectric device. In an exemplary embodiment, the X and Y dimensions can be less than or equal to 10 mm by 10 mm, or less than or equal to 10 mm in diameter. In another exemplary embodiment, the X and Y dimensions can be less than or equal to 7 mm by 7 mm, or less than or equal to 7 mm in diameter. In another exemplary embodiment, the X and Y dimensions can be less than or equal to 5 mm by 5 mm, or less than or equal to 5 mm in diameter. In another exemplary embodiment, the X and Y dimensions can be less than or equal to 3 mm by 3 mm, or less than or equal to 3 mm in diameter. In another exemplary embodiment, the X and Y dimensions can be less than or equal to 2 mm by 2 mm, or less than or equal to 2 mm in diameter. The Z dimension is typically established by the needs of fabrication of the thermoelectric devices. For many of the embodiments described herein, the Z dimension is relatively unimportant and can virtually any dimension that would be anticipated from a thermoelectric device. However, for some embodiments, for example, those positioned in the frames or nose pieces of eyeglasses, the thickness or Z dimension of a thermoelectric device is more important. An exemplary Z dimension or thickness of a thermoelectric device is less than or equal to 17 mm. Another exemplary Z dimension or thickness of a thermoelectric device is less than or equal to 10 mm. Yet another exemplary Z dimension or thickness of a thermoelectric cooler is less than or equal to 6 mm. In another exemplary embodiment, the Z dimension or thickness is less than 4.5 mm. In yet another exemplary embodiment, the Z dimension or thickness is less than 3 mm, with this dimension generally being desirable for most embodiments where the thermoelectric device is embedded in a frame of some type.

Figure 87:
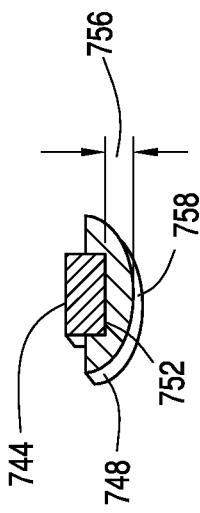
FIG. 87 is a cross sectional view of a thermoelectric device embedded in a frame or support in accordance with an exemplary embodiment of the present disclosure.
Figure 88:
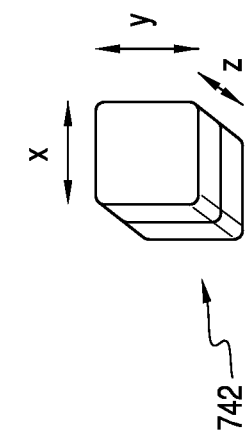
FIG. 88 is another cross sectional view of a thermoelectric device embedded in a frame or support in accordance with an exemplary embodiment of the present disclosure.

Thermoelectric coolers described herein may be positioned in a variety of configurations, depending on application. For example, FIG. 87 shows a cross-sectional view of a thermoelectric device 744 positioned in a frame, support, nose piece, plastic band, flexible strap, etc., 746. FIG. 88 shows thermoelectric device 744 positioned in another frame, support, nosepiece, etc., 748. As can be seen by comparing FIG. 87 to FIG. 88, a distance 750 from a bottom 752 of thermoelectric device 744 to an exterior surface 754 of frame 746 can be significantly more than a distance 756 from bottom 752 of thermoelectric device 744 to an exterior surface 758 of frame 748. The difference between these two configurations is that the greater the distance from bottom 752 to an exterior surface of a support or frame, the more heat from thermoelectric device 744 spreads, and the longer it takes for heating to occur. However, in some circumstances, the spread of heat may accommodate some misalignment with ABTT terminus 20, and reduces the rate of heat buildup, which may be advantageous in some therapeutic applications of heat and cold to ABTT terminus 20. The structure containing thermoelectric devices in many embodiments I configured to be deformable, flexible, bendable, etc., and can be configured to include a sponge or foam for better comfort and apposition to the skin.

Figure 89:
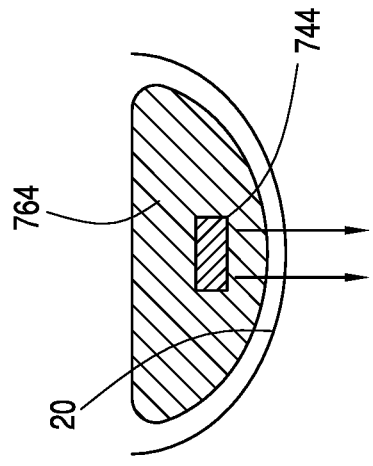
FIG. 89 is yet another cross sectional view of a thermoelectric device embedded in a frame or support in accordance with an exemplary embodiment of the present disclosure.
Figure 90:
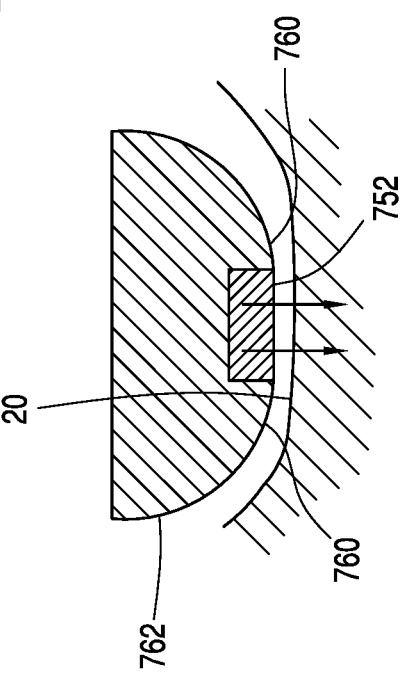
FIG. 90 is a further cross sectional view of a thermoelectric device embedded in a frame or support in accordance with an exemplary embodiment of the present disclosure.

As shown in FIG. 89, thermoelectric device 744 may also be positioned such that bottom 752 is contiguous with a curvilinear surface 760 of a support, frame or nose piece 762, which provides relatively localized heating or cooling as compared to the configurations of FIGS. 87 and 88. FIG. 90 is a view of yet another configuration, in which thermoelectric device 744 is fully embedded or surrounded by a support, frame, or nose piece 764, thus capturing all heat generated by thermoelectric device 744 and conferring the benefits of the configurations of FIGS. 87 and 88.

Figures 91, 91A:
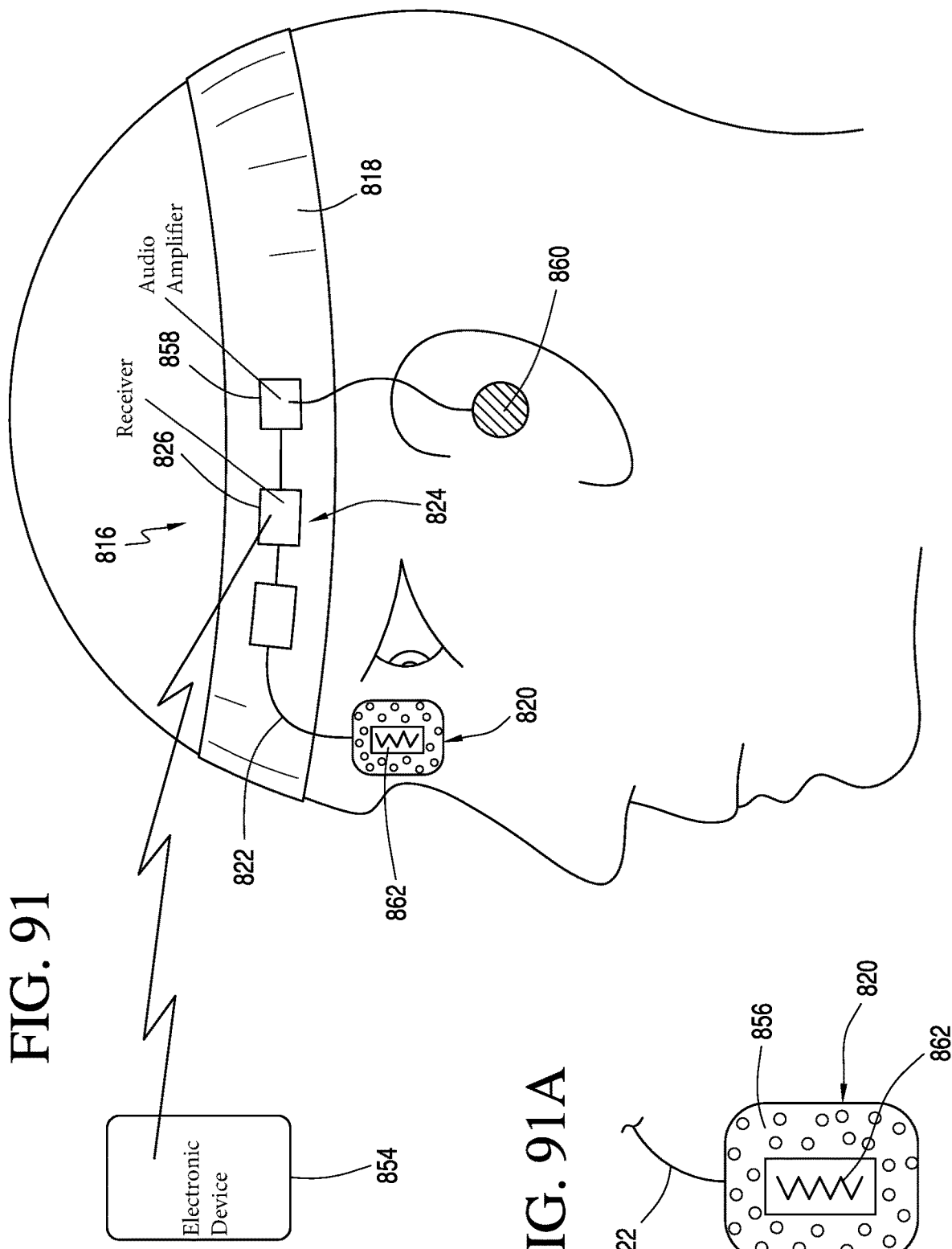
FIG. 91 is a view of another active thermal exchange device in accordance with an exemplary embodiment of the present disclosure.
FIG. 91A is a view of a portion of the active thermal exchange device of FIG. 91.

FIG. 91 is a view of a further active thermal exchange device in accordance with an exemplary embodiment of the present disclosure, indicated generally at 816. Device 816 includes a support structure 818, which in the exemplary embodiment of FIG. 91 is a headband. Device 816 further includes a thermoelectric apparatus 820 configured to be positioned on an ABTT terminus 20. Thermoelectric apparatus 820 is configured to be attached by a wire or cable 822 to support structure 818. Support structure 818 is configured to include a plurality of electronics 824, including a transceiver, transmitter, or receiver 826 for communication with a separate electronic device 854. Other electronics can include a controller or processor, a power supply, and an audio amplifier 858 for providing signals to one or more earphones 860, which permits audio communication by device 816 to a user. As shown in FIG. 91A, thermoelectric apparatus 820 may include a thermally retentive substance or material 856 configured to surround a thermoelectric device 862.

While various embodiments of the disclosure have been shown and described, it is understood that these embodiments are not limited thereto. The embodiments may be changed, modified, and further applied by those skilled in the art. Therefore, these embodiments are not limited to the detail shown and described previously, but also include all such changes and modifications.

I claim:

1. A device configured to apply heat or cold to an Abreu brain thermal tunnel (ABTT) terminus, the device comprising:
   a support structure configured as eyeglass frames; and
   a resistive heater positioned on the support structure, the resistive heater being positioned to heat a portion of the support structure that extends along the superior palpebral vein when the support structure is worn by a user and the resistive heater being configured to provide thermal exchange with the superior palpebral vein when the support structure is worn by a user,
   wherein the resistive heater extends away from the ABTT terminus along an upper eyelid region and alongside the superior palpebral vein of the user when the structure is worn by the user on both a left side of the user and a right side of the user, the resistive heater terminating before reaching the end of the superior palpebral vein of the user on the left side of the user and terminating before reaching the end of the superior palpebral vein of the user on the right side of the user.

2. The device of claim 1, further comprising:
   a flexible support configured to hold the resistive heater on the support structure,
   wherein the flexible support allows for the position of the resistive heater to be adjusted on the face of the user along the superior palpebral vein.

3. The device of claim 1, further comprising:
   a power supply configured to supply power to the resistive heater; and
   a transmitter configured to communicate wirelessly with a separate electronic device.

4. The device of claim 3, wherein the electronic device is at least one selected from the group consisting of a cell phone, a watch, a laptop, and a tablet.

5. The device of claim 1, wherein the resistive heater comprises a body connected to an adjustable arm, the body having a cylindrical configuration.

6. The device of claim 5, wherein the body of the thermal device has a length of from 7 mm to 40 mm, and a diameter of from 2.5 mm to 20 mm.

7. The device of claim 1, further comprising:
   a hood configured to create air pockets around the superior palpebral vein to augment the thermal effect of the device.

* * * * *